United States Patent
Mo et al.

(10) Patent No.: US 12,185,627 B2
(45) Date of Patent: Dec. 31, 2024

(54) HETEROCYCLIC COMPOUND AND ORGANIC LIGHT-EMITTING DEVICE COMPRISING SAME

(71) Applicant: LT MATERIALS CO., LTD., Yongin-Si (KR)

(72) Inventors: Jun-Tae Mo, Osan-si (KR); Mi-Jin Kim, Ulju-gun (KR); Ji-Yoon Byun, Osan-si (KR); Jong-Su Lee, Osan-si (KR); Dong-Jun Kim, Yongin-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 712 days.

(21) Appl. No.: 17/041,170

(22) PCT Filed: Apr. 16, 2019

(86) PCT No.: PCT/KR2019/004599
§ 371 (c)(1),
(2) Date: Sep. 24, 2020

(87) PCT Pub. No.: WO2019/203550
PCT Pub. Date: Oct. 24, 2019

(65) Prior Publication Data
US 2021/0013411 A1    Jan. 14, 2021

(30) Foreign Application Priority Data
Apr. 17, 2018  (KR) .................. 10-2018-0044407

(51) Int. Cl.
*H01L 51/50*   (2006.01)
*C07D 405/14*  (2006.01)
*H10K 99/00*   (2023.01)

(52) U.S. Cl.
CPC .......... *H10K 99/00* (2023.02); *C07D 405/14* (2013.01)

(58) Field of Classification Search
None
See application file for complete search history.

(56) References Cited

U.S. PATENT DOCUMENTS

| | | | |
|---|---|---|---|
| 10,840,457 B2 | 11/2020 | Mun et al. | |
| 2003/0137239 A1* | 7/2003 | Matsuura | H10K 50/14 313/503 |
| 2013/0256637 A1 | 10/2013 | Seo et al. | |
| 2017/0005276 A1* | 1/2017 | Kim | C07D 401/14 |
| 2017/0179401 A1 | 6/2017 | Kim et al. | |

(Continued)

FOREIGN PATENT DOCUMENTS

KR  10-2013-0025268 A   3/2013
KR  10-2014-0046541 A   4/2014
(Continued)

OTHER PUBLICATIONS

International Search Report (Form PCT/ISA/210) for International Application No. PCT/KR2019/004599, dated Jul. 16, 2019.
(Continued)

*Primary Examiner* — Gregory D Clark
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

10 Claims, 2 Drawing Sheets

(56) References Cited

U.S. PATENT DOCUMENTS

| | | | |
|---|---|---|---|
| 2017/0186975 A1 | 6/2017 | Kim et al. | |
| 2018/0123051 A1 | 6/2018 | Lee et al. | |
| 2019/0237880 A1 | 8/2019 | Kim et al. | |
| 2020/0136058 A1* | 4/2020 | Kim | C07D 403/14 |

FOREIGN PATENT DOCUMENTS

| | | | | |
|---|---|---|---|---|
| KR | 2014/046541 | * | 7/2014 | C09K 11/06 |
| KR | 10-2017-0035232 A | | 3/2017 | |
| KR | 10-2017-0096769 A | | 5/2017 | |
| KR | 10-2017-0075118 A | | 7/2017 | |
| KR | 10-2017-0078977 A | | 7/2017 | |
| KR | 2017-096769 | * | 8/2017 | H01L 51/00 |
| KR | 10-2017-0112865 A | | 10/2017 | |
| KR | 10-2018-0015546 A | | 2/2018 | |
| KR | 10-2018-0020822 A | | 2/2018 | |
| KR | 10-2018-0022325 A | | 3/2018 | |
| KR | 10-2018-0022608 A | | 3/2018 | |
| KR | 10-2018-0031385 A | | 3/2018 | |
| KR | 10-2018-0109747 A | | 10/2018 | |
| KR | 10-2018-0109748 A | | 10/2018 | |
| KR | 10-2019-0002206 A | | 1/2019 | |
| WO | WO 2013-032284 A1 | * | 3/2013 | H01L 51/54 |

OTHER PUBLICATIONS

Kuwabara et al., "Thermally Stable Multilayered Organic Electroluminescent Devices Using Novel Starburst Molecules, 4,4' 4"-Tri(N-carbazolyl)triphenylamine (TCTA) and 4,4',4"-Tris(3-methylphenylphenylamino)triphenylamine (m-MTDATA), as Hole-Transport Materials", Advanced Materials, vol. 6, No. 9, 1994, pp. 677-679.

* cited by examiner

【FIG. 1】
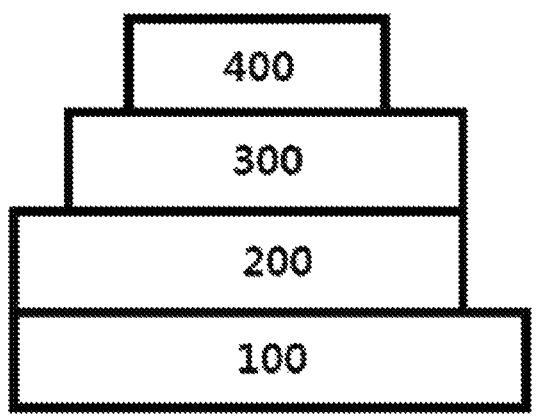
【FIG. 2】
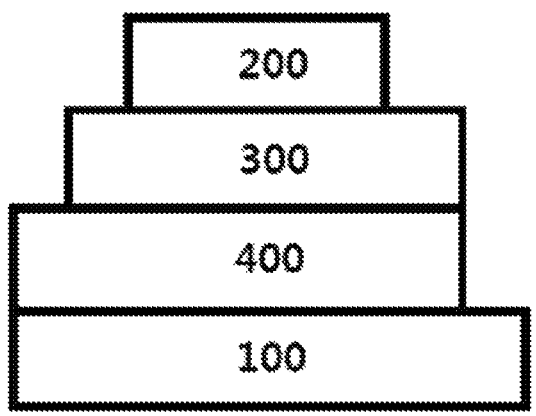

【FIG. 3】
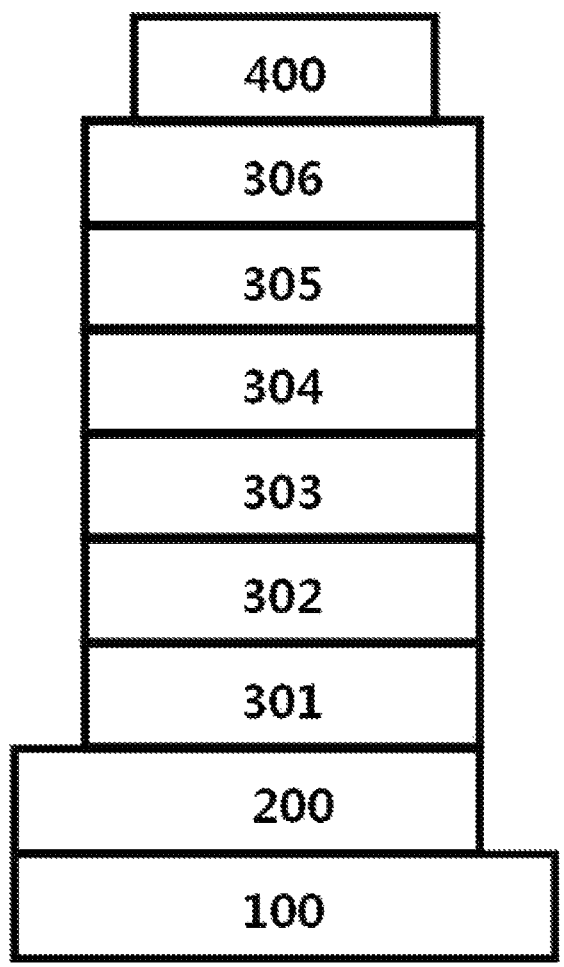

HETEROCYCLIC COMPOUND AND ORGANIC LIGHT-EMITTING DEVICE COMPRISING SAME

TECHNICAL FIELD

The present application claims priority to and the benefits of Korean Patent Application No. 10-2018-0044407, filed with the Korean Intellectual Property Office on Apr. 17, 2018, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present application is directed to providing a novel heterocyclic compound, and an organic light emitting device comprising the same.

Technical Solution

One embodiment of the present application provides a heterocyclic compound represented by the following Chemical Formula 1.

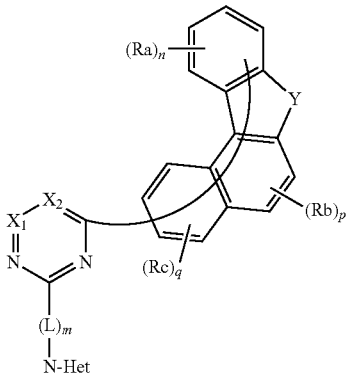

[Chemical Formula 1]

In Chemical Formula 1,
$X_1$ is N or $CR_1$,
$X_2$ is N or $CR_2$,
Y is O; S; CRR'; or NR",
L is a direct bond; a substituted or unsubstituted arylene group; or a substituted or unsubstituted heteroarylene group,
m is an integer of 0 to 5,
N-Het is a monocyclic or polycyclic heterocyclic group substituted or unsubstituted and comprising one or more Ns,
$R_1$ and $R_2$ are the same as or different from each other, and each independently selected from the group consisting of hydrogen; a substituted or unsubstituted alkyl group; a substituted or unsubstituted aryl group; and a substituted or unsubstituted heteroaryl group, or two or more groups adjacent to each other bond to each other to form a substituted or unsubstituted aliphatic or aromatic hydrocarbon ring or a substituted or unsubstituted aliphatic or aromatic heteroring,
$R_a$ to $R_c$, R, R' and R" are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or a substituted or unsubstituted aliphatic or aromatic heteroring, n and q are each an integer of 0 to 4, and when n is 2 or greater, Pas are the same as or different from each other, when q is 2 or greater, $R_c$s are the same as or different from each other, p is an integer of 0 to 2, and when p is an integer of 2, $R_b$s are the same as or different from each other, and
$n+p+q \leq 9$.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like in the organic light emitting device. Particularly, the compound can be used as a light emitting layer material of the organic light emitting device. For example, the compound alone can be used as a light emitting material, or the compound can be used as a host material of a light emitting layer.

Particularly, by substituting a heterocyclic compound having an electron transfer ability with a polycyclic compound, Chemical Formula 1 shows stability in the electron transfer ability, and has properties of improving a lifetime. Particularly, properties of increasing a lifetime are obtained in various N-containing heterocyclic compounds having a hole transfer ability by N-Het, and particularly in carbazole-based compounds, lifetime properties are excellent, and properties of improving efficiency and driving are obtained depending on structural characteristics of the heteroring.

DESCRIPTION OF DRAWINGS

FIG. 1 to FIG. 3 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group.

The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a terphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the fluorenyl group may be substituted, and adjacent substituents may bond to each other to form a ring.

When the fluorenyl group is substituted, the following structures may be obtained, however, the structure is not limited thereto.

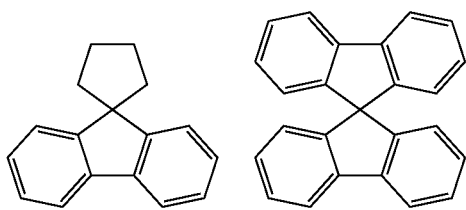

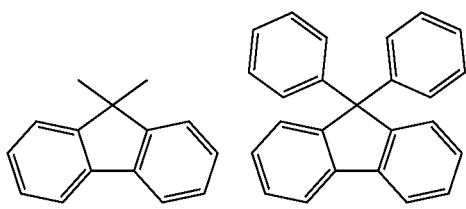

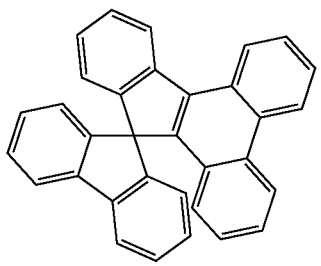

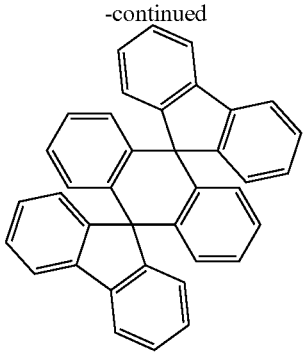

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinoxalinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH₂; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the phosphine oxide group may specifically be substituted with an aryl group, and the examples described above may be applied to the aryl group. Examples of the phosphine oxide group may comprise a diphenylphosphine oxide group, a dinaphthylphosphine oxide group and the like, but are not limited thereto.

In the present specification, the arylene group means the aryl group having two bonding sites, that is, a divalent group. Descriptions on the aryl group provided above may be applied thereto except for those that are each a divalent. In addition, the heteroarylene group means the heteroaryl group having two bonding sites, that is, a divalent group. Descriptions on the heteroaryl group provided above may be applied thereto except for those that are each a divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

The structures illustrated as the cycloalkyl group described above may be applied to the aliphatic hydrocarbon ring that adjacent groups may form except for those that are not a monovalent group, the structures illustrated as the aryl group described above may be applied to the aromatic hydrocarbon ring except for those that are not a monovalent group, the structures illustrated as the heterocycloalkyl group described above may be applied to the aliphatic heteroring except for those that are not a monovalent group, and the structures illustrated as the heteroaryl group described above may be applied to the aromatic heteroring except for those that are not a monovalent group.

One embodiment of the present application provides a compound represented by Chemical Formula 1.

In one embodiment of the present application, Chemical Formula 1 may be represented by any one of the following Chemical Formulae 2 to 5.

[Chemical Formula 2]

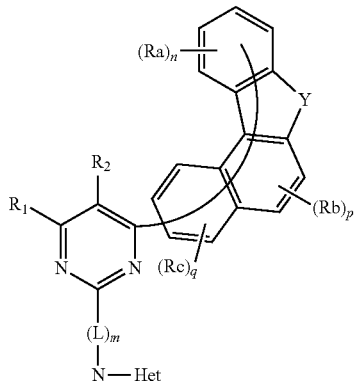

[Chemical Formula 3]

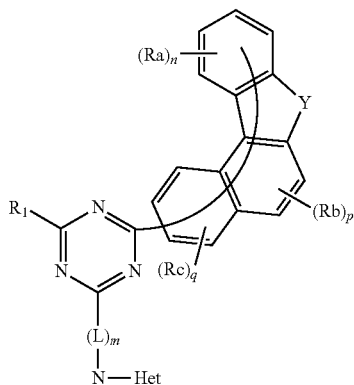

[Chemical Formula 4]

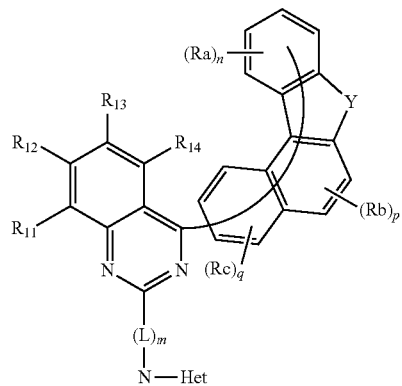

[Chemical Formula 5]

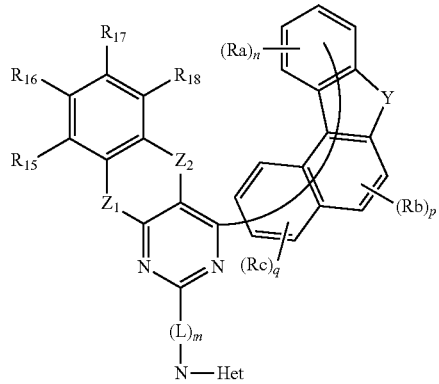

In Chemical Formulae 2 to 5, $R_1$, $R_2$, and $R_{11}$ to $R_{18}$ are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, $Z_1$ and $Z_2$ are the same as or different from each other, and each independently a direct bond; O; or S, and $R_a$ to $R_c$, Y, N-Het, L, m, n, p and q have the same definitions as in Chemical Formula 1.

In one embodiment of the present application, $X_1$ may be N or $CR_1$.

In one embodiment of the present application, $X_1$ may be N.

In one embodiment of the present application, $X_1$ may be $CR_1$.

In one embodiment of the present application, $X_2$ may be N or $CR_2$.

In one embodiment of the present application, $X_2$ may be N.

In one embodiment of the present application, $X_2$ may be $CR_2$.

In one embodiment of the present application, $R_1$ and $R_2$ are the same as or different from each other, and each independently selected from the group consisting of hydrogen; a substituted or unsubstituted alkyl group; a substituted or unsubstituted aryl group; and a substituted or unsubstituted heteroaryl group, or two or more groups adjacent to each other may bond to each other to form a substituted or unsubstituted aliphatic or aromatic hydrocarbon ring or a substituted or unsubstituted aliphatic or aromatic heteroring.

In another embodiment, $R_1$ and $R_2$ are the same as or different from each other, and each independently selected from the group consisting of hydrogen; and a substituted or unsubstituted aryl group, or two or more groups adjacent to each other may bond to each other to form a substituted or unsubstituted aromatic hydrocarbon ring or a substituted or unsubstituted aromatic heteroring.

In another embodiment, $R_1$ and $R_2$ are the same as or different from each other, and each independently selected from the group consisting of hydrogen; and a substituted or unsubstituted C6 to C60 aryl group, or two or more groups adjacent to each other may bond to each other to form a substituted or unsubstituted C6 to C60 aromatic hydrocarbon ring or a substituted or unsubstituted C2 to C60 aromatic heteroring.

In another embodiment, $R_1$ and $R_2$ are the same as or different from each other, and each independently selected from the group consisting of hydrogen; and a substituted or unsubstituted C6 to C40 aryl group, or two or more groups adjacent to each other may bond to each other to form a substituted or unsubstituted C6 to C40 aromatic hydrocarbon ring or a substituted or unsubstituted C2 to C40 aromatic heteroring.

In another embodiment, $R_1$ and $R_2$ are the same as or different from each other, and each independently selected from the group consisting of hydrogen; and a C6 to C40 aryl group, or two or more groups adjacent to each other may bond to each other to form a C6 to C40 aromatic hydrocarbon ring or a C2 to C40 aromatic heteroring.

In another embodiment, $R_1$ and $R_2$ are the same as or different from each other, and each independently selected from the group consisting of hydrogen; and a phenyl group, or two or more groups adjacent to each other may bond to each other to form a benzene ring, a benzothiophene ring or a benzofuran ring.

In one embodiment of the present application, Y may be O; S; CRR'; or NR".

In another embodiment, Y may be O; or S.

In one embodiment of the present application, L may be a direct bond; a substituted or unsubstituted arylene group; or a substituted or unsubstituted heteroarylene group.

In another embodiment, L may be a direct bond; or a substituted or unsubstituted arylene group.

In another embodiment, L may be a direct bond; or a substituted or unsubstituted C6 to C60 arylene group.

In another embodiment, L may be a direct bond; or a substituted or unsubstituted C6 to C40 arylene group.

In another embodiment, L may be a direct bond; or a C6 to C40 arylene group.

In another embodiment, L may be a direct bond; or a C6 to C40 monocyclic arylene group.

In another embodiment, L may be a direct bond; or a phenylene group.

In one embodiment of the present application, $R_a$ to $R_c$, R, R' and R" are the same as or different from each other, and may be each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group.

In another embodiment, $R_a$ to $R_c$, R, R' and R" are the same as or different from each other, and may be each independently selected from the group consisting of hydrogen; a substituted or unsubstituted aryl group; and a substituted or unsubstituted heteroaryl group.

In another embodiment, $R_a$ to $R_c$, R, R' and R" are the same as or different from each other, and may be each independently selected from the group consisting of hydrogen; a substituted or unsubstituted C6 to C60 aryl group; and a substituted or unsubstituted C2 to C60 heteroaryl group.

In another embodiment, $R_a$ to $R_c$, R, R' and R" are the same as or different from each other, and may be each independently selected from the group consisting of hydrogen; a substituted or unsubstituted C6 to C40 aryl group; and a substituted or unsubstituted C2 to C40 heteroaryl group.

In another embodiment, $R_a$ to $R_e$ may be hydrogen.

In another embodiment, R, R' and R" are the same as or different from each other, and may be each independently hydrogen; or a phenyl group.

In one embodiment of the present application, $R_{11}$ to $R_{14}$ may be hydrogen.

In one embodiment of the present application, $R_{15}$ to $R_{18}$ may be hydrogen.

In one embodiment of the present application, N-Het is a monocyclic or polycyclic heteroring substituted or unsubstituted and comprising one or more Ns.

In one embodiment of the present application, N-Het is a monocyclic or polycyclic heteroring substituted or unsubstituted and comprising one or more and three or less Ns.

In one embodiment of the present application, N-Het is a monocyclic or polycyclic heteroring unsubstituted or substituted with one or more substituents selected from the group consisting of a C1 to C60 alkyl group, a substituted or unsubstituted C6 to C60 aryl group, a substituted or unsubstituted C2 to C60 heteroaryl group and a substituted or unsubstituted amine group, and comprising one N.

In one embodiment of the present application, N-Het may be a carbazole-based substituent.

The carbazole-based substituent may comprise both an unsubstituted carbazole group and a substituted carbazole group, and the substituted carbazole group may also comprise a carbazole group fused to form a ring.

In one embodiment of the present application, Chemical Formula 1 may be represented by any one of the following Chemical Formulae 6 to 9.

[Chemical Formula 6]

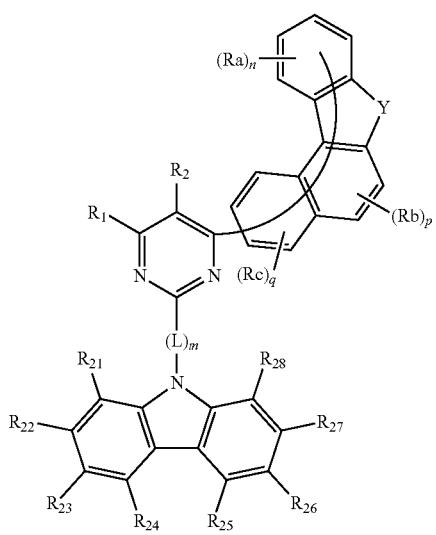

[Chemical Formula 7]

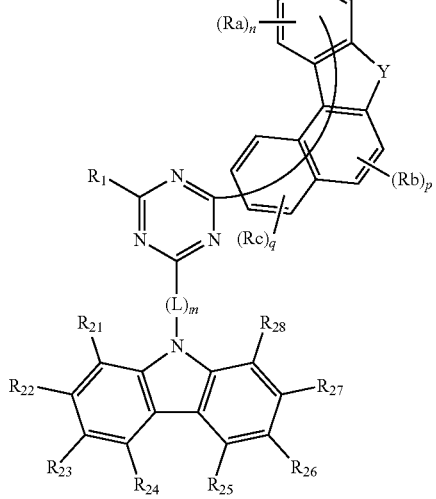

[Chemical Formula 8]

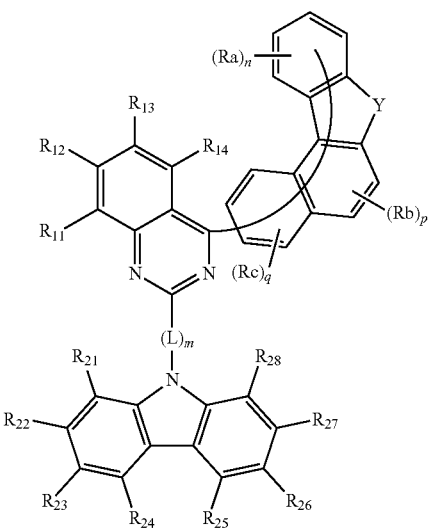

[Chemical Formula 9]

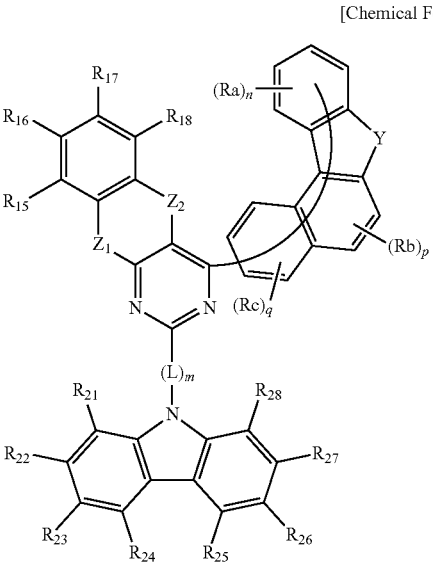

In Chemical Formulae 6 to 9, $R_1$, $R_2$, and $R_{11}$ to $R_{18}$ are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, $R_{21}$ to $R_{28}$ are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group;

a substituted or unsubstituted phosphine oxide group; and a substituted or unsubstituted amine group, or two or more groups adjacent to each other bond to each other to form a substituted or unsubstituted aliphatic or aromatic hydrocarbon ring or a substituted or unsubstituted aliphatic or aromatic heteroring, $Z_1$ and $Z_2$ are the same as or different from each other, and each independently a direct bond; O; or S, and $R_a$ to $R_c$, Y, L, m, n, p and q have the same definitions as in Chemical Formula 1.

In one embodiment of the present application, $R_{21}$ to $R_{28}$ are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other may bond to each other to form a substituted or unsubstituted aliphatic or aromatic hydrocarbon ring or a substituted or unsubstituted aliphatic or aromatic heteroring.

In another embodiment, $R_{21}$ to $R_{28}$ are the same as or different from each other, and each independently selected from the group consisting of hydrogen; a substituted or unsubstituted aryl group; a substituted or unsubstituted heteroaryl group; and a substituted or unsubstituted amine group, or two or more groups adjacent to each other may bond to each other to form a substituted or unsubstituted aromatic hydrocarbon ring or a substituted or unsubstituted aromatic heteroring.

In another embodiment, $R_{21}$ to $R_{28}$ are the same as or different from each other, and each independently selected from the group consisting of hydrogen; a substituted or unsubstituted C6 to C60 aryl group; a substituted or unsubstituted C2 to C60 heteroaryl group; and a diarylamine group, or two or more groups adjacent to each other may bond to each other to form a substituted or unsubstituted C6 to C60 aromatic hydrocarbon ring or a substituted or unsubstituted C2 to C60 aromatic heteroring.

In another embodiment, $R_{21}$ to $R_{28}$ are the same as or different from each other, and each independently selected from the group consisting of hydrogen; a substituted or unsubstituted C6 to C40 aryl group; a substituted or unsubstituted C2 to C40 heteroaryl group; and a diarylamine group, or two or more groups adjacent to each other may bond to each other to form a substituted or unsubstituted C6 to C40 aromatic hydrocarbon ring or a substituted or unsubstituted C2 to C40 aromatic heteroring.

In another embodiment, $R_{21}$ to $R_{28}$ are the same as or different from each other, and each independently selected from the group consisting of hydrogen; a C6 to C40 aryl group unsubstituted or substituted with one or more substituents selected from the group consisting of a C2 to C40 heteroaryl group and a diarylamine group; a C2 to C40 heteroaryl group unsubstituted or substituted with a C6 to C40 aryl group; and a diarylamine group, or two or more groups adjacent to each other may bond to each other to form a C6 to C40 aromatic hydrocarbon ring unsubstituted or substituted with a C1 to C40 alkyl group, or a C2 to C40 aromatic heteroring unsubstituted or substituted with a C6 to C40 aryl group.

In another embodiment, $R_{21}$ to $R_{28}$ are the same as or different from each other, and each independently selected from the group consisting of hydrogen; a phenyl group unsubstituted or substituted with one or more substituents selected from the group consisting of a carbazole group and an arylamine group; a naphthyl group; a carbazole group unsubstituted or substituted with a phenyl group; and an arylamine group, or two or more groups adjacent to each other may bond to each other to form a benzene ring; an indene ring unsubstituted or substituted with a methyl group; a benzofuran ring; a benzothiophene ring; or an indole ring unsubstituted or substituted with a phenyl group.

In an embodiment of the present application,

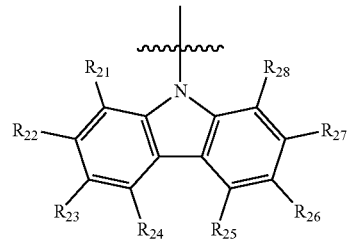

may be represented by the following Chemical Formula 10. Herein,

is a site linked to L.

[Chemical Formula 10]

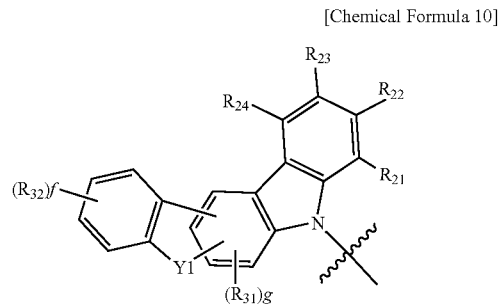

In Chemical Formula 10, $R_{21}$ to $R_{24}$ are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or a substituted or unsubstituted aliphatic or aromatic heteroring, Y1 is O; S; $CR_{41}R_{42}$; or $NR_{43}$, $R_{31}$, $R_{32}$ and $R_{41}$ to $R_{43}$ are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, f is an integer of 0 to 4, and when f is 2 or greater, $R_{32}$s are the same as or different from each other, g is an integer of 0 to 2, and when g is 2 or greater, $R_{31}$s are the same as or different from each other.

In another embodiment, Chemical Formula 10 may be selected from among the following structural formulae.

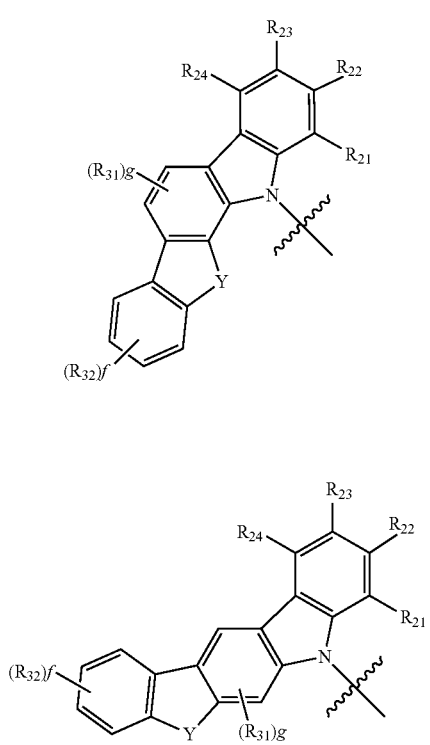

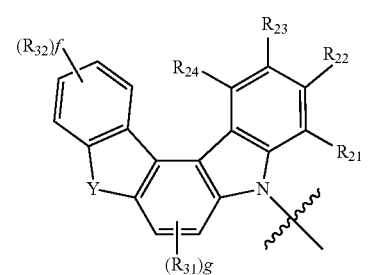

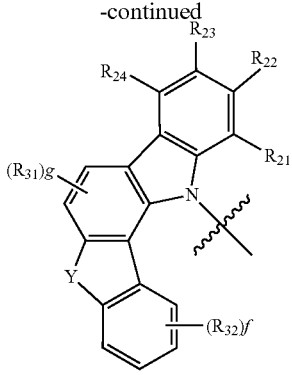

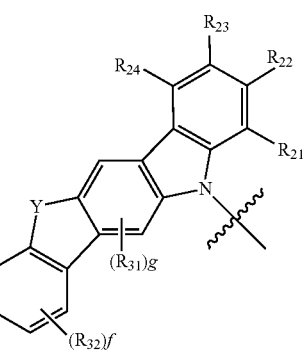

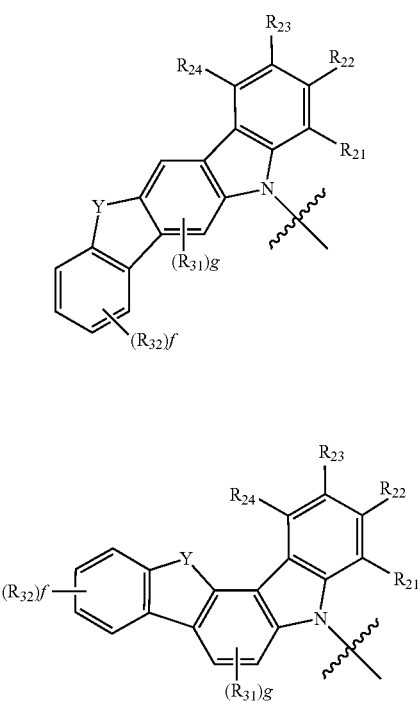

In the structural formulae,
substituents have the same definitions as in Chemical Formula 10.

In one embodiment of the present application,

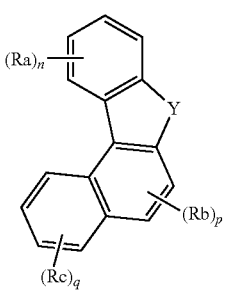

of Chemical Formula 1 may bond to

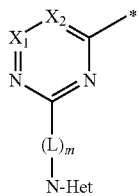

as follows, which means that the site represented by ⌇* of

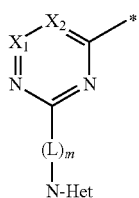

and the site represented by ⌇* of the following structural formulae bond to each other.

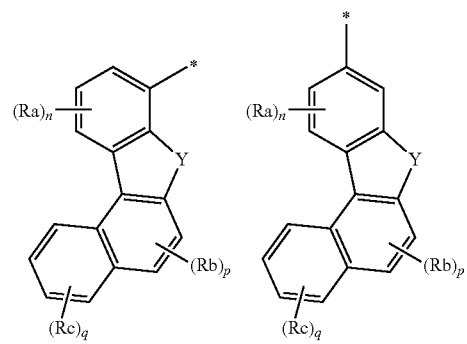

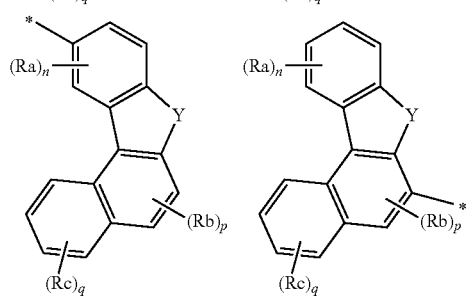

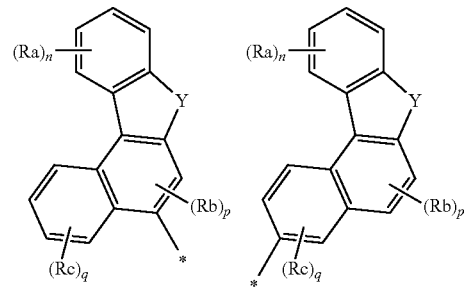

In the structural formulae, substituents have the same definitions as in Chemical Formula 1.

In one embodiment of the present application,

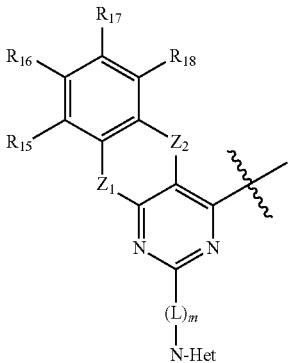

of Chemical Formula 5 may be represented by any one of the following structural formulae. Herein,

means a linking site.

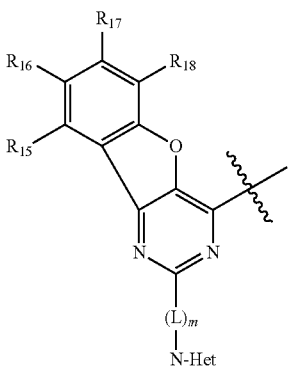

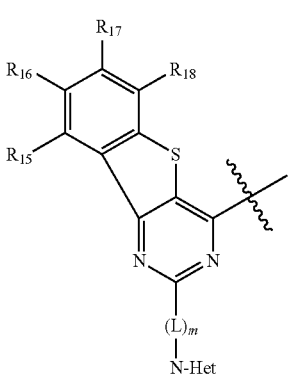

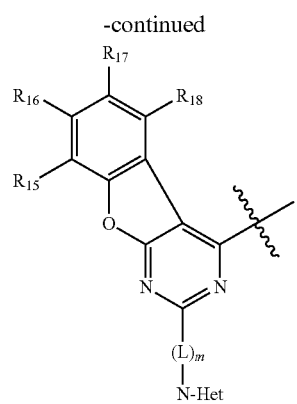
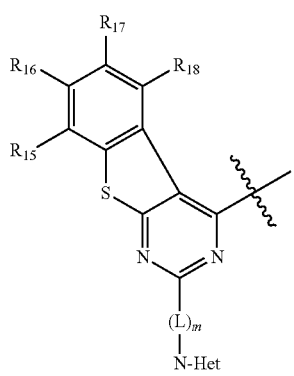
In the structural formulae, $R_{15}$ to $R_{18}$, m, L and N-Het have the same definitions as in Chemical Formula 5.
According to one embodiment of the present application, Chemical Formula 1 may be represented by any one of the following compounds, but is not limited thereto.
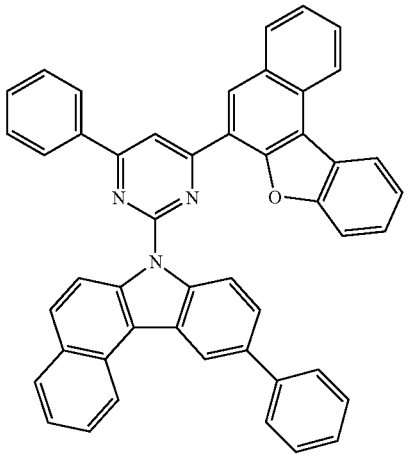
I2
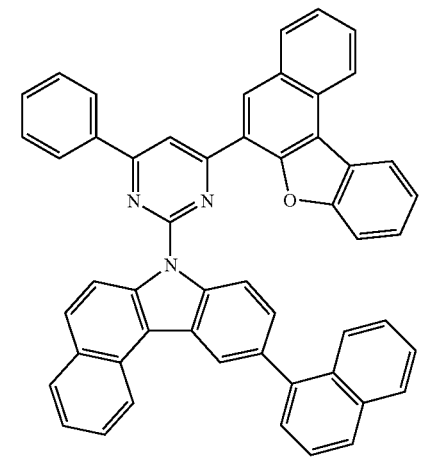
I3
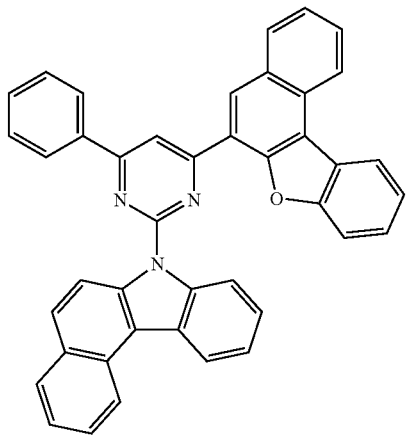
I1
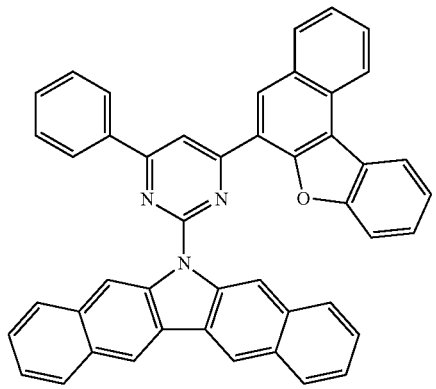
I4

-continued
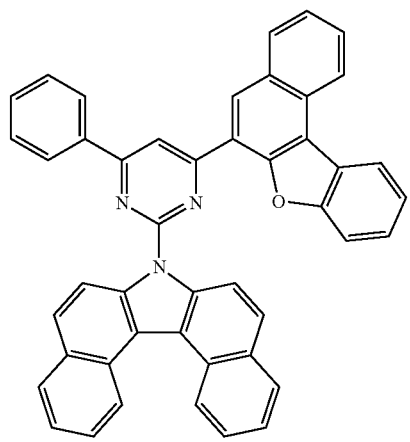
I5
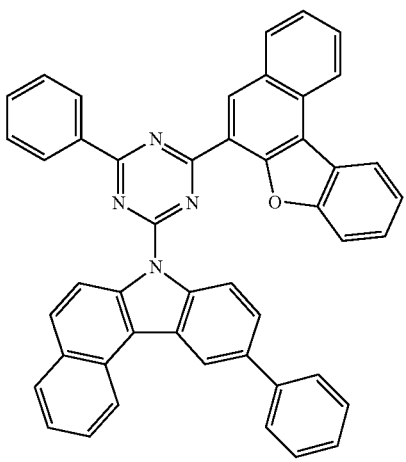
I8
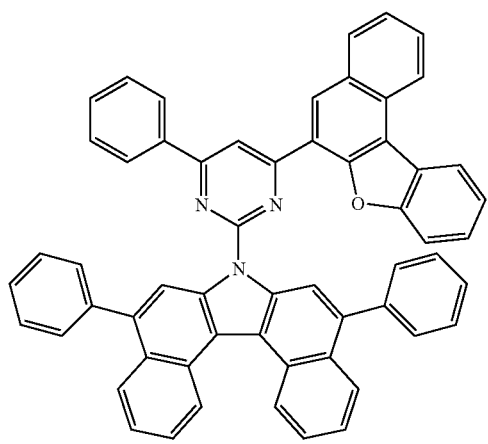
I6
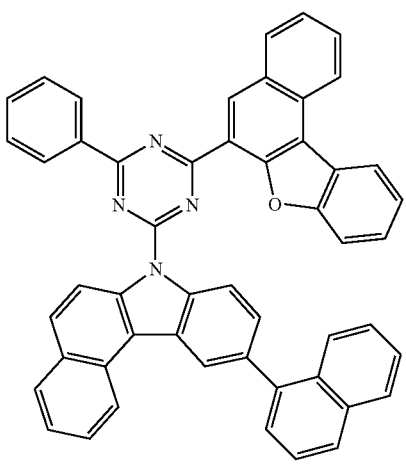
I9
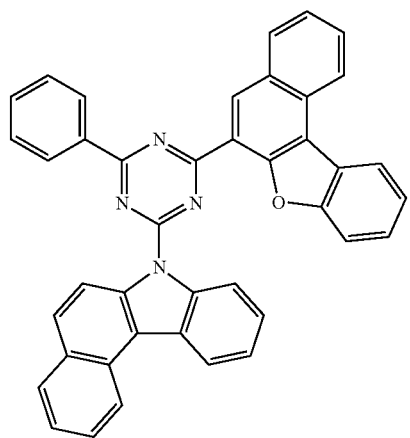
I7
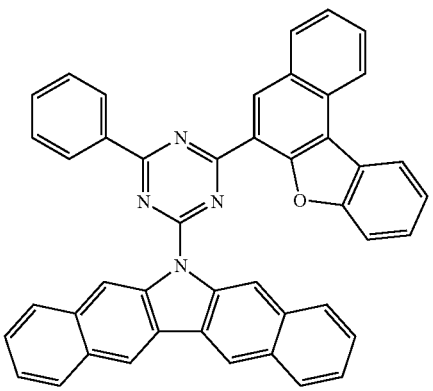
I10

I11
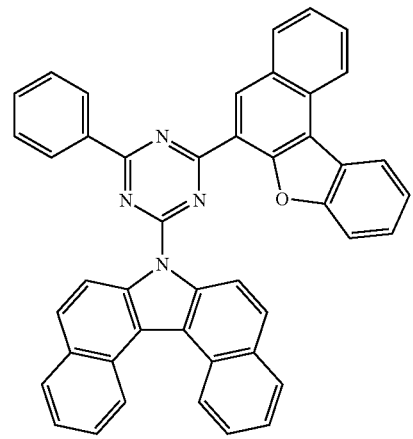
I12
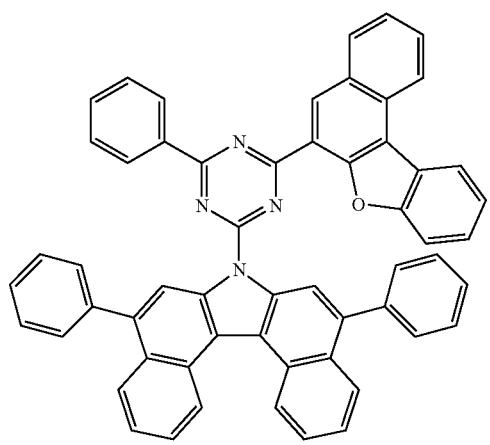
I13
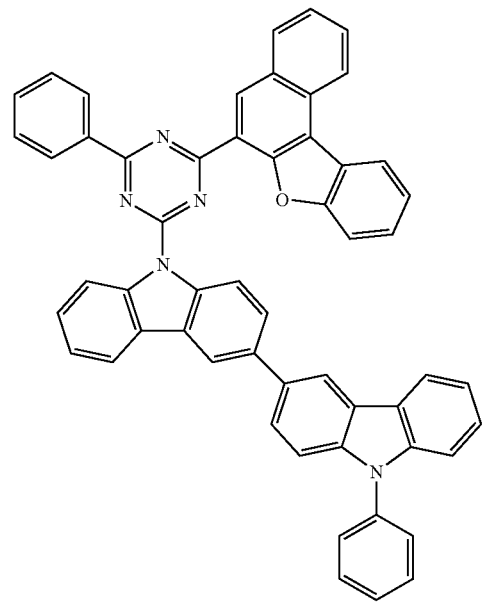
I14
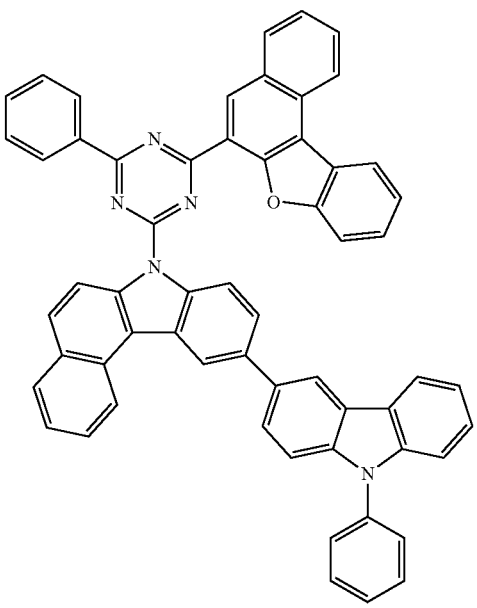
I15
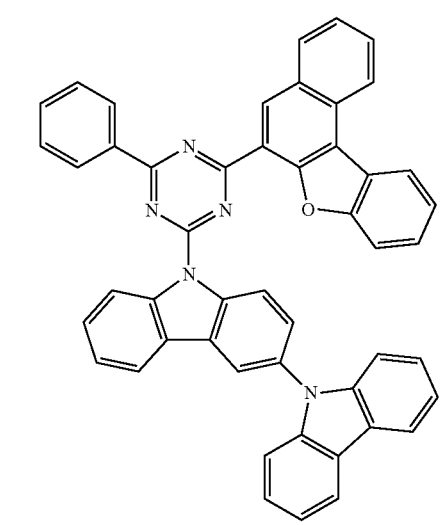
I16
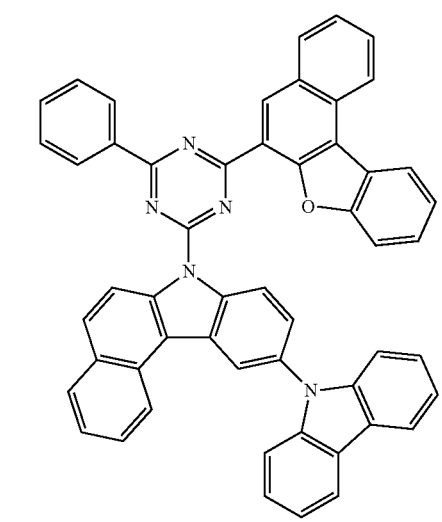

I17
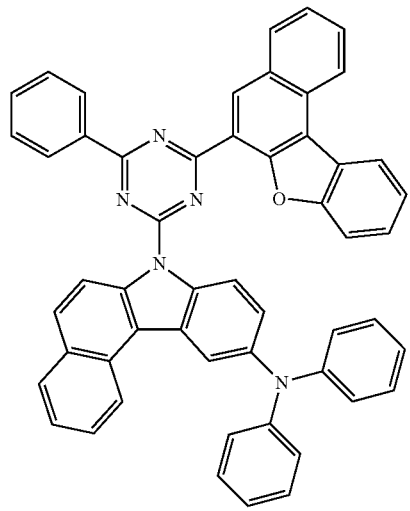
I18
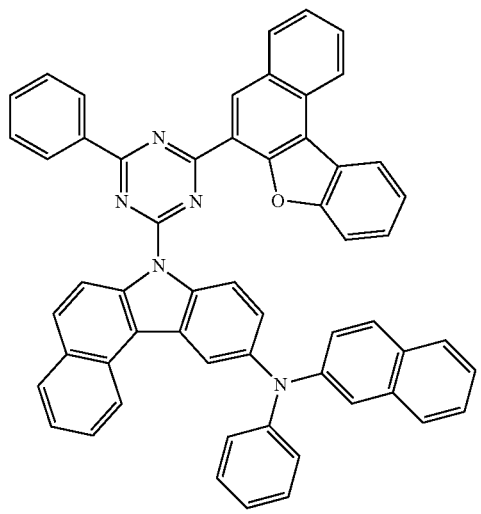
I19
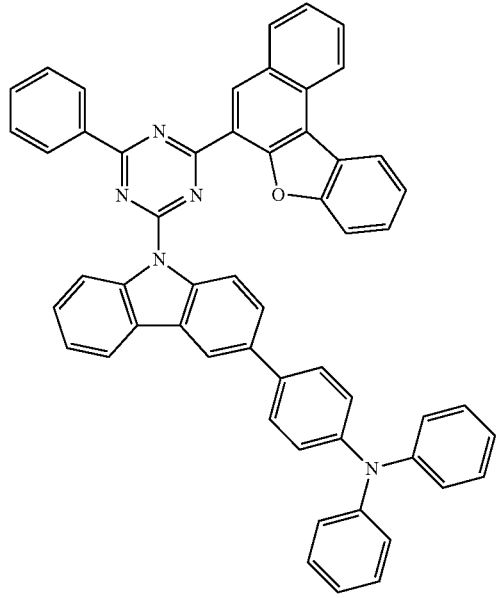
I20
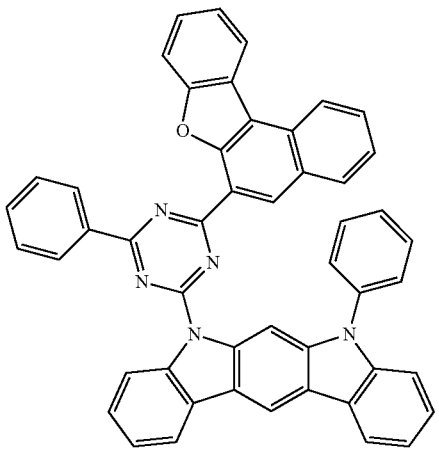
I21
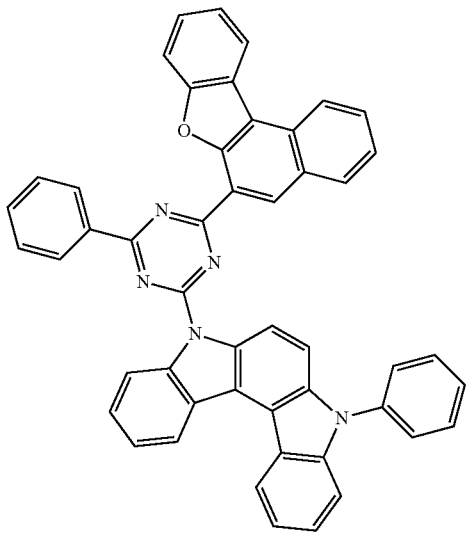
I22
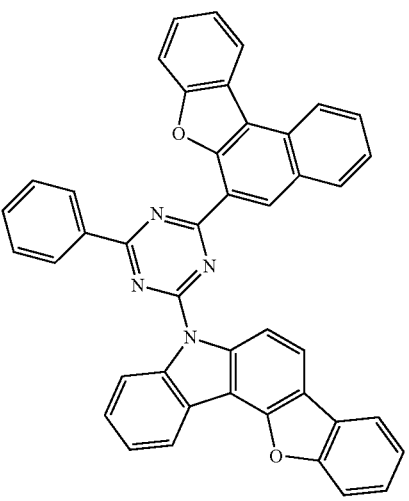

I 23
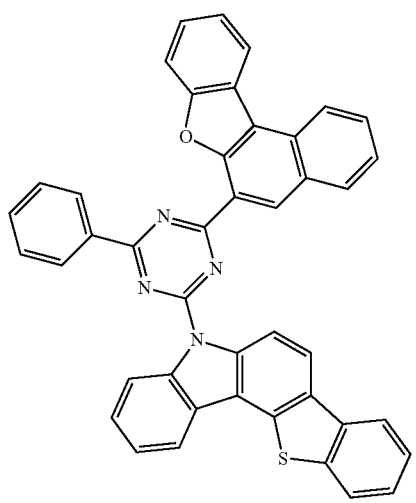
I 24
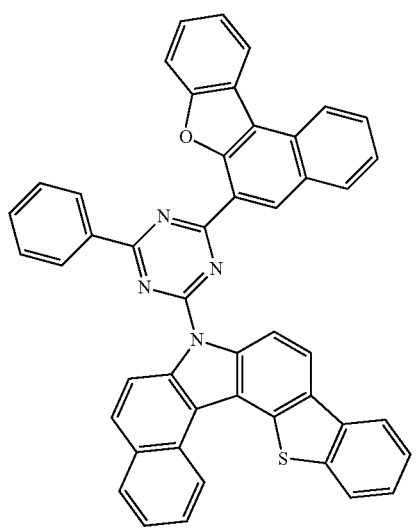
I 25
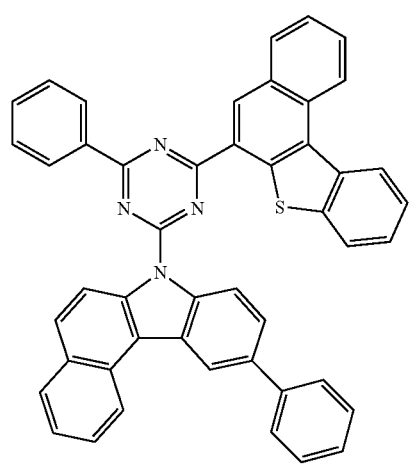
I 26
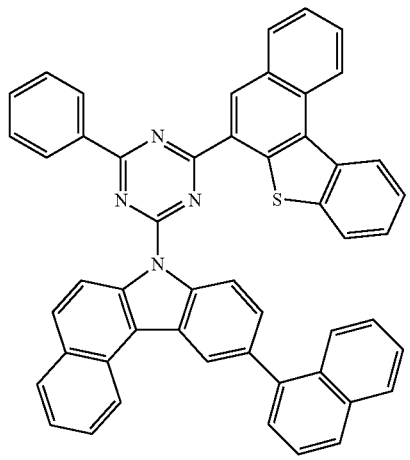
I 27
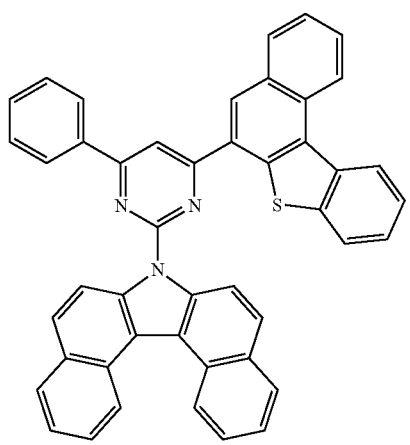
I 28
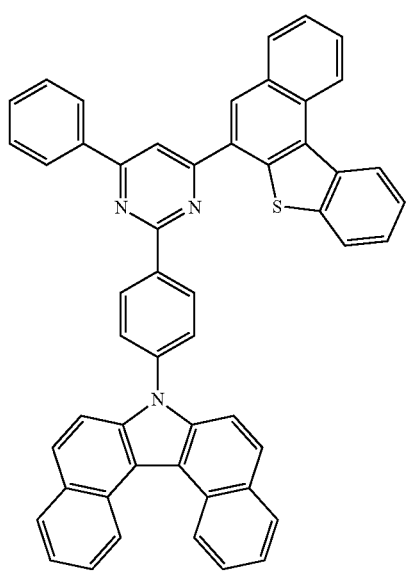

I 29
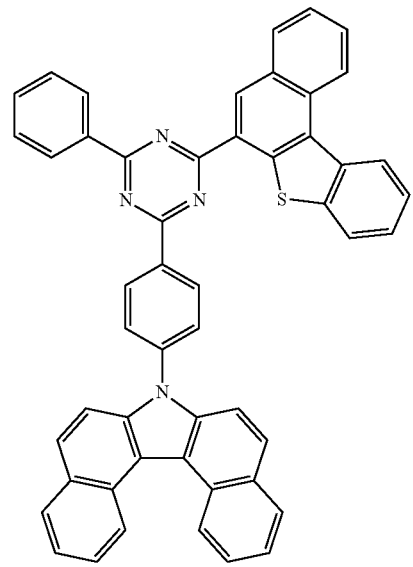
I 32
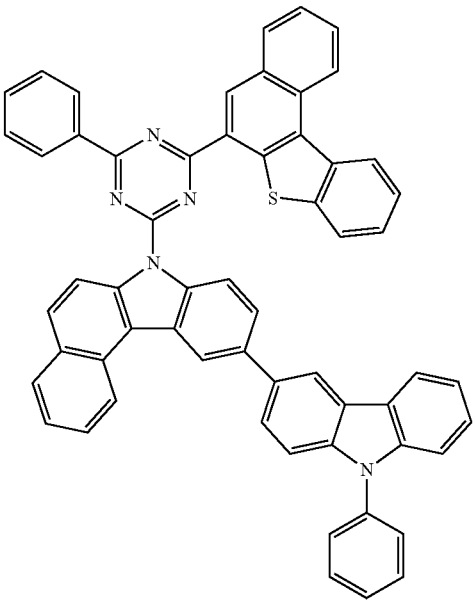
I 30
I 33
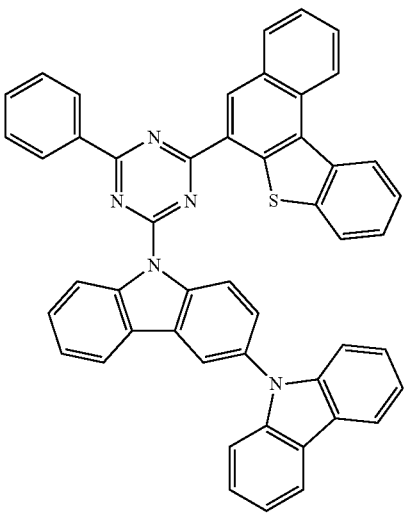
I 31
I 34
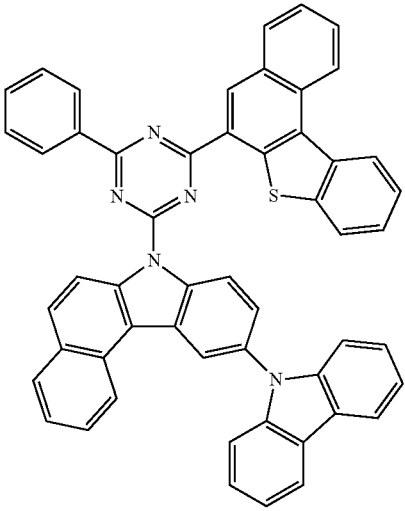

I 35
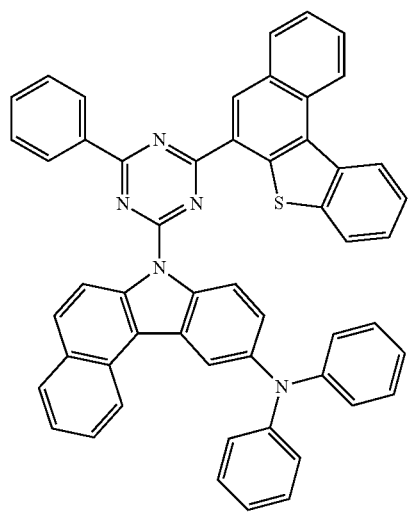
I 38
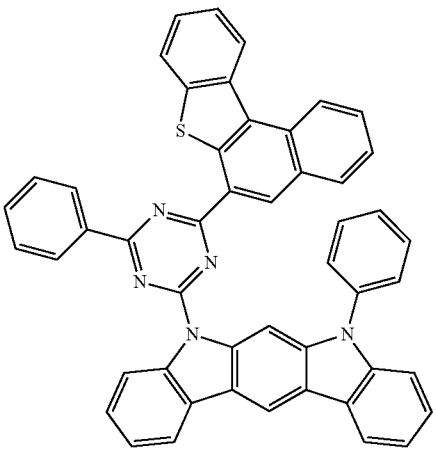
I 36
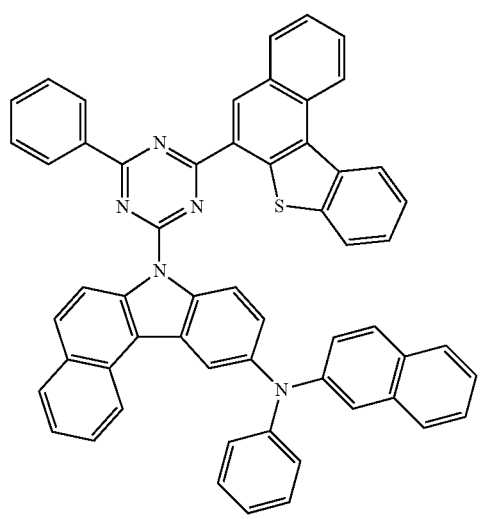
I 39
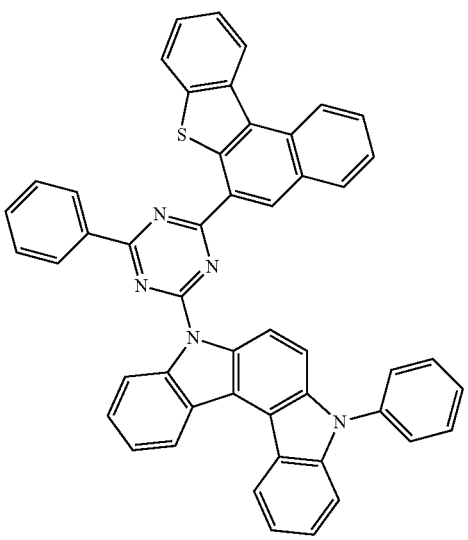
I 37
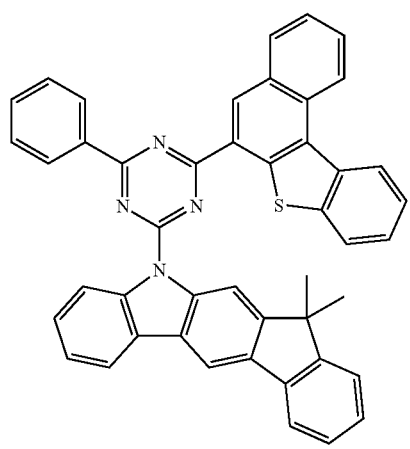
I 40
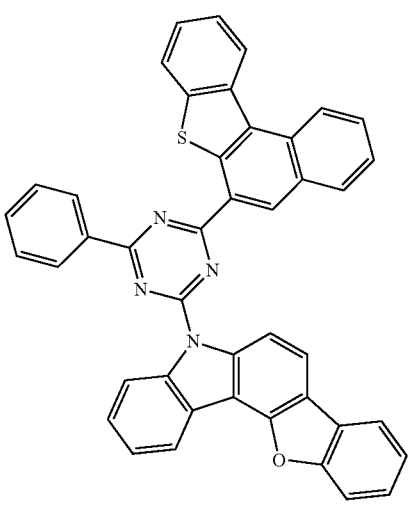

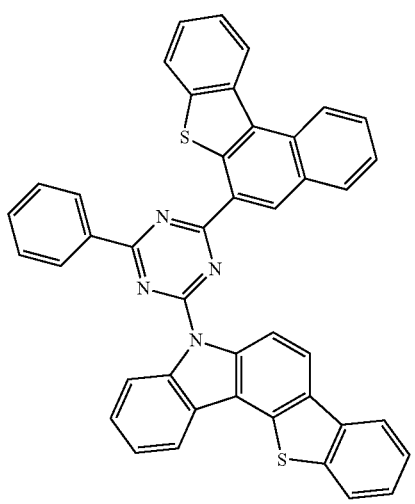
I41
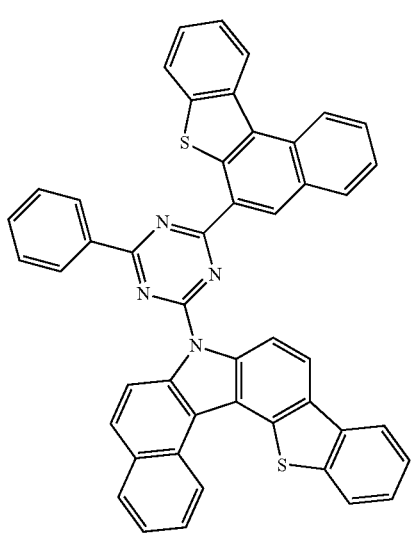
I42
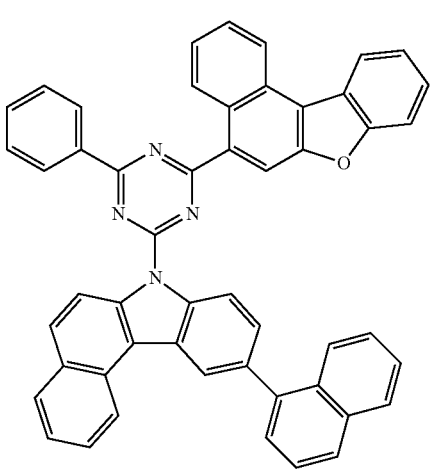
I43
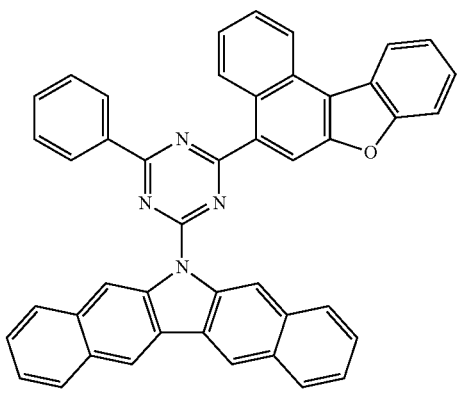
I44
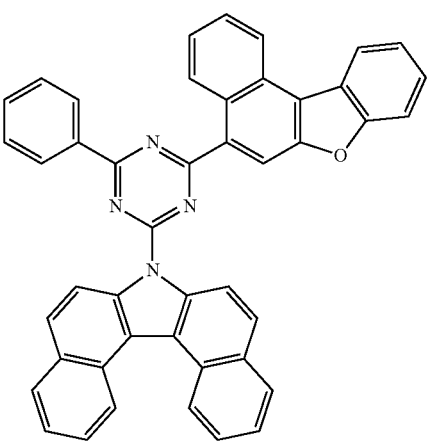
I45
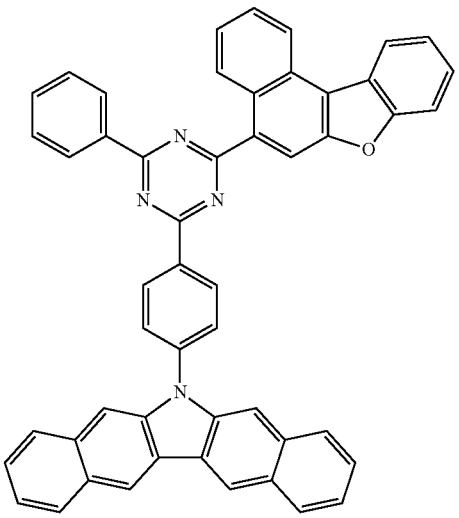
I46

-continued
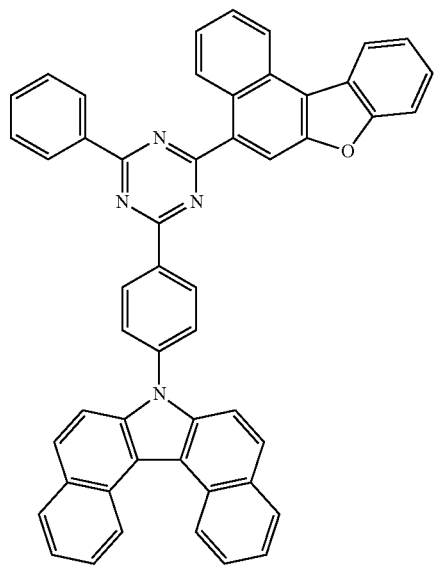
I 47
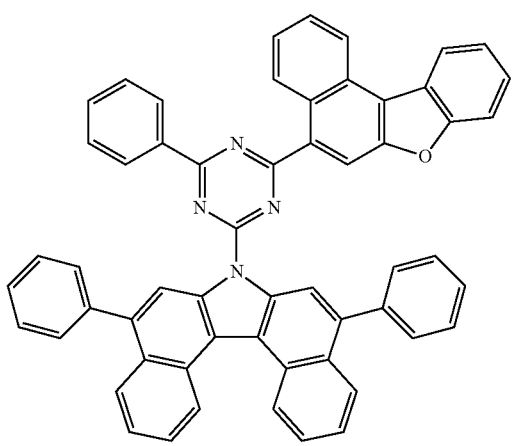
I 48
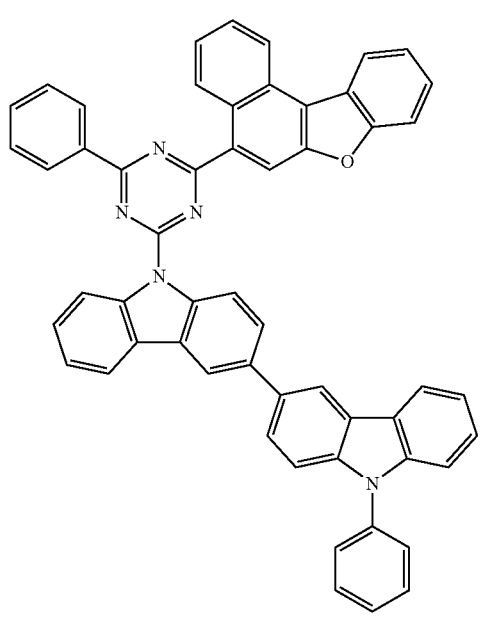
I 49
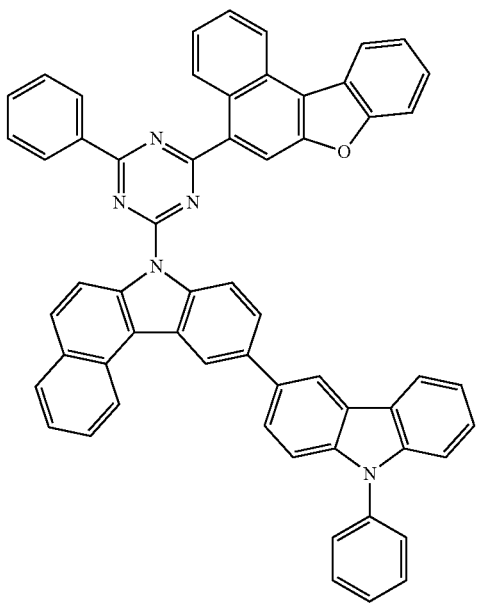
I 50
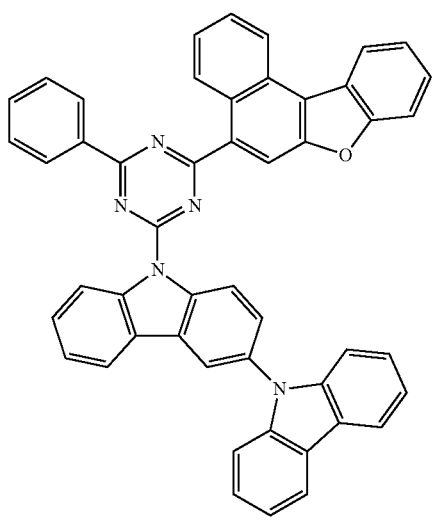
I 51
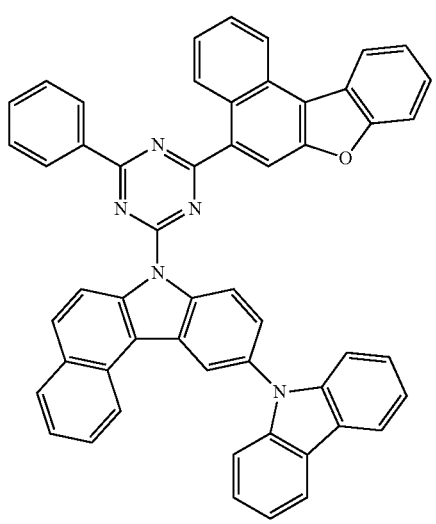
I 52

-continued
I53
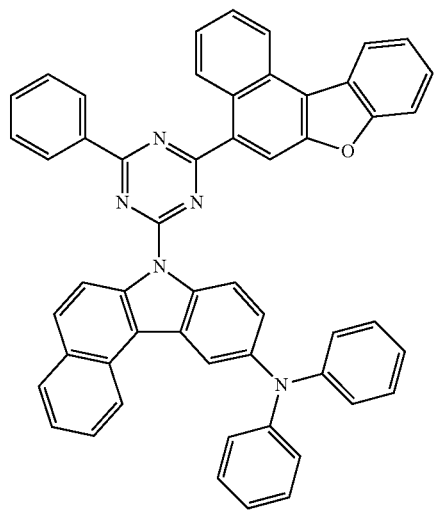
I54
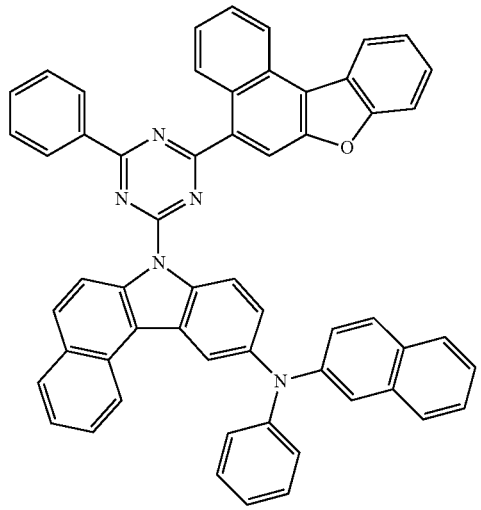
I55
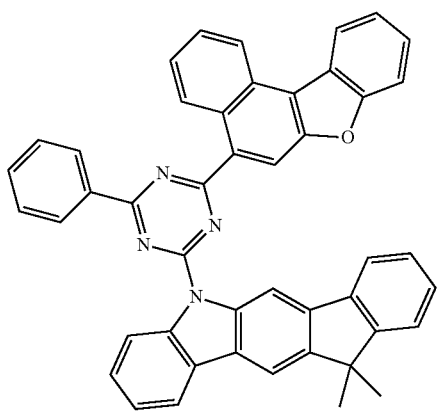
-continued
I56
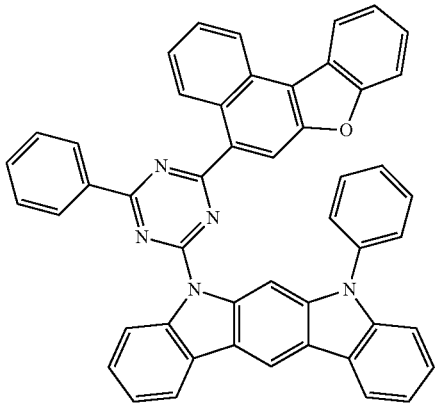
I57
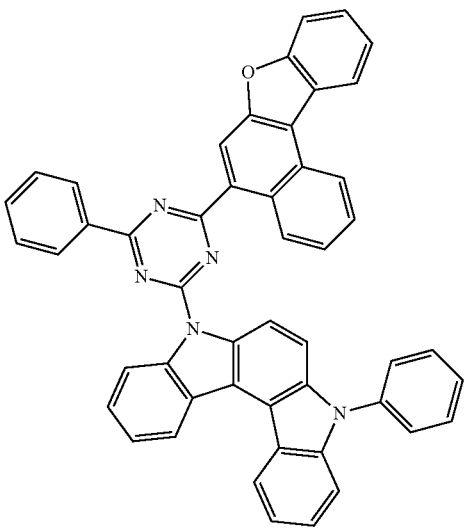
I58
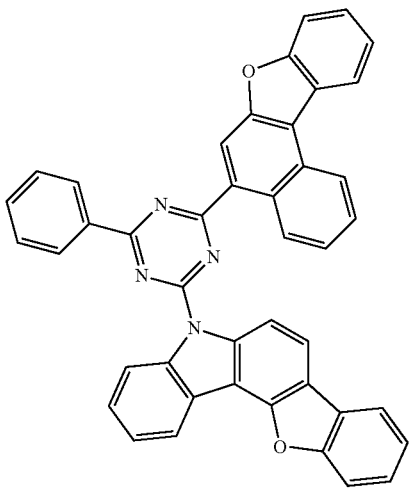

I 59
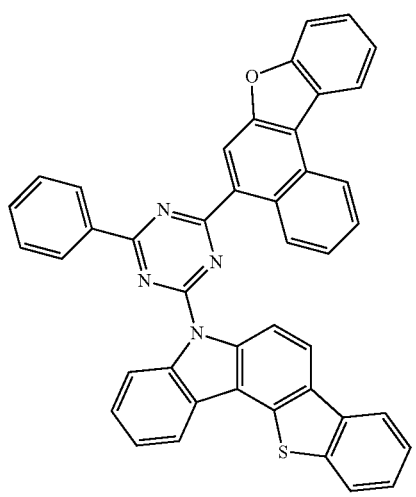
I 60
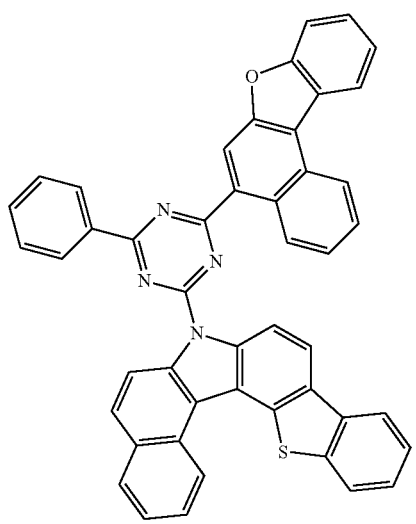
I 61
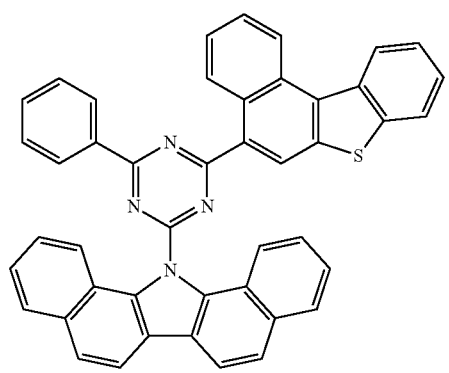
I 62
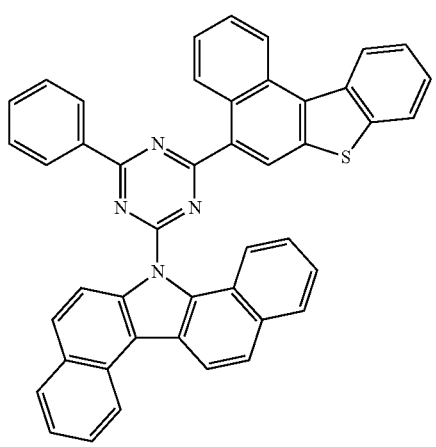
I 63
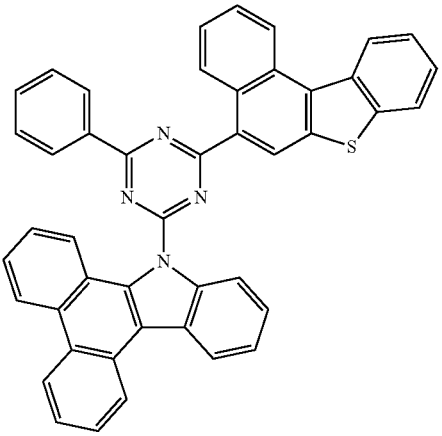
I 64
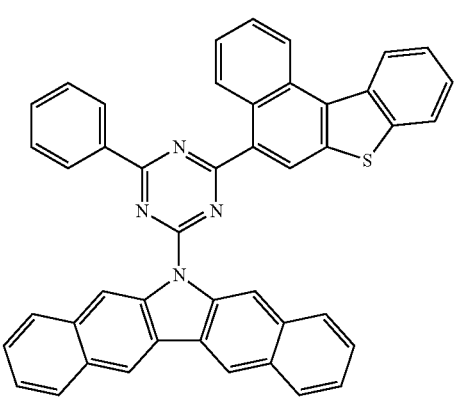

I-65
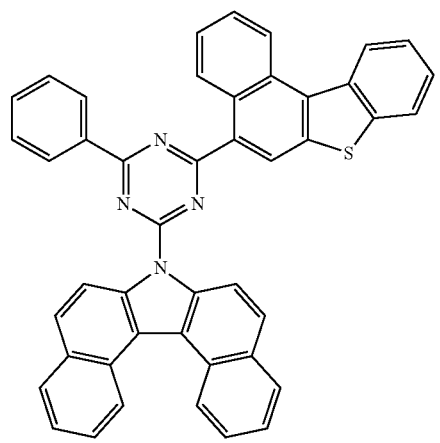
I-66
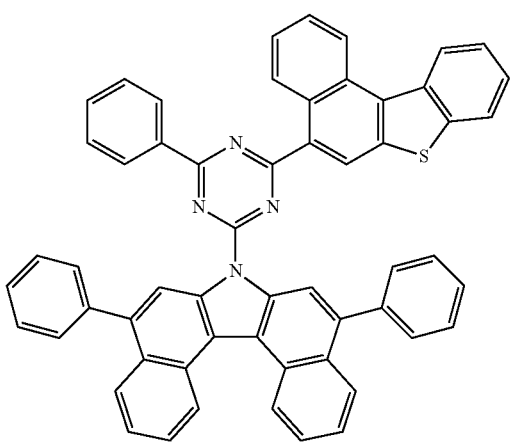
I-67
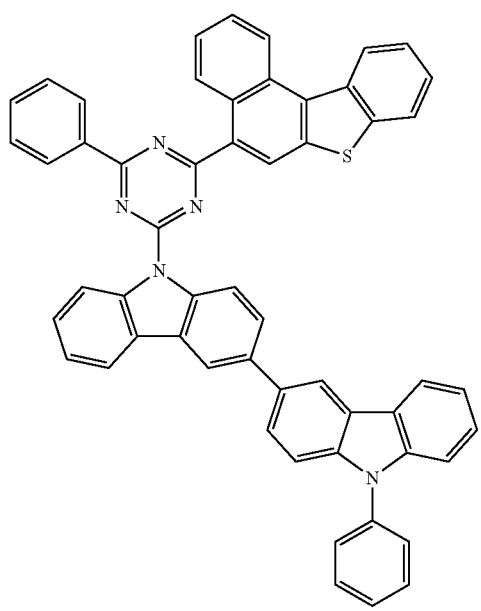
I-68
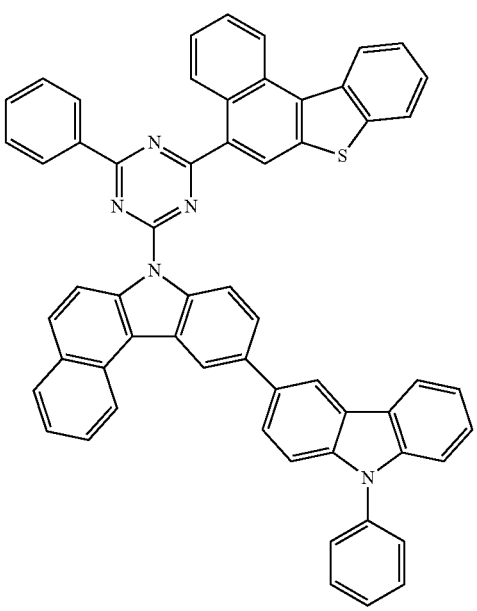
I-69
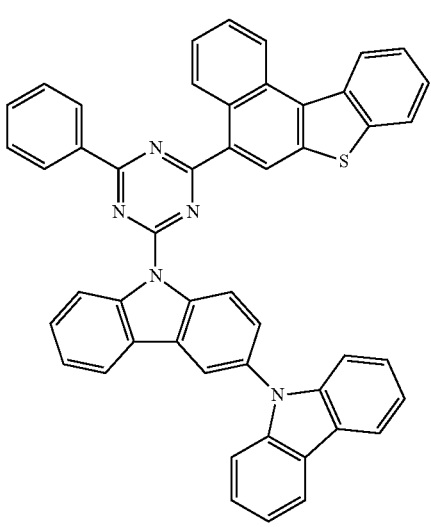
I-70
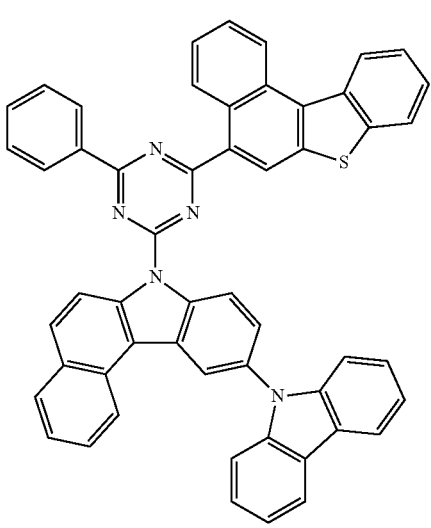

I 71
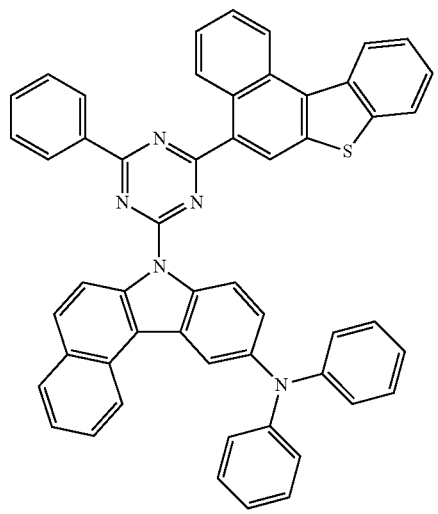
I 72
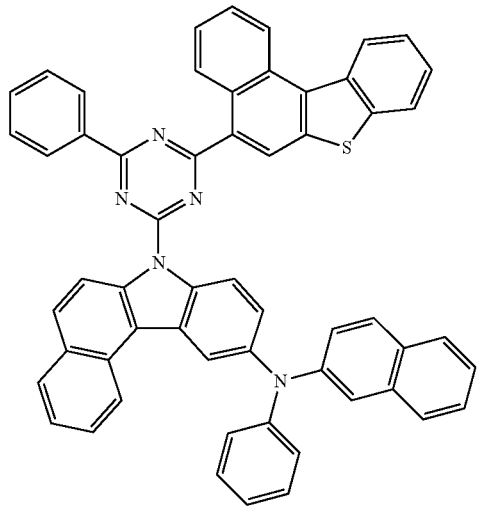
I 73
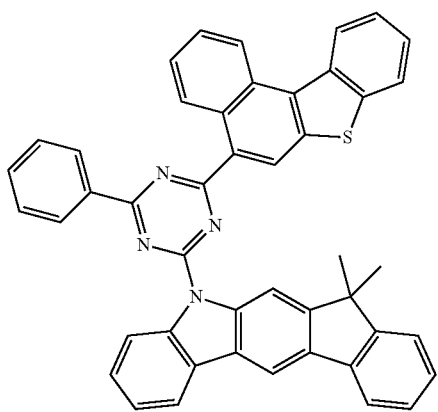
I 74
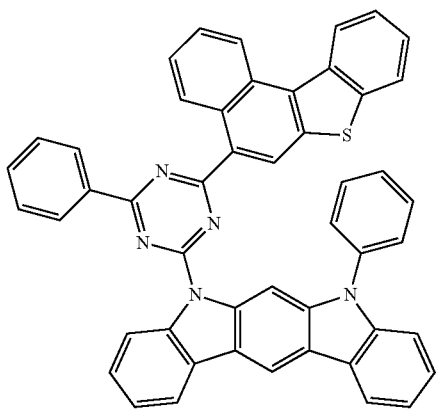
I 75
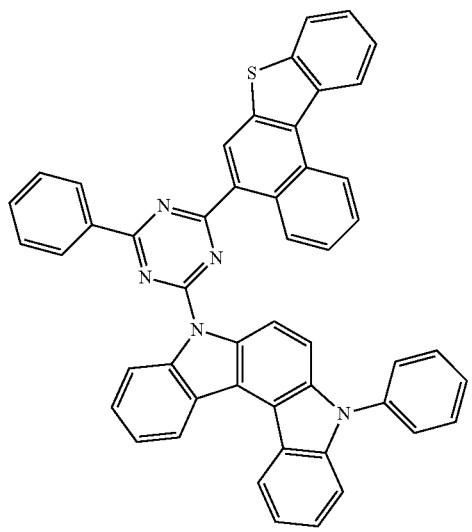
I 76
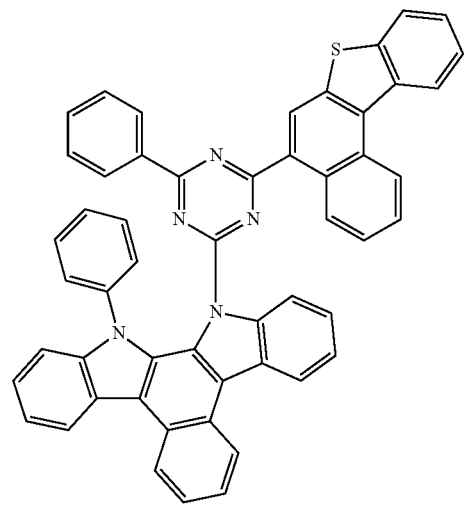

-continued
I 77
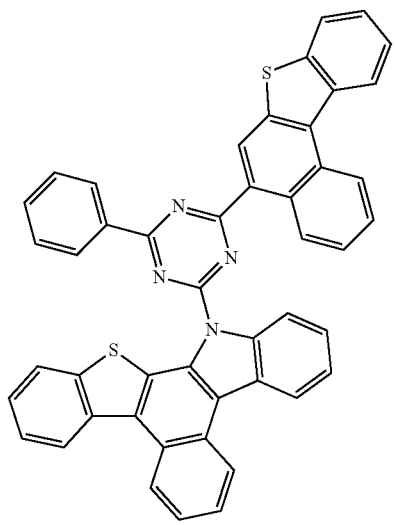
I 78
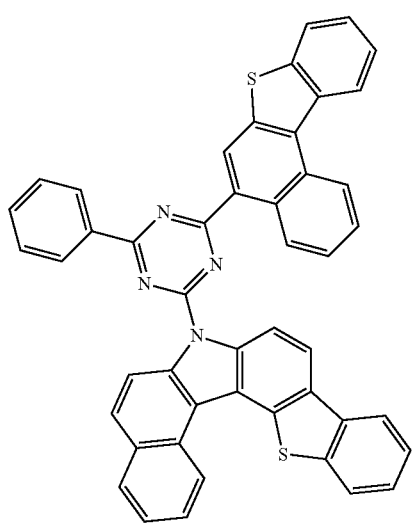
I 79
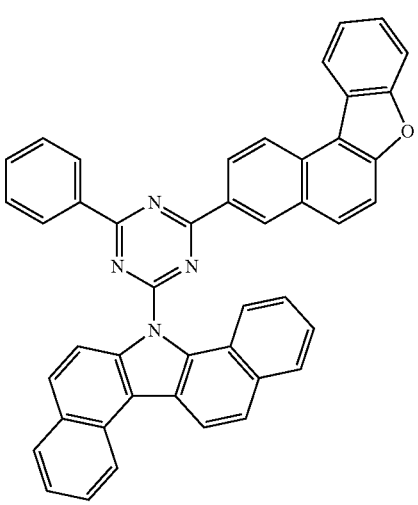
-continued
I 80
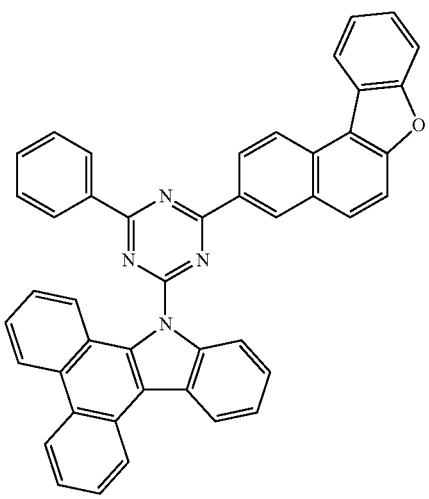
I 81
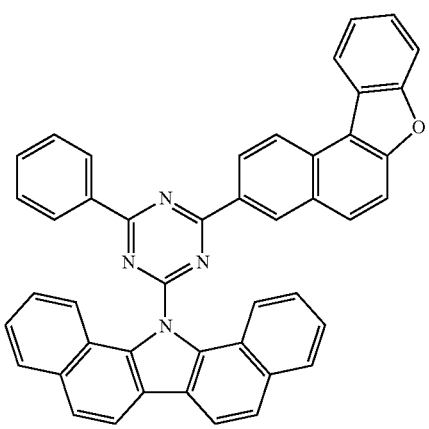
I 82
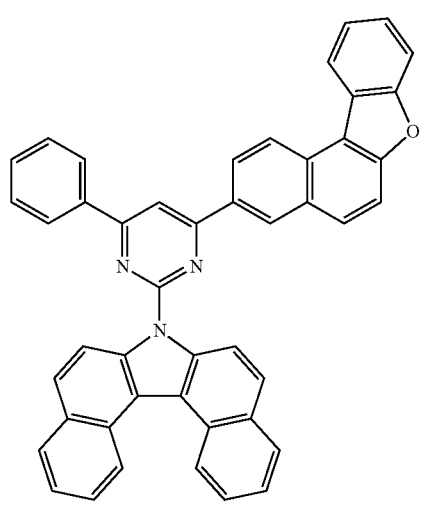

I 83
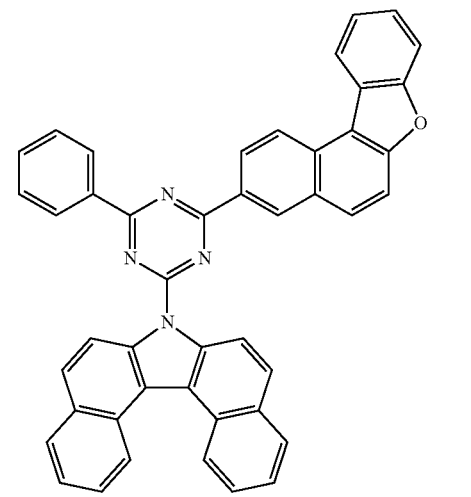
I 84
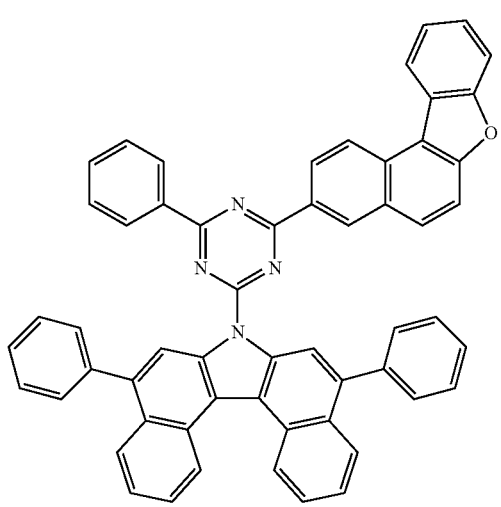
I 85
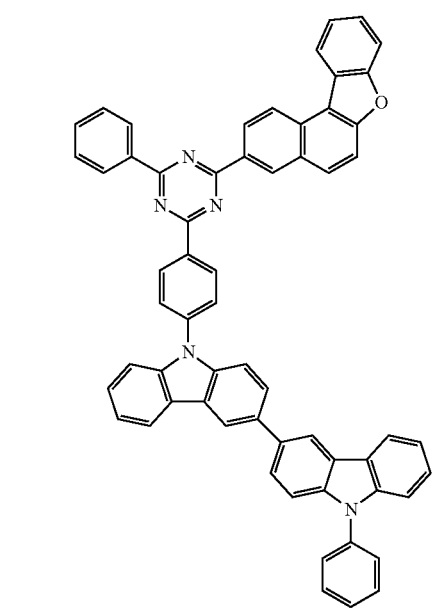
I 86
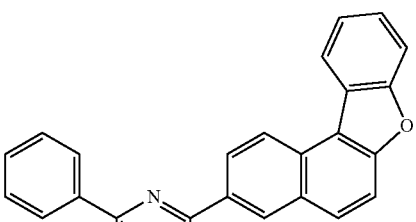
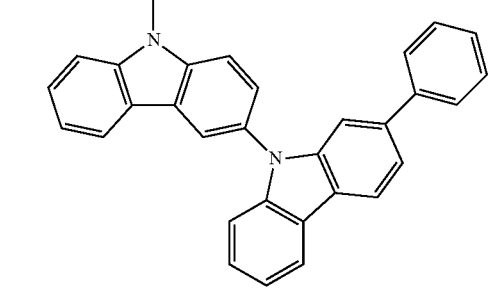
I 87
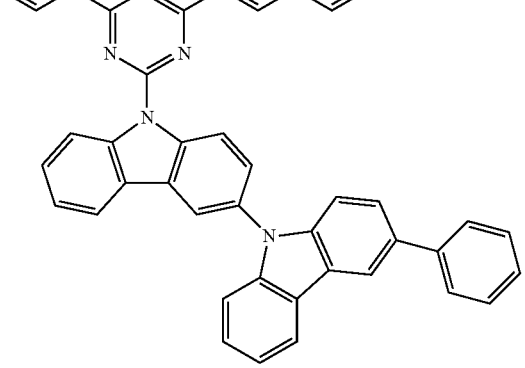

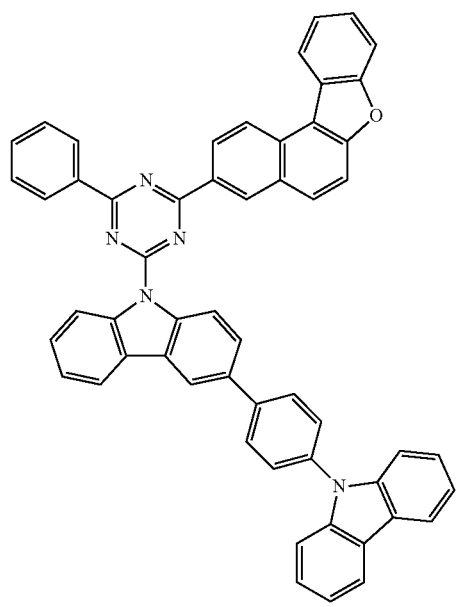
I 88
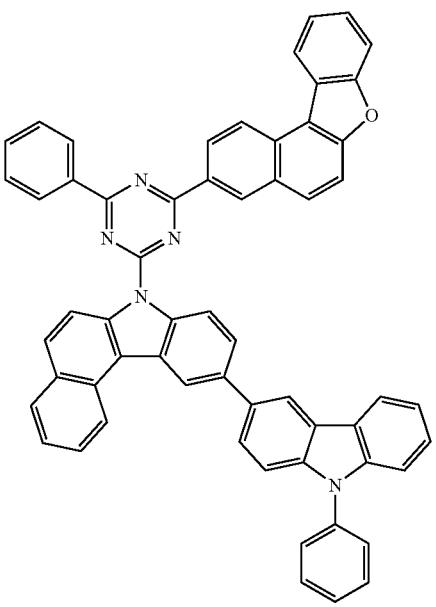
I 90
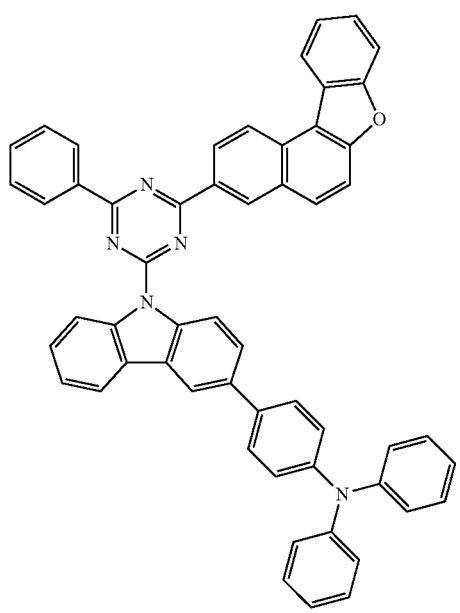
I 89
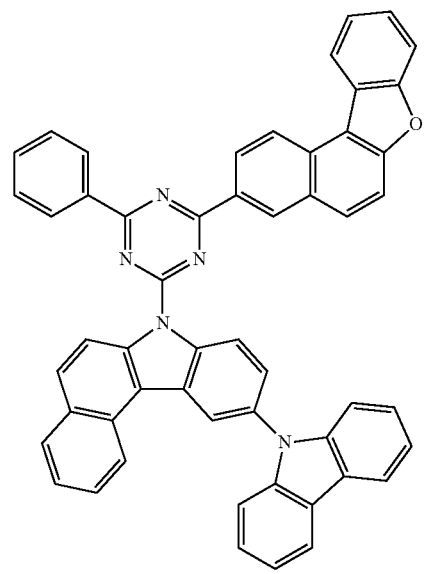
I 91

I 92
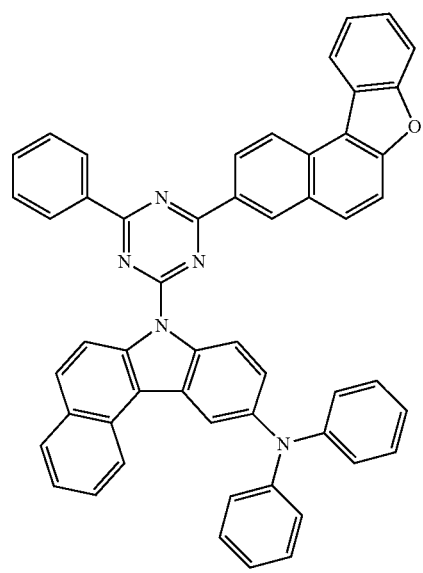
I 93
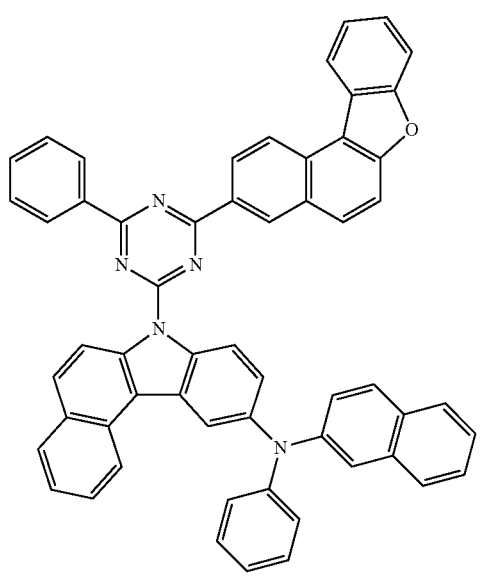
I 94
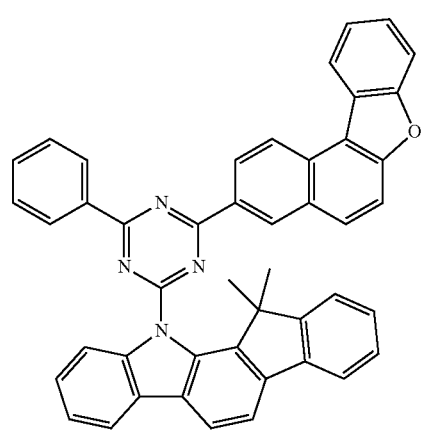
I 95
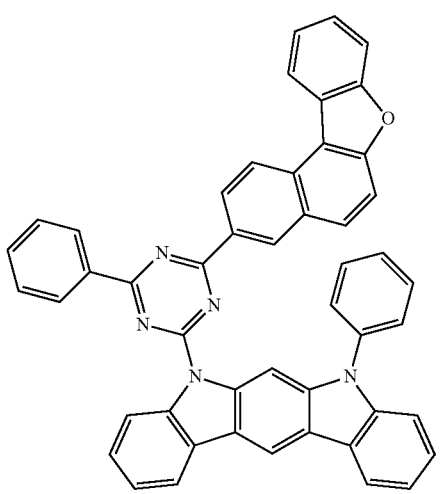
I 96
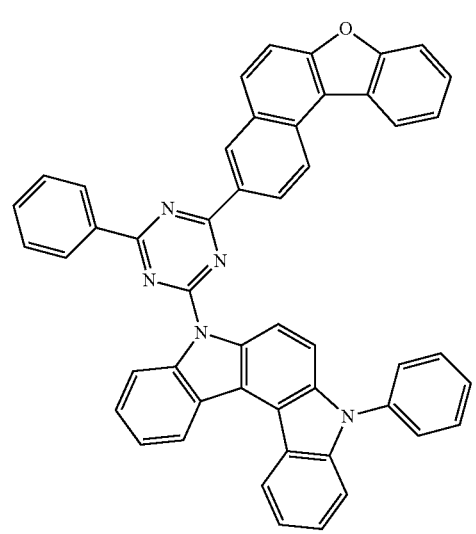
I 97
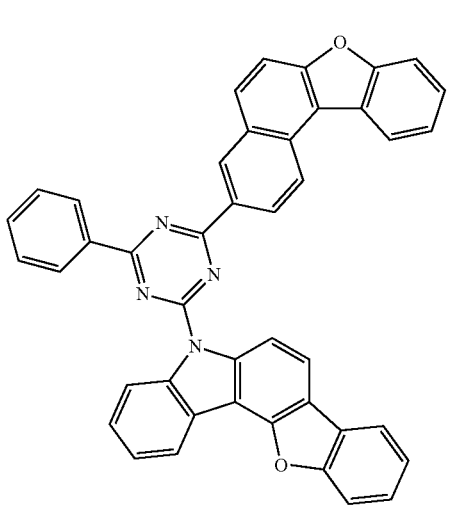

-continued
I98
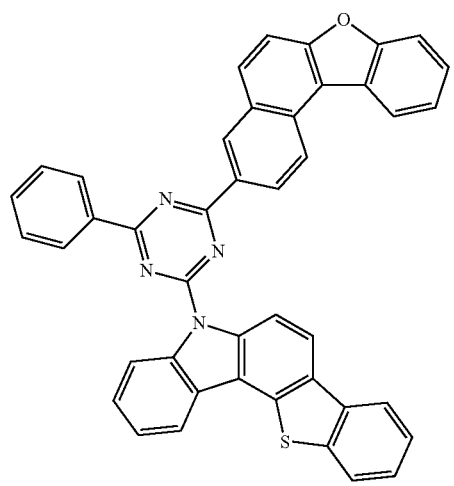
I99
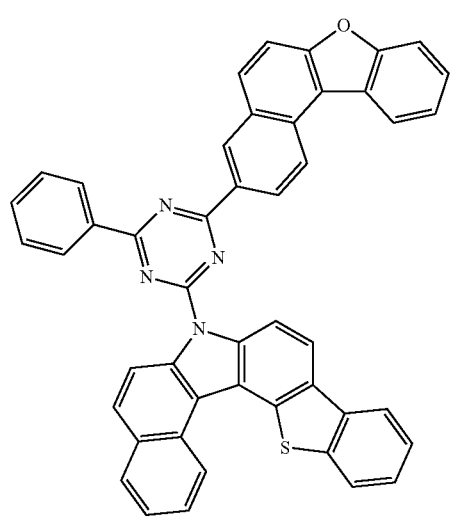
I100
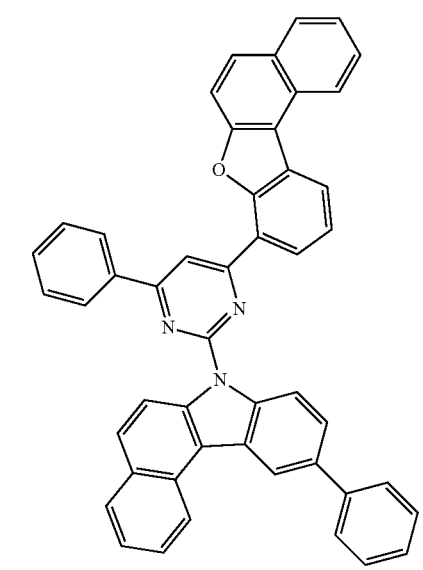
-continued
I101
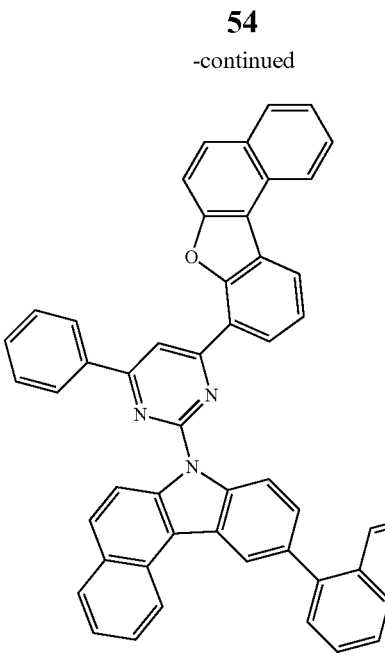
I102
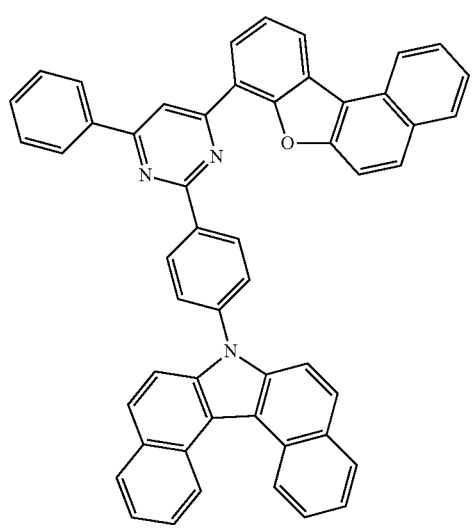
I103
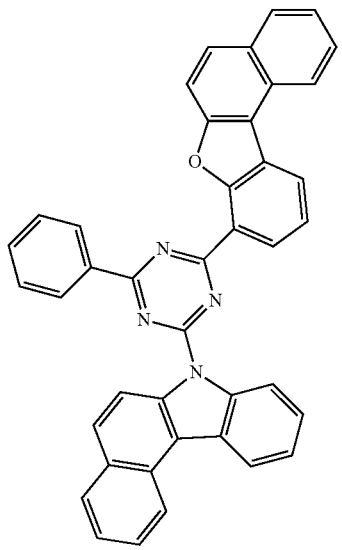

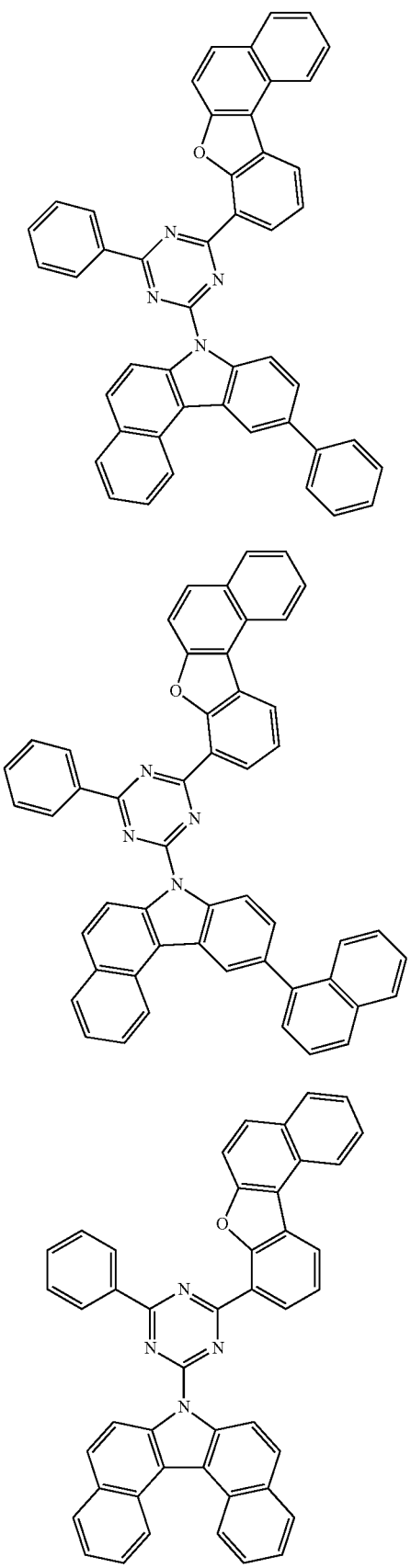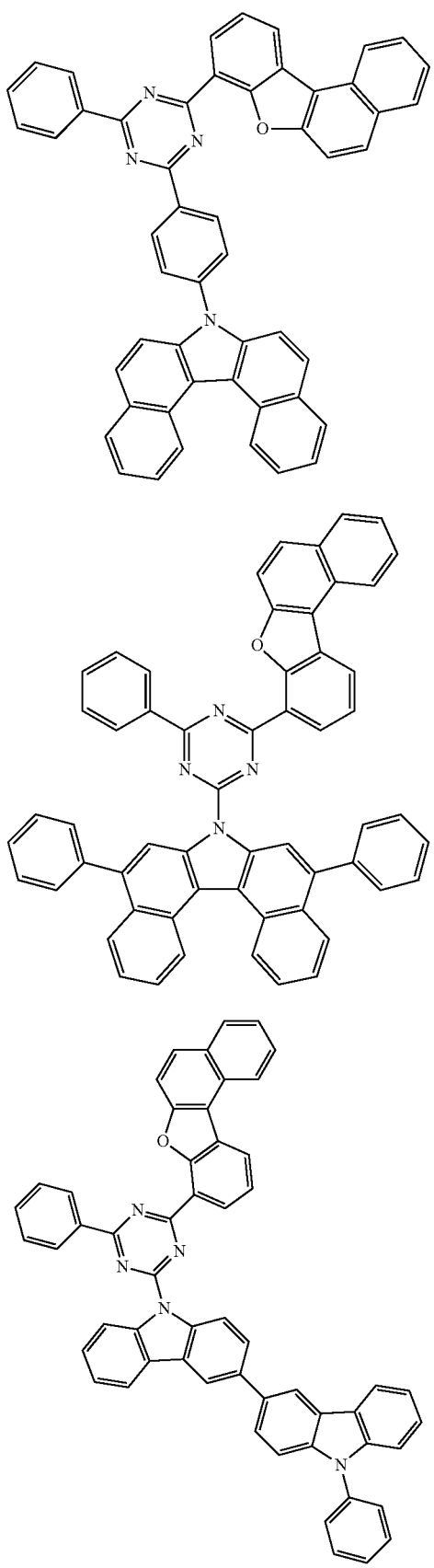

I 110
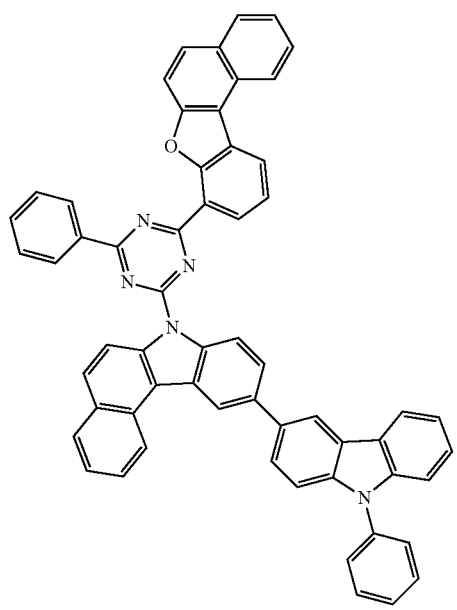
I 111
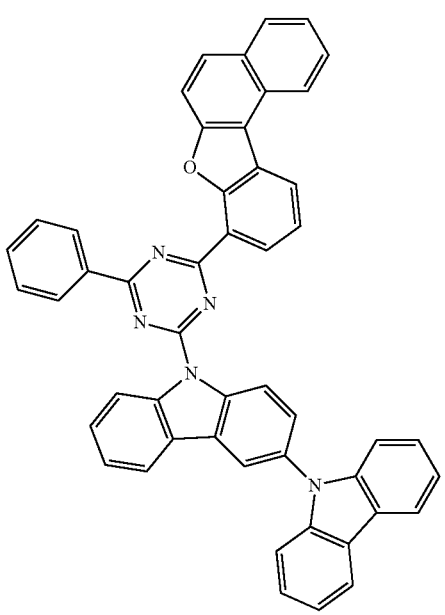
I 112
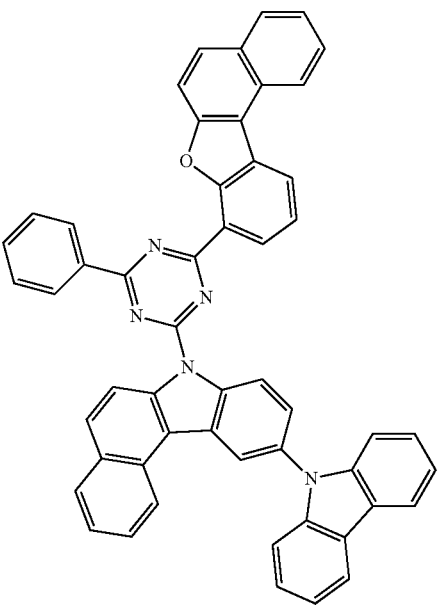
I 113
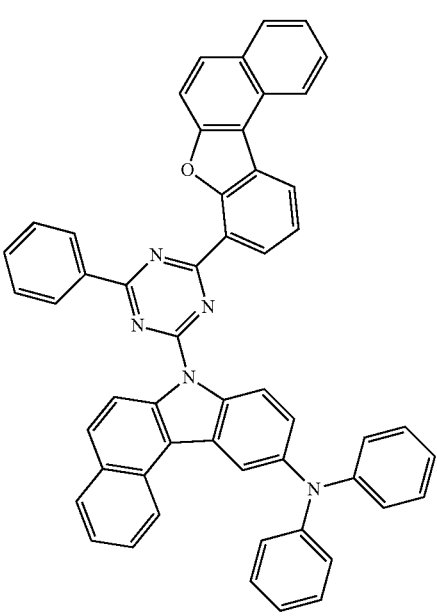

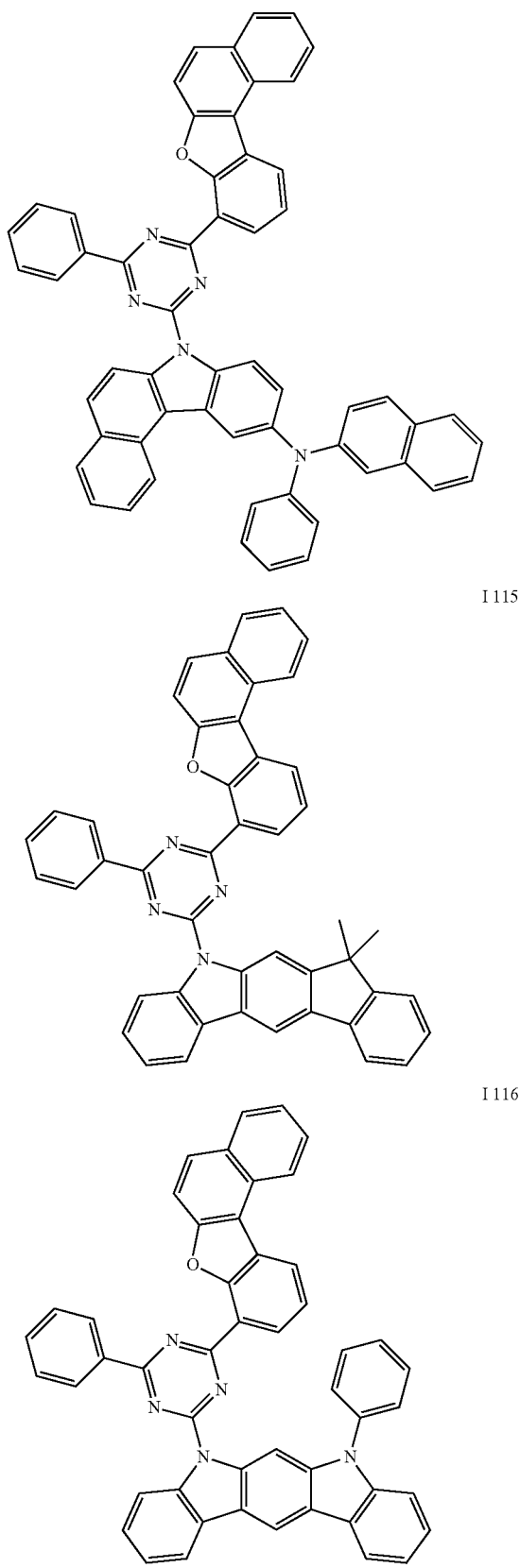
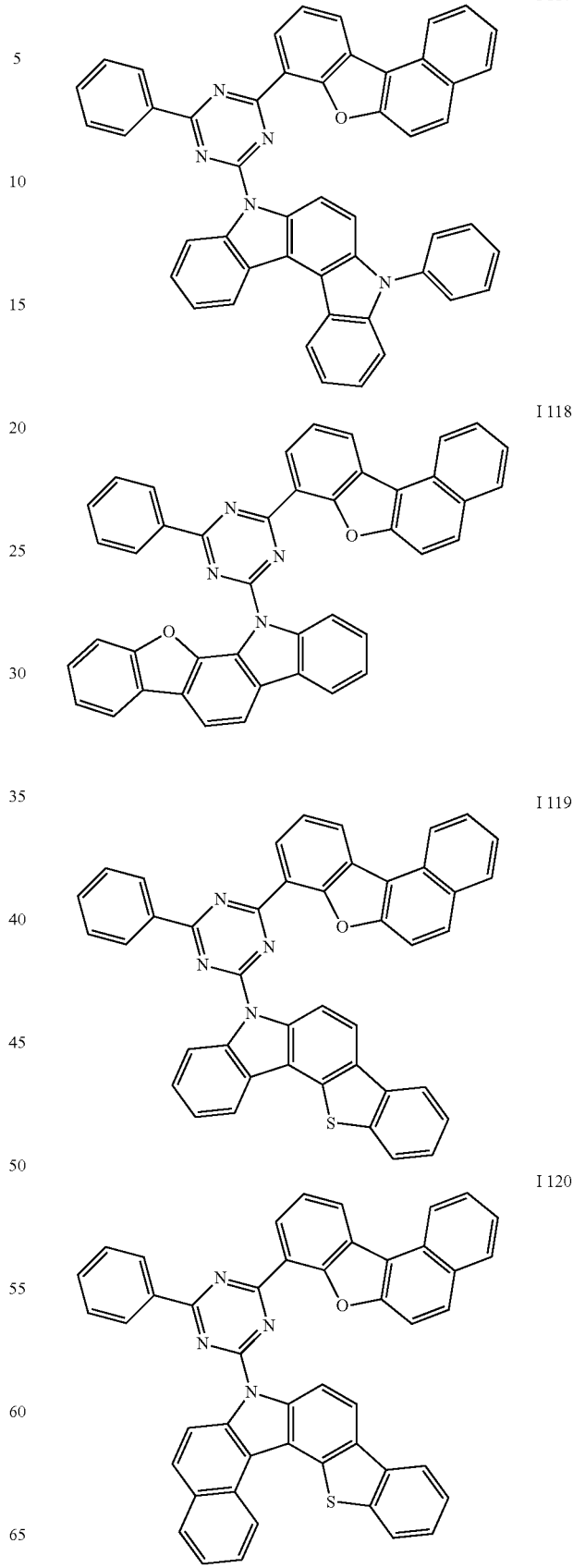

-continued
I 121
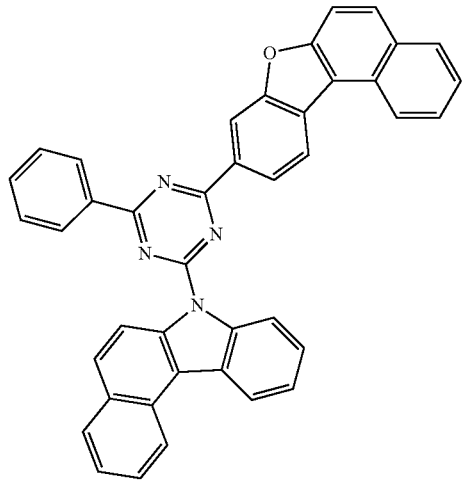
I 122
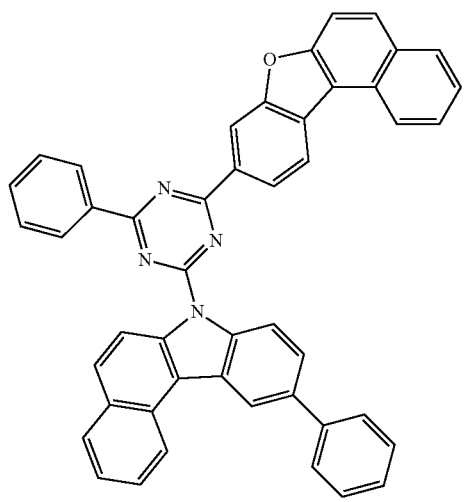
I 123
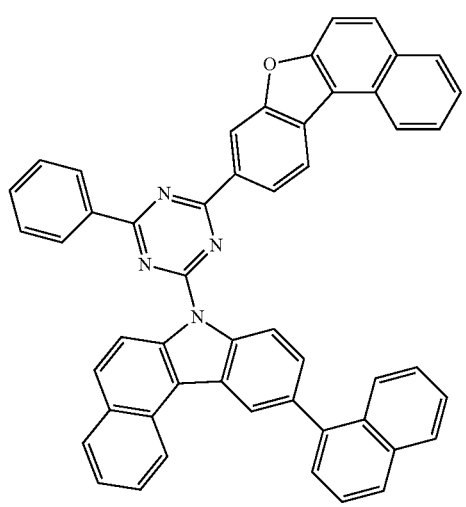
-continued
I 124
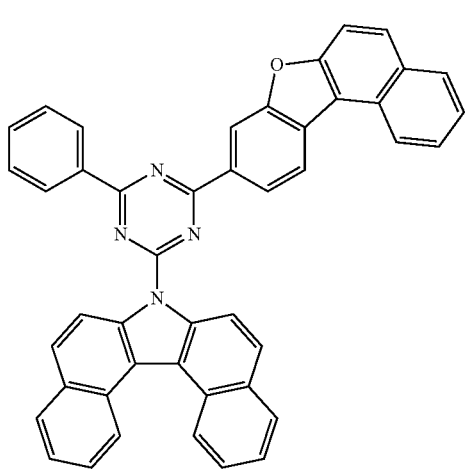
I 125
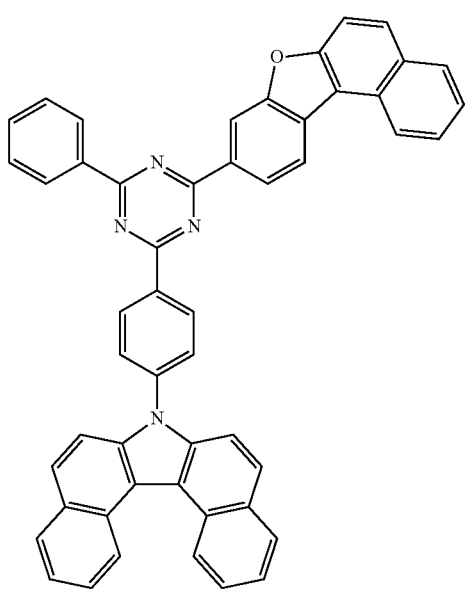
I 126
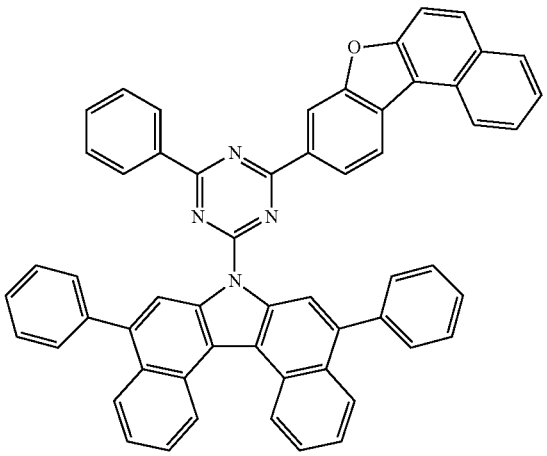

I 127
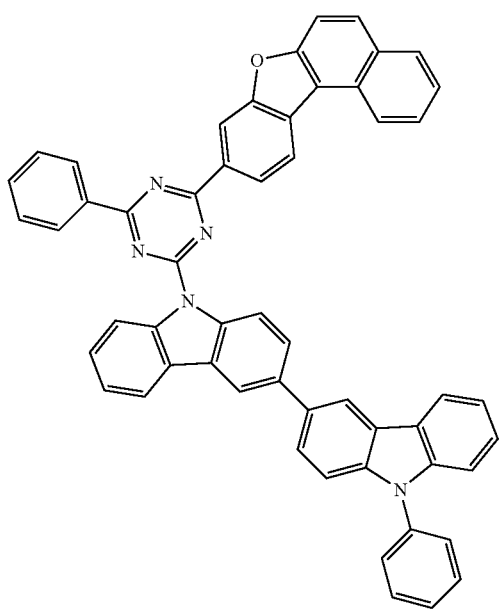
I 128
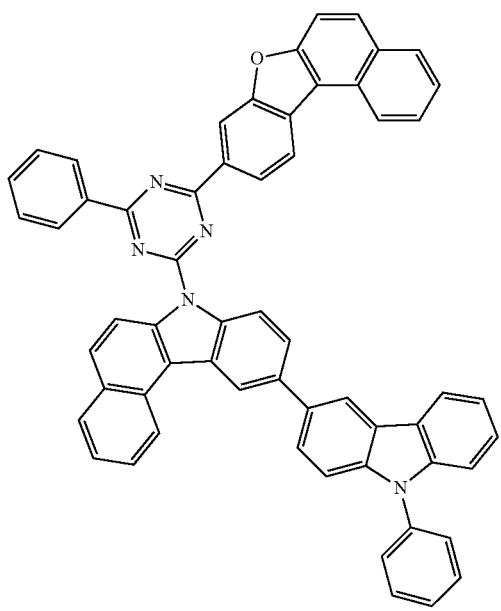
I 129
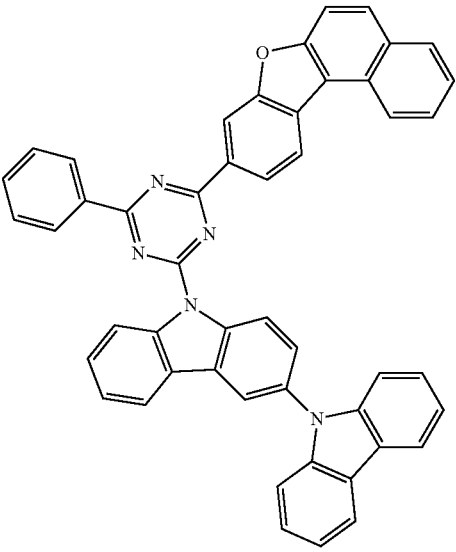
I 130
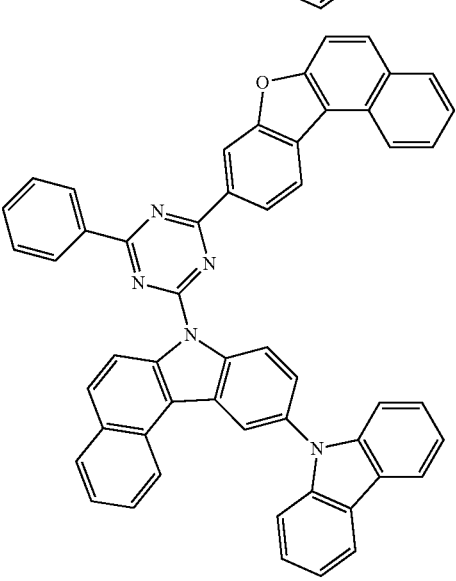
I 131
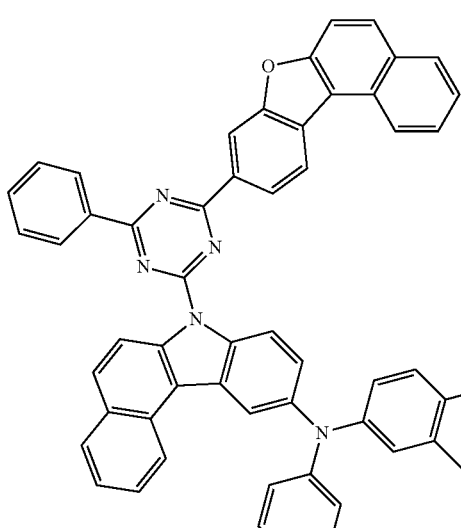

I 132
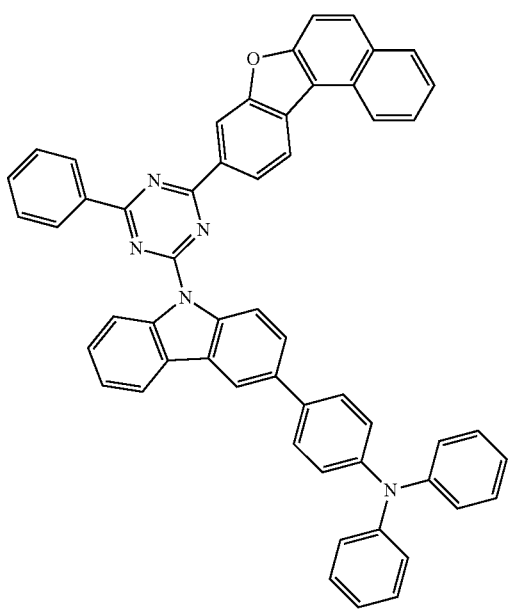
I 133
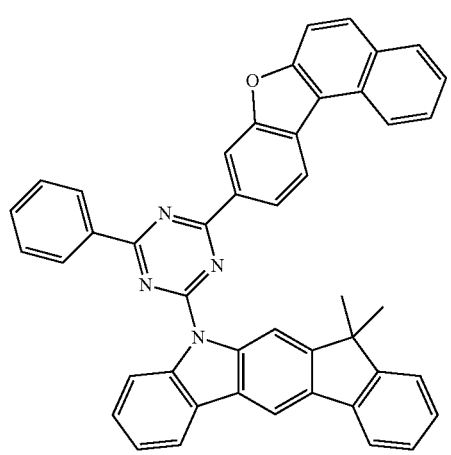
I 134
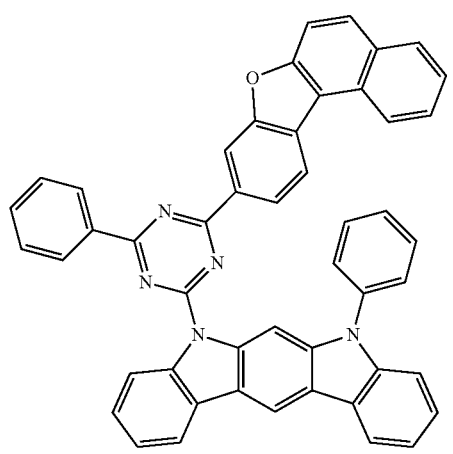
I 135
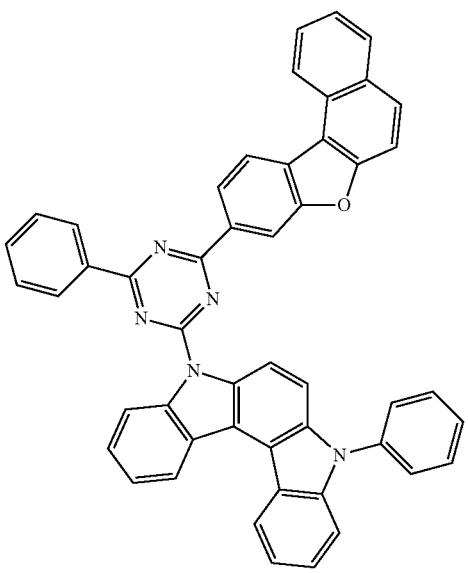
I 136
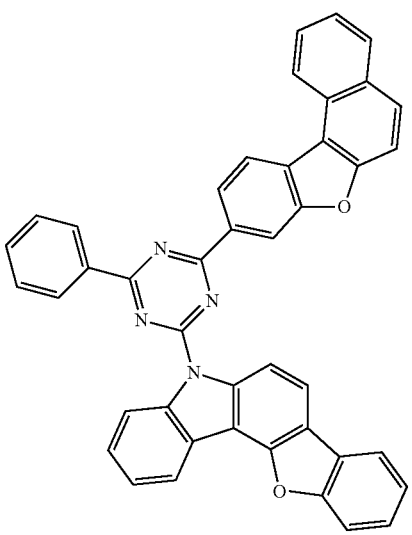
I 137
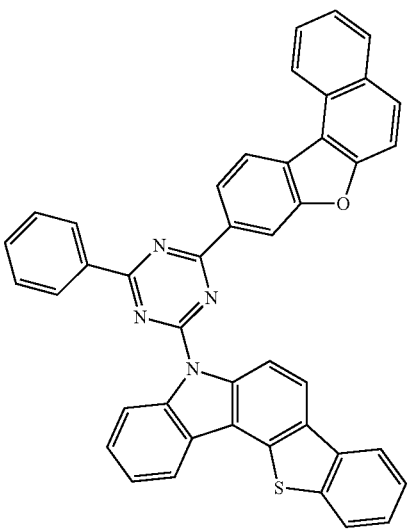

I 138
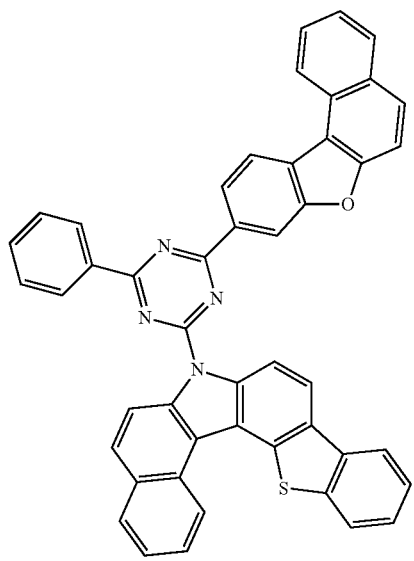
I 139
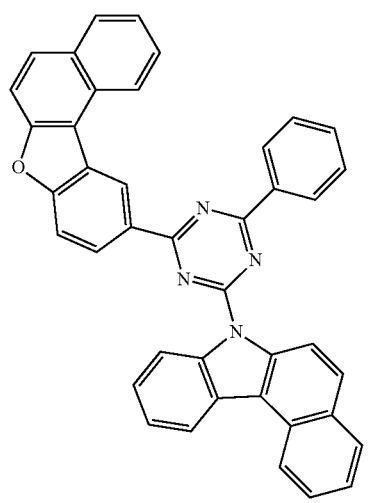
I 140
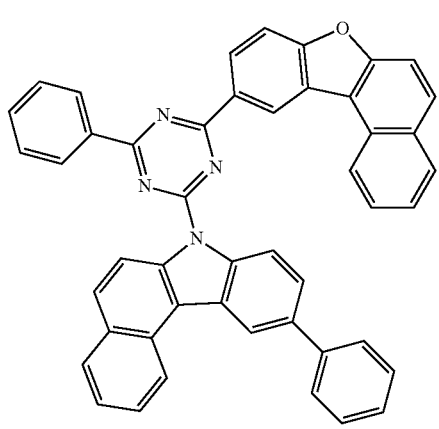
I 141
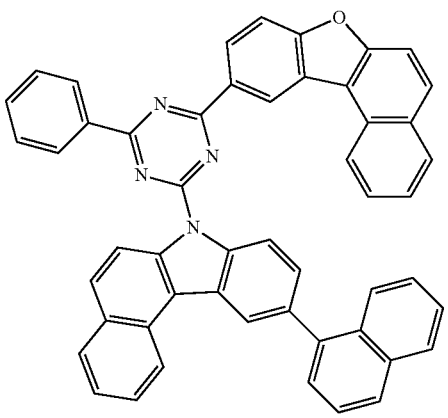
I 142
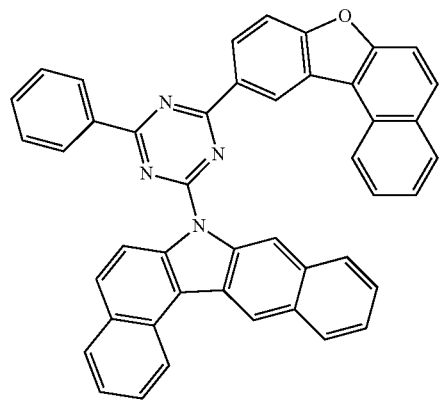
I 143
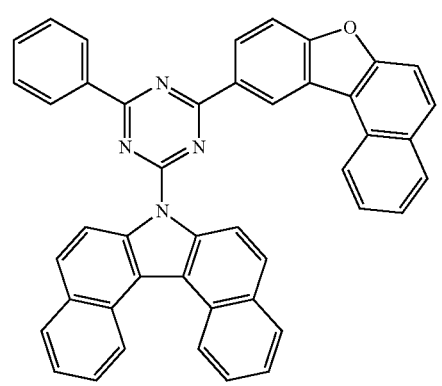

I 144
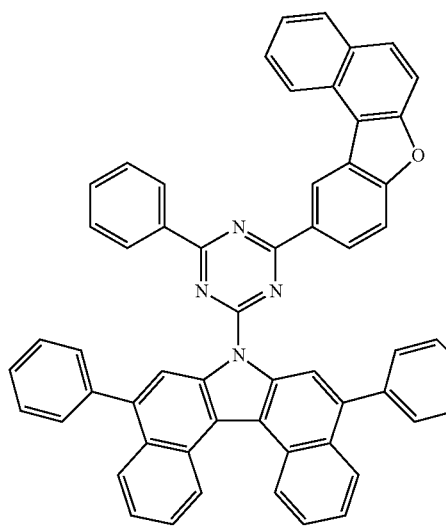
I 145
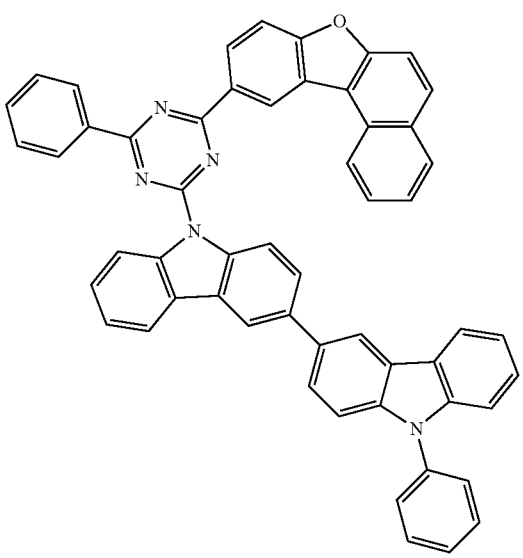
I 146
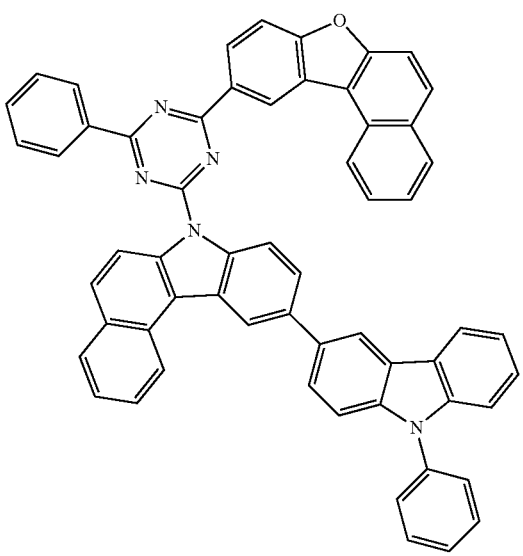
I 147
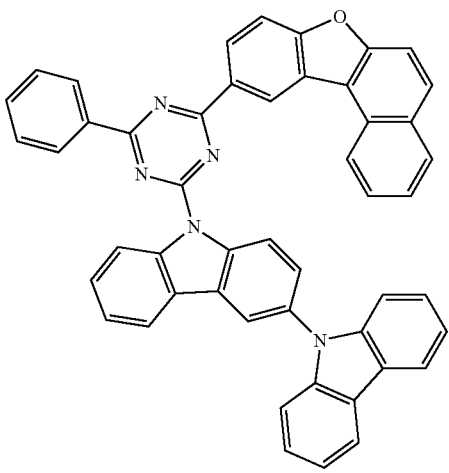
I 148
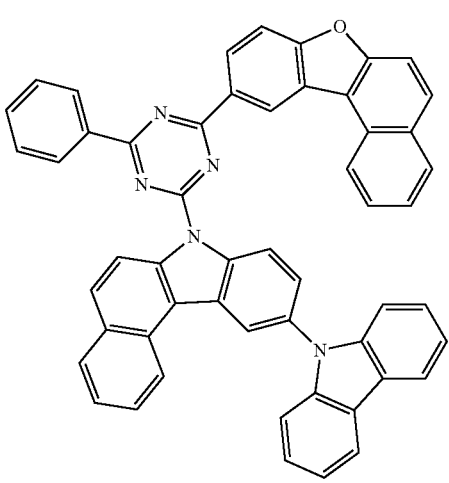
I 149
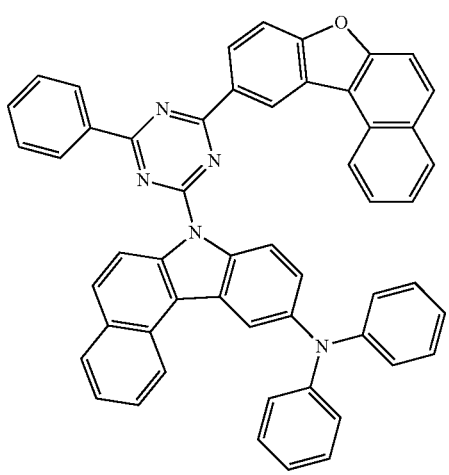

I-150
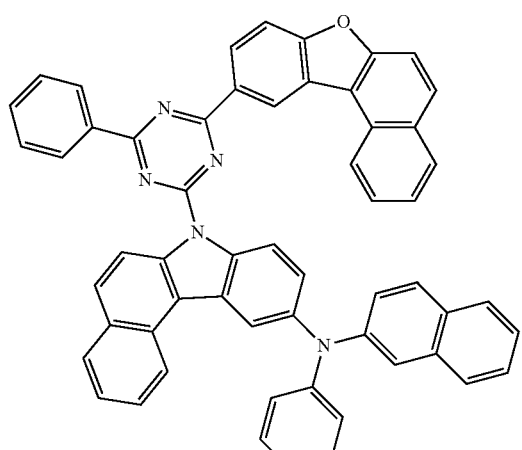
I-151
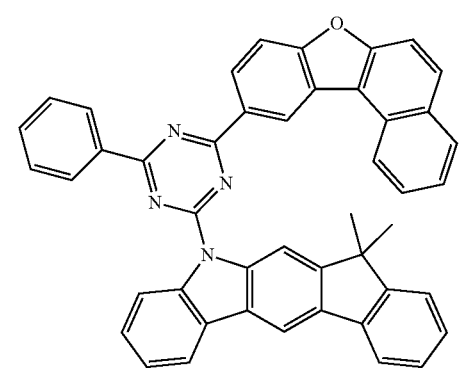
I-152
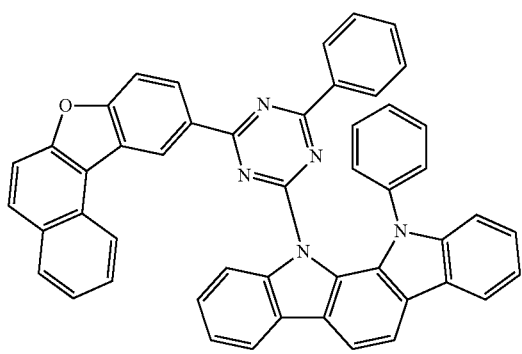
I-153
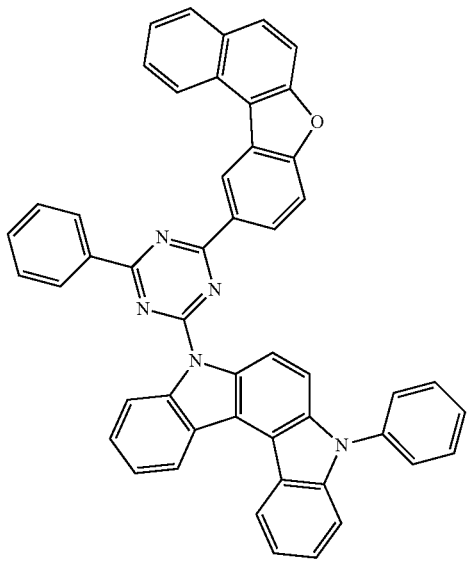
I-154
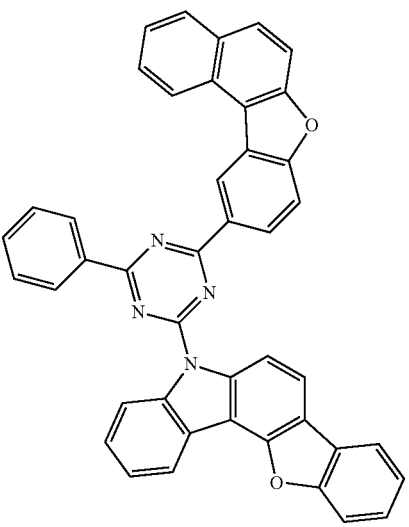
I-155
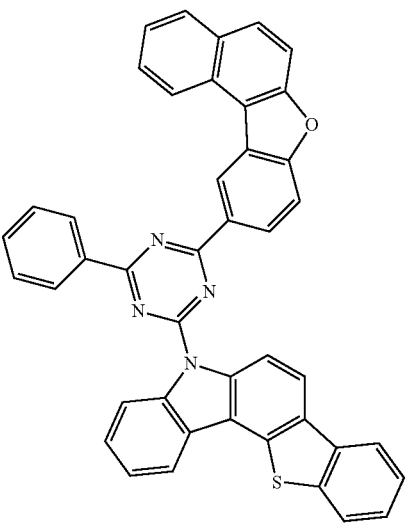

I 156
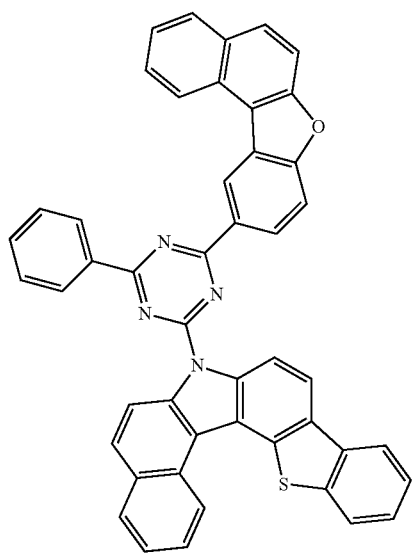
I 157
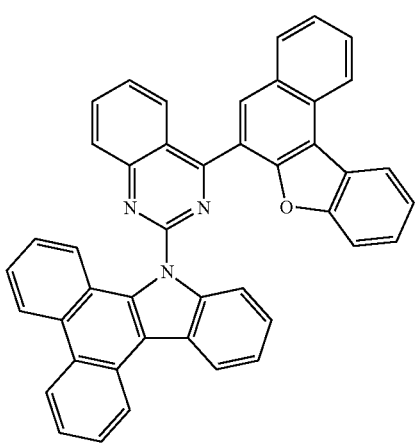
I 158
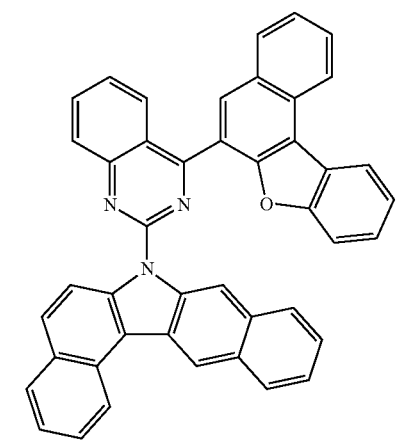
I 159
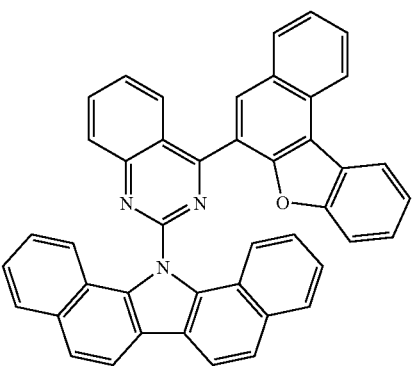
I 160
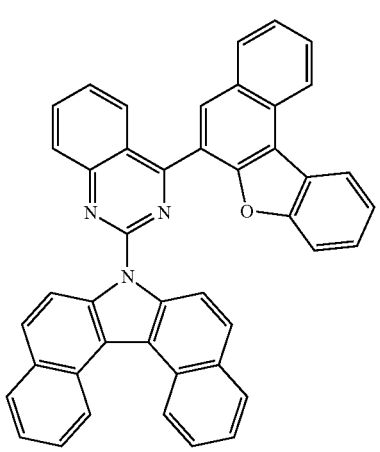
I 161
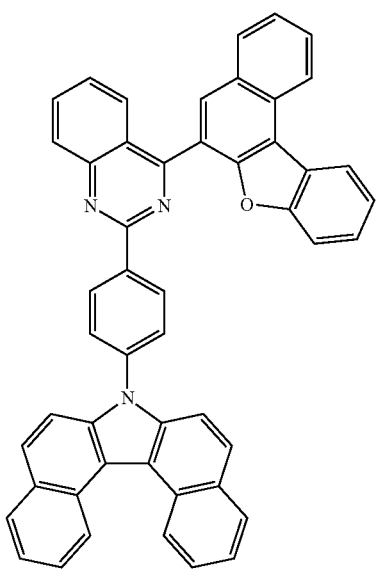

I-162
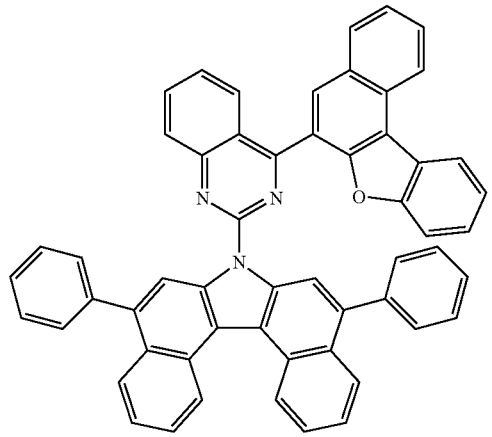
I-163
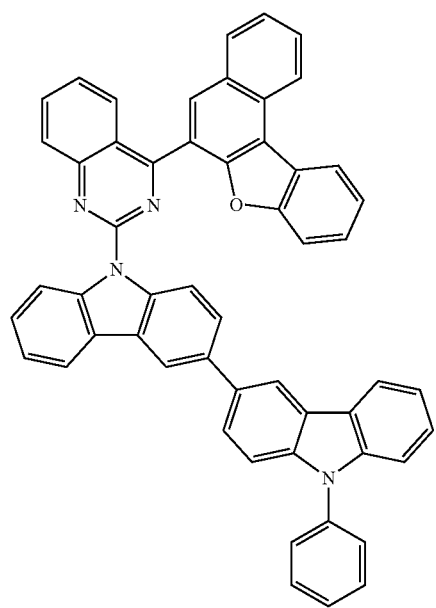
I-164
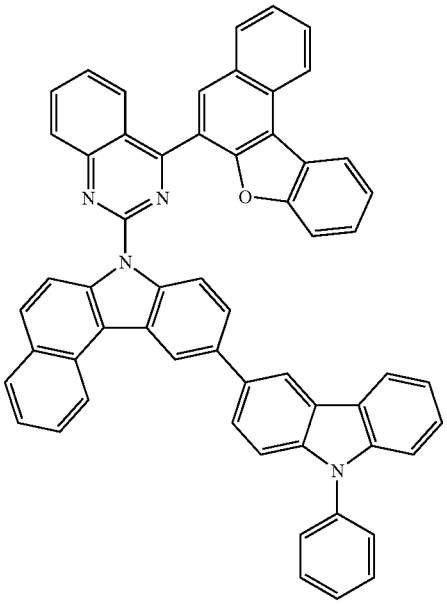
I-165
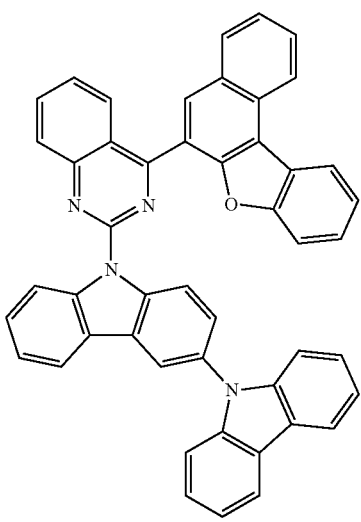
I-166
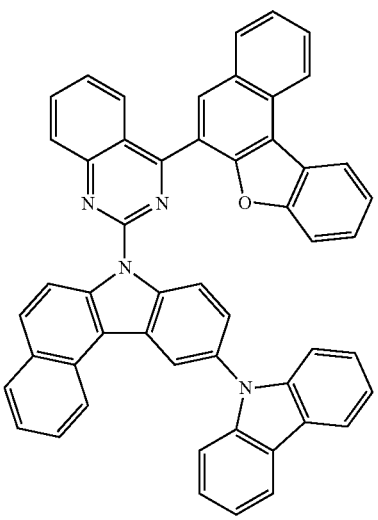

I 167
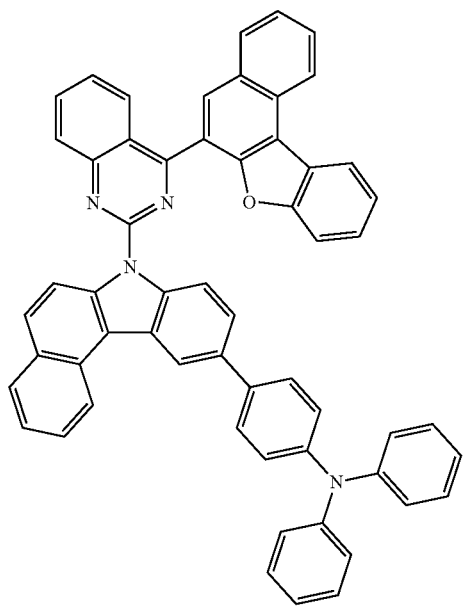
I 168
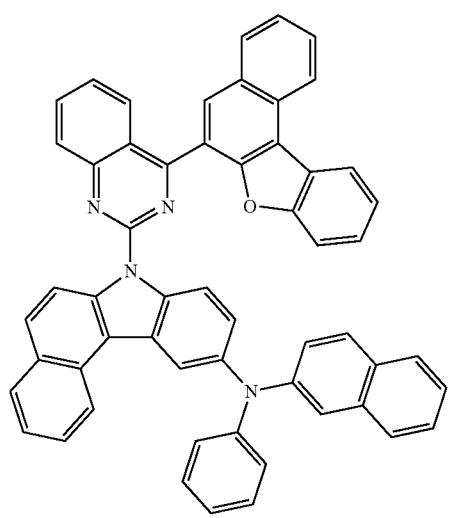
I 169
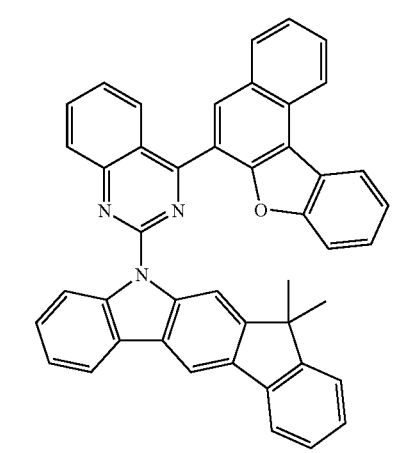
I 170
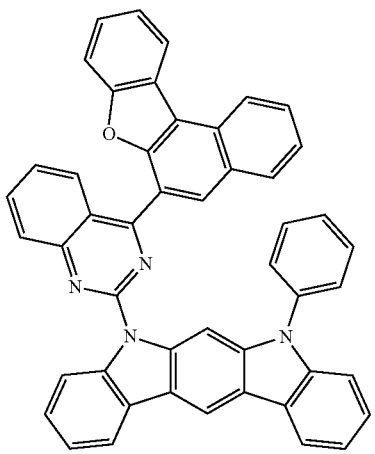
I 171
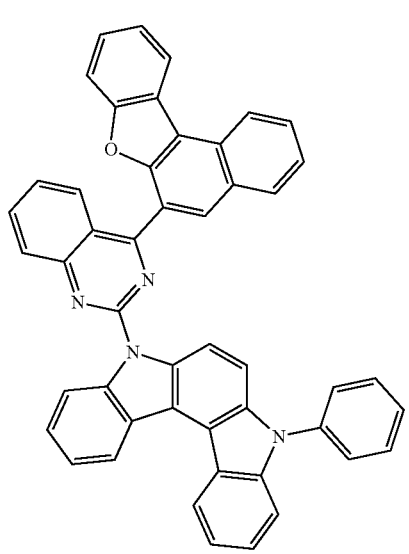
I 172
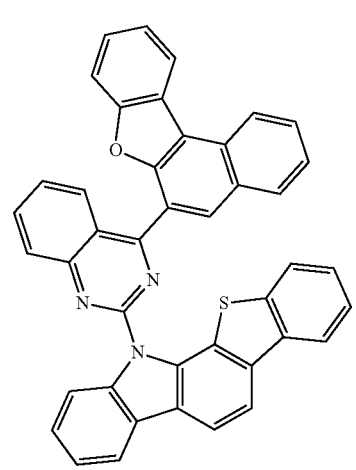

-continued
I 173
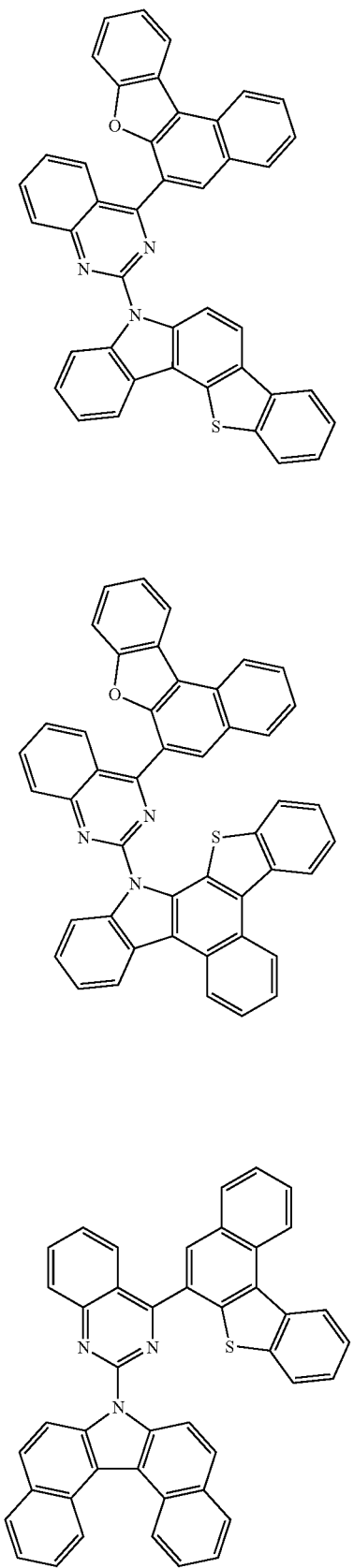
I 174
I 175
-continued
I 176
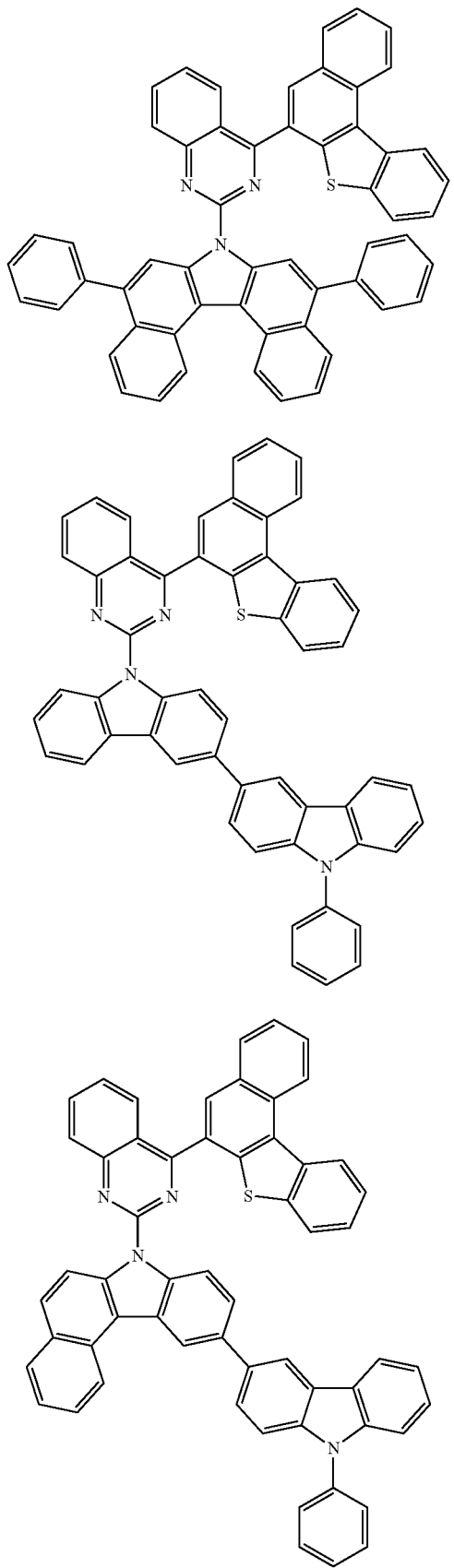
I 177
I 178

I179
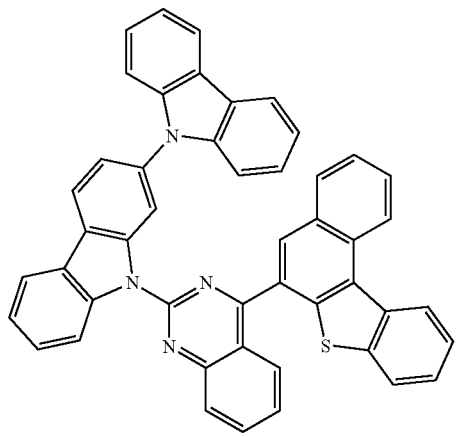
I180
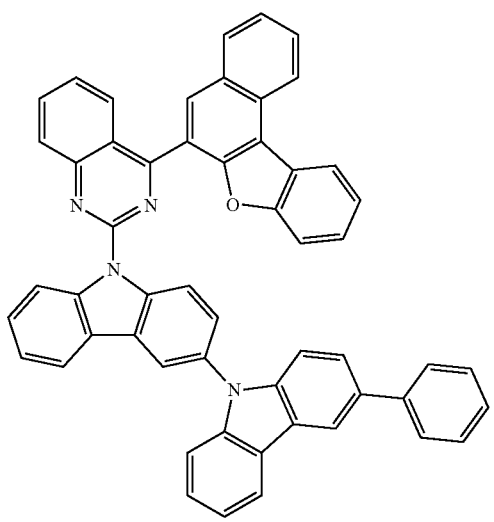
I181
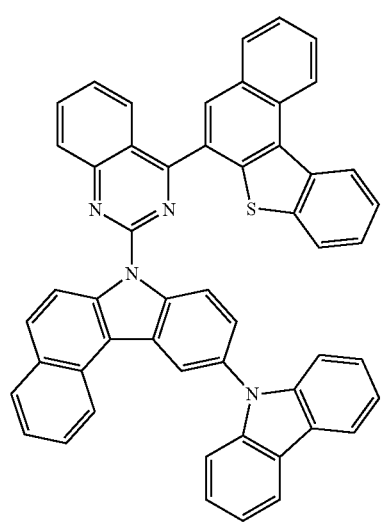
I182
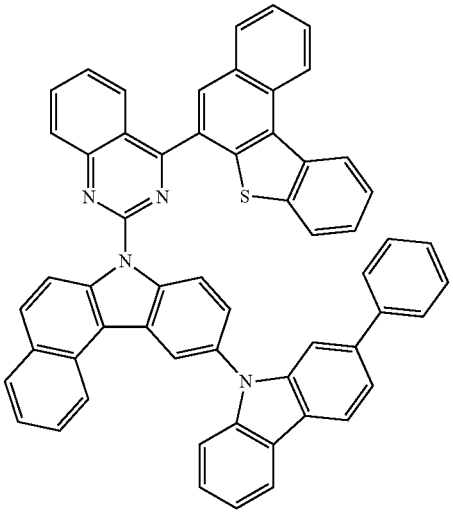
I183
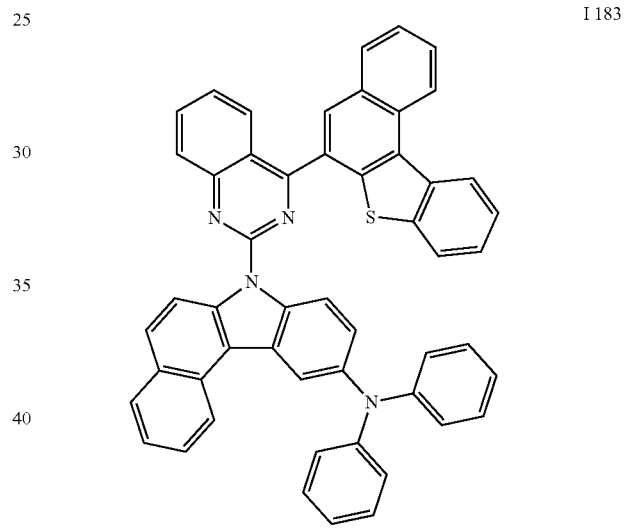
I184
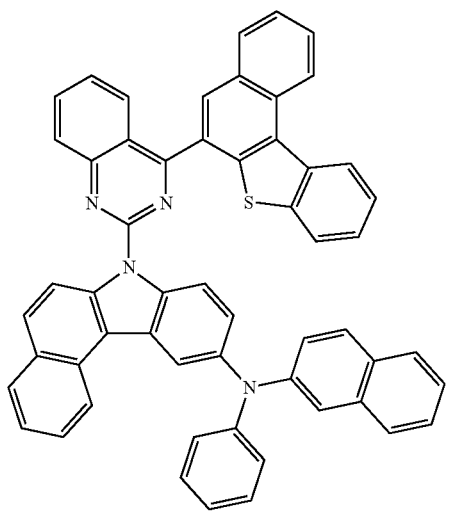

I 185
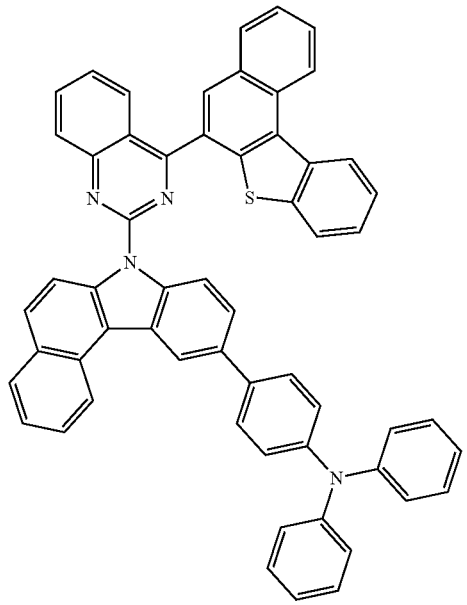
I 186
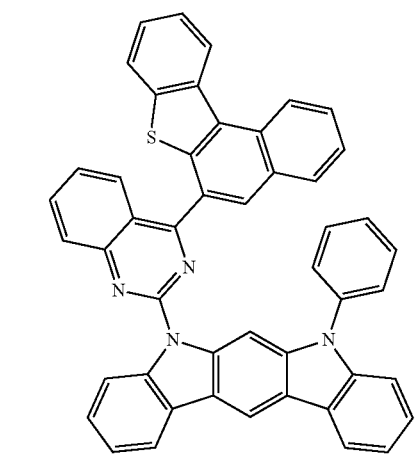
I 187
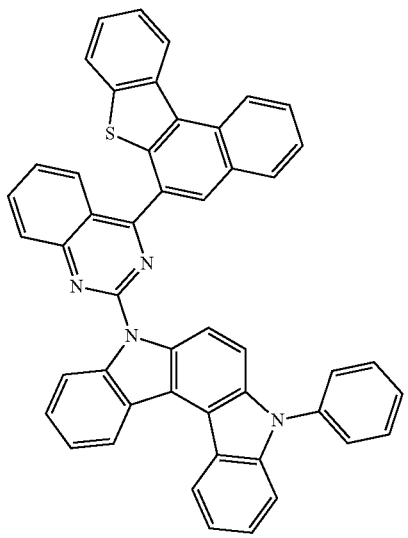
I 188
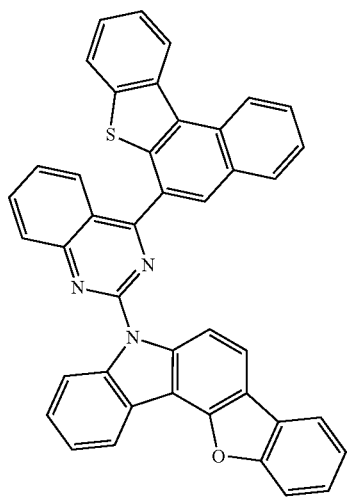
I 189
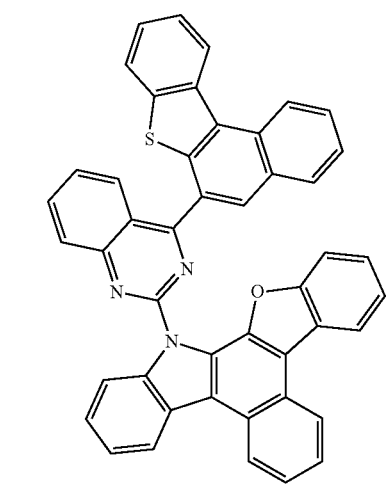
I 190
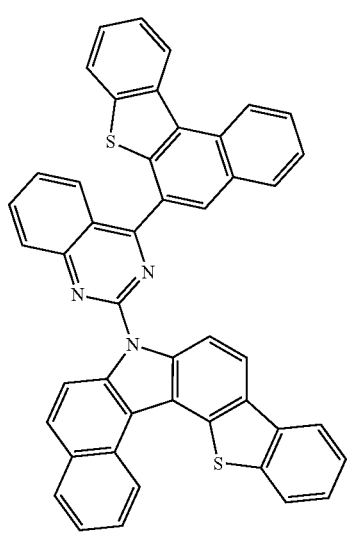

I 191
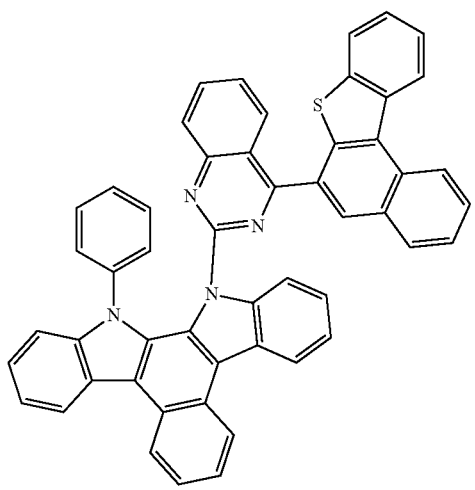
I 194
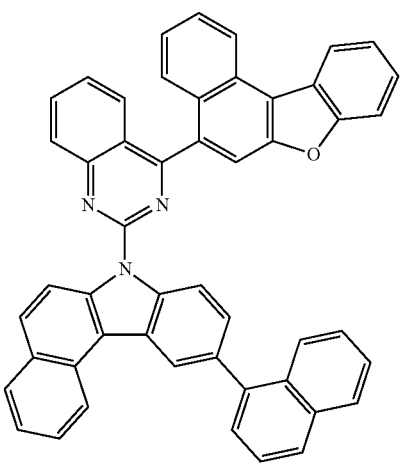
I 192
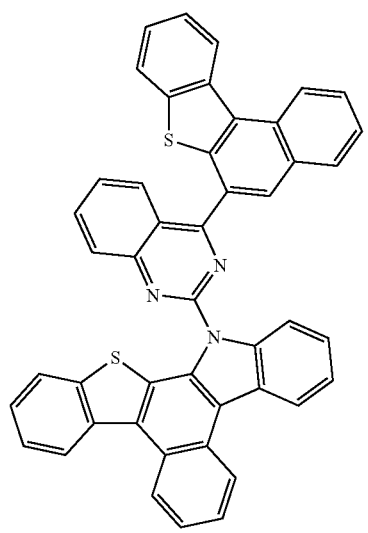
I 195
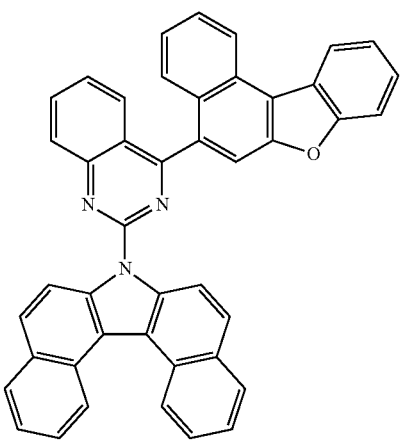
I 193
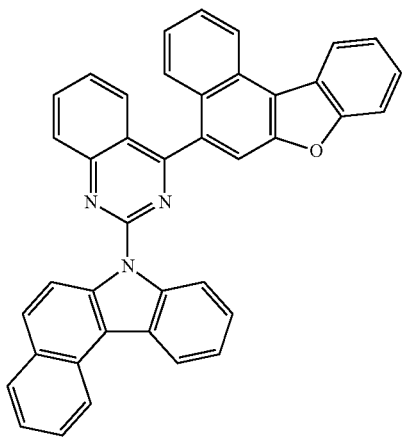
I 196
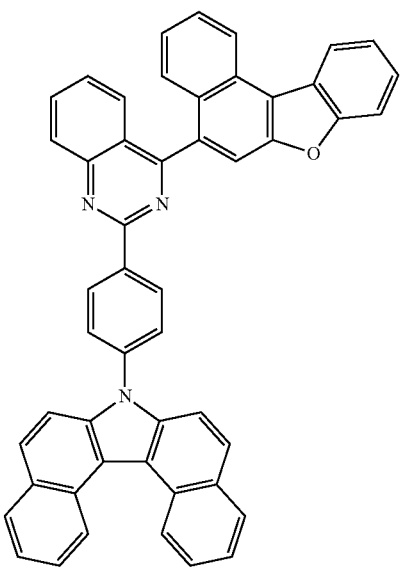

-continued
I 197
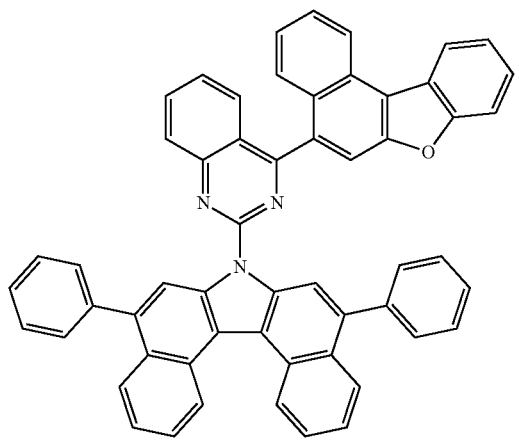
I 198
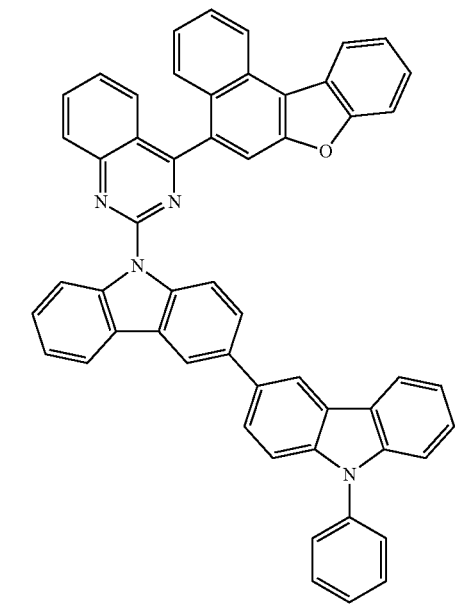
I 199
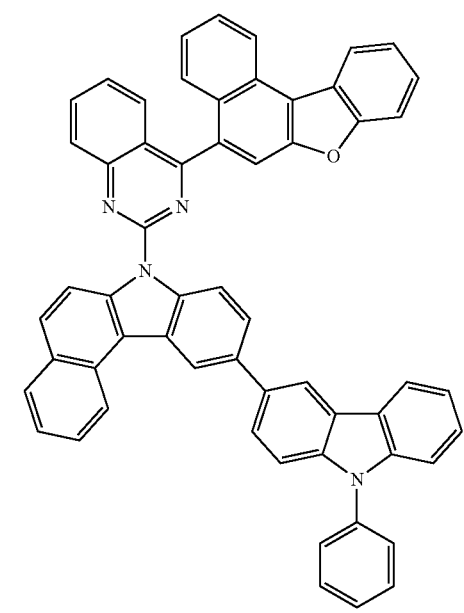
-continued
I 200
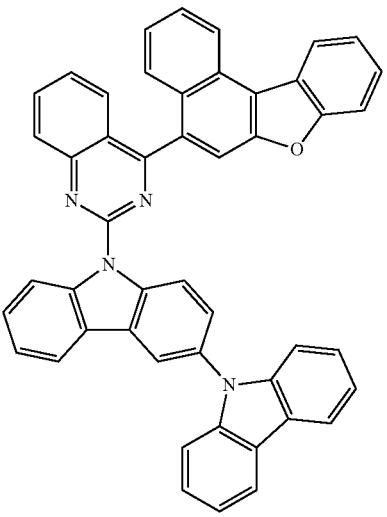
I 201
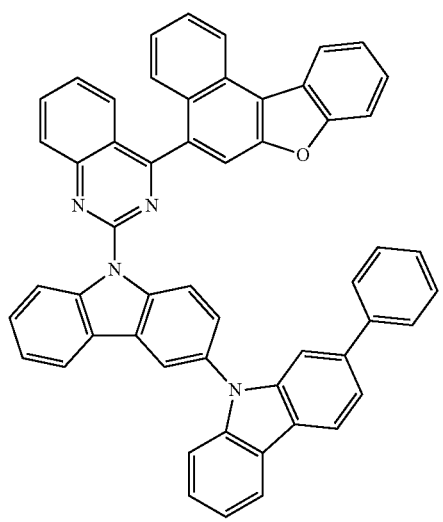
I 202
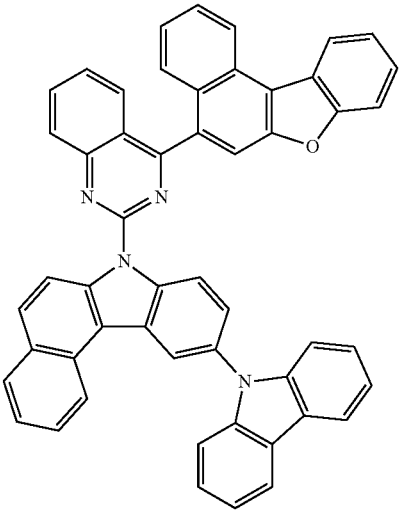

I 203
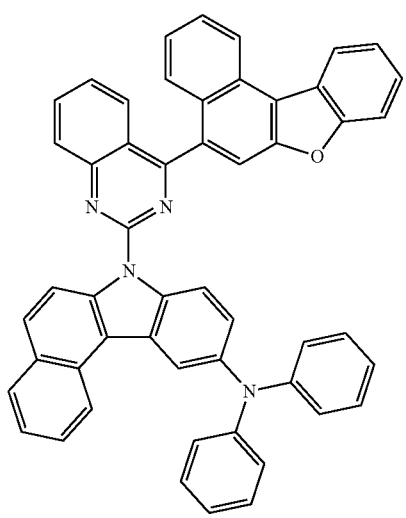
I 204
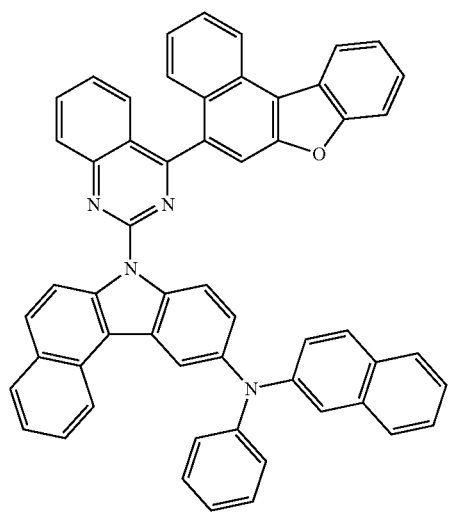
I 205
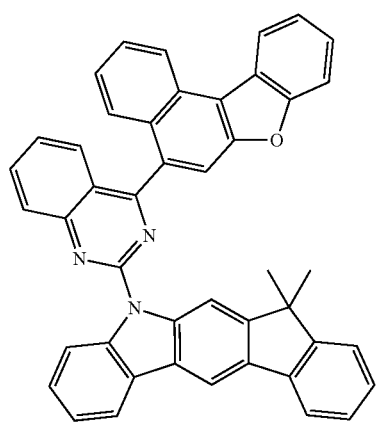
I 206
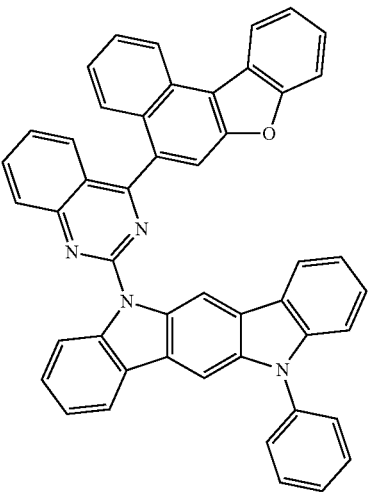
I 207
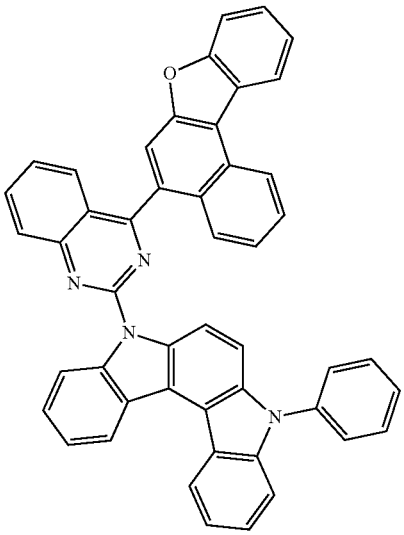
I 208
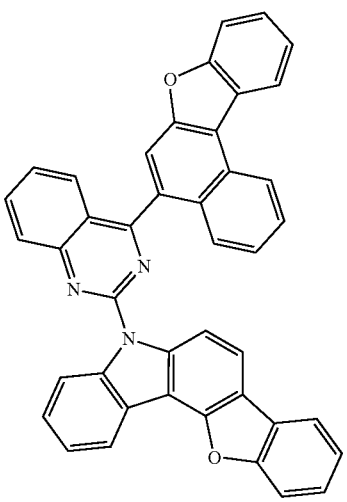

I 209
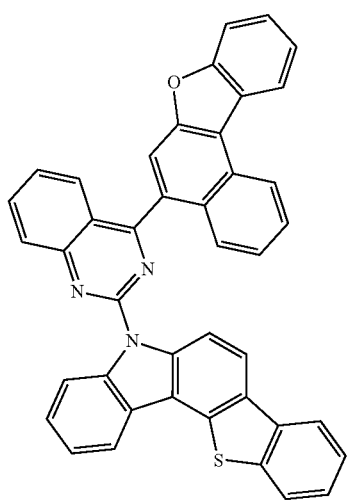
I 210
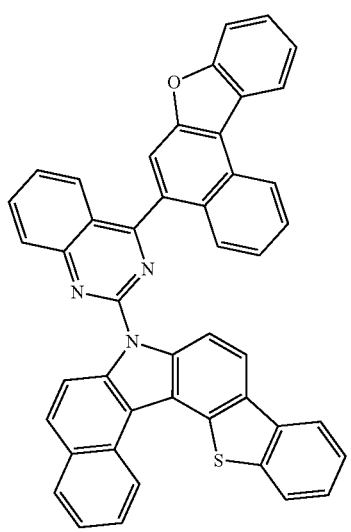
I 211
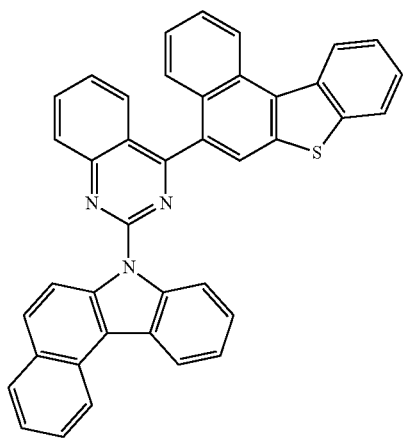
I 212
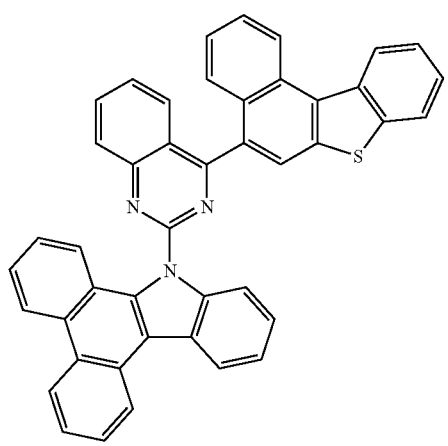
I 213
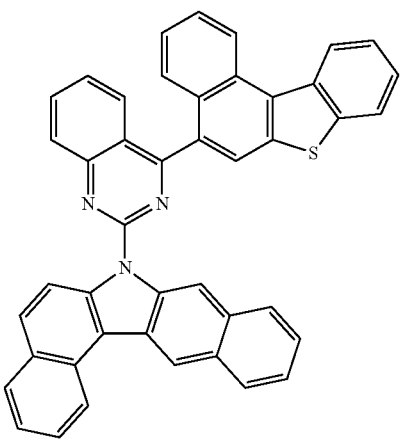
I 214
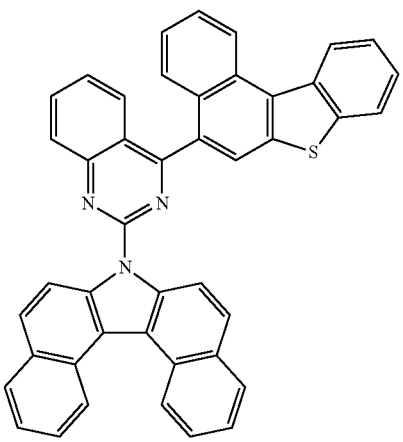

I 215
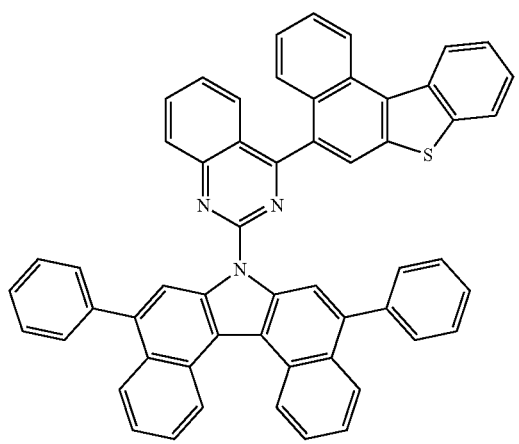
I 216
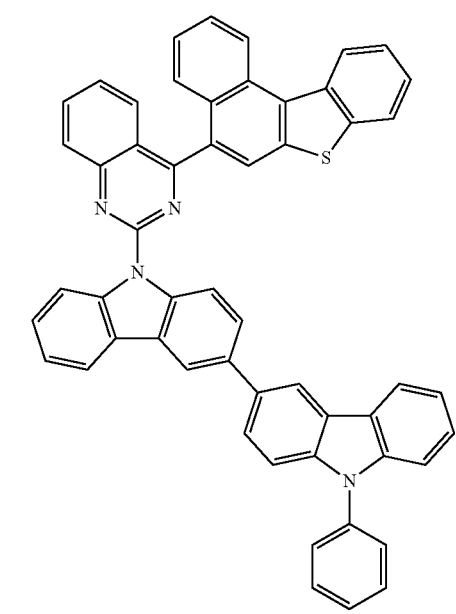
I 217
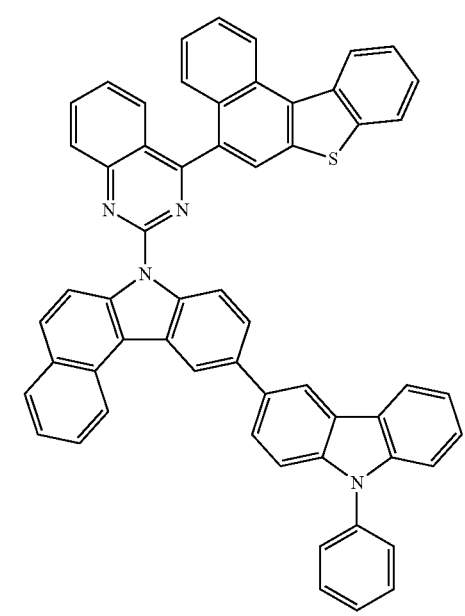
I 218
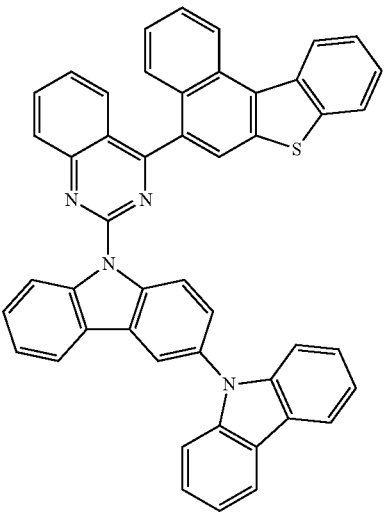
I 219
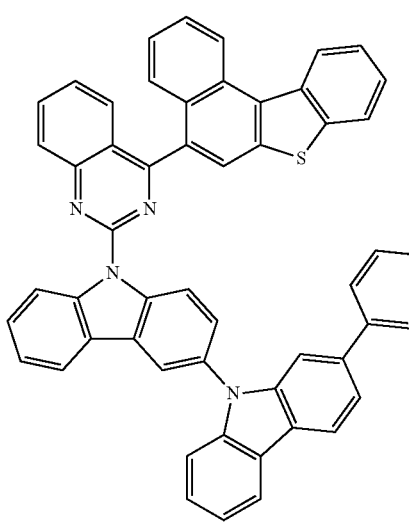
I 220
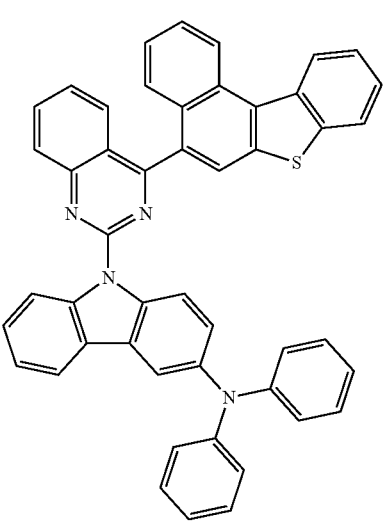

I 221
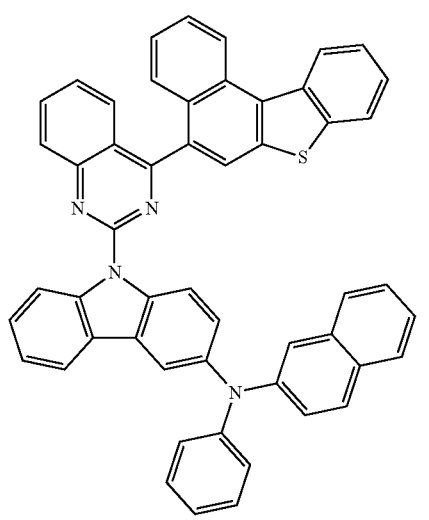
I 222
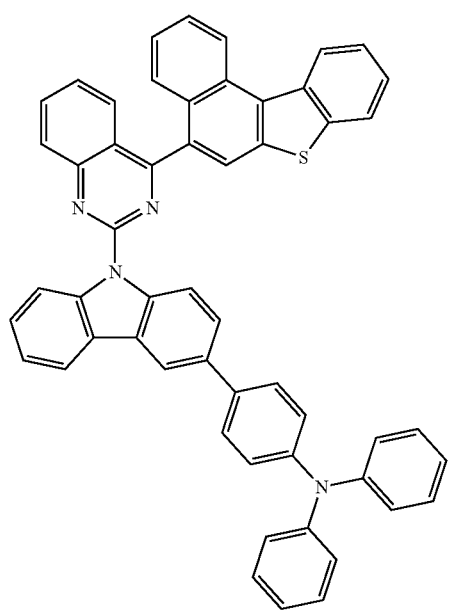
I 223
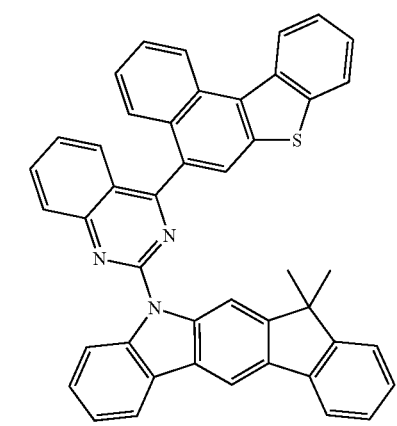
I 224
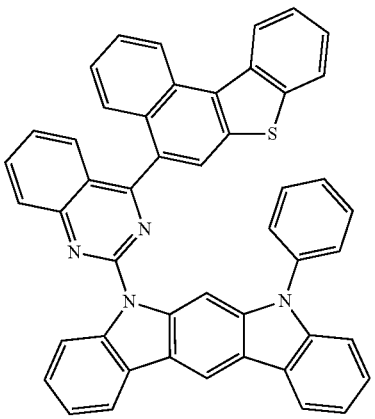
I 225
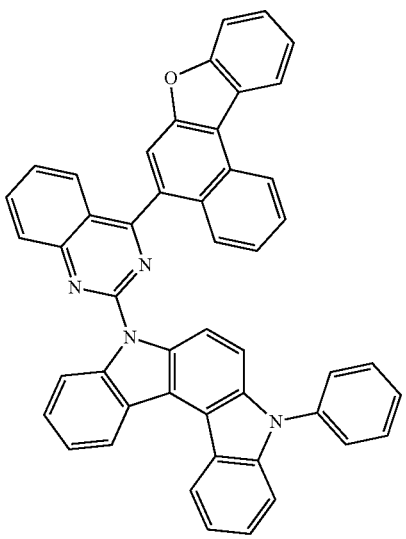
I 226
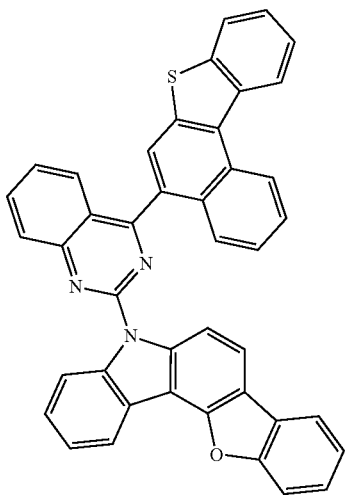

-continued
I 227
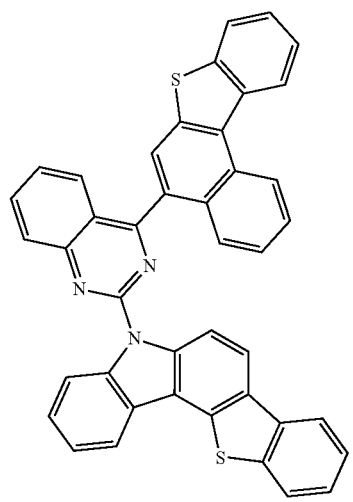
I 228
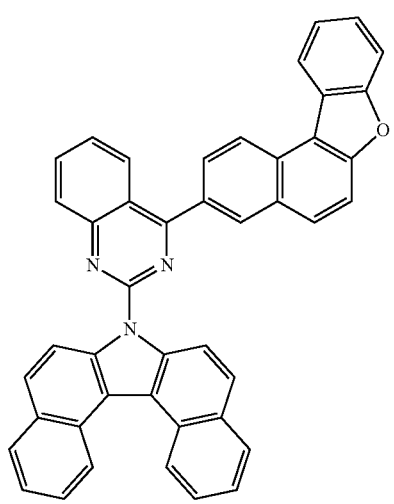
I 229
-continued
I 230
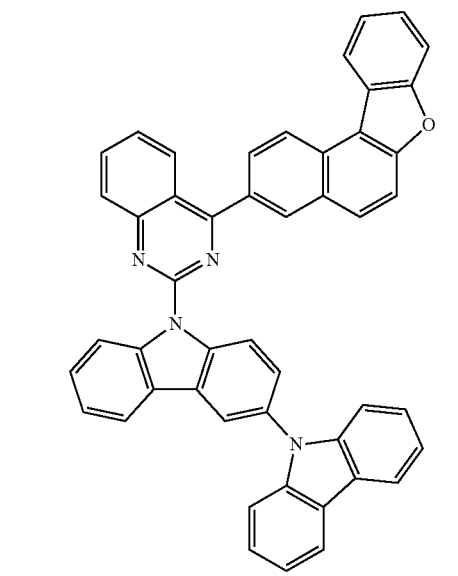
I 231
I 232
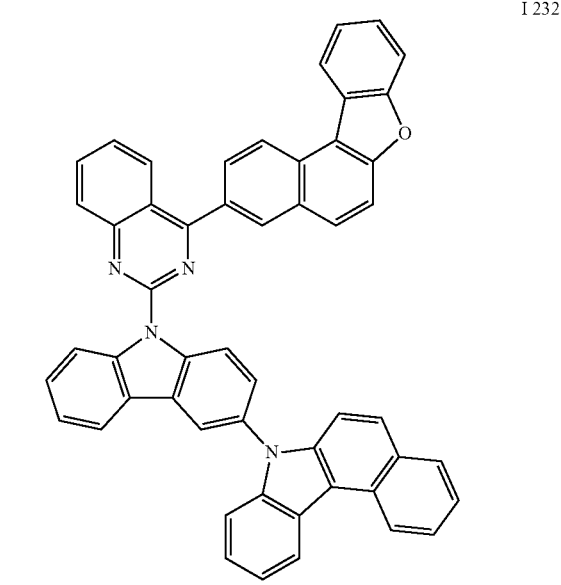

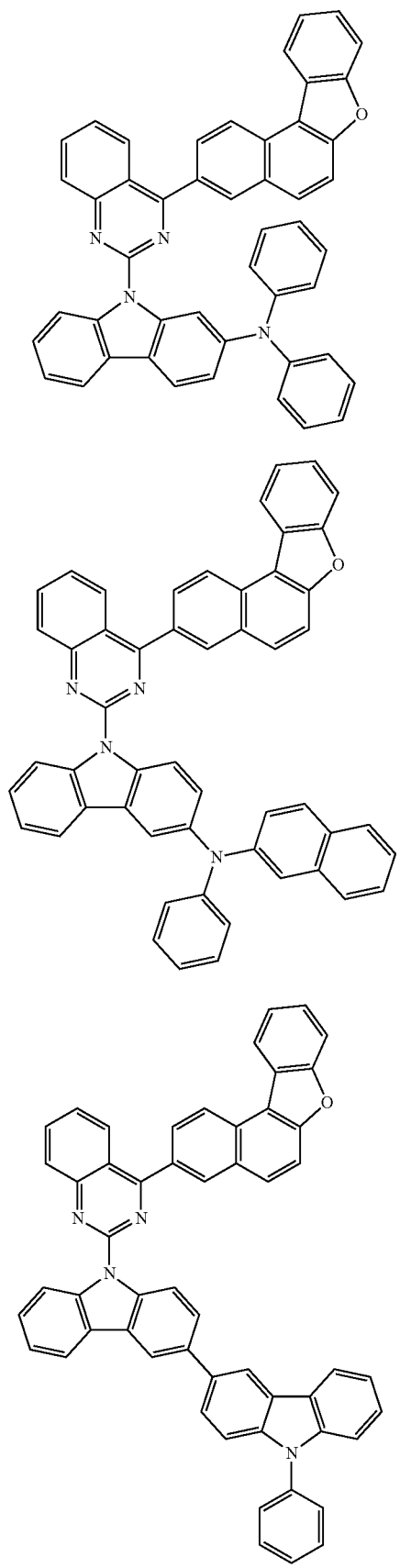

I 238
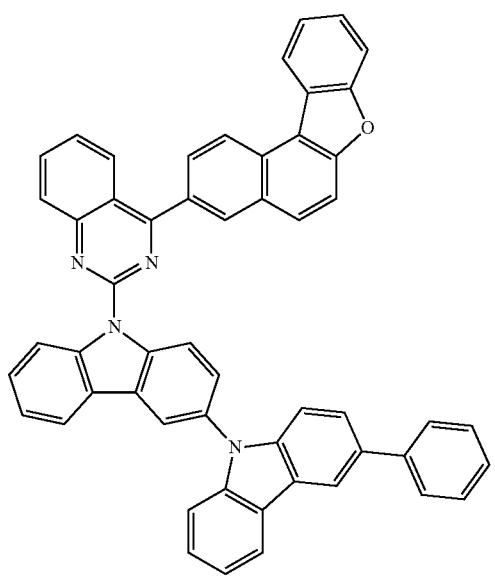
I 239
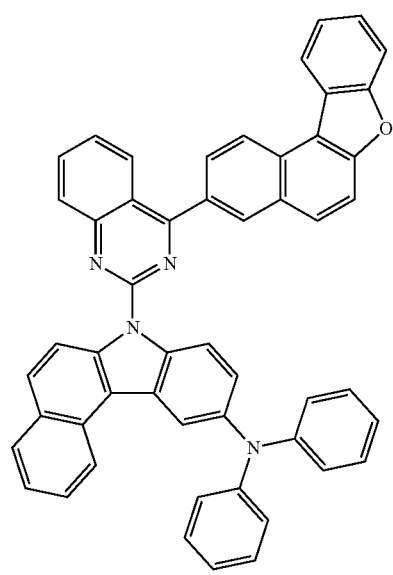
I 240
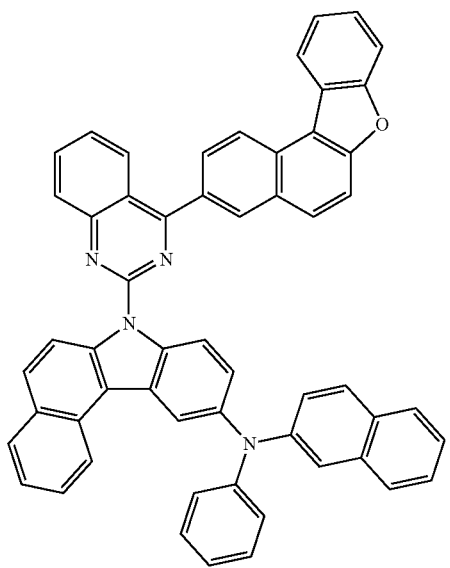
I 241
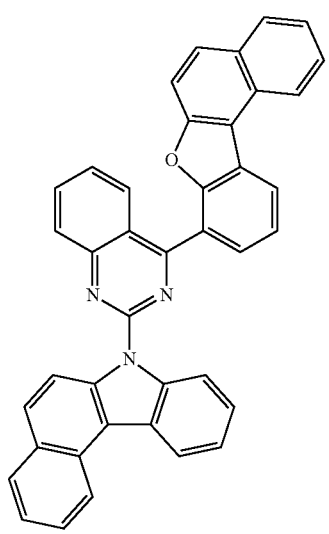
I 242
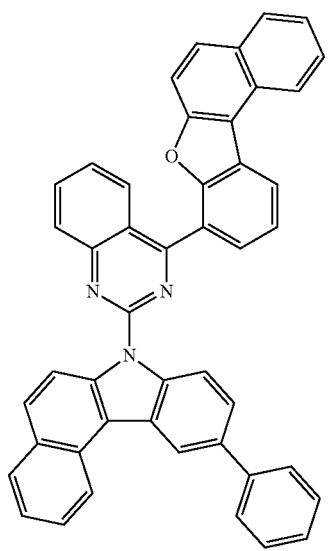

I 243
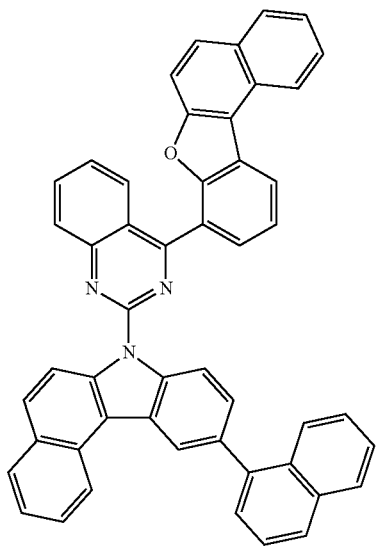
I 245
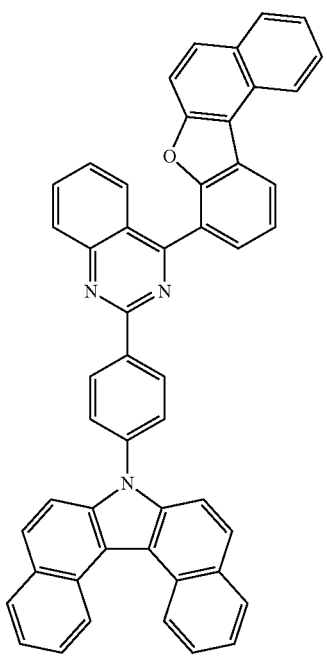
I 244
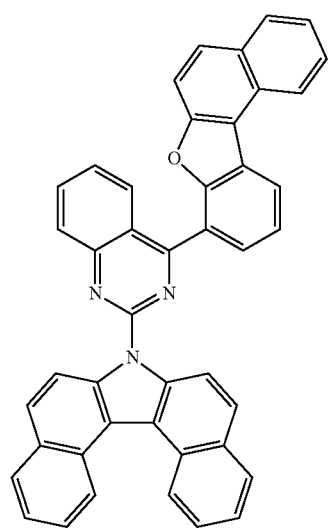
I 246
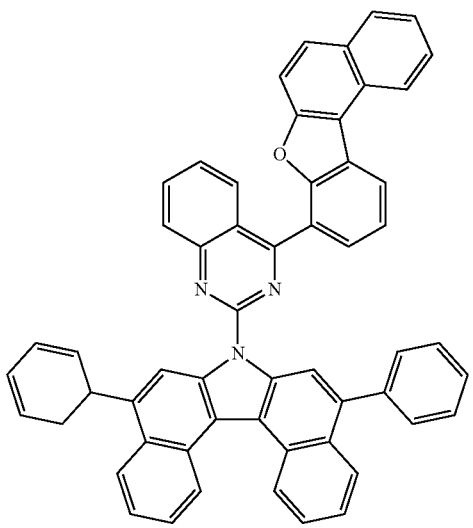

I 247
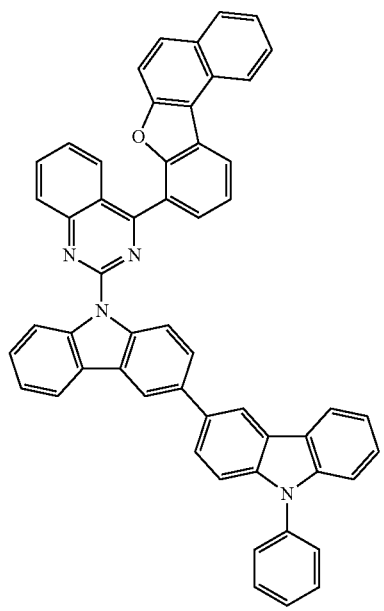
I 248
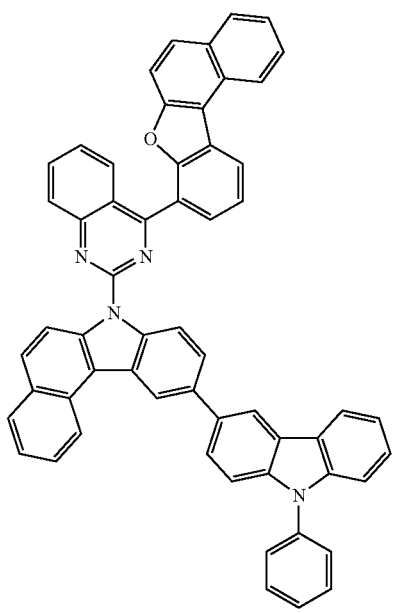
I 249
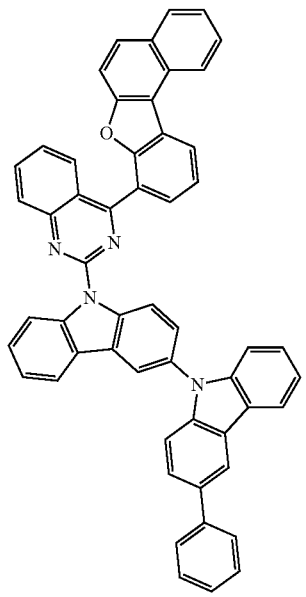
I 250
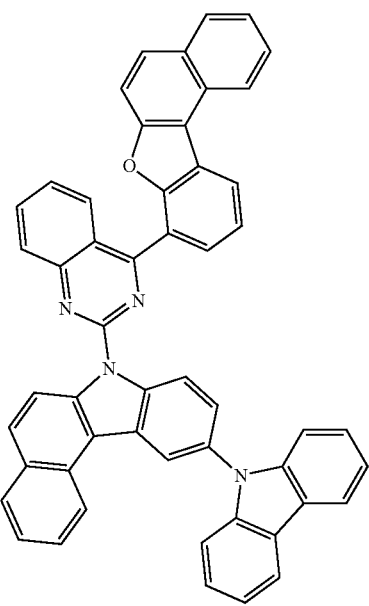

I 251
I 252
I 253
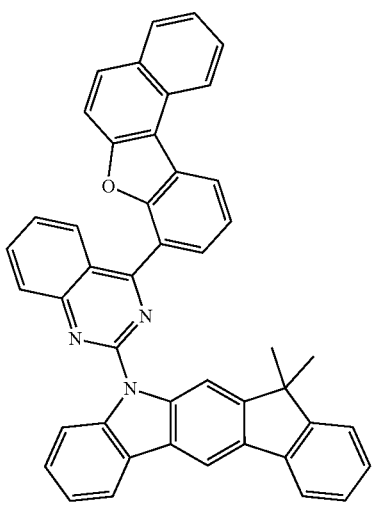
I 254
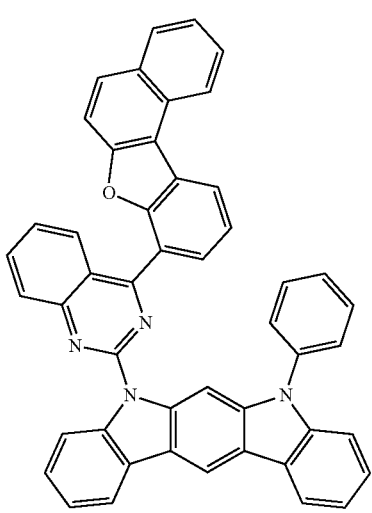
I 255
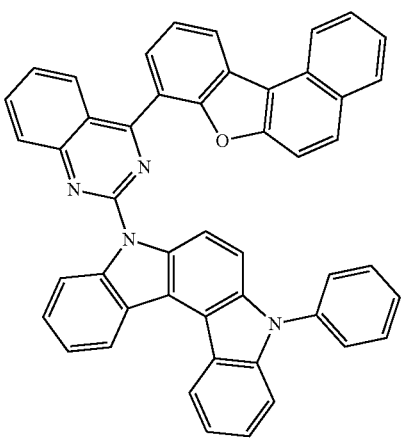

-continued
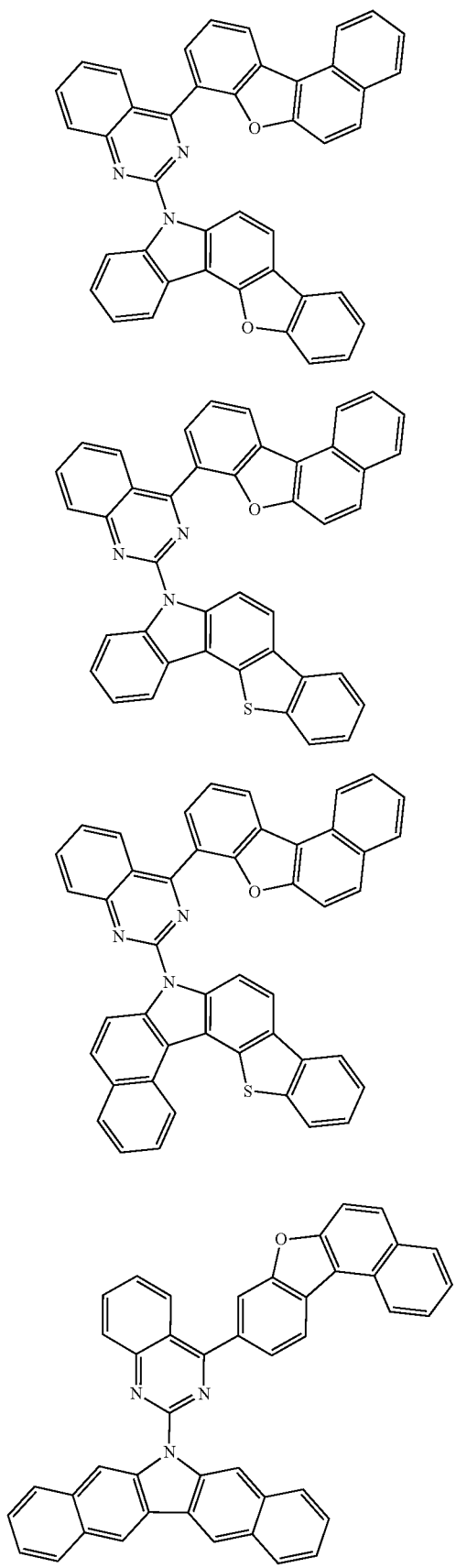
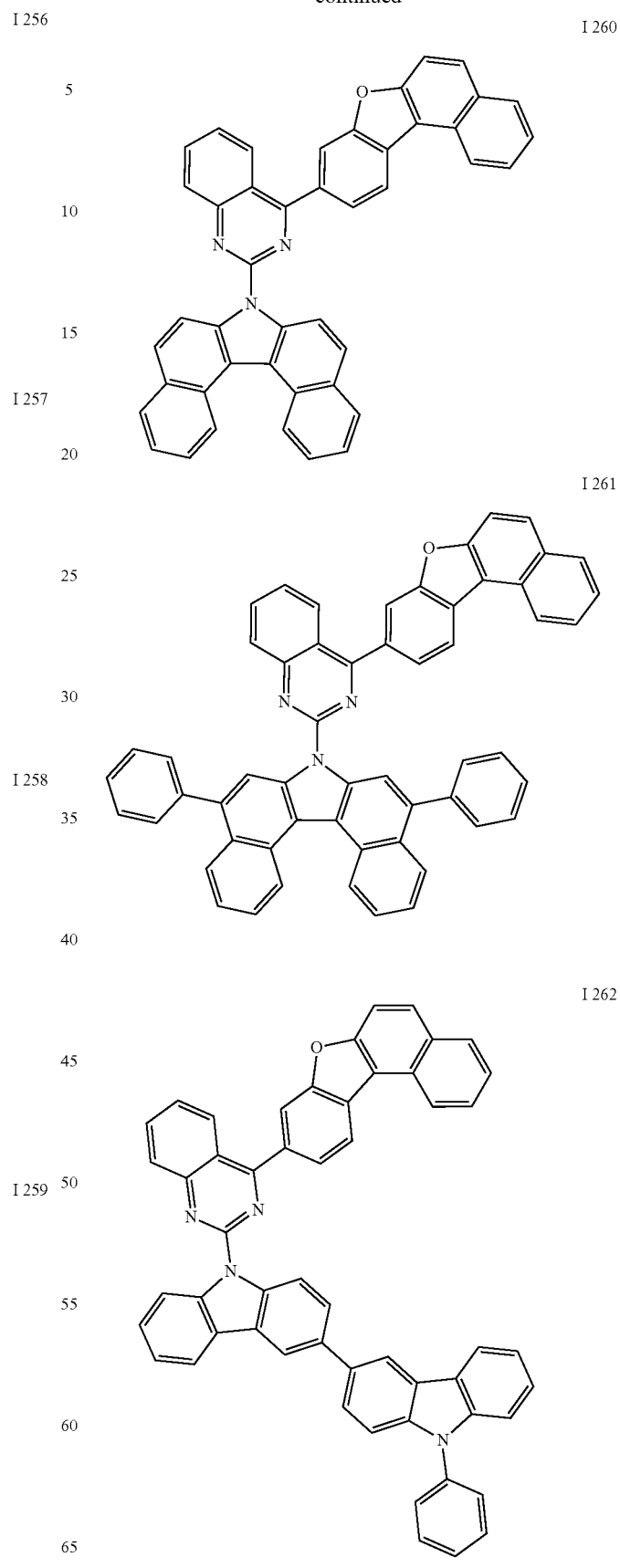

-continued
I 263
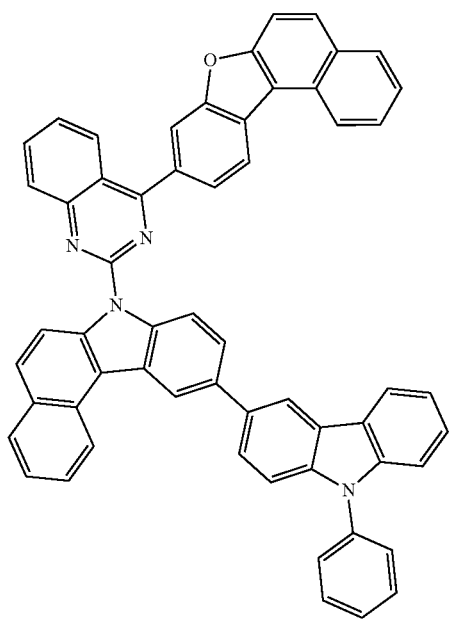
I 264
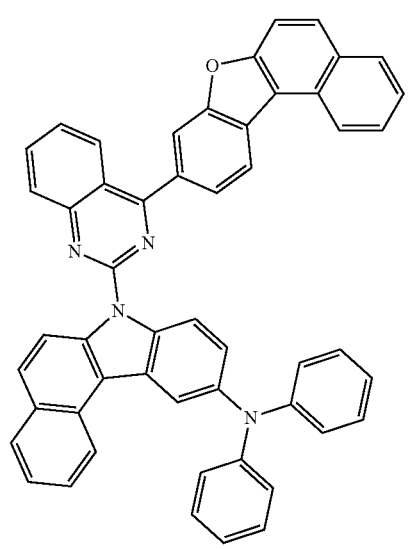
I 265
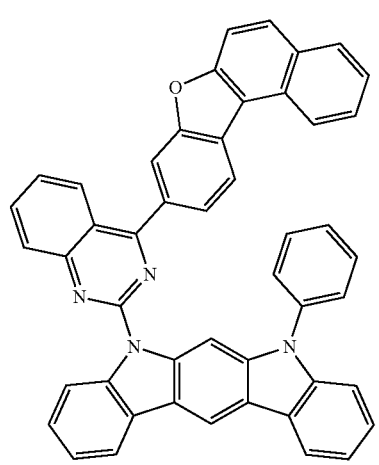
-continued
I 266
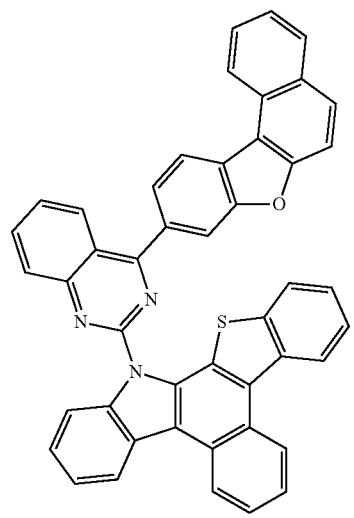
I 267
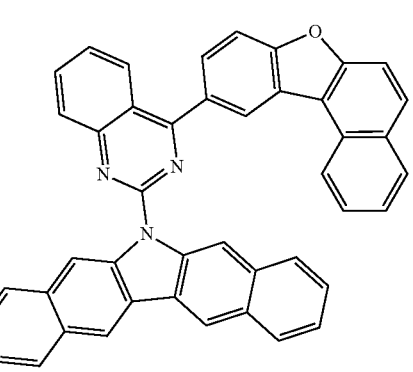
I 268
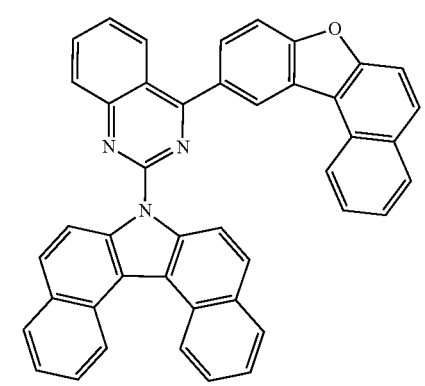

I 269
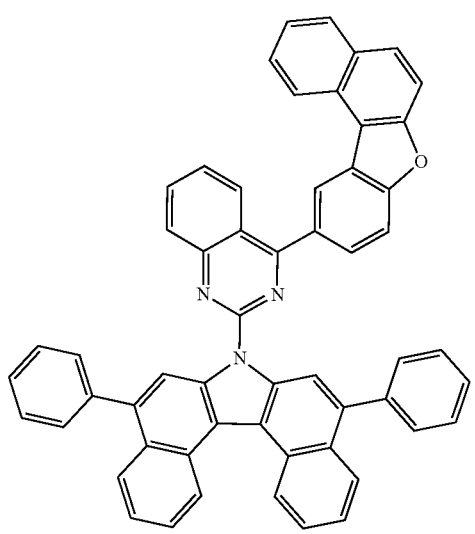
I 270
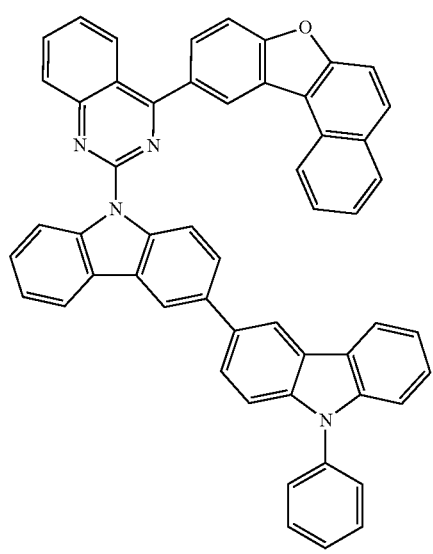
I 271
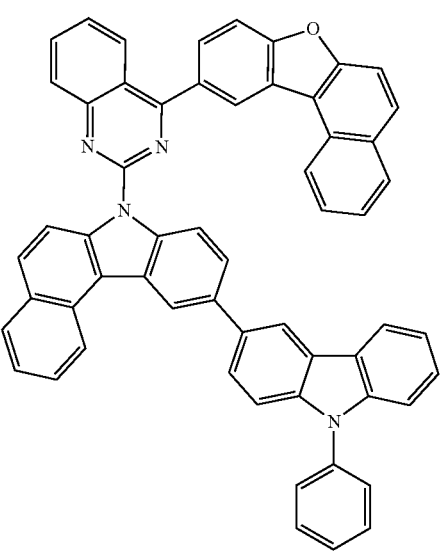
I 272
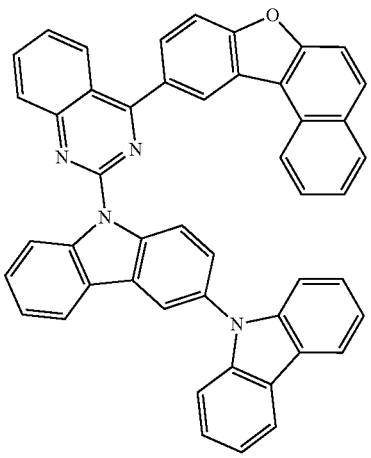
I 273
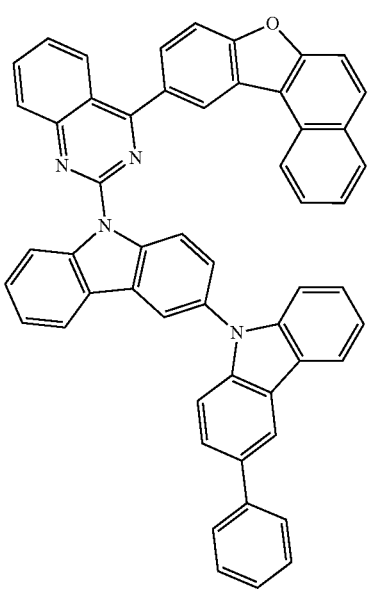
I 274
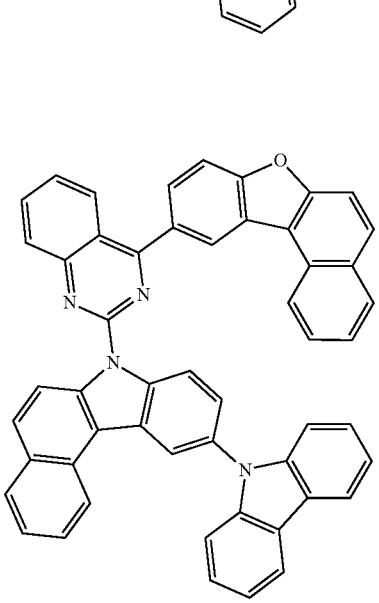

I 275
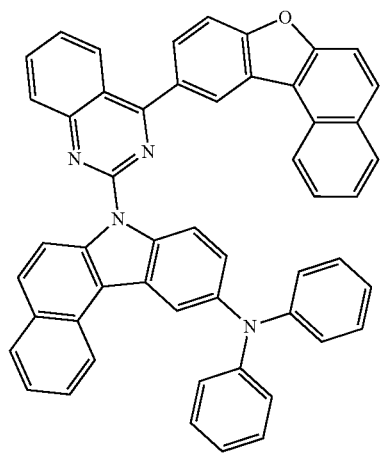
I 276
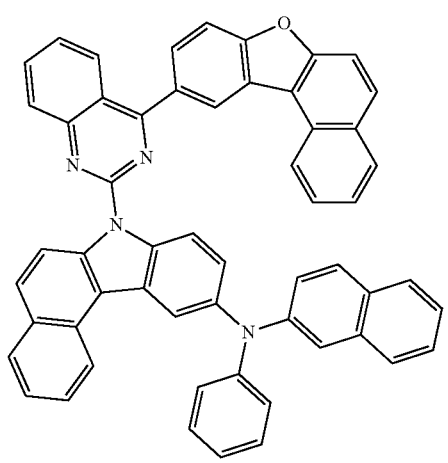
I 277
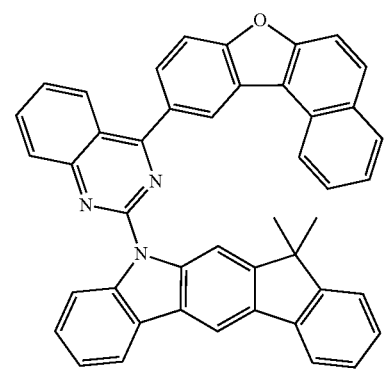
I 278
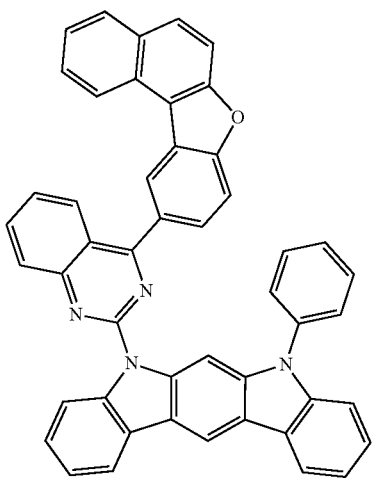
I 279
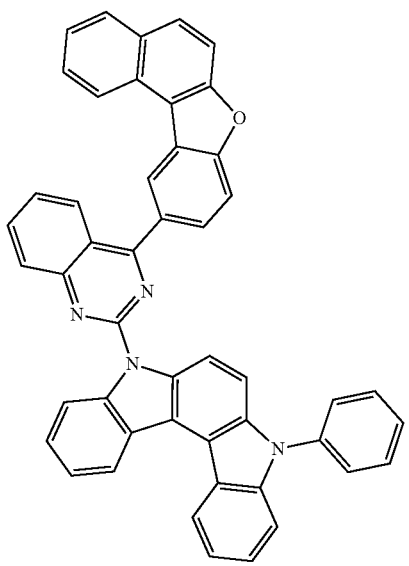
I 280
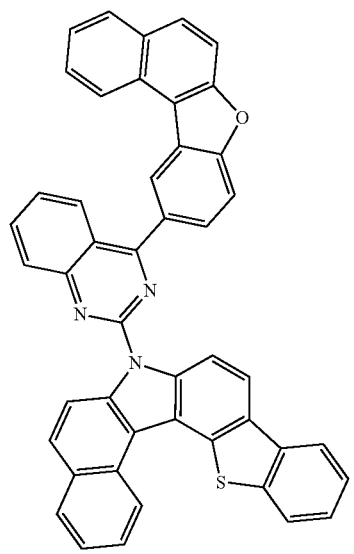

-continued
I 281
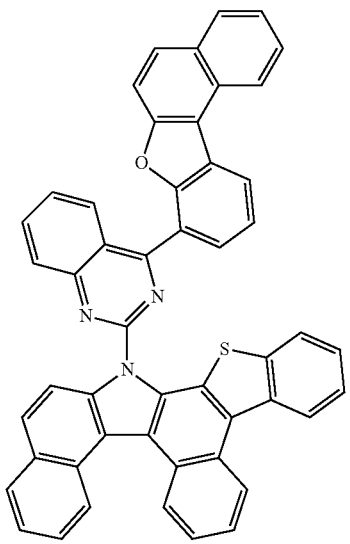
I 282
I 283
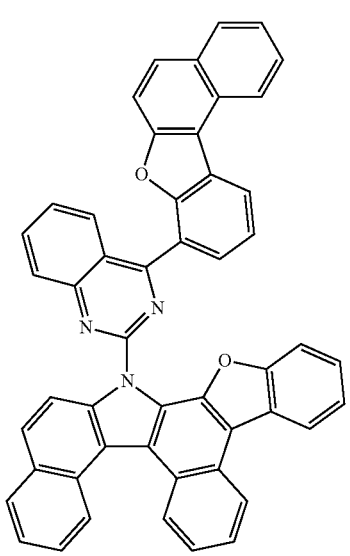
I 284
I 285
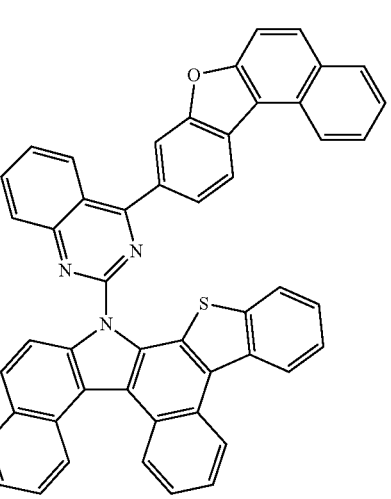

I 286
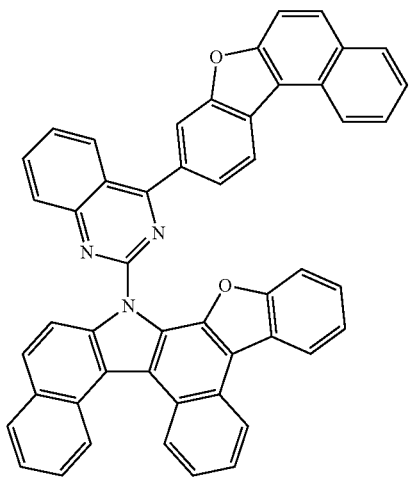
I 287
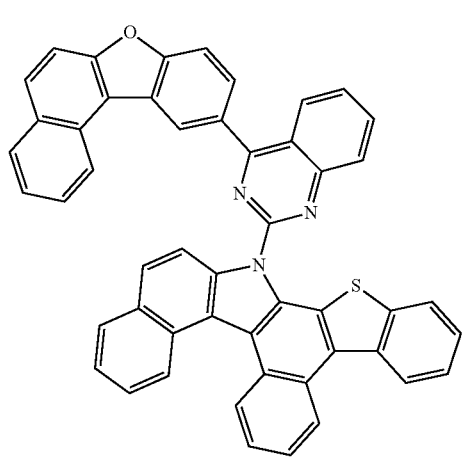
I 288
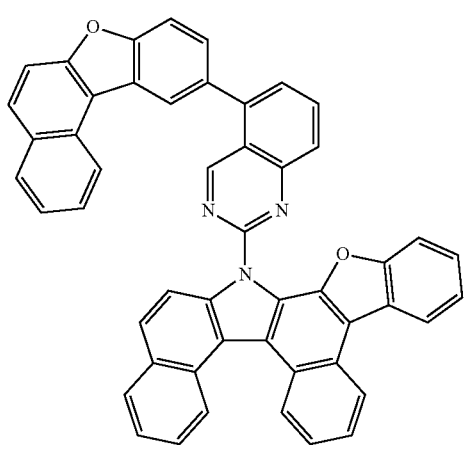
I 289
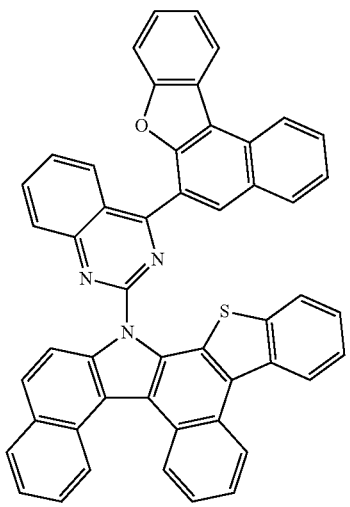
I 290
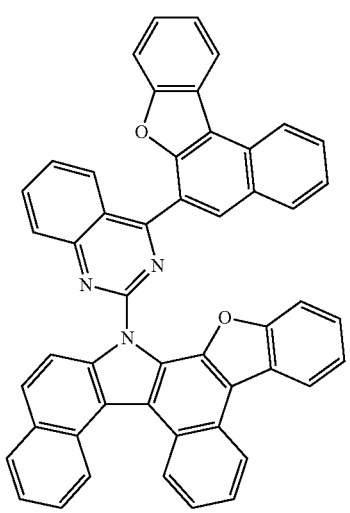
I 291
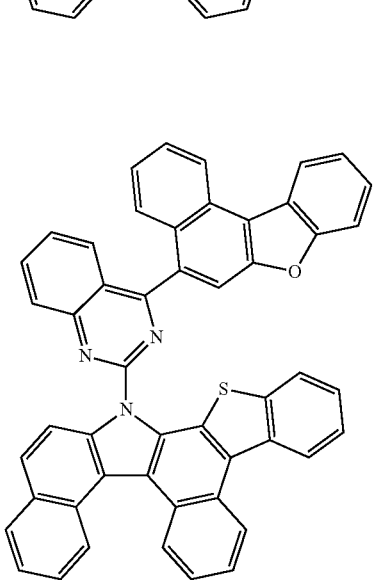

I 292
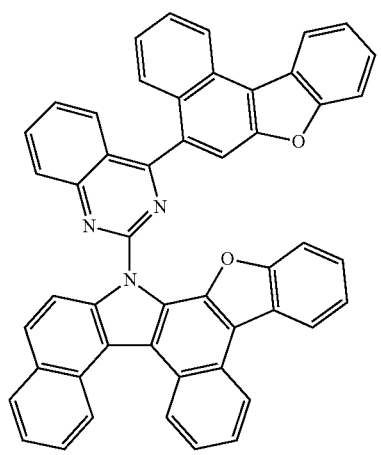
I 293
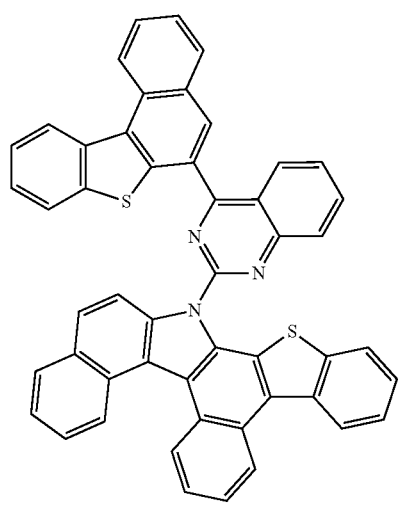
I 294
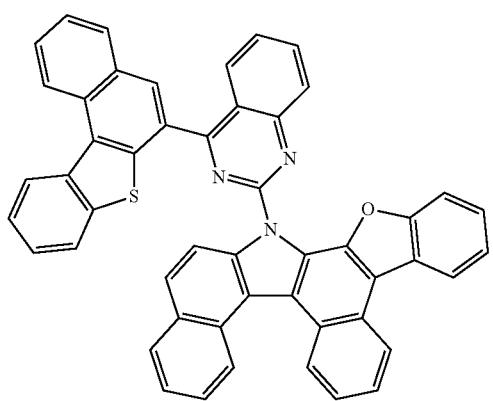
I 295
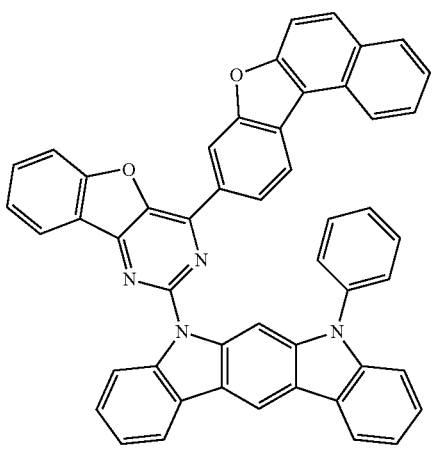
I 296
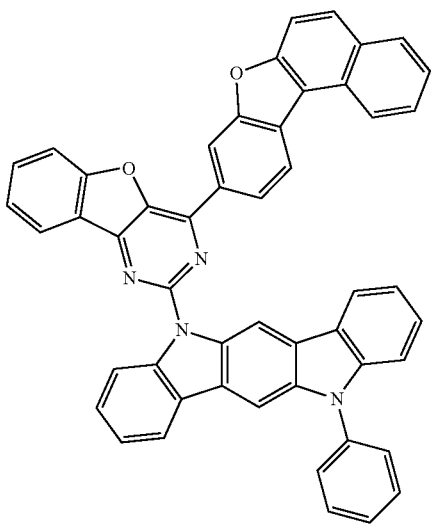
I 297
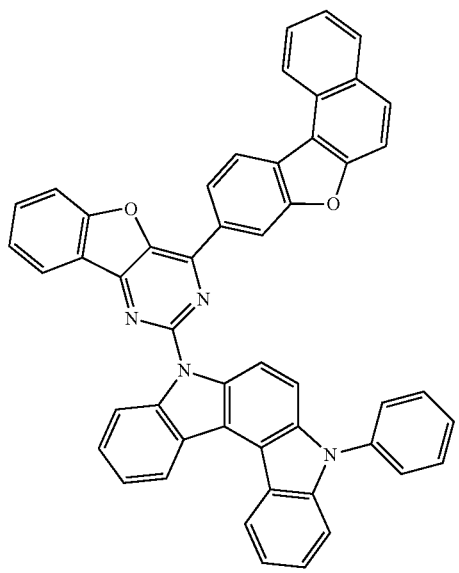

I 298
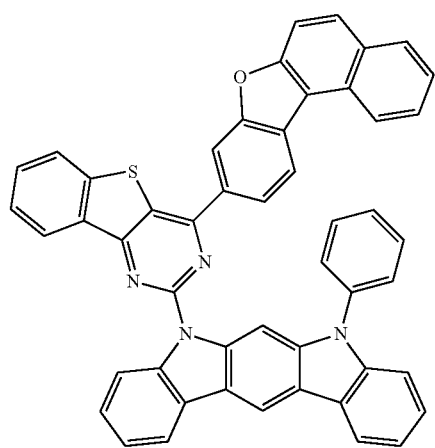
I 299
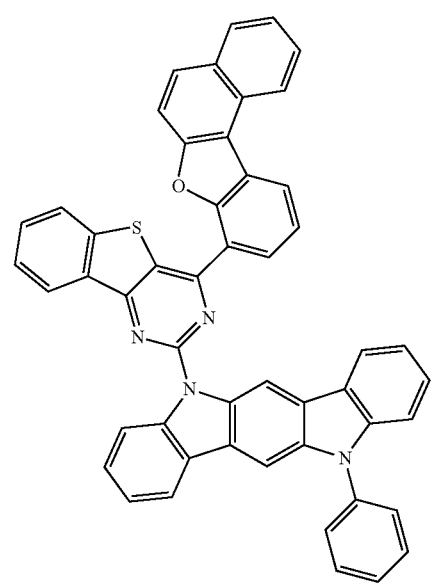
I 300
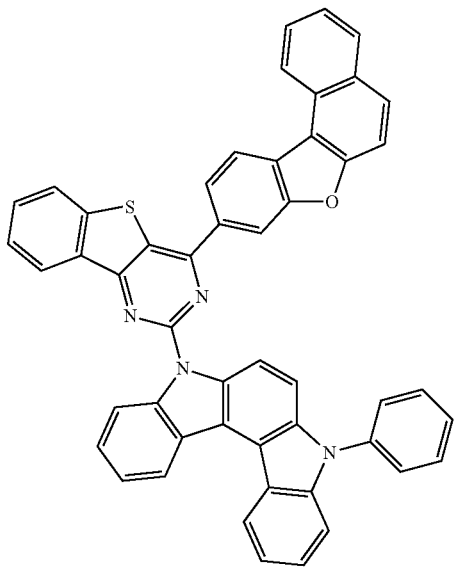
I 301
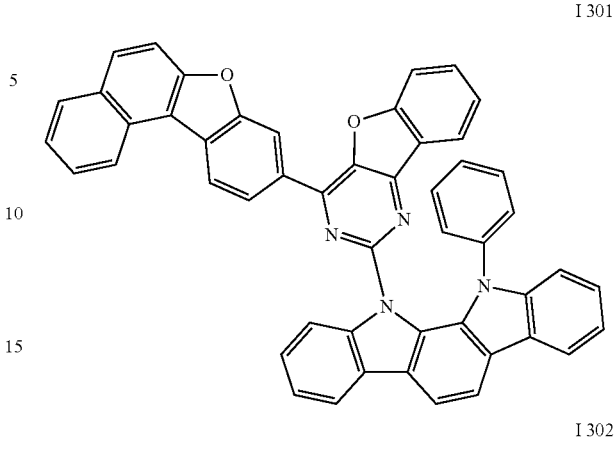
I 302
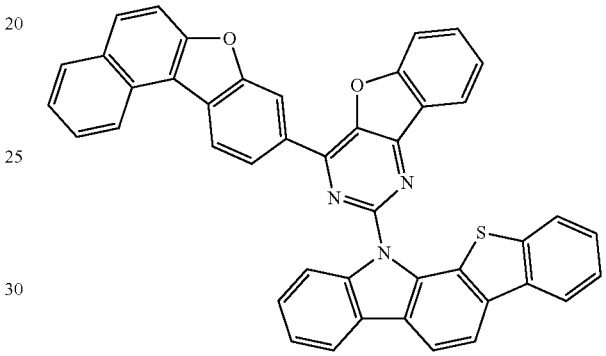
I 303
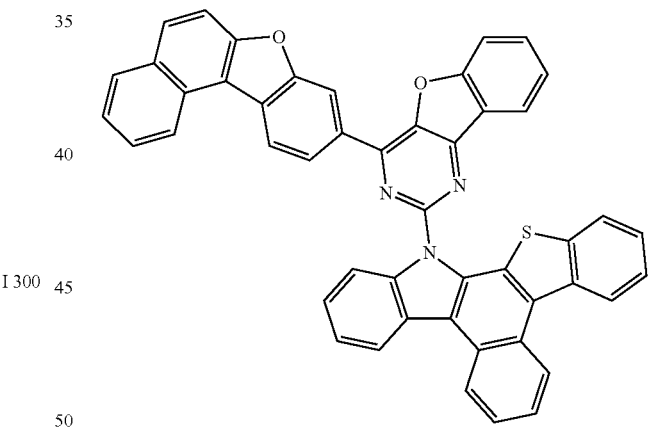
I 304
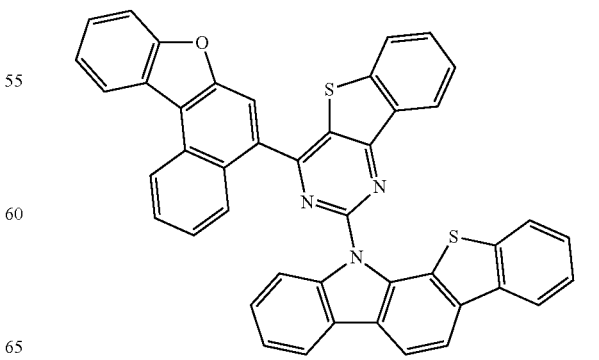

I 305
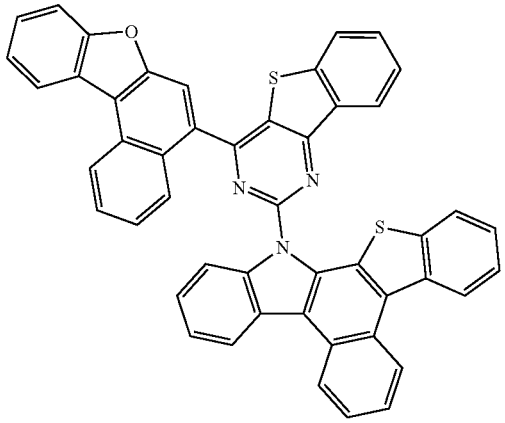
I 306
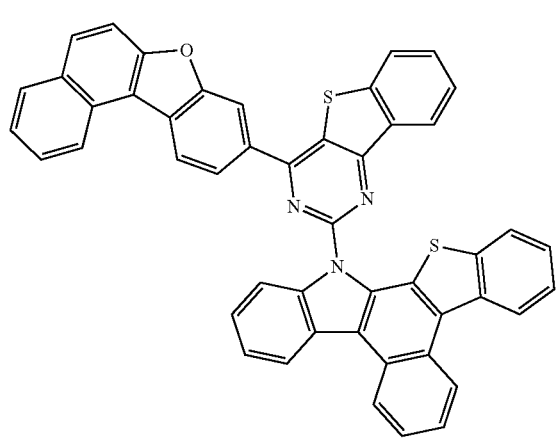
I 307
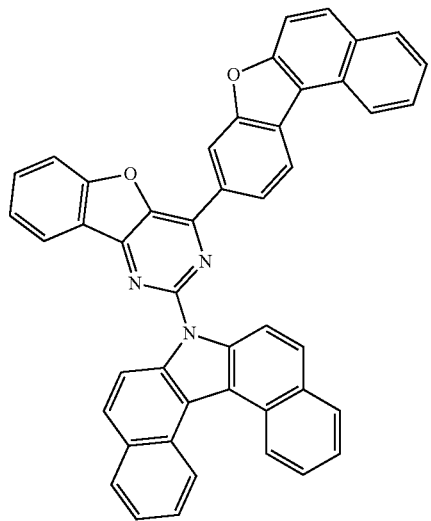
I 308
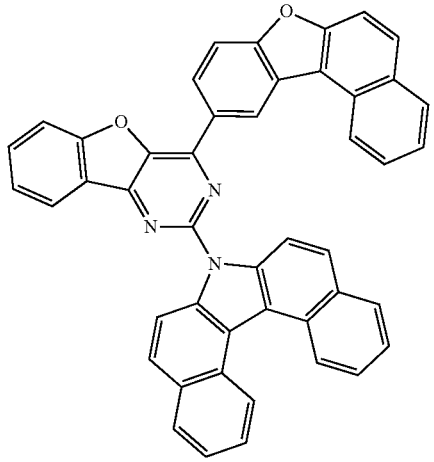
I 309
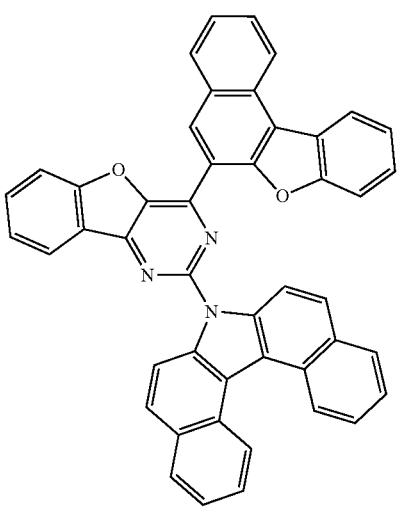
I 310
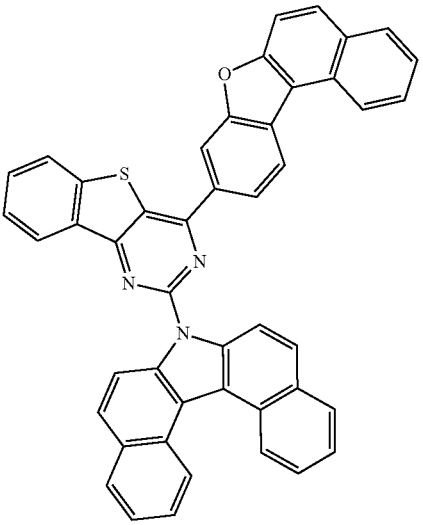

-continued
I311
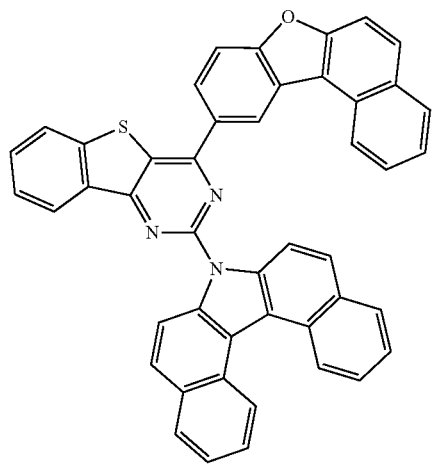
I312
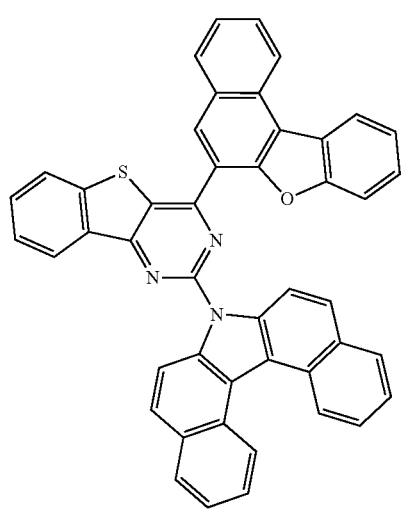
I313
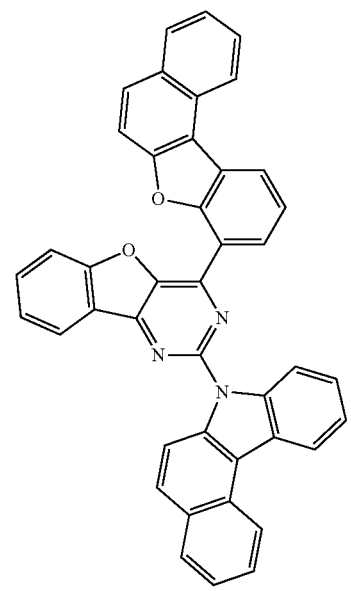
-continued
I314
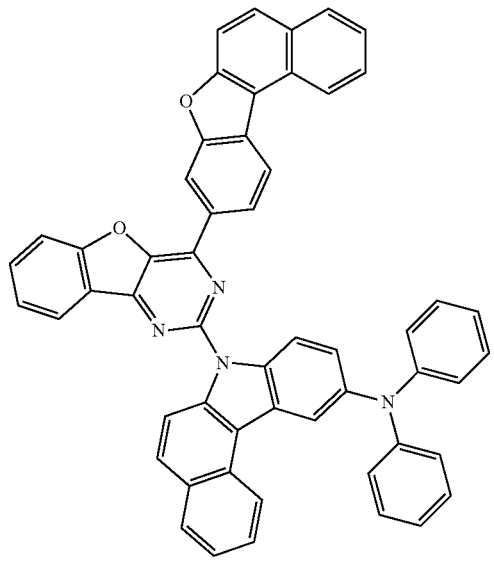
I315
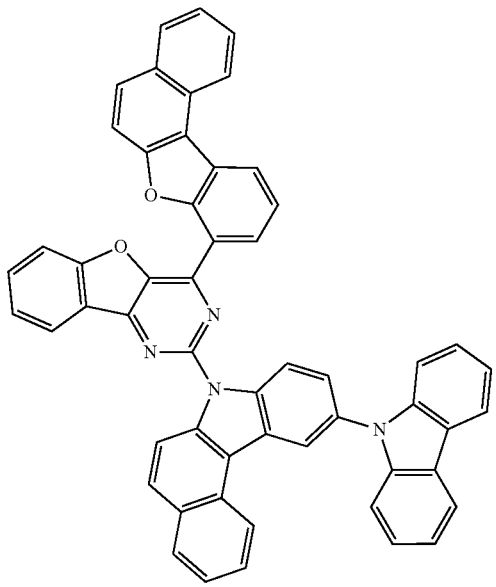

I 316
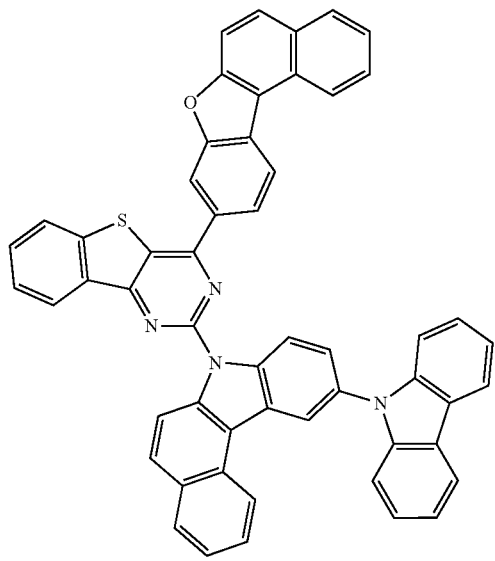
I 317
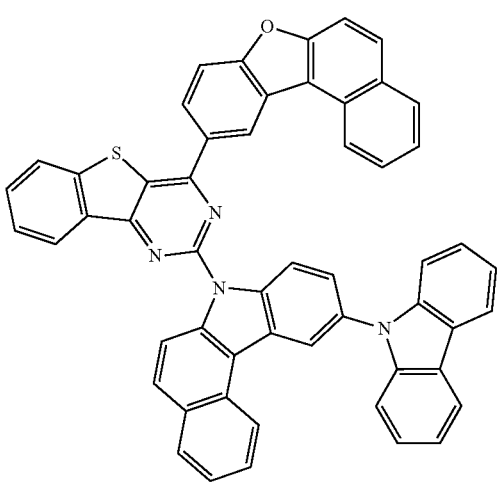
I 318
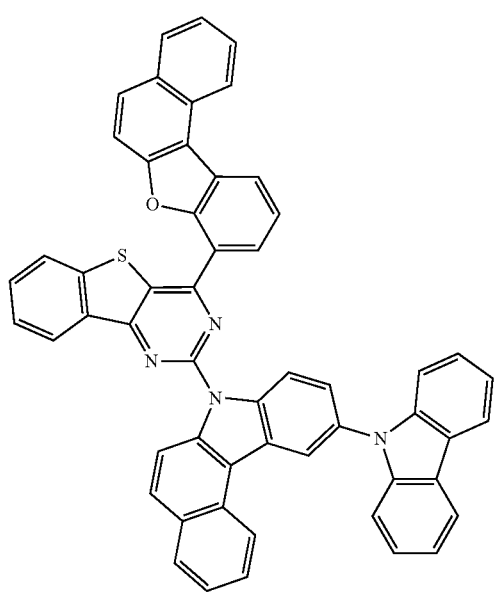
I 319
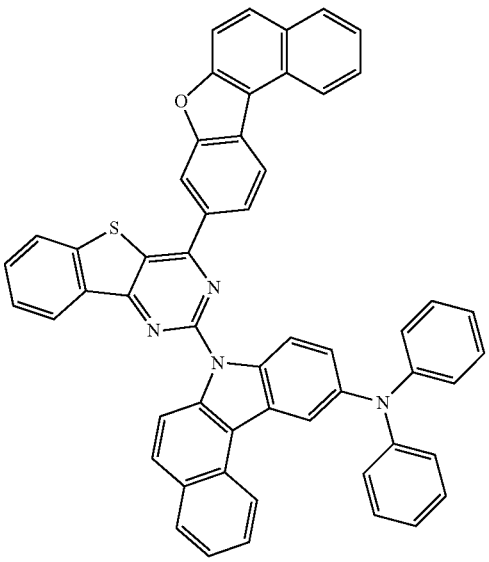
I 320
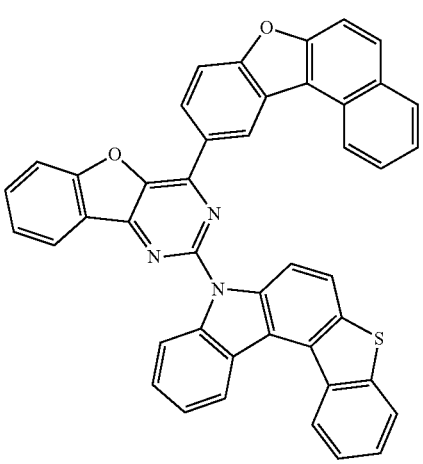
I 321
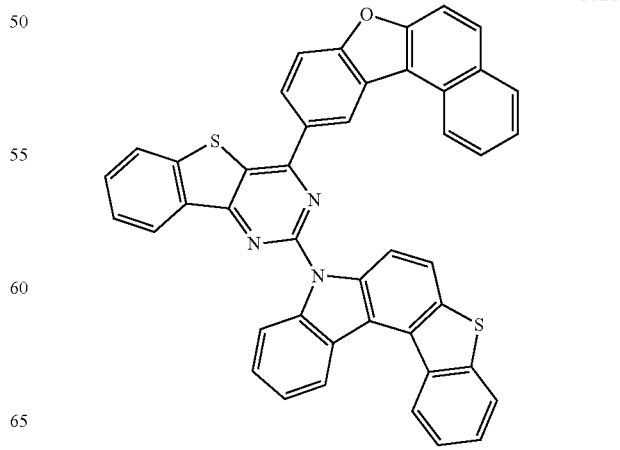

I322
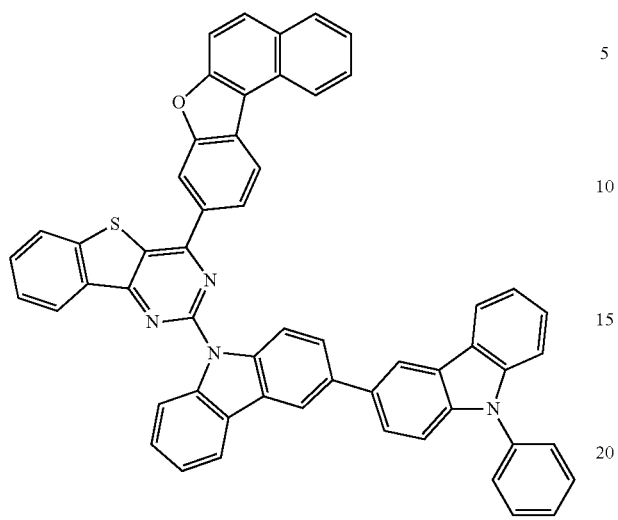
I323
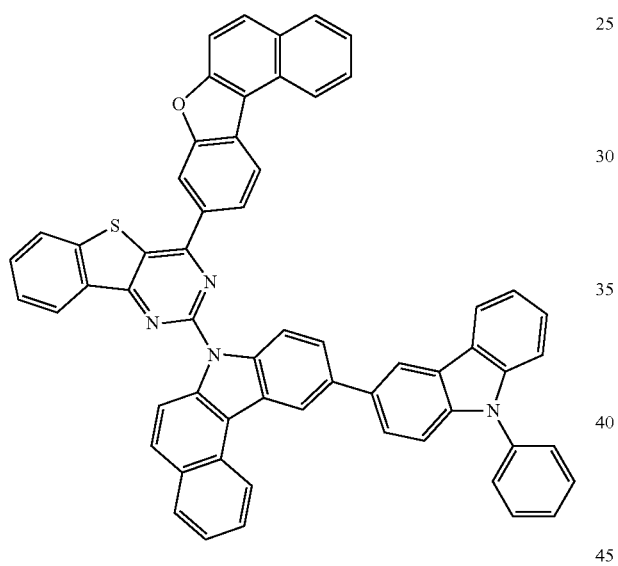
I324
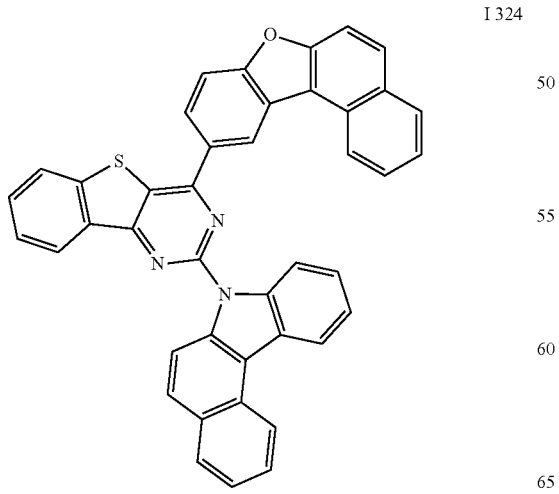
I325
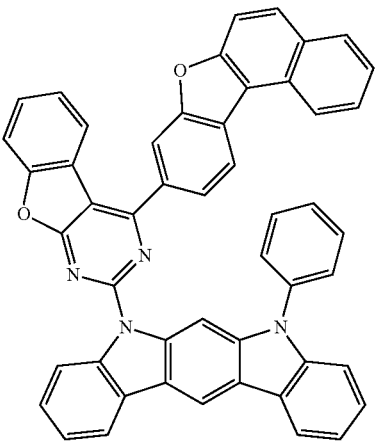
I326
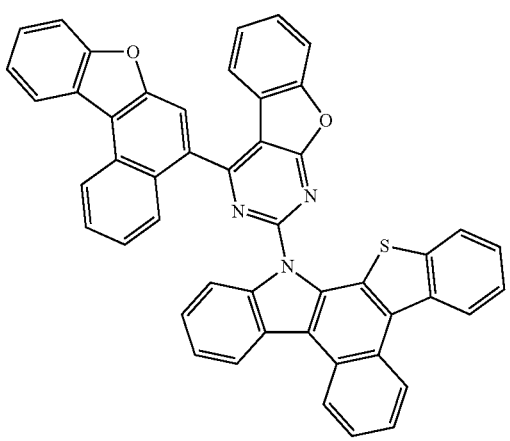
I327
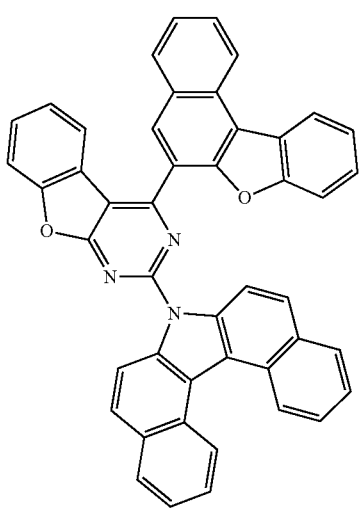

I 328
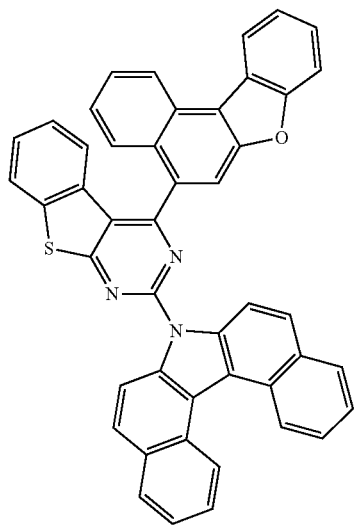
I 329
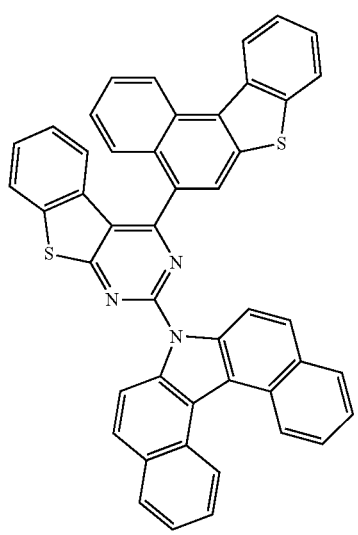
I 330
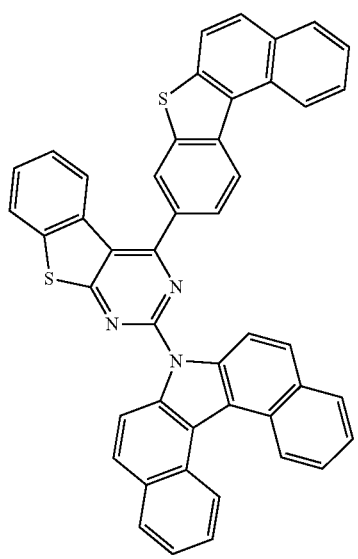
I 331
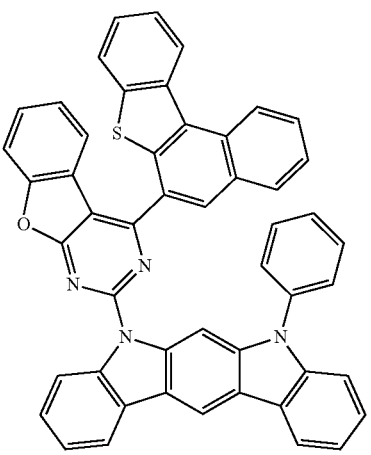
I 332
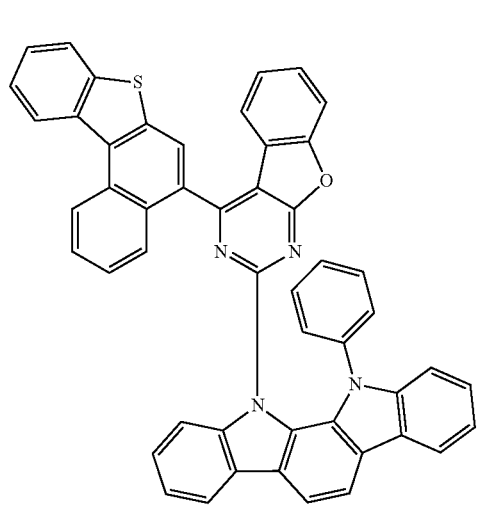
I 333
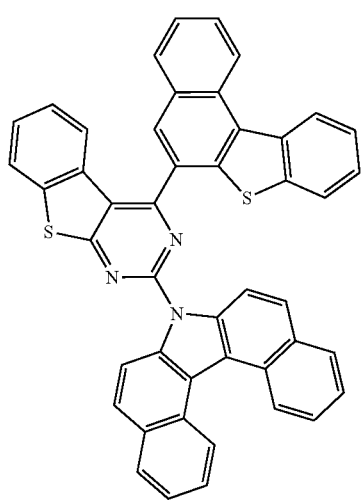

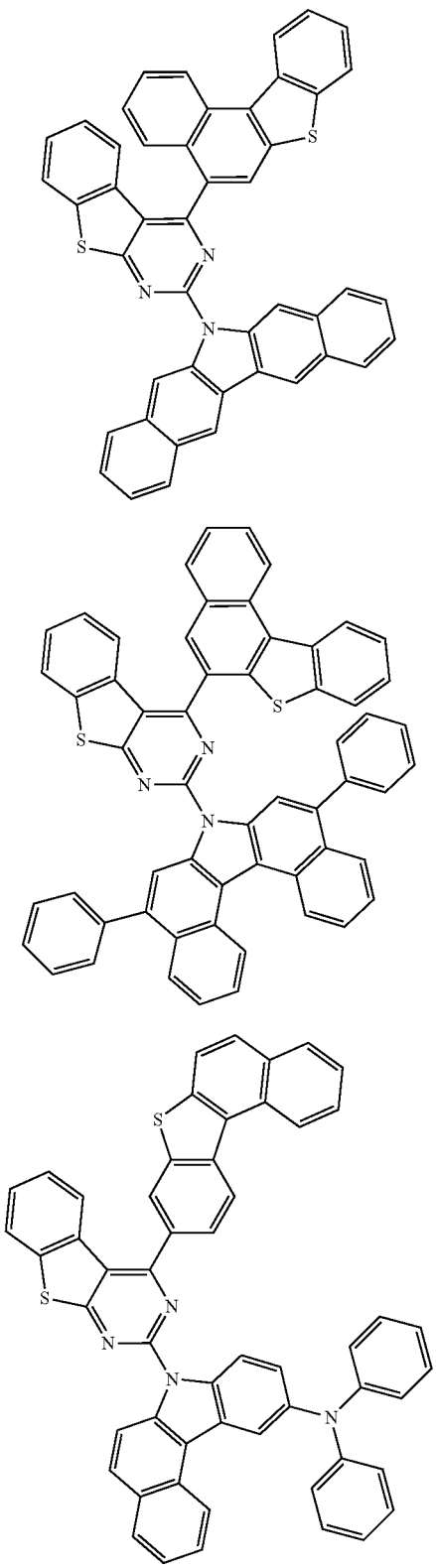

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

Specific details on the heterocyclic compound represented by Chemical Formula 1 are the same as the descriptions provided above.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in a host material of a blue light emitting layer of the blue organic light emitting device.

In one embodiment of the present application, the organic light emitting device may be a green organic light emitting device, and the heterocyclic compound according to Chemical Formula 1 may be used as a material of the green organic light emitting device. For example, the heterocyclic compound according to Chemical Formula 1 may be included in a host material of a green light emitting layer of the green organic light emitting device.

In one embodiment of the present application, the organic light emitting device may be a red organic light emitting device, and the heterocyclic compound according to Chemical Formula 1 may be used as a material of the red organic light emitting device. For example, the heterocyclic compound according to Chemical Formula 1 may be included in a host material of a red light emitting layer of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises a light emitting layer, and the light emitting layer may comprise the heterocyclic compound.

In another organic light emitting device, the organic material layer comprises a light emitting layer, the light emitting layer comprises a host material, and the host material may comprise the heterocyclic compound.

As another embodiment, the organic material layer comprising the heterocyclic compound comprises the heterocyclic compound represented by Chemical Formula 1 as a host, and an iridium-based dopant may be used therewith.

In the organic light emitting device of the present disclosure, the organic material layer comprises an electron injection layer or an electron transfer layer, and the electron transfer layer or the electron injection layer may comprise the heterocyclic compound.

In another organic light emitting device, the organic material layer comprises an electron blocking layer or a hole blocking layer, and the electron blocking layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound of Chemical Formula 1 may further comprise other materials as necessary.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrenesulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed.

For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

<Preparation Example 1>—Syntheses of Compounds E1 and E2

C. When the reaction was completed, the temperature was lowered to room temperature, water was introduced thereto, and the result was extracted with methylene chloride (MC). The organic layer was dried with $Mg_2SO_4$ and concentrated, and then purified using a silica-gel column to obtain Compound C1 (18 g, 75.5 mmol, 53%).

Synthesis of Compound D1

C1 (18 g, 75.5 mmol) was introduced to a 250 mL round bottom flask, dissolved in dimethylacetamide (DMA) (150 mL), and then $Cs_2CO_3$ (49 g, 151 mmol) was added thereto. The result was stirred at a reaction temperature of 140° C., and after the reaction was completed, the temperature was lowered to room temperature, and the result was filtered using paper to remove $Cs_2CO_3$. The filtered solids were washed with water and MeOH, and then dried to obtain Compound D1 (16 g, 73.3 mmol, 97%).

Synthesis of Compound E1

D1 (8 g, 36.6 mmol) was introduced to a 250 mL round bottom flask, and, after substituting the flask with the nitrogen atmosphere, was dissolved by introducing THF

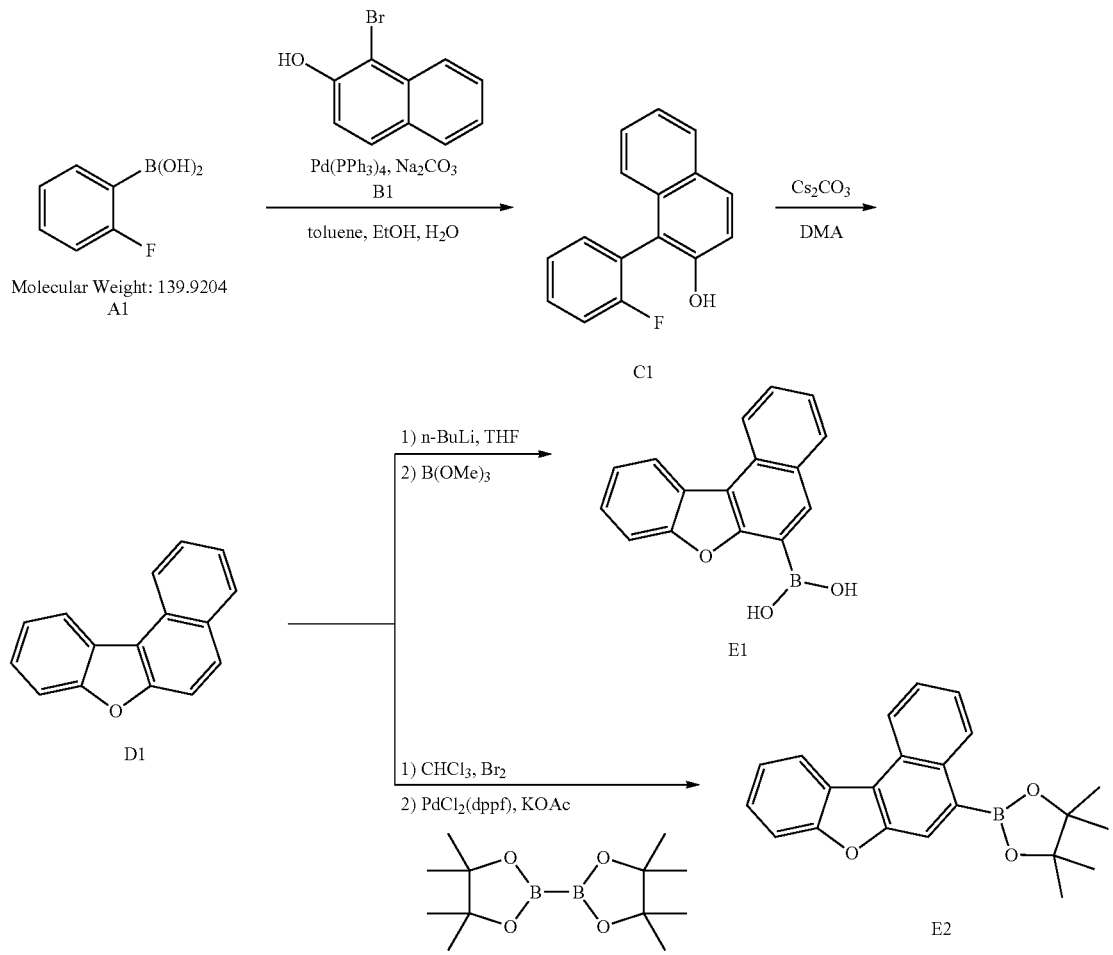

Synthesis of Compound C1

A1 (20 g, 142.9 mmol), B1 (31.9 g, 142.9 mmol), $Pd(PPh_3)_4$ (8.2 g, 7.15 mmol) and $Na_2CO_3$ (30.3 g, 285.8 mmol) were introduced to a 500 mL round bottom flask, and dissolved by introducing toluene (200 mL), EtOH (40 mL) and $H_2O$ (40 mL) thereto, and the result was refluxed at 120°

(150 mL) thereto. After lowering an external temperature of the reactor to −78° C., n-BuLi (2.5 M solution in Hx, 15 mL) was introduced thereto, and the result was stirred for 1 hour (external temperature: −30° C.). The external temperature was lowered again to −78° C., then $B(OMe)_3$ (54.9 mmol) was introduced thereto, and the result was stirred for 4 hours at room temperature. After the reaction was completed, cold water was introduced thereto, and the result was extracted with MC. The extracted organic layer was dried with $Mg_2SO_4$, and then concentrated. The result was silica-gel columned and recrystallized to obtain Compound E1 (25.6 mmol, 70%).

Synthesis of Compound E2

D1 (20 g, 85.35 mmol) was introduced to a 500 mL round bottom flask, and dissolved in $CHCl_3$ (250 mL). $Br_2$ (4.6 mL, 84.6 mmol) was slowly added dropwise to the reactor. After the reaction was completed, MeOH (150 mL) was introduced thereto, and solids were precipitated and then filtered using filter paper. The filtered solids were washed several times with MeOH (50 mL×3) and vacuum dried. The dried solids were introduced to a 500 mL round bottom flask, and dissolved in dioxane (300 mL), then $PdCl_2(dppf)$ (2.5 g, 3.46 mmol), 4,4,4',4', 5,5,5',5'-octamethyl-2,2'-bi(1,3,2-dioxaborolane) (21.1 g, 83.14 mmol) and KOAc (20 g, 207.6 mmol) were introduced thereto, and the result was stirred at 120° C. After the second reaction was completed, the reaction temperature was lowered to room temperature, water was introduced thereto, and the result was extracted with MC. The extracted organic solvent was dried with $Mg_2SO_4$, and then concentrated. The result was purified using a silica-gel column to obtain Compound E2 (21.5 g, 59.7 mmol).

<Preparation Example 2>—Syntheses of Compounds E3 and E4

Synthesis of Compound E3

Compound E3 was obtained in the same manner as in the method for synthesizing E1 of Preparation Example 1 except that, as the starting material, D2 was used instead of D1.

Synthesis of Compound E4

Compound E4 was obtained in the same manner as in the method for synthesizing E2 of Preparation Example 1 except that, as the starting material, D2 was used instead of D1.

<Preparation Example 3>—Synthesis of Compound E6

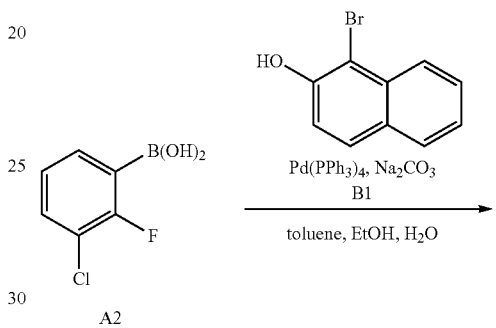

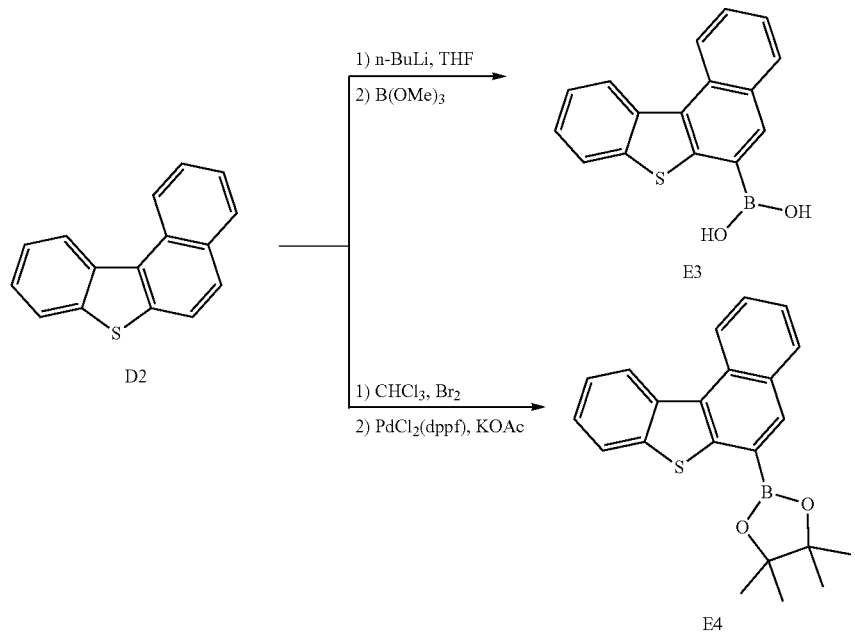

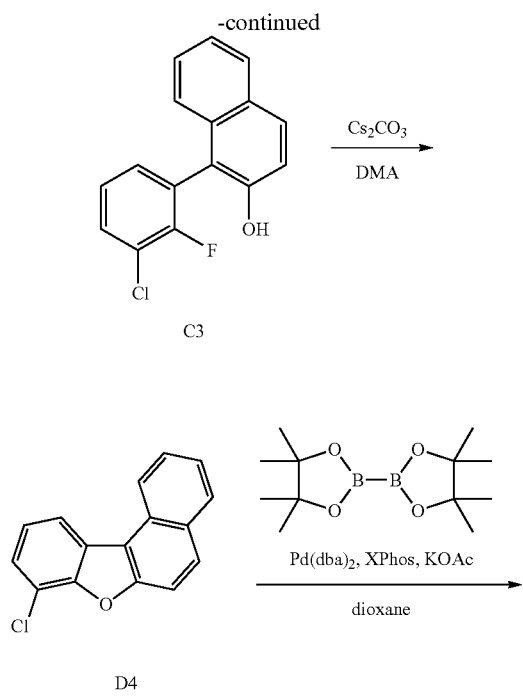

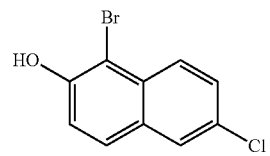
[Compound B2]

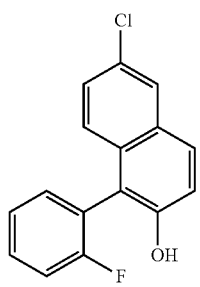
[Compound C2]

Synthesis of Compound C4

Compound C4 (64%) was obtained in the same manner as in the method for synthesizing C1 of Preparation Example 1 except that, as the starting material, A3 was used instead of A1.

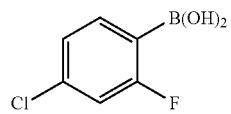
[Compound A3]

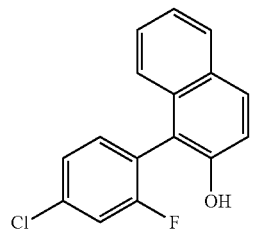
[Compound C4]

Synthesis of Compound C3

Compound C3 was obtained in the same manner as in the method for synthesizing C1 of Preparation Example 1 except that, as the starting material, A2 was used instead of A1.

Synthesis of Compound D4 Compound D4 was obtained in the same manner as in the method for synthesizing D1 of Preparation Example 1 except that, as the starting material, C3 was used instead of C1.

Synthesis of Compound E6 Compound E6 (64%) was obtained in the same manner as in the method for synthesizing E2 of Preparation Example 1 except that, as the starting material, D4 was used instead of D1, and $Pd(dba)_2$ and XPhos were used as a catalyst and a ligand, respectively.

Hereinafter, the following compounds were synthesized, and resulting Compounds E5, E7 and E8 were synthesized.

Synthesis of Compound C2

Compound C2 (50%) was obtained in the same manner as in the method for synthesizing C1 of Preparation Example 1 except that, as the starting material, B2 was used instead of B1.

Synthesis of Compound C5

Compound C5 was obtained in the same manner as in the method for synthesizing C1 of Preparation Example 1 except that, as the starting material, A4 was used instead of A1.

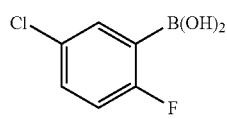
[Compound A4]

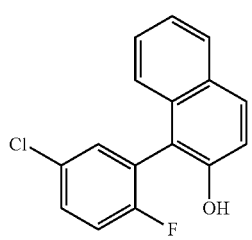
[Compound C5]

Synthesis of Compound E5

Compound E5 (60%) was obtained in the same manner as in the method for synthesizing E2 of Preparation Example 1 except that, as the starting material, D3 was used instead of D1, and Pd(dba)$_2$ and XPhos were used as a catalyst and a ligand, respectively.

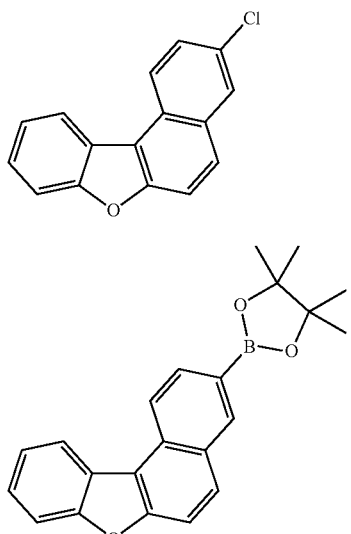

[Compound D3]

[Compound E5]

Synthesis of Compound E7

Compound E7 (74%) was obtained in the same manner as in the method for synthesizing E2 of Preparation Example 1 except that, as the starting material, D5 was used instead of D1, and Pd(dba)$_2$ and XPhos were used as a catalyst and a ligand, respectively.

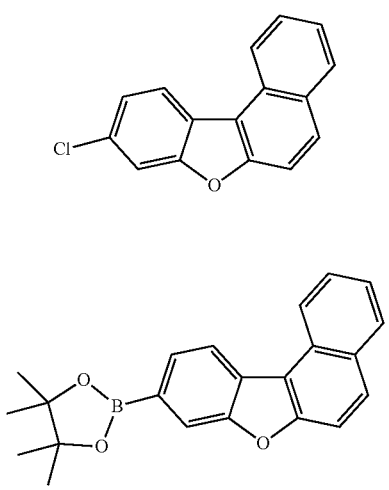

[Compound D5]

[Compound E7]

Synthesis of Compound E8

Compound E8 (80%) was obtained in the same manner as in the method for synthesizing E2 of Preparation Example 1 except that, as the starting material, D6 was used instead of D1, and Pd(dba)$_2$ and XPhos were used as a catalyst and a ligand, respectively.

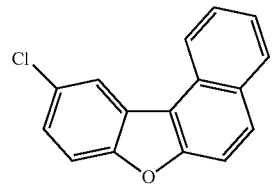

[Compound D6]

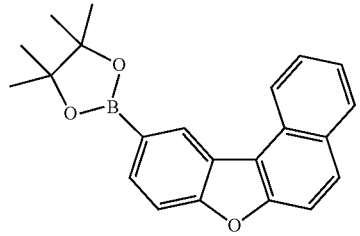

[Compound E8]

<Preparation Example 4>—Synthesis of Compound G1

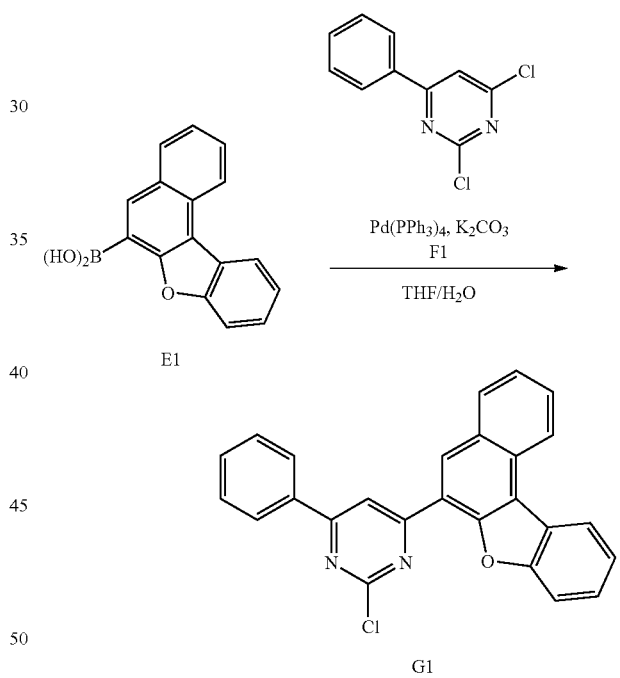

Synthesis of Compound G1

E1 (10 g, 38.1 mmol), F1 (8.6 g, 38.1 mmol), Pd(PPh$_3$)$_4$ (2.2 g, 1.90 mmol) and K$_2$CO$_3$ (10.5 g, 76.2 mmol) were introduced to a 100 mL round bottom flask, and after introducing THF (120 mL) and water (30 mL) thereto, the result was stirred at 80° C. After the reaction was completed, the temperature was lowered to room temperature, water was introduced thereto, and the result was extracted with MC. The extracted organic solvent was dried with Mg$_2$SO$_4$, and then concentrated. The result was silica-gel columned and recrystallized to obtain Compound G1 (8 g, 19.8 mmol, 52%).

Target compounds were obtained in the same manner as in the method for synthesizing Compound G1 of Preparation Example 4 except that any one of E1 to E8 of the following Table 1 was used instead of E1, and any one of F1 to F7 of the following Table 1 was used instead of F1.
TABLE 1
| E | F | G | G Yield |
|---|---|---|---------|
| E1 | F1 | G1 | 52% |
| E1 | F2 | G2 | 59% |
| E1 | F3 | G3 | 88% |
| E2 | F2 | G4 | 71% |
| E2 | F3 | G5 | 93% |
| E3 | F1 | G6 | 66% |
| E3 | F2 | G7 | 64% |
| E3 | F3 | G8 | 97% |
| E4 | F2 | G9 | 67% |
| E4 | F3 | G10 | 94% |
| E5 | F1 | G11 | 47% |
| E5 | F2 | G12 | 48% |
| E5 | F3 | G13 | 90% |
| E6 | F1 | G14 | 60% |
| E6 | F2 | G15 | 66% |
| E6 | F3 | G16 | 94% |
| E7 | F2 | G17 | 66% |
| E7 | F3 | G18 | 92% |
| E8 | F2 | G19 | 70% |
| E8 | F3 | G20 | 94% |
| E7 | F4 | G21 | 72% |
| E7 | F5 | G22 | 80% |
| E8 | F4 | G23 | 79% |
| E4 | F5 | G24 | 81% |
| E8 | F5 | G25 | 76% |
| E2 | F5 | G26 | 88% |
| E8 | F6 | G27 | 65% |
| E4 | F7 | G28 | 80% |
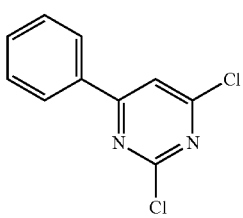
F1
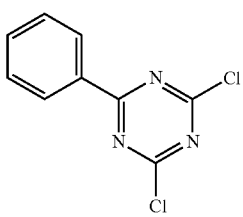
F2
F3
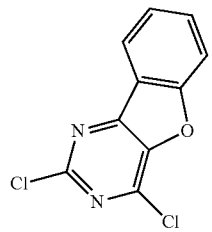
F4
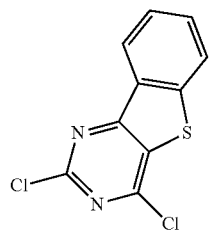
F5
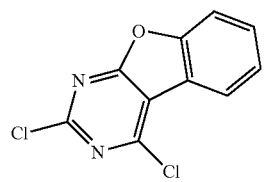
F6
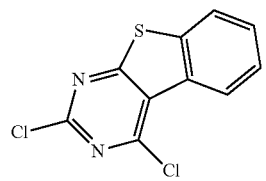
F7
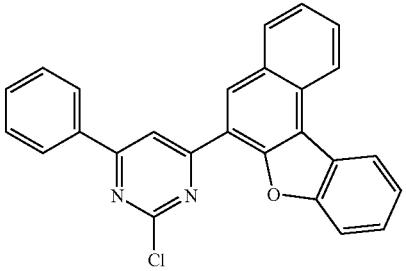
G1
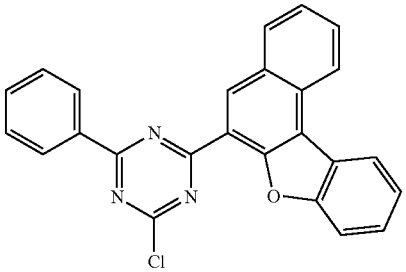
G2

G3
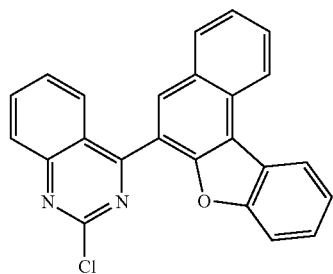
G4
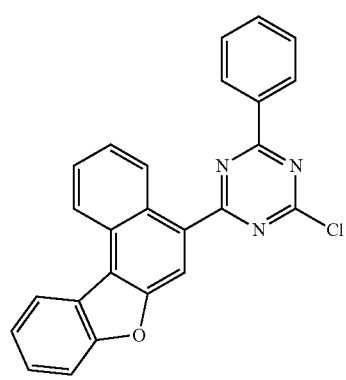
G5
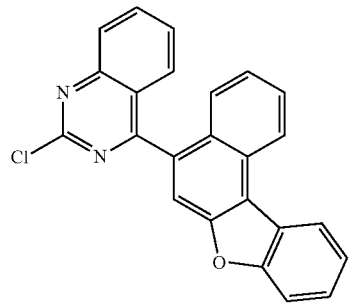
G6
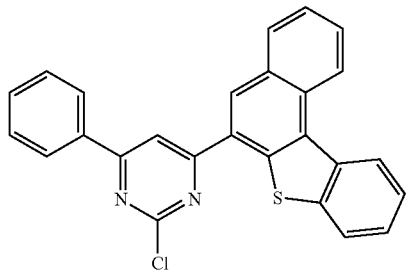
G7
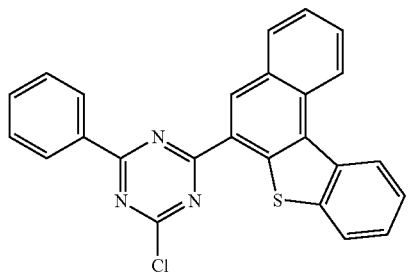
G8
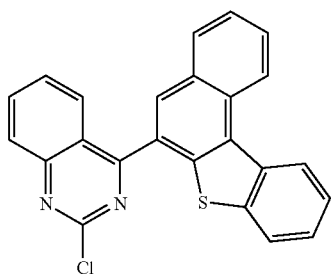
G9
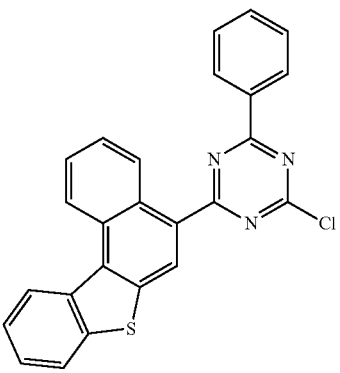
G10
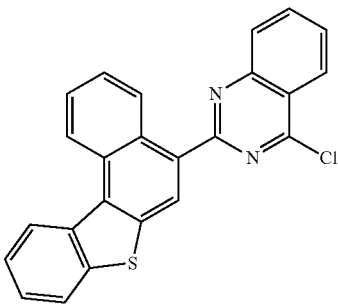
G11
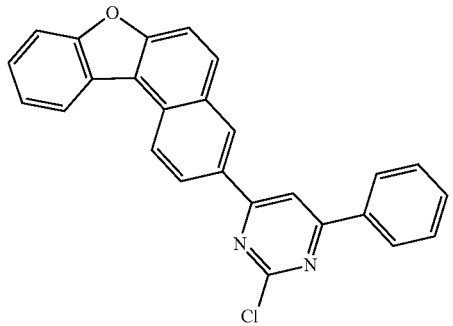
G12
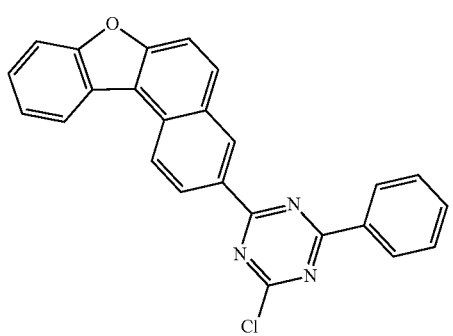

-continued
G13
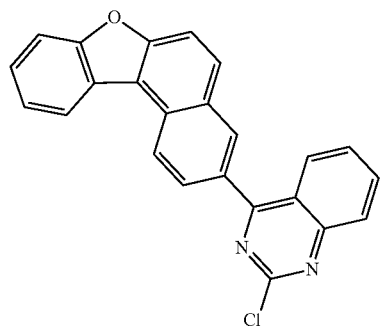
G14
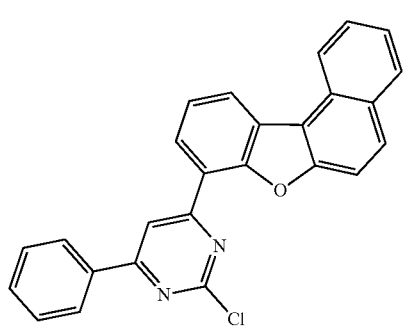
G15
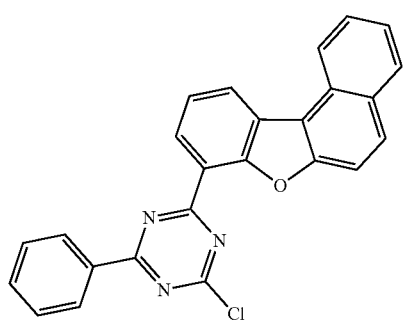
G16
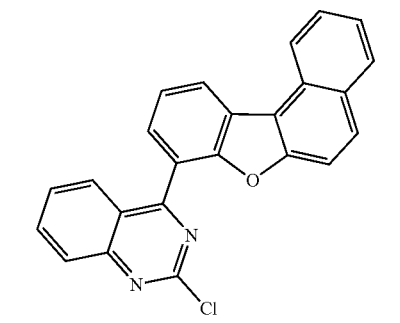
G17
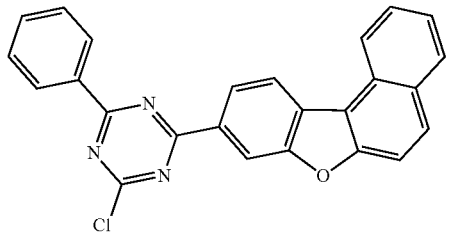
-continued
G18
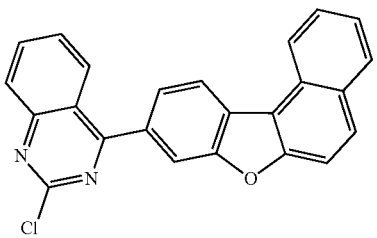
G19
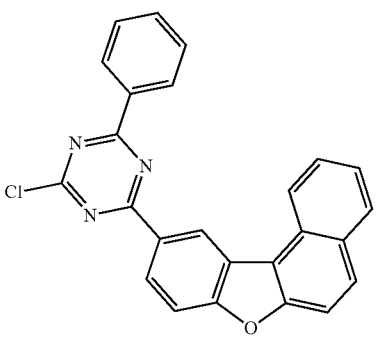
G20
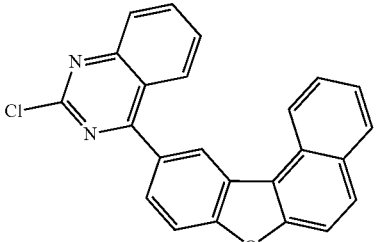
G21
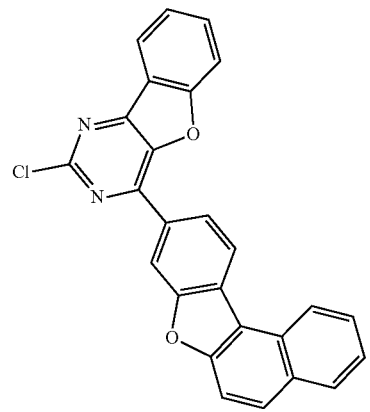

G22
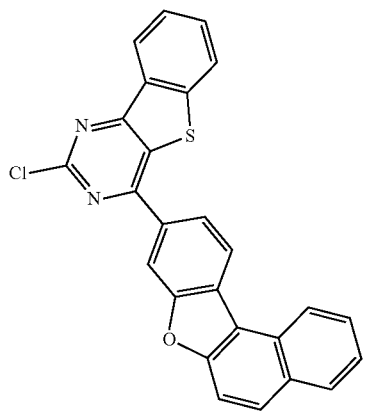
G23
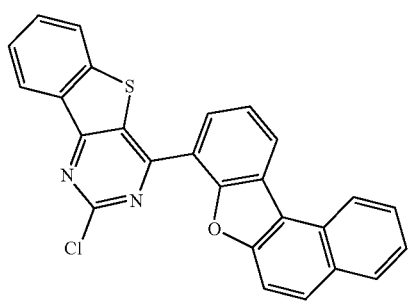
G24
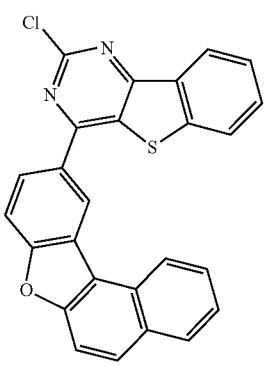
G25
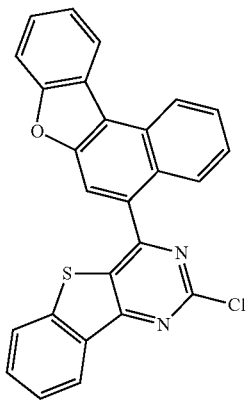
G26
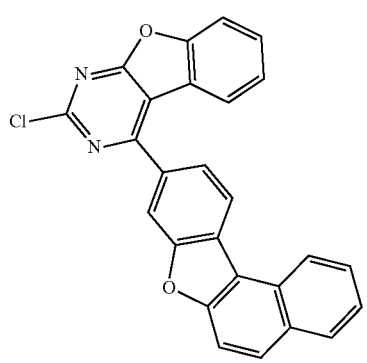
G27
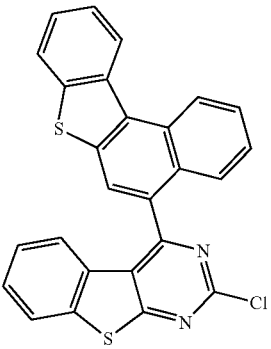
G28
<Preparation Example 5>—Synthesis of Compound I1
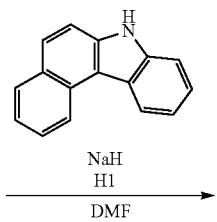

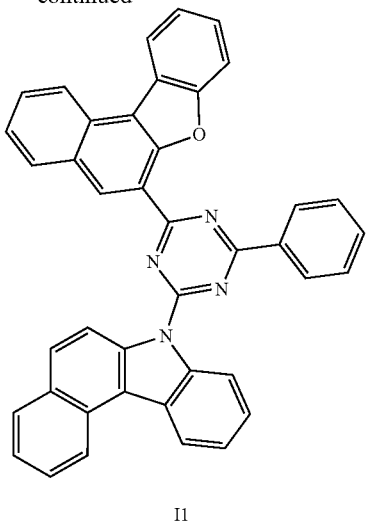

I1

Synthesis of Compound I1

G1 (5 g, 12.3 mmol) and H1 (2.66 g, 12.3 mmol) were introduced to a 100 mL round bottom flask, and dissolved in DMF (60 mL). To this mixture, NaH 60% in mineral oil (1.2 g, 18.45 mmol) was added portion wise, and then the result was stirred at 50° C. After the reaction was completed, produced solids were filtered using filter paper, washed with water and MeOH (40 mL), and then vacuum dried. The dried solids were recrystallized with toluene to obtain Compound I1 (7.0 g, 11.9 mmol, 97%).

Target compounds were obtained in the same manner as in the method for synthesizing Compound I1 of Preparation Example 5 except that any one of G1 to G28 of the following Table 2 was used instead of G1, and any one of the following H1 to H46 was used instead of H1.

TABLE 2

| Entry | G | H | I | I Yield |
|---|---|---|---|---|
| 1 | G1 | H1 | I1 | 97% |
| 2 | G1 | H2 | I2 | 96% |
| 3 | G1 | H4 | I4 | 80% |
| 4 | G1 | H5 | I5 | 84% |
| 5 | G1 | H11 | I6 | 88% |
| 6 | G2 | H4 | I10 | 86% |
| 7 | G2 | H5 | I11 | 86% |
| 8 | G2 | H11 | I12 | 90% |
| 9 | G2 | H27 | I17 | 76% |
| 10 | G2 | H22 | I18 | 69% |
| 11 | G2 | H24 | I19 | 74% |
| 12 | G6 | H5 | I27 | 94% |
| 13 | G6 | H7 | I28 | 88% |
| 14 | G7 | H7 | I29 | 90% |
| 15 | G7 | H12 | I31 | 68% |
| 16 | G7 | H25 | I32 | 59% |
| 17 | G7 | H14 | I33 | 69% |
| 18 | G7 | H26 | I34 | 69% |
| 19 | G7 | H27 | I35 | 59% |
| 20 | G7 | H30 | I37 | 88% |
| 21 | G7 | H33 | I38 | 88% |
| 22 | G7 | H35 | I39 | 94% |
| 23 | G7 | H37 | I40 | 89% |
| 24 | G7 | H38 | I41 | 80% |
| 25 | G7 | H39 | I42 | 93% |
| 26 | G4 | H3 | I43 | 88% |
| 27 | G4 | H5 | I45 | 92% |
| 28 | G4 | H6 | I46 | 77% |
| 29 | G4 | H7 | I47 | 78% |
| 30 | G4 | H11 | I48 | 88% |
| 31 | G4 | H28 | I54 | 86% |
| 32 | G4 | H31 | I55 | 73% |
| 33 | G4 | H33 | I56 | 96% |
| 34 | G4 | H35 | I57 | 94% |
| 35 | G9 | H10 | I61 | 49% |
| 36 | G9 | H9 | I62 | 89% |
| 37 | G9 | H8 | I63 | 60% |
| 38 | G9 | H4 | I64 | 71% |
| 39 | G9 | H5 | I65 | 88% |
| 40 | G9 | H12 | I67 | 90% |
| 41 | G9 | H25 | I68 | 66% |
| 42 | G9 | H40 | I76 | 59% |
| 43 | G9 | H45 | I77 | 84% |
| 44 | G12 | H9 | I79 | 88% |
| 45 | G12 | H8 | I80 | 76% |
| 46 | G12 | H10 | I81 | 60% |
| 47 | G11 | H5 | I82 | 94% |
| 48 | G12 | H5 | I83 | 90% |
| 49 | G12 | H13 | I85 | 92% |
| 50 | G12 | H16 | I86 | 75% |
| 51 | G12 | H14 | I87 | 77% |
| 52 | G12 | H19 | I88 | 89% |
| 53 | G12 | H24 | I89 | 94% |
| 54 | G12 | H25 | I90 | 96% |
| 55 | G12 | H26 | I91 | 70% |
| 56 | G12 | H27 | I92 | 89% |
| 57 | G12 | H28 | I93 | 94% |
| 58 | G12 | H29 | I94 | 79% |
| 59 | G12 | H33 | I95 | 90% |
| 60 | G12 | H35 | I96 | 93% |
| 61 | G14 | H3 | I101 | 88% |
| 62 | G14 | H7 | I102 | 90% |
| 63 | G15 | H7 | I107 | 89% |
| 64 | G16 | H35 | I117 | 94% |
| 65 | G16 | H41 | I118 | 88% |
| 66 | G16 | H38 | I119 | 89% |
| 67 | G16 | H39 | I120 | 89% |
| 68 | G17 | H12 | I127 | 89% |
| 69 | G17 | H25 | I128 | 90% |
| 70 | G17 | H26 | I130 | 68% |
| 71 | G17 | H24 | I132 | 92% |
| 72 | G19 | H9 | I142 | 70% |
| 73 | G19 | H5 | I143 | 95% |
| 74 | G19 | H11 | I144 | 93% |
| 75 | G19 | H12 | I145 | 88% |
| 76 | G12 | H32 | I152 | 77% |
| 77 | G3 | H9 | I158 | 74% |
| 78 | G3 | H5 | I160 | 92% |
| 79 | G3 | H11 | I162 | 88% |
| 80 | G3 | H12 | I163 | 90% |
| 81 | G3 | H25 | I164 | 69% |
| 82 | G3 | H35 | I171 | 78% |
| 83 | G3 | H43 | I172 | 82% |
| 84 | G3 | H38 | I173 | 89% |
| 85 | G3 | H44 | I174 | 88% |
| 86 | G8 | H15 | I179 | 60% |
| 87 | G8 | H17 | I180 | 90% |
| 88 | G8 | H33 | I186 | 88% |
| 89 | G8 | H42 | I189 | 77% |
| 90 | G8 | H32 | I191 | 69% |
| 91 | G8 | H44 | I192 | 81% |
| 92 | G5 | H5 | I195 | 91% |
| 93 | G5 | H7 | I196 | 96% |
| 94 | G5 | H12 | I198 | 90% |
| 95 | G5 | H23 | I199 | 76% |
| 96 | G5 | H14 | I200 | 90% |
| 97 | G5 | H22 | I204 | 79% |
| 98 | G5 | H34 | I206 | 80% |
| 99 | G10 | H5 | I214 | 88% |
| 100 | G10 | H18 | I218 | 79% |
| 101 | G10 | H24 | I222 | 77% |
| 102 | G13 | H5 | I229 | 80% |
| 103 | G13 | H25 | I230 | 72% |
| 104 | G13 | H18 | I232 | 77% |
| 105 | G13 | H21 | I233 | 68% |
| 106 | G13 | H12 | I235 | 86% |
| 107 | G16 | H5 | I244 | 90% |
| 108 | G16 | H7 | I245 | 88% |

TABLE 2-continued
| Entry | G | H | I | I Yield |
|---|---|---|---|---|
| 109 | G16 | H11 | I246 | 95% |
| 110 | G16 | H12 | I247 | 90% |
| 111 | G16 | H25 | I248 | 88% |
| 112 | G16 | H16 | I249 | 72% |
| 113 | G16 | H26 | I250 | 69% |
| 114 | G16 | H22 | I252 | 79% |
| 115 | G16 | H39 | I258 | 64% |
| 116 | G18 | H11 | I261 | 78% |
| 117 | G18 | H24 | I262 | 88% |
| 118 | G18 | H25 | I263 | 85% |
| 119 | G18 | H32 | I266 | 77% |
| 120 | G20 | H4 | I267 | 78% |
| 121 | G20 | H5 | I268 | 70% |
| 122 | G20 | H26 | I274 | 89% |
| 123 | G20 | H20 | I275 | 74% |
| 124 | G20 | H23 | I276 | 90% |
| 125 | G20 | H33 | I278 | 70% |
| 126 | G20 | H35 | I279 | 88% |
| 127 | G20 | H36 | I281 | 57% |
| 128 | G20 | H44 | I282 | 79% |
| 129 | G16 | H46 | I283 | 77% |
| 130 | G18 | H46 | I285 | 82% |
| 131 | G18 | H45 | I286 | 83% |
| 132 | G3 | H46 | I290 | 90% |
| 133 | G8 | H46 | I293 | 88% |
| 134 | G8 | H45 | I294 | 79% |
| 135 | G21 | H33 | I295 | 90% |
| 136 | G21 | H34 | I296 | 87% |
| 137 | G21 | H35 | I297 | 84% |
| 138 | G22 | H33 | I298 | 86% |
| 139 | G22 | H34 | I299 | 94% |
| 140 | G22 | H35 | I300 | 90% |
| 141 | G26 | H43 | I304 | 87% |
| 142 | G26 | H44 | I305 | 84% |
| 143 | G22 | H44 | I306 | 89% |
| 144 | G23 | H5 | I308 | 93% |
| 145 | G22 | H26 | I316 | 90% |
| 146 | G25 | H26 | I317 | 87% |
| 147 | G25 | H36 | I321 | 82% |
| 148 | G22 | H12 | I322 | 92% |
| 149 | G27 | H33 | I325 | 88% |
| 150 | G28 | H4 | I334 | 86% |
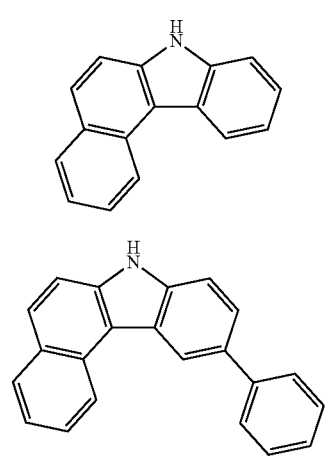
H1
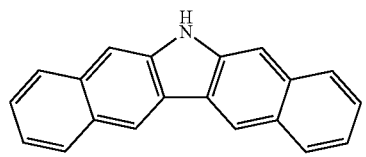
H2
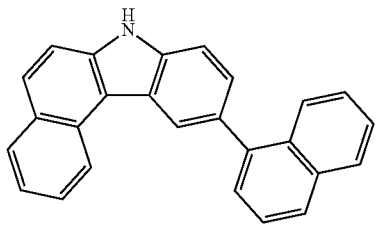
H3
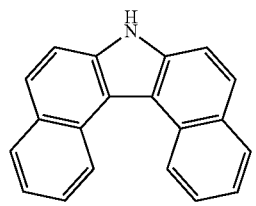
H4
H5
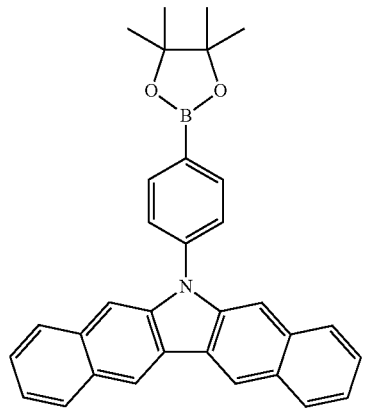
H6
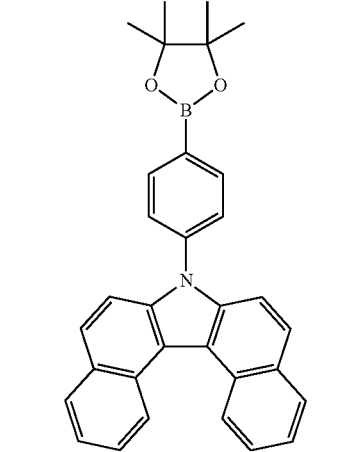
H7

H8 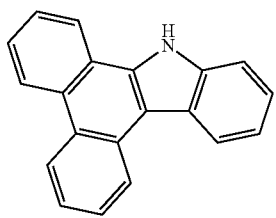
H9 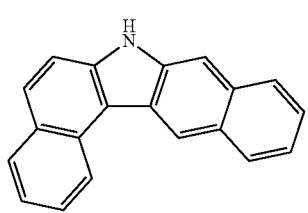
H10 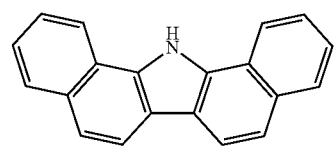
H11 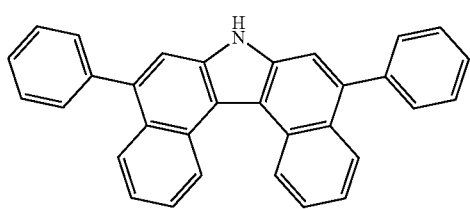
H12 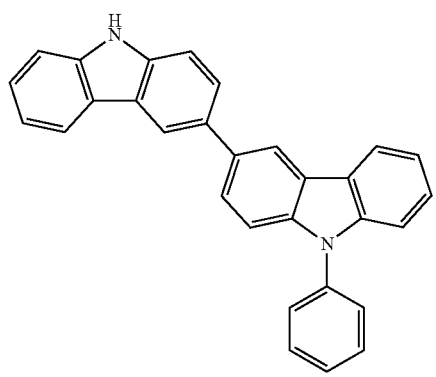
H13 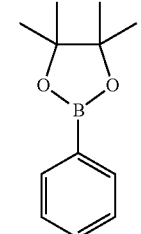
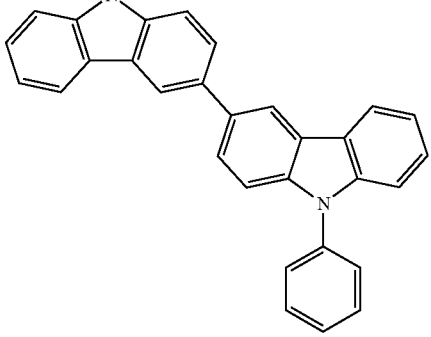
H14 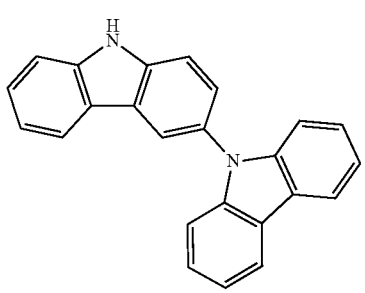
H15 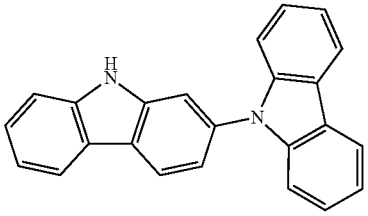
H16 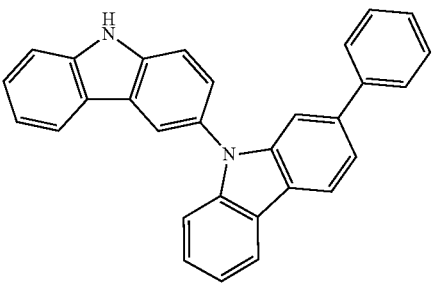

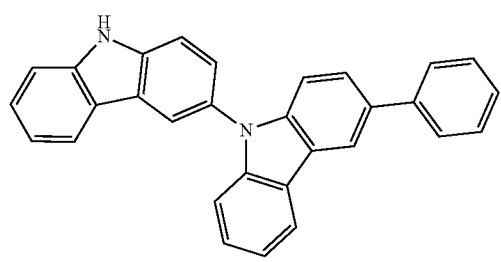
H17
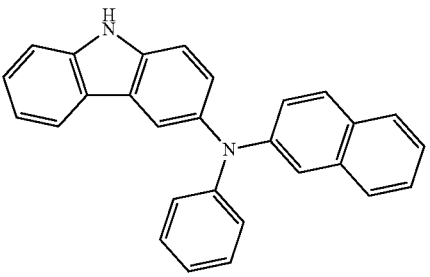
H22
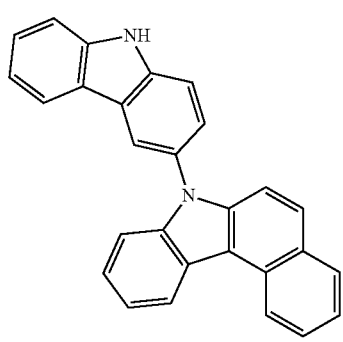
H18
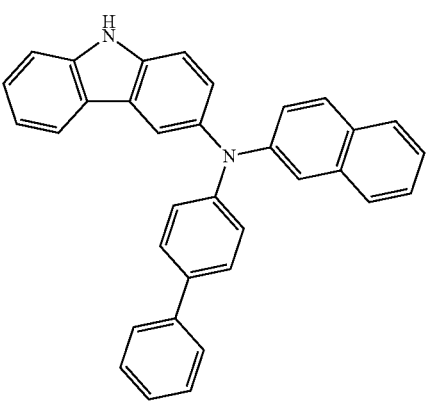
H23
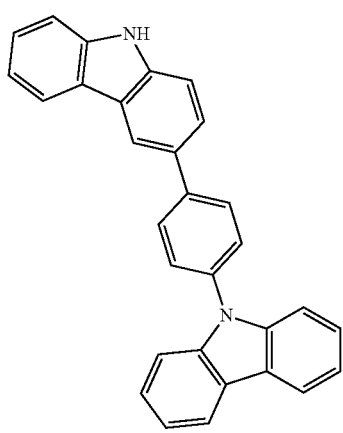
H19
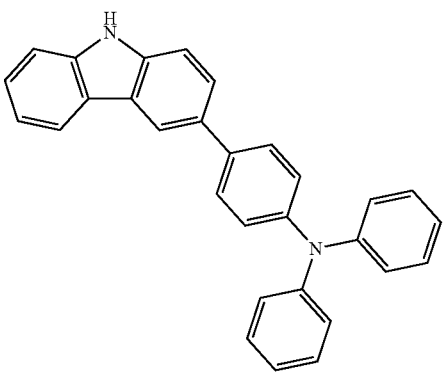
H24
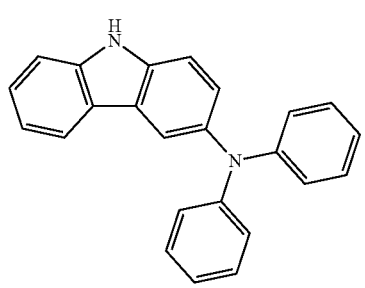
H20
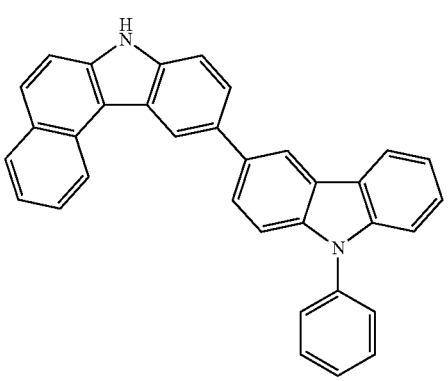
H25
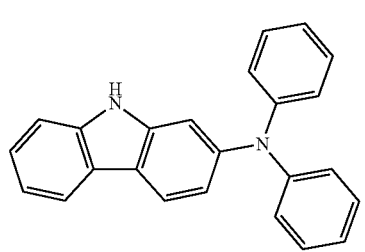
H21

H26
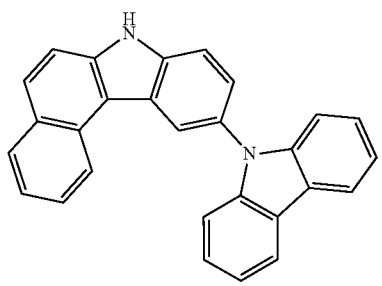
H27
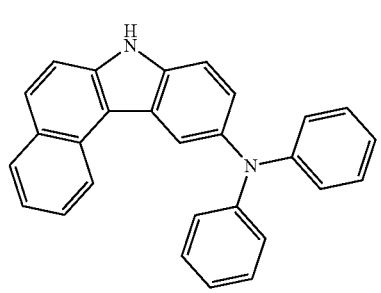
H28
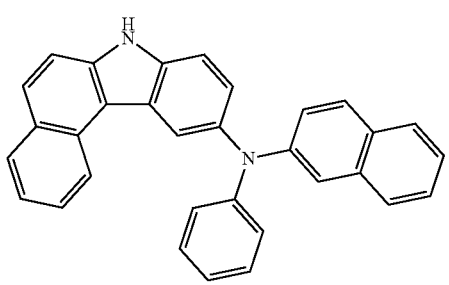
H29
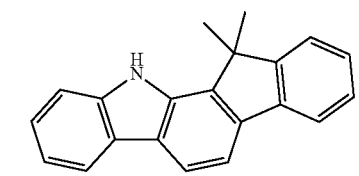
H30
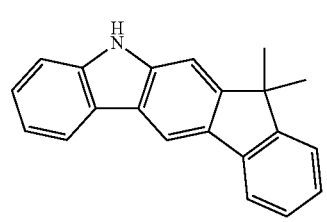
H31
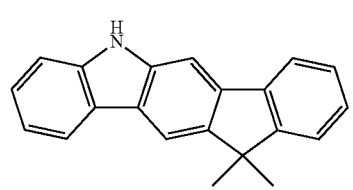
H32
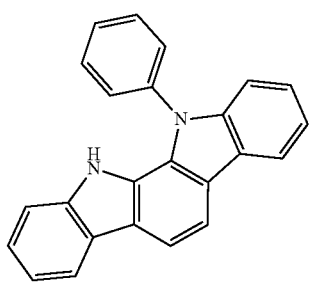
H33
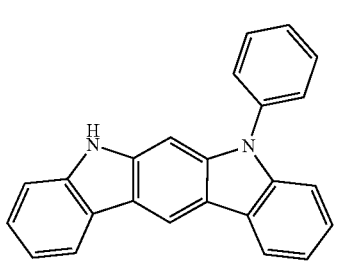
H34
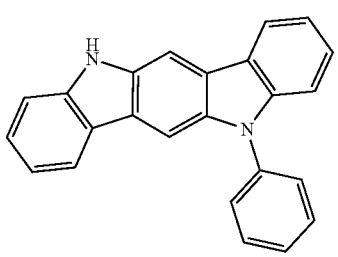
H35
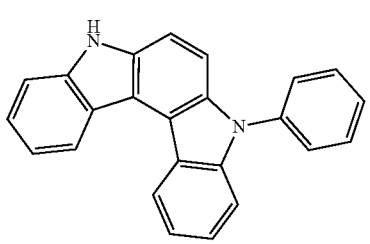
H36
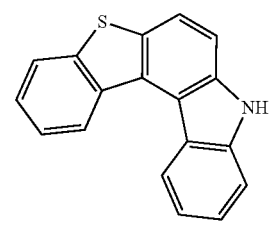
H37
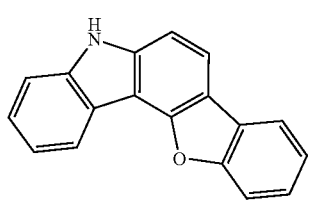

-continued

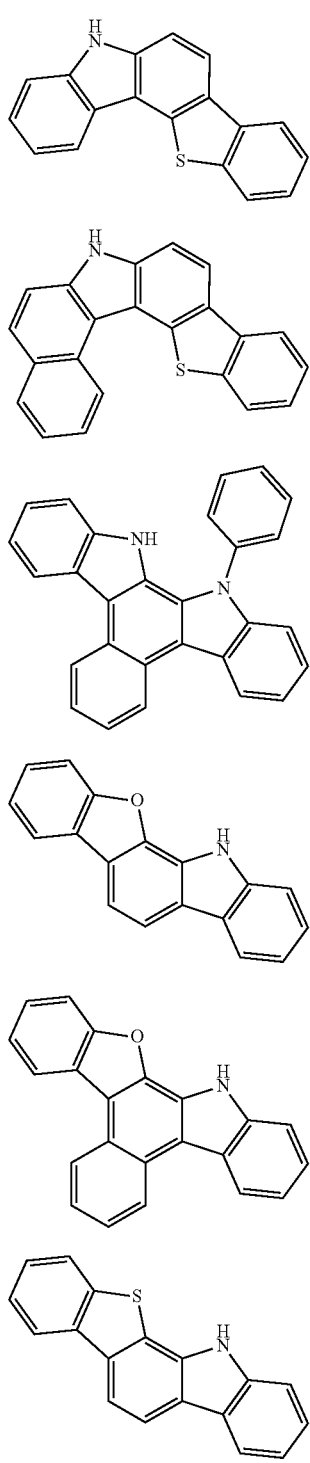

Compounds I1 to I336 other than the compounds described in the preparation examples were also prepared in the same manner as in the methods described in the preparation examples provided above.

Synthesis identification data for the compounds prepared above are as described in the following [Table 3] and [Table 4].

TABLE 3

| Compound | FD-Mass | Compound | FD-Mass |
| --- | --- | --- | --- |
| 1 | m/z = 587.6820 (C42H25N3O, 587.1998) | 2 | m/z = 663.7800 (C48H29N3O, 663.2311) |
| 3 | m/z = 713.8400 (C52H31N3O, 713.2467) | 4 | m/z = 637.7420 (C46H27N3O, 637.2154) |
| 5 | m/z = 637.7420 (C46H27N3O, 637.2154) | 6 | m/z = 789.9380 (C58H35N3O, 789.2780) |
| 7 | m/z = 588.6780 (C41H24N4O, 588.1950) | 3 | m/z = 664.7680 (C47H28N4O, 664.2263) |
| 9 | m/z = 714.8280 (C51H30N4O, 714.2420) | 10 | m/z = 638.7300 (C45H26N4O, 638.2107) |
| 11 | m/z = 638.7300 (C45H26N4O, 638.2107) | 12 | m/z = 790.9260 (C57H34N4O, 790.2733) |

TABLE 3-continued

| Compound | FD-Mass | Compound | FD-Mass |
|---|---|---|---|
| 13 | m/z = 779.9030 (C55H33N5O, 779.2685) | 14 | m/z = 829.9630 (C59H35N5O, 829.2842) |
| 15 | m/z = 703.8050 (C49H29N5O, 703.2372) | 16 | m/z = 753.8650 (C53H31N5O, 753.2529) |
| 17 | m/z = 755.8810 (C53H33N5O, 755.2685) | 18 | m/z = 805.9410 (C57H35N5O, 805.2842) |
| 19 | m/z = 781.9190 (C55H35N5O, 781.2841) | 20 | m/z = 703.8050 (C49H29N5O, 703.2372) |
| 21 | m/z = 703.8050 (C49H29N5O, 703.2372) | 22 | m/z = 628.6910 (C43H24N4O2, 628.1899) |
| 23 | m/z = 644.7520 (C43H24N4OS, 644.1671) | 24 | m/z = 694.8120 (C47H26N4OS, 694.1827) |
| 25 | m/z = 680.8290 (C47H28N4S, 680.2035) | 26 | m/z = 730.8890 (C51H1N4S, 730.2191) |
| 27 | m/z = 653.8030 (C46H27N3S, 653.1926) | 28 | m/z = 729.9010 (C52H31N3S, 729.2239) |
| 29 | m/z = 730.8890 (C51H31N4S, 730.2191) | 30 | m/z = 806.9870 C57H34N4S, 806.2904) |
| 31 | m/z = 795.9460 (C55H33N5S, 795.2457) | 32 | m/z = 846.0240 (C59H35N5S, 845.2613) |
| 33 | m/z = 719.8660 (C49H29N5S, 719.2144) | 34 | m/z = 769.9260 (C53H31N5S, 769.2300) |
| 35 | m/z = 771.9420 (C53H33N5S, 771.2457) | 36 | m/z = 822.0020 (C57H35N5S, 821.2613) |
| 37 | m/z = 670.8340 (C46H30N4S, 670.2191) | 38 | m/z = 719.8660 (C49H29N5S, 719.2144) |
| 39 | m/z = 719.8660 (C49H29N5S, 719.2144) | 40 | m/z = 644.7520 (C43H24N4OS, 644.1671) |
| 41 | m/z = 660.8130 (C43H24N4S2, 660.1442) | 42 | m/z = 710.8730 (C47H26N4S2, 710.1599) |
| 43 | m/z = 714.8280 (C51H30N4O, 714.2420) | 44 | m/z = 638.7300 (C45H26N4C, 638.2107) |
| 45 | m/z = 638.7300 (C45H26N4O, 638.2107) | 46 | m/z = 714.8280 (C51H30N4O, 714.2420) |
| 47 | m/z = 714.8280 (C51H30N4O, 714.2420) | 48 | m/z = 790.9260 (C57H34N4O, 790.2733) |
| 49 | m/z = 779.9030 (C55H33N5O, 779.2685) | 50 | m/z = 829.9630 (C59H35N5C, 829.2842) |
| 51 | m/z = 703.8050 (C49H29N5O, 703.2372) | 52 | m/z = 753.8650 (C53H31N5O, 753.2529) |
| 53 | m/z = 755.8810 (C53H33N5O, 755.2685) | 54 | m/z = 805.9410 (C57H35N5O, 805.2842) |
| 55 | m/z = 654.7730 (C46H30N4O, 654.2420) | 56 | m/z = 703.8050 (C49H29N5O, 703.2372) |
| 57 | m/z = 703.8050 (C49H29N5O, 703.2372) | 58 | m/z = 628.6910 (C43H24N4O2, 628.1899) |
| 59 | m/z = 644.7520 (C43H24N4OS, 644.1671) | 60 | m/z = 694.8120 (C47H26N4OS, 694.1827) |
| 61 | m/z = 653.8030 (C46H27N3S, 653.1926) | 62 | m/z = 653.8030 (C46H27N3S, 653.1926) |
| 63 | m/z = 653.8030 (C46H27N3S, 653.1926) | 64 | m/z = 653.8030 (C46H27N3S, 653.1926) |
| 65 | m/z = 653.8030 (C46H27N3S, 653.1926) | 66 | m/z = 806.9870 C57H34N4S, 806.2904) |
| 67 | m/z = 795.9460 (C55H33N5S, 795.2457) | 68 | m/z = 846.0240 (C59H35N5S, 845.2613) |
| 69 | m/z = 719.8660 (C49H29N5S, 719.2144) | 70 | m/z = 769.9260 (C53H31N5S, 769.2300) |
| 71 | m/z = 771.9420 (C53H33N5S, 771.2457) | 72 | m/z = 822.0020 (C57H35N5S, 821.2613) |
| 73 | m/z = 670.8340 (C46H30N4S, 670.2191) | 74 | m/z = 719.8660 (C49H29N5S, 719.2144) |
| 75 | m/z = 719.8660 (C49H29N5S, 719.2144) | 76 | m/z = 710.8730 (C47H26N4S2, 710.1599) |
| 77 | m/z = 769.9260 (C53H31N5S, 769.2300) | 78 | m/z = 710.8730 (C47H26N4S2, 710.1599) |
| 79 | m/z = 638.7300 (C45H26N4O, 638.2107) | 80 | m/z = 638.7300 (C45H26N4O, 638.2107) |
| 81 | m/z = 638.7300 (C45H26N4O, 638.2107) | 82 | m/z = 637.7420 (C46H27N3O, 637.2154) |
| 83 | m/z = 638.7300 (C45H26N4O, 638.2107) | 84 | m/z = 790.9260 (C57H34N4O, 790.2733) |
| 85 | m/z = 779.9030 (C55H33N5O, 779.2685) | 86 | m/z = 779.9030 (C55H33N5O, 779.2685) |
| 87 | m/z = 779.9030 (C55H33N5O, 779.2685) | 88 | m/z = 779.9030 (C55H33N5O, 779.2685) |
| 89 | m/z = 781.9190 (C55H35N5O, 781.2842) | 90 | m/z = 829.9630 (C59H35N5O, 829.2842) |
| 91 | m/z = 753.8650 (C53H31N5O, 753.2529) | 92 | m/z = 755.8810 (C53H33N5O, 755.2685) |
| 93 | m/z = 805.9410 (C57H35N5O, 805.2842) | 94 | m/z = 654.7730 (C46H30N4O, 654.2420) |
| 95 | m/z = 703.8050 (C49H29N5O, 703.2372) | 96 | m/z = 703.8050 (C49H29N5O, 703.2372) |
| 97 | m/z = 628.6910 (C43H24N4O2, 628.1899) | 98 | m/z = 644.7520 (C43H24N4OS, 644.1671) |
| 99 | m/z = 694.8120 (C47H26N4OS, 694.1827) | 100 | m/z = 663.7800 (C48H29N3O, 663.2311) |
| 101 | m/z = 713.8400 (C52H31N3O, 713.2467) | 102 | m/z = 713.8400 (C52H31N3O, 713.2467) |
| 103 | m/z = 588.6780 (C41H24N4O, 588.1950) | 104 | m/z = 664.7680 (C47H28N4O, 664.2263) |
| 105 | m/z = 714.8280 (C51H30N4O, 714.2420) | 106 | m/z = 638.7300 (C45H26N4O, 638.2107) |
| 107 | m/z = 714.8280 (C51H30N4O, 714.2420) | 108 | m/z = 790.9260 (C57H34N4O, 790.2733) |
| 109 | m/z = 779.9030 (C55H33N5O, 779.2685) | 110 | m/z = 829.9630 (C59H35N5O, 829.2842) |
| 111 | m/z = 703.8050 (C49H29N5O, 703.2372) | 112 | m/z = 753.8650 (C53H31N5O, 753.2529) |
| 113 | m/z = 755.8810 (C53H33N5O, 755.2685) | 114 | m/z = 805.9410 (C57H35N5O, 805.2842) |
| 115 | m/z = 654.7730 (C46H30N4O, 654.2420) | 116 | m/z = 703.8050 (C49H29N5O, 703.2372) |
| 117 | m/z = 703.8050 (C49H29N5O, 703.2372) | 118 | m/z = 628.6910 (C43H24N4O2, 628.1899) |
| 119 | m/z = 644.7520 (C43H24N4OS, 644.1671) | 120 | m/z = 694.8120 (C47H26N4OS, 694.1827) |
| 121 | m/z = 588.6780 (C41H24N4O, 588.1950) | 122 | m/z = 664.7680 (C47H28N4O, 664.2263) |
| 123 | m/z = 714.8280 (C51H30N4O, 714.2420) | 124 | m/z = 638.7300 (C45H26N4O, 638.2107) |
| 125 | m/z = 714.8280 (C51H30N4O, 714.2420) | 126 | m/z = 790.9260 (C57H34N4O, 790.2733) |
| 127 | m/z = 779.9030 (C55H33N5O, 779.2685) | 128 | m/z = 829.9630 (C59H35N5O, 829.2842) |
| 129 | m/z = 703.8050 (C49H29N5O, 703.2372) | 130 | m/z = 753.8650 (C53H31N5O, 753.2529) |
| 131 | m/z = m/z = 805.9410 (C57H35N5O, 805.2842) | 132 | m/z = 781.9190 (C55H35N5O, 781.2841) |
| 133 | m/z = 654.7730 (C46H30N4O, 654.2420) | 134 | m/z = 703.8050 (C49H29N5O, 703.2372) |
| 135 | m/z = 703.8050 (C49H29N5O, 703.2372) | 136 | m/z = 628.6910 (C43H24N4O2, 628.1899) |
| 137 | m/z = 644.7520 (C43H24N4OS, 644.1671) | 138 | m/z = 694.8120 (C47H26N4OS, 694.1827) |
| 139 | m/z = 588.6780 (C41H24N4O, 588.1950) | 140 | m/z = 664.7680 (C47H28N4O, 664.2263) |
| 141 | m/z = 714.8280 (C51H30N4O, 714.2420) | 142 | m/z = 638.7300 (C45H26N4O, 638.2107) |
| 143 | m/z = 638.7300 (C45H26N4O, 638.2107) | 144 | m/z = 790.9260 (C57H34N4O, 790.2733) |
| 145 | m/z = 779.9030 (C55H33N5O, 779.2685) | 146 | m/z = 829.9630 (C59H35N5O, 829.2842) |
| 147 | m/z = 703.8050 (C49H29N5O, 703.2372) | 148 | m/z = 753.8650 (C53H31N5O, 753.2529) |
| 149 | m/z = 755.8810 (C53H33N5O, 755.2685) | 150 | m/z = 805.9410 (C57H35N5O, 805.2842) |
| 151 | m/z = 654.7730 (C46H30N4O, 654.2420) | 152 | m/z = 703.8050 (C49H29N5O, 703.2372) |
| 153 | m/z = 703.8050 (C49H29N5O, 703.2372) | 154 | m/z = 628.6910 (C43H24N4O2, 628.1899) |
| 155 | m/z = 644.7520 (C43H24N4OS, 644.1671) | 156 | m/z = 694.8120 (C47H26N4OS, 694.1827) |
| 157 | m/z = 611.7040 (C44H25N3O, 611.1998) | 158 | m/z = 611.7040 (C44H25N3O, 611.1998) |
| 159 | m/z = 611.7040 (C44H25N3O, 611.1998) | 160 | m/z = 611.7040 (C44H25N3O, 611.1998) |
| 161 | m/z = 687.8020 (C50H29N3O, 687.2311) | 162 | m/z = 763.9000 (C56H33N3O, 763.2624) |
| 163 | m/z = 752.8770 (C54H32N4O, 752.2576) | 164 | m/z = 802.9370 (C58H34N4O, 802.2733) |
| 165 | m/z = 676.7790 (C48H28N4O, 676.2263) | 166 | m/z = 726.8390 (C52H30N4O, 726.2420) |

TABLE 3-continued

| Compound | FD-Mass | Compound | FD-Mass |
|---|---|---|---|
| 167 | m/z = 728.8550 (C52H32N4O, 728.2576) | 168 | m/z = 778.9150 (C56H34N4O, 778.2733) |
| 169 | m/z = 627.7470 (C45H29N3O, 627.2311) | 170 | m/z = 676.7790 (C48H28N4O, 676.2263) |
| 171 | m/z = 676.7790 (C48H28N4O, 676.2263) | 172 | m/z = 617.7260 (C42H23N3OS, 617.1562) |
| 173 | m/z = 617.7260 (C42H23N3OS, 617.1562) | 174 | m/z = 667.7860 (C46H25N3OS, 667.1718) |
| 175 | m/z = 627.7650 (C44H25N3S, 627.1769) | 176 | m/z = 779.9610 (C56H33N3S, 779.2395) |
| 177 | m/z = 768.9380 (C54H32N4S, 768.2348) | 178 | m/z = 818.9980 (C58H34N4S, 828.2504) |
| 179 | m/z = 692.8400 (C48H28N4S, 692.2035) | 180 | m/z = 768.9380 (C54H32N4S, 768.2348) |
| 181 | m/z = 742.9000 (C52H30N4S, 742.2191) | 182 | m/z = 818.9980 (C58H34N4S, 828.2504) |
| 183 | m/z = 744.9160 (C52H32N4S, 744.2348) | 184 | m/z = 794.9760 (C56H34N4S, 794.2504) |
| 185 | m/z = 856.0010 (C61H37N5O, 855.2998) | 186 | m/z = 692.8400 (C48H28N4S, 692.2035) |
| 187 | m/z = 692.8400 (C48H28N4S, 692.2035) | 188 | m/z = 617.7260 (C42H23N3OS, 617.1562) |
| 189 | m/z = 667.7860 (C46H25N3OS, 667.1718) | 190 | m/z = 683.8470 (C46H25N3S2, 683.1490) |
| 191 | m/z = 742.9000 (C52H30N4S, 742.2191) | 192 | m/z = 683.8470 (C46H25N3S2, 683.1490) |
| 193 | m/z = 561.6440 (C40H23N3O, 561.1841) | 194 | m/z = 687.8020 (C50H29N3O, 687.2311) |
| 195 | m/z = 611.7040 (C44H25N3O, 611.1998) | 196 | m/z = 687.8020 (C50H29N3O, 687.2311) |
| 197 | m/z = 763.9000 (C56H33N3O, 763.2624) | 198 | m/z = 752.8770 (C54H32N4O, 752.2576) |
| 199 | m/z = 802.9370 (C58H34N4O, 802.2733) | 200 | m/z = 676.7790 (C48H28N4O, 676.2263) |
| 201 | m/z = 752.8770 (C54H32N4O, 752.2576) | 202 | m/z = 726.8390 (C52H30N4O, 726.2420) |
| 203 | m/z = 728.8550 (C52H32N4O, 728.2576) | 204 | m/z = 778.9150 (C56H34N4O, 778.2733) |
| 205 | m/z = 627.7470 (C45H29N3O, 627.2311) | 206 | m/z = 676.7790 (C48H28N4O, 676.2263) |
| 207 | m/z = 676.7790 (C48H28N4O, 676.2263) | 208 | m/z = 601.6650 (C42H23N3O2, 601.1790) |
| 209 | m/z = 617.7260 (C42H23N3OS, 617.1562) | 210 | m/z = 667.7860 (C46H25N3OS, 667.1718) |
| 211 | m/z = 577.7050 (C40H23N3S, 577.1613) | 212 | m/z = 627.7650 (C44H25N3S, 627.1769) |
| 213 | m/z = 627.7650 (C44H25N3S, 627.1769) | 214 | m/z = 627.7650 (C44H25N3S, 627.1769) |
| 215 | m/z = 779.9610 (C56H33N3S, 779.2395) | 216 | m/z = 768.9380 (C54H32N4S, 768.2348) |
| 217 | m/z = 818.9980 (C58H34N4S, 828.2504) | 218 | m/z = 692.8400 (C48H28N4S, 692.2035) |
| 219 | m/z = 768.9380 (C54H32N4S, 768.2348) | 220 | m/z = 744.9160 (C52H32N4S, 744.2348) |
| 221 | m/z = 794.9760 (C56H34N4S, 794.2504) | 222 | m/z = 821.0140 (C58H36N4S, 821.0140) |
| 223 | m/z = 643.8080 (C45H29N3S, 643.2082) | 224 | m/z = 692.8400 (C48H28N4S, 692.2035) |
| 225 | m/z = 692.8400 (C48H28N4S, 692.2035) | 226 | m/z = 617.7260 (C42H23N3OS, 617.1562) |
| 227 | m/z = 633.7870 (C42H23N3S2, 633.1333) | 228 | m/z = 683.8470 (C46H25N3S2, 683.1490) |
| 229 | m/z = 611.7040 (C44H25N3O, 611.1998) | 230 | m/z = 763.9000 (C56H33N3O, 763.2624) |
| 231 | m/z = 676.7790 (C48H28N4O, 676.2263) | 232 | m/z = 802.9370 (C58H34N4O, 802.2733) |
| 233 | m/z = 728.8550 (C52H32N4O, 728.2576) | 234 | m/z = 778.9150 (C56H34N4O, 778.2733) |
| 235 | m/z = 752.8770 (C54H32N4O, 752.2576) | 236 | m/z = 802.9370 (C58H34N4O, 802.2733) |
| 237 | m/z = 752.8770 (C54H32N4O, 752.2576) | 238 | m/z = 752.8770 (C54H32N4O, 752.2576) |
| 239 | m/z = 728.8550 (C52H32N4O, 728.2576) | 240 | m/z = 778.9150 (C56H34N4O, 778.2733) |
| 241 | m/z = 561.6440 (C40H23N3O, 561.1841) | 242 | m/z = 637.7420 (C46H27N3O, 737.2154) |
| 243 | m/z = 687.8020 (C50H29N3O, 687.2311) | 244 | m/z = 611.7040 (C44H25N3O, 611.1998) |
| 245 | m/z = 687.8020 (C50H29N3O, 687.2311) | 246 | m/z = 763.9000 (C56H33N3O, 763.2624) |
| 247 | m/z = 752.8770 (C54H32N4O, 752.2576) | 248 | m/z = 802.9370 (C58H34N4O, 802.2733) |
| 249 | m/z = 752.8770 (C54H32N4O, 752.2576) | 250 | m/z = 802.9370 (C58H34N4O, 802.2733) |
| 251 | m/z = 728.8550 (C52H32N4O, 728.2576) | 252 | m/z = 778.9150 (C56H34N4O, 778.2733) |
| 253 | m/z = 627.7470 (C45H29N3O, 627.2311) | 254 | m/z = 676.7790 (C48H28N4O, 676.2263) |
| 255 | m/z = 676.7790 (C48H28N4O, 676.2263) | 256 | m/z = 601.6650 (C42H23N3O2, 601.1790) |
| 257 | m/z = 617.7260 (C42H23N3OS, 617.1562) | 258 | m/z = 667.7860 (C46H25N3OS, 667.1718) |
| 259 | m/z = 611.7040 (C44H25N3O, 611.1998) | 260 | m/z = 611.7040 (C44H25N3O, 611.1998) |
| 261 | m/z = 763.9000 (C56H33N3O, 763.2624) | 262 | m/z = 752.8770 (C54H32N4O, 752.2576) |
| 263 | m/z = 802.9370 (C58H34N4O, 802.2733) | 264 | m/z = 728.8550 (C52H32N4O, 728.2576) |
| 265 | m/z = 676.7790 (C48H28N4O, 676.2263) | 266 | m/z = 667.7860 (C46H25N3OS, 667.1718) |
| 267 | m/z = 611.7040 (C44H25N3O, 611.1998) | 268 | m/z = 611.7040 (C44H25N3O, 611.1998) |
| 269 | m/z = 763.9000 (C56H33N3O, 763.2624) | 270 | m/z = 752.8770 (C54H32N4O, 752.2576) |
| 271 | m/z = 802.9370 (C58H34N4O, 802.2733) | 272 | m/z = 676.7790 (C48H28N4O, 676.2263) |
| 273 | m/z = 752.8770 (C54H32N4O, 752.2576) | 274 | m/z = 726.8390 (C52H30N4O, 726.2420) |
| 275 | m/z = 728.8550 (C52H32N4O, 728.2576) | 276 | m/z = 778.9150 (C56H34N4O, 778.2733) |
| 277 | m/z = 627.7470 (C45H29N3O, 627.2311) | 278 | m/z = 676.7790 (C48H28N4O, 676.2263) |
| 279 | m/z = 676.7790 (C48H28N4O, 676.2263) | 280 | m/z = 667.7860 (C46H25N3OS, 667.1718) |
| 281 | m/z = 617.7260 (C42H23N3OS, 617.1562) | 282 | m/z = 667.7860 (C46H25N3OS, 667.1718) |
| 283 | m/z = 717.8460 (C50H27N3OS, 717.1875) | 284 | m/z = 701.7850 (C50H27N3O2, 701.2103) |
| 285 | m/z = 717.8460 (C50H27N3OS, 717.1875) | 286 | m/z = 701.7850 (C50H27N3O2, 701.2103) |
| 287 | m/z = 717.8460 (C50H27N3OS, 717.1875) | 288 | m/z = 701.7850 (C50H27N3O2, 701.2103) |
| 289 | m/z = 717.8460 (C50H27N3OS, 717.1875) | 290 | m/z = 701.7850 (C50H27N3O2, 701.2103) |
| 291 | m/z = 717.8460 (C50H27N3OS, 717.1875) | 292 | m/z = 701.7850 (C50H27N3O2, 701.2103) |
| 293 | m/z = 733.9070 (C50H27N3S2, 733.1646) | 294 | m/z = 717.8460 (C50H27N3OS, 717.1875) |
| 295 | m/z = 716.8000 (C50H28N4O2, 716.2212) | 296 | m/z = 716.8000 (C50H28N4O2, 716.2212) |
| 297 | m/z = 716.8000 (C50H28N4O2, 716.2212) | 298 | m/z = 732.8610 (C50H28N4OS, 732.1984) |
| 299 | m/z = 732.8610 (C50H28N4OS, 732.1984) | 300 | m/z = 732.8610 (C50H28N4OS, 732.1984) |
| 301 | m/z = 716.8000 (C50H28N4O2, 716.2212) | 302 | m/z = 657.7470 (C44H23N3O2S, 657.1511) |
| 303 | m/z = 707.8070 (C48H25N3O2S, 707.1667) | 304 | m/z = 673.8080 (C44H23N3OS2, 673.1283) |
| 305 | m/z = 723.8680 (C48H25N3OS2, 723.1439) | 306 | m/z = 723.8680 (C48H25N3OS2, 723.1439) |
| 307 | m/z = 651.7250 (C46H25N3O2, 651.1947) | 308 | m/z = 651.7250 (C46H25N3O2, 651.1947) |
| 309 | m/z = 651.7250 (C46H25N3O2, 651.1947) | 310 | m/z = 667.7860 (C46H25N3OS, 667.1718) |
| 311 | m/z = 667.7860 (C46H25N3OS, 667.1718) | 312 | m/z = 667.7860 (C46H25N3OS, 667.1718) |
| 313 | m/z = 601.6650 (C42H23N3O2, 601.1790) | 314 | m/z = 768.8760 (C54H32N4O2, 7678.2525) |
| 315 | m/z = 766.8600 (C54H30N4O2, 766.2369) | 316 | m/z = 782.9210 (C54H30N4OS, 782.2140) |
| 317 | m/z = 782.9210 (C54H30N4OS, 782.2140) | 318 | m/z = 782.9210 (C54H30N4OS, 782.2140) |
| 319 | m/z = 784.9370 (C54H32N4OS, 784.2297) | 320 | m/z = 657.7470 (C44H23N3O2S, 657.1511) |
| 321 | m/z = 673.8080 (C44H23N3OS2, 673.1283) | 322 | m/z = 808.9590 (C56H32N4OS, 808.2297) |

TABLE 3-continued

| Compound | FD-Mass | Compound | FD-Mass |
|---|---|---|---|
| 323 | m/z = 859.0190 (C60H34N4OS, 858.2453) | 324 | m/z = 617.7260 (C42H23N3OS, 617.1562) |
| 325 | m/z = 716.8000 (C50H28N4O2, 716.2212) | 326 | m/z = 707.8070 (C48H25N3O2S, 707.1667) |
| 327 | m/z = 651.7250 (C46H25N3O2, 651.1947) | 328 | m/z = 667.7860 (C46H25N3OS, 667.1718) |
| 329 | m/z = 683.8470 (C46H25N3S2, 683.1490) | 330 | m/z = 683.8470 (C46H25N3S2, 683.1490) |
| 331 | m/z = 732.8610 (C50H28N4OS, 732.1984) | 332 | m/z = 732.8610 (C50H28N4OS, 732.1984) |
| 333 | m/z = 683.8470 (C46H25N3S2, 683.1490) | 334 | m/z = 683.8470 (C46H25N3S2, 683.1490) |
| 335 | m/z = 836.0430 (C58H33N3S2, 835.2116) | 336 | m/z = 800.9980 (C54H32N4S2, 800.2068) |

TABLE 4

| Example | $^1$H NMR (CDCL$_3$, 200 Mz) |
|---|---|
| I1 | δ = 8.91(d, 1H), 8.88(d, 1H), 8.76(s, 1H), 8.73(d, 1H), 8.59(d, 1H), 8.18(d, 1H), 7.94~7.74(m, 7H), 7.59~7.38(m, 8H), 7.30~7.21(m, 4H). |
| I2 | δ = 8.90(d, 1H), 8.88(d, 1H), 8.76(s, 1H), 8.71(d, 1H), 8.60(d, 1H), 7.81~7.69(m, 9H), 7.52~7.28 (m, 10H), 7.28~7.15(m, 5H). |
| I4 | δ = 8.91(s, 1H), 8.65(d, 2H), 8.59(d, 2H), 8.18~7.90(m, 5H), 7.82~7.64(m, 4H), 7.59~7.53(m, 8H), 7.41~7.36(m, 5H). |
| I5 | δ = 8.9(s, 1H), 8.69(d, 2H), 8.58(d, 2H), 8.24~8.11 (m, 3H), 7.76~7.54 (m, 6H), 7.59~7.34 (m, 7H), 7.29~7.17 (m, 6H). |
| I6 | δ = 8.85 (s, 1H), 8.69(s, 2H), 8.38~8.24(m, 7H), 8.22~8.11(m, 8H), 7.76~7.54 (m, 6H), 7.44~7.39(m, 5H), 7.37(t, 2H), 7.32~7.27(m, 4H). |
| I10 | δ = 8.64 (d, 2H), 8.59(d, 2H), 8.30~8.15(m, 5H), 7.78~7.64(m, 4H), 7.52~7.40(m, 8H), 7.30~7.20(m, 5H). |
| I11 | δ = 9.18 (d, 2H), 9.14(d, 2H), 8.83~8.81(m, 3H), 7.90~7.79(m, 10H), 7.59~7.54(m, 3H), 7.43~7.40 (m, 6H). |
| I12 | δ = 9.20(s, 2H), 9.14(d, 2H), 8.48~8.44(m, 5H), 8.29~8.18(m, 8H), 7.80~7.76(m, 6H), 7.54~7.51(m, 5H), 7.39(t, 2H), 7.24~7.18(m, 4H). |
| I17 | δ = 8.59(d, 1H), 8.40(d, 2H), 8.27~8.18(m, 6H), 7.82~7.69(m, 11H), 7.59~7.34(m, 6H), 7.29~7.17(m, 6H). 6.71(d, 1H). |
| I18 | δ = 8.59(d, 1H), 8.37(d, 2H), 8.27~8.16(m, 7H), 8.12(s, 1H), 7.81~7.66(m, 12H), 7.57~7.30(m, 6H), 7.29~7.17(m, 5H). 6.71(d, 1H). |
| I19 | δ = 8.7(s, 1H), 8.49 (d, 2H), 8.24~8.11 (m, 5H), 7.76 (d, 2H), 7.60~7.51 (m, 11H), 7.50~7.35 (m, 8H), 7.29~7.16 (m, 6H). |
| I27 | δ = 8.9(s, 1H), 8.82(d, 2H), 8.79(d, 2H), 8.27~8.25(m, 3H), 7.77~7.65(m, 6H), 7.54~7.45(m, 7H), 7.31~7.27(m, 6H). |
| I28 | δ = 8.88(s, 1H), 8.62(d, 2H), 8.59 (d, 2H), 8.42(d, 2H), 8.27~8.25(m, 3H), 7.77(d, 2H), 7.67~7.59 (m, 6H), 7.62~7.53(m, 7H), 7.27~7.19(m, 6H). |
| I29 | δ = 8.66(d, 2H), 8.52(d, 2H), 8.41(d, 2H), 8.35~8.18(m, 3H), 7.9(d, 2H), 7.77~7.61(m, 6H), 7.72~7.43(m, 7H), 7.29~7.15(m, 5H), 7.11~7.09(m, 1H). |
| I31 | δ = 9.20(dd, 2H), 9.04(d, 3H), 8.62(s, 1H), 8.58 (s, 1H), 8.27(s, 1H), 8.19~8.15(m, 4H), 8.11(d, 1H), 8.05~8.00(m, 2H), 8.00~7.88(m, 4H), 7.79~7.51(m, 14H), 7.47(d, 1H), 7.41~7.39(m, 1H). |
| I32 | δ = 9.19(dd, 2H), 9.08(d, 3H), 8.61(s, 1H), 8.58 (s, 1H), 8.56(d, 1H), 8.28(s, 1H), 8.19~8.15(m, 4H), 8.11(d, 1H), 8.05~8.00(m, 2H), 7.90~7.79(m, 5H), 7.74~7.60(m, 14H), 7.48(d, 1H), 7.40(t, 1H). |
| I33 | δ = 8.86(d, 1H), 8.59 (d, 2H), 8.36(s, 1H), 8.27~8.19(m, 5H), 7.88~7.72(m, 9H), 7.57(d, 2H), 7.49~7.40(m, 4H), 7.38(d, 2H), 7.27~7.17(m, 4H). 6.71(d, 1H) |
| I34 | δ = 8.87(d, 1H), 8.66(d, 2H), 8.48(d, 1H), 8.36(s, 1H), 8.30~8.19 (m, 6H), 7.81~7.68(m, 9H), 7.58(d, 2H), 7.51~7.44 (m, 4H), 7.39 (d, 2H), 7.33~7.22 (m, 4H). 6.84(d, 1H) |
| I35 | δ = 8.65 (d, 1H), 8.48(d, 2H), 8.29~8.20(m, 6H), 7.91~7.77(m, 11H), 7.60~7.36(m, 6H), 7.28~7.18(m, 6H). 6.89(d, 1H) |
| I37 | δ = 8.55 (d, 1H), 8.46 (d, 1H), 8.43(d, 2H), 8.29~8.17 (m, 4H), 7.76 (d, 1H), 7.7(s, 1H), 7.59(d, 1H), 7.48~7.38 (m, 8H), 7.28 (s, 1H), 7.36~7.31 (m, 3H), 7.20 (t, 1H), 1.77 (s, 6H). |
| I38 | δ = 8.55(d, 1H), 8.47(d, 1H), 8.40(d, 2H), 8.27~8.16 (m, 4H), 7.73(d, 1H), 7.9(s, 1H), 7.59(d, 1H), 7.48~7.38(m, 8H), 7.36~7.27(m, 7H), 7.24(s, 1H), 7.20~7.18(m, 2H). |
| I39 | δ = 8.57(d, 2H), 8.48(d, 1H), 8.38(d, 2H), 8.16~8.09(m, 5H), 7.56~7.41(m, 14H), 7.33(t, 2H), 7.21 (d, 1H), 7.19-7.18(m, 2H). |
| I40 | δ = 8.55(d, 1H), 8.48(d, 1H), 8.37(d, 2H), 8.07~7.99(m, 3H), 7.97(d, 2H), 7.66(d, 1H), 7.59~7.52 (m, 7H), 7.48~7.44(m, 4H), 7.29~7.23(m, 3H). |
| I41 | δ = 8.54(d, 1H), 8.49(d, 1H), 8.37(dd, 2H), 8.07~7.99(m, 3H), 7.98(d, 2H), 7.89(d, 1H), 7.60~7.55 (m, 7H), 7.49~7.43(m, 4H), 7.30~7.24(m, 3H). |
| I42 | δ = 8.49(d, 1H), 8.38(d, 1H), 8.38(dd, 2H), 8.07~7.80(m, 3H), 7.98(d, 2H), 7.89(d, 1H), 7.60~7.52 (m, 8H), 7.48~7.40 (m, 5H), 7.29~7.25(m, 3H). |
| I43 | δ = 9.0(d, 1H), 8.9(d, 1H), 8.56(d, 1H), 8.55(d, 1H), 8.42(d, 1H), 8.39(d, 2H), 8.20~8.13(m, 3H), 8.07~8.01(m, 3H), 7.94(s, 1H), 7.88(s, 1H), 7.79-7.78(m, 1H), 7.47~7.44 (m, 11H), 7.36~7.32(m, 3H). |
| I45 | δ = 8.56(d, 2H), 8.43 (d, 2H), 8.34~8.29(m, 3H), 7.91~7.84(m, 6H), 7.67(s, 1H), 7.59~7.48(m, 6H), 7.33~7.21(m, 6H). |
| I46 | δ = 8.39(d, 2H), 8.36(d, 2H), 8.27(d, 2H), 8.18~7.95(m, 3H), 7.92(d, 2H), 7.82~7.66(m, 4H), 7.59~7.49 (m, 5H), 4.46 (s, 2H), 7.44-7.37(m, 3H), 7.28~7.15(m, 5H). |
| I47 | δ = 8.54(d, 2H), 8.42(d, 2H), 8.34~8.30(m, 3H), 8.27(d, 2H), 7.91~7.84(m, 6H), 7.67(s, 1H), 7.59(d, 2H), 7.52~7.38(m, 6H), 7.33~7.21(m, 6H). |

TABLE 4-continued

| Example | $^1$H NMR (CDCL$_3$, 200 Mz) |
|---|---|
| I48 | δ = 8.55(d, 2H), 8.42(d, 2H), 8.36~8.31(m, 3H), 8.26(d, 2H), 7.90~7.85(m, 6H), 7.68(s, 1H), 7.54(d, 2H), 7.52~7.33(m, 9H), 7.31~7.19(m, 9H), 7.17(t, 2H). |
| I54 | δ = 8.58(d, 1H), 8.33(d, 2H), 8.27~8.16(m, 7H), 8.05~8.01(m, 4H), 7.77~7.64(m, 9H), 7.42~7.36(m, 4H), 7.29~7.25(m, 2H), 7.29~7.17(m, 5H). 6.69(d, 1H) |
| I55 | δ = 8.55(d, 1H), 8.46(d, 1H), 8.43(d, 2H), 8.29~8.16(m, 4H), 7.76(d, 1H), 7.58(s, 1H), 7.57(d, 1H), 7.46~7.37(m, 8H), 7.27(s, 1H), 7.36~7.31(m, 3H), 7.20~7.19(m, 1H), 1.77(s, 6H). |
| I56 | δ = 8.54(d, 1H), 8.44(d, 1H), 8.40(d, 2H), 8.19~8.14 (m, 4H), 7.71(d, 1H), 7.79(s, 1H), 7.56(d, 1H), 7.47~7.36(m, 8H), 7.36~7.26(m, 7H), 7.23(s, 1H), 7.21~7.18(m, 2H). |
| I57 | δ = 8.55(d, 2H), 8.47(d, 1H), 8.38(d, 2H), 8.14~8.09(m, 5H), 7.56~7.51(m, 8H), 7.50~7.44(m, 6H), 7.33(t, 2H), 7.20(d, 1H), 7.19~7.18(m, 2H). |
| I61 | δ = 8.59(d, 2H), 8.48(s, 1H), 8.44(d, 2H), 8.39(d, 2H), 7.76~7.70(m, 5H), 7.39(d, 2H), 7.33(d, 2H), 7.32~7.26(m, 5H), 7.24~7.20(m, 4H), 7.14(t, 1H). |
| I62 | δ = 8.59(d, 2H), 8.46(s, 1H), 8.43(d, 1H), 8.36(d, 1H), 8.22(d, 1H), 8.19(d, 1H), 7.72~7.66(m, 5H), 7.36(d, 2H), 7.35~7.31(m, 7H), 7.28~7.23(m, 4H), 7.17(t, 1H). |
| I63 | δ = 8.59(d, 2H), 8.46(s, 1H), 8.45(d, 1H), 8.43(d, 1H), 8.33(d, 1H), 8.22(d, 1H), 8.19(d, 1H), 7.77(d, 2H), 7.49~7.42(m, 3H), 7.72~7.66(m, 4H), 7.38(d, 2H), 7.36(d, 2H), 7.35~7.31(d, 4H), 7.22~7.20(m, 1H). |
| I64 | δ = 8.66(d, 2H), 8.54(s, 1H), 8.49(s, 2H), 8.49(d, 2H), 8.38(s, 2H), 8.03(d, 4H), 7.76(d, 4H), 7.49~7.45 (m, 5H), 7.42~7.38(m, 3H), 7.19~7.17(m, 1H). |
| I65 | δ = 9.31(d, 2H), 9.24 (d, 2H), 9.06 (d, 3H), 8.39 (d, 1H), 8.29 (s, 1H), 8.15 (d, 1H), 8.11 (d, 2H), 8.04 (t, 1H), 8.00~7.89 (m, 4H), 7.80~7.61 (m, 8H), 7.56 (t, 1H). |
| I67 | δ = 9.33(d, 1H), 9.21(dd, 2H), 9.09(d, 3H), 8.62(s, 1H), 8.56(s, 1H), 8.17~8.15(m, 4H), 8.11(d, 1H), 8.04~8.00 (m, 2H), 8.00~7.89(m, 4H), 7.80~7.51(m, 13H), 7.41~7.39(m, 1H). |
| I68 | δ = 9.24 (dd, 2H), 9.02(d, 3H), 8.64(d, 1H), 8.59(s, 1H), 8.56(s, 1H), 8.19~8.16(m, 4H), 8.12(d, 1H), 8.09~8.04(dd, 2H), 8.01~7.89(m, 4H), 7.80~8.64(m, 8H), 7.60~7.51(m, 6H), 7.43~7.39(m, 2H). |
| I76 | δ = 9.42(d, 2H), 9.32(s, 1H), 9.28(d, 1H), 9.15(d, 1H), 8.9(d, 1H), 8.71(d, 1H), 8.52~8.49(m, 2H), 8.39~8.37(m, 1H), 8.04(d, 1H), 7.87~7.83(m, 2H), 7.83~7.75(m, 4H), 7.66(d, 1H), 7.64~7.49(m, 10H), 7.38(t, 2H). |
| I77 | δ = 9.38(d, 2H), 9.3(s, 1H), 9.27(d, 1H), 9.11(d, 1H), 8.87(d, 1H), 8.74(d, 1H), 8.54~8.49(m, 2H), 8.40~8.38(m, 1H), 8.04(d, 1H), 7.87~7.84(m, 2H), 7.83~7.75(m, 4H), 7.61~7.49(m, 8H), 7.36(t, 1H). |
| I79 | δ = 8.76(d, 1H), 8.55(d, 1H), 8.46(d, 2H), 8.36(d, 1H), 8.34(d, 1H), 8.29(d, 1H), 7.90~7.86(m, 6H), 7.77(s, 1H), 7.62~7.51(m, 6H), 7.35~7.26(m, 6H). |
| I80 | δ = 8.74(d, 1H), 8.71(d, 1H), 8.55(d, 2H), 8.46(d, 2H), 8.36(d, 1H), 8.34~8.30(m, 3H), 7.90~7.84(m, 6H), 7.70(s, 1H), 7.52~7.48(m, 4H), 7.31~7.26(m, 5H). |
| I81 | δ = 8.76(d, 2H), 8.71(d, 2H), 8.46(d, 2H), 8.34~8.29(m, 3H), 7.93~7.85(m, 6H), 7.66(s, 1H), 7.50~7.46(m, 4H), 7.27~7.22(m, 6H). |
| I82 | δ = 8.55(d, 2H), 8.46(d, 2H), 8.34~8.29(m, 3H), 7.93~7.88(m, 6H), 7.73(s, 1H), 7.62~7.48(m, 6H), 7.34~7.27(m, 6H). |
| I83 | δ = 8.78(s, 1H), 8.52(d, 2H), 8.40(d, 2H), 8.33~8.28(m, 3H), 7.93~7.87(m, 6H), 7.70(s, 1H), 7.61~7.51(m, 6H), 7.34~7.27(m, 6H). |
| I85 | δ = 9.36(s, 1H), 8.71(d, 1H), 8.68(d, 1H), 8.46(d, 1H), 8.29(d, 1H), 8.27(d, 2H), 8.24~8.11(m, 5H), 7.76(d, 1H), 7.49~7.44(m, 7H), 7.39~7.36(m, 9H), 7.28~7.23(m, 6H), 7.18~7.16(m, 2H). |
| I86 | δ = 9.34(s, 1H), 8.89(d, 1H), 8.85(d, 1H), 8.43(d, 1H), 8.28(d, 1H), 8.27(d, 2H), 8.24~8.19(m, 3H), 7.76(d, 1H), 7.49~7.44(m, 5H), 7.39(s, 1H), 7.38~7.28(m, 9H), 7.26~7.20(m, 6H), 7.18~7.16(m, 2H). |
| I87 | δ = 9.34(s, 1H), 8.89(d, 1H), 8.85(d, 1H), 8.42(d, 1H), 8.29(d, 1H), 8.27(d, 2H), 8.15~8.11(m, 3H), 7.77(d, 1H), 7.47~7.43(m, 5H), 7.38~7.27(m, 9H), 7.26~7.20(m, 6H), 7.18~7.17(m, 2H). |
| I88 | δ = 9.30(s, 1H), 8.82(d, 1H), 8.88(d, 1H), 8.44(s, 1H), 8.26(d, 1H), 8.25(d, 2H), 8.18~8.11(m, 3H), 7.72(d, 1H), 7.47~7.43(m, 5H), 7.38~7.27(m, 6H), 7.28~7.23(m, 8H), 7.20(d, 2H), 7.18(t, 1H). |
| I89 | δ = 9.30(s, 1H), 8.89(d, 1H), 8.86(d, 1H), 8.79(s, 1H), 8.32(d, 1H), 8.17~8.13(m, 3H), 7.66(d, 1H), 7.42~7.36(m, 5H), 7.35~7.30(m, 6H), 7.28~7.21(m, 12H), 7.14~7.11(m, 3H). |
| I90 | δ = 9.27(s, 1H), 8.95(d, 2H), 8.87(d, 1H), 8.74(d, 1H), 8.77(d, 1H), 8.75(d, 1H), 8.58 (d, 2H), 8.56(d, 1H), 8.22(d, 1H), 8.19~8.15(m, 4H), 8.12(d, 1H), 8.05~8.00(m, 2H), 7.90~7.79(m, 5H), 7.74~7.59 (m, 10H), 7.44(d, 1H), 7.36(t, 1H). |
| I91 | δ = 9.29(s, 1H), 8.87(d, 1H), 8.86(d, 2H), 8.70(d, 2H), 8.68(s, 1H), 8.48(d, 1H), 8.24~8.19(m, 5H), 7.81~7.68(m, 7H), 7.58(d, 2H), 7.51~7.44 (m, 4H), 7.39 (d, 2H), 7.33~7.29(m, 2H), 7.22 (t, 1H). |
| I92 | δ = 9.26(s, 1H), 8.85(d, 1H), 8.81(d, 2H), 8.66(d, 2H), 8.46(d, 1H), 8.24~8.19(m, 5H), 8.07(s, 1H), 7.81~7.72(m, 6H), 7.46~7.41(m, 4H), 7.33~7.29(m, 8H), 7.17(t, 2H). |
| I93 | δ = 9.26(s, 1H), 8.86(d, 1H), 8.83(d, 2H), 8.65(d, 2H), 8.46(d, 1H), 8.31(d, 1H), 8.25~8.19(m, 4H), 8.04(s, 1H), 7.76(d, 1H), 7.64(d, 1H), 7.59(d, 1H), 7.48~7.47(m, 2H), 7.46~7.41(m, 7H), 7.33~7.27(m, 10H), 7.19(t, 1H). |
| I94 | δ = 8.76(d, 1H), 8.45(d, 2H), 8.29~8.17(m, 4H), 7.76(d, 1H), 7.81(s, 1H), 7.59(d, 1H), 7.56(s, 1H), 7.53~7.51(m, 3H), 7.48~7.42(m, 6H), 7.40~7.38(m, 3H), 7.30(s, 1H), 1.75(s, 6H). |
| I95 | δ = 9.12(d, 1H), 9.08(s, 1H), 8.89(d, 2H), 8.40(d, 2H), 8.26(d, 2H), 8.25(s, 1H), 8.24~8.16 (m, 4H), 7.73(d, 1H), 7.59(d, 1H), 7.48~7.38(m, 6H), 7.36~7.27(m, 5H), 7.24(s, 1H), 7.20~7.17(m, 2H). |
| I96 | δ = 9.14(d, 1H), 9.08(s, 1H), 8.90(d, 2H), 8.68(d, 2H), 8.41(d, 2H), 8.28(d, 2H), 8.26(s, 1H), 8.24~8.21(m, 2H), 7.61(d, 1H), 7.59(d, 1H), 7.46~7.38(m, 6H), 7.36~7.27(m, 5H), 7.23(s, 1H), 7.20~7.18(m, 2H). |

TABLE 4-continued

| Example | ¹H NMR (CDCL₃, 200 Mz) |
|---|---|
| I101 | δ = 8.98(s, 1H), 8.87(d, 1H), 8.79(d, 1H), 8.64(d, 2H), 8.62(s, 1H), 8.34~8.30(m, 3H), 8.27(d, 2H), 8.02(d, 1H), 7.77(d, 1H), 7.70~7.61(m, 6H), 7.59(d, 2H), 7.52~7.43(m, 4H), 7.27~7.21(m, 6H). |
| I102 | δ = 8.98(s, 1H), 8.85~8.83(m, 3H), 8.60(d, 2H), 8.49(d, 2H), 8.26~8.22(m, 3H), 8.21(d, 2H), 7.71~7.61(m, 6H), 7.59(d, 2H), 7.52~7.43(m, 4H), 7.27~7.20(m, 6H). |
| I107 | δ = 8.87~8.86(m, 3H), 8.64(d, 2H), 8.62(d, 2H), 8.34~8.30(m, 3H), 8.27(d, 2H), 7.71~7.61(m, 6H), 7.59(d, 2H), 7.52~7.43(m, 4H), 7.27~7.21(m, 6H). |
| I117 | δ = 8.67(d, 2H), 8.59(s, 1H), 8.58(d, 1H), 8.38(d, 2H), 8.27(d, 1H), 8.24(d, 1H), 8.16(d, 1H), 7.51~7.40(m, 14H), 7.33~7.29(m, 3H), 7.21 (d, 1H), 7.19-7.18(m, 2H). |
| I118 | δ = 8.69(d, 2H), 8.61(s, 1H), 8.58(d, 1H), 8.40(d, 2H), 8.18(d, 1H), 8.16(d, 1H), 8.12(d, 1H), 7.48~7.44(m, 5H), 7.39~7.31(m, 8H), 7.29(d, 1H), 7.24(t, 1H). |
| I119 | δ = 8.89(d, 2H), 8.80(s, 1H), 8.68(d, 1H), 8.60(d, 2H), 8.32(d, 1H), 8.24(d, 1H), 8.21(d, 1H), 7.56~7.50(m, 5H), 7.49~7.39(m, 8H), 7.32(d, 1H), 7.28(t, 1H). |
| I120 | δ = 8.86(d, 2H), 8.77(s, 1H), 8.58(d, 2H), 8.32(d, 1H), 8.30(d, 1H), 8.26(d, 1H), 7.55~7.48(m, 6H), 7.50~7.39(m, 10H), 7.30(d, 1H), 7.24(t, 1H). |
| I127 | δ = 9.18(dd, 2H), 8.72(d, 1H), 8.65(d, 1H), 8.51(s, 1H), 8.42(s, 1H), 8.34(s, 1H), 8.28(d, 1H), 8.26~8.20(m, 3H), 8.14~8.08(m, 2H), 8.03(d, 1H), 7.97-7.90(m, 2H), 7.86~7.78(m, 3H), 7.63~7.41 (m, 12H), 7.32(t, 1H) |
| I128 | δ = 9.16(dd, 2H), 8.70(d, 1H), 8.59(d, 1H), 8.46(s, 1H), 8.40(s, 1H), 8.33(s, 1H), 8.19(d, 1H), 8.27~8.22(m, 4H), 8.14~8.06(m, 2H), 8.01(d, 1H), 7.97~7.92(m, 2H), 7.88~7.79(m, 4H), 7.65~7.41 (m, 14H), 7.34-7.30(m, 1H) |
| I130 | δ = 8.92(d, 1H), 8.87(d, 1H), 8.86(d, 2H), 8.70(d, 1H), 8.69(d, 1H), 8.66(s, 1H), 8.60(s, 1H), 8.48(d, 1H), 8.29(d, 2H), 8.24~8.20(m, 3H), 7.83~7.66(m, 6H), 7.57(d, 2H), 7.50~7.45(m, 4H), 7.39 (d, 2H), 7.33~7.30(m, 2H), 7.19(t, 1H). |
| I132 | δ = 8.90(d, 1H), 8.86(d, 1H), 8.84(d, 2H), 8.69(d, 1H), 8.66(d, 1H), 8.64(s, 1H), 8.59(s, 1H), 8.48(d, 1H), 8.29(d, 2H), 8.17~8.13(m, 3H), 7.66(d, 1H), 7.42~7.36(m, 4H), 7.35~7.30(m, 4H), 7.28~7.21(m, 9H), 7.14~7.11(m, 3H). |
| I142 | δ = 9.23(d, 2H), 9.17(d, 1H), 8.90(s, 1H), 8.82(d, 2H), 8.76(d, 2H), 8.60(s, 1H), 8.54(d, 1H), 8.26(s, 1H), 7.71~7.63(m, 8H), 7.40~7.37(m, 3H), 7.33~7.28(m, 4H). |
| I143 | δ = 9.23(d, 2H), 9.17(d, 2H), 8.82(d, 3H), 8.80(s, 1H), 8.26(d, 1H), 8.25(d, 2H), 7.77~7.65(m, 10H), 7.42~7.39(m, 2H), 7.38~7.35(m, 4H). |
| I144 | δ = 9.20(s, 2H), 9.16(d, 2H), 8.80(d, 3H), 8.79(s, 1H), 8.24(d, 1H), 8.22(d, 2H), 7.78~7.67(m, 13H), 7.42~7.38(m, 4H), 7.37~7.33(m, 6H). |
| I145 | δ = 9.19(dd, 2H), 8.73(d, 1H), 8.62(d, 1H), 8.57(s, 1H), 8.42(s, 1H), 8.34(s, 1H), 8.28(d, 1H), 8.26~8.20(m, 3H), 8.14~8.08(m, 2H), 8.03(d, 1H), 7.95-7.89(m, 2H), 7.87~7.76(m, 3H), 7.61~7.40 (m, 12H), 7.32(t, 1H) |
| I152 | δ = 9.15(d, 2H), 9.11(s, 1H), 9.09(d, 1H), 8.92(s, 1H), 8.90(d, 1H), 8.45(d, 1H), 8.43(d, 1H), 7.65~7.61(m, 5H), 7.56~7.51(m, 7H), 7.48(d, 1H), 7.36~7.32(m, 5H), 7.28(s, 1H), 7.27~7.25(m, 2H) |
| I158 | δ = 9.03(d, 2H), 8.97(s, 1H), 8.72(d, 1H), 8.70(d, 2H), 8.52(s, 1H), 8.49~8.47(m, 2H), 8.23(d, 2H), 7.74~7.67(m, 6H), 7.44~7.37(m, 5H), 7.34~7.31 (m, 4H). |
| I160 | δ = 8.88 (d, 2H), 8.74(d, 2H), 8.33~8.21(m, 3H), 8.16(d, 1H), 7.70~7.59(m, 8H), 7.49~7.44(m, 5H), 7.38~7.31 (m, 6H). |
| I162 | δ = 8.89 (s, 2H), 8.71(d, 2H), 8.32~8.21(m, 3H), 8.19(d, 1H), 7.69~7.64(m, 5H), 7.59~7.56(m, 3H), 7.49~7.44(m, 7H), 7.36~7.30 (m, 8H), 7.27(t, 2H). |
| I163 | δ = 9.19(dd, 2H), 8.73(d, 1H), 8.67(d, 1H), 8.49(s, 1H), 8.41(s, 1H), 8.29(d, 1H), 8.25~8.20(m, 3H), 8.15~8.07(m, 3H), 8.03(d, 1H), 7.98-7.91(m, 2H), 7.85~7.78(m, 3H), 7.66~7.42 (m, 12H), 7.34-7.30 (m, 1H) |
| I164 | δ = 9.16(dd, 2H), 8.70(d, 1H), 8.59(d, 1H), 8.46(s, 1H), 8.40(s, 1H), 8.33(s, 1H), 8.19(d, 1H), 8.27~8.22(m, 4H), 8.14~8.06(m, 2H), 8.01(d, 1H), 7.97~7.92(m, 2H), 7.88~7.79(m, 4H), 7.65~7.41 (m, 14H), 7.34-7.30(m, 1H) |
| I171 | δ = 8.92(d, 1H), 8.80(d, 1H), 8.79(d, 1H), 8.68(s, 1H), 8.43(d, 1H), 8.34(d, 2H), 8.30~8.28(m, 2H), 7.66~7.58(m, 10H), 7.54~7.52(m, 2H), 7.29(t, 1H). |
| I172 | δ = 8.94(d, 1H), 8.69(s, 1H), 8.67(d, 1H), 8.43(d, 1H), 8.28(dd, 2H), 8.24(d, 2H), 8.20~8.18(m, 3H), 7.70~7.64(m, 7H), 7.49~7.44(m, 5H). |
| I173 | δ = 8.99(d, 1H), 8.84(d, 1H), 8.71(s, 1H), 8.62(d, 1H), 8.40(d, 1H), 8.35(d, 1H), 8.23(d, 2H), 8.22~8.18(m, 3H), 7.70~7.64(m, 7H), 7.42~7.39(m, 4H). |
| I174 | δ = 9.26(d, 1H), 9.15(d, 1H), 8.96(d, 1H), 8.61(s, 1H), 8.47~8.44(m, 1H), 8.39~8.37(m, 1H), 8.21~8.18(m, 2H), 8.05(d, 1H), 7.86(t, 1H), 7.84~7.63(m, 3H), 7.62~7.51(m, 9H), 7.34~7.28(m, 3H). |
| I179 | δ = 9.18(d, 2H), 9.15 (d, 1H), 8.89(d, 1H), 8.80(s, 1H), 8.79~8.78(m, 2H), 8.63(s, 1H), 8.59(d, 1H), 8.26(dd, 2H), 8.24(d, 1H), 7.76~7.65(m, 10H), 7.49~7.44 (m, 6H). |
| I180 | δ = 9.18(d, 2H), 9.14 (d, 1H), 8.87(d, 1H), 8.80(s, 1H), 8.79~8.77(m, 2H), 8.63(s, 1H), 8.62(d, 1H), 8.25(dd, 2H), 8.22(d, 1H), 7.75~7.54 (m, 12H), 7.49~7.43 (m, 8H), 7.31(t, 1H). |
| I186 | δ = 9.11(s, 1H), 8.82(d, 1H), 8.80(d, 1H), 8.67(s, 1H), 8.59(d, 1H), 8.46(d, 1H), 8.38~8.36(m, 2H), 7.57~7.54 (m, 8H), 7.44~7.40(m, 4H), 7.36~7.30(m, 6H), 7.28(s, 1H), 7.11(t, 1H). |
| I189 | δ = 8.99(d, 1H), 8.82(d, 2H), 8.77(s, 1H), 8.49~8.47(m, 3H), 8.26(d, 1H), 7.78~7.74(m, 5H), 7.56~7.51(m, 6H), 7.39~7.33(m, 6H). |
| I191 | δ = 8.82(d, 1H), 8.62(d, 1H), 8.44(s, 1H), 8.37(d, 1H), 8.26~8.11(m, 3H), 8.09(d, 1H), 7.76~7.62 (m, 3H), 7.59~7.50(m, 12H), 7.29~7.26(m, 6H), 7.20(t, 1H). |
| I192 | δ = 8.78(d, 2H), 8.70(d, 2H), 8.46(d, 2H), 8.23~8.22(m, 2H), 8.21(d, 2H), 8.14(s, 1H), 8.16(d, 1H), 7.89(d, 1H), 7.44~7.38(m, 6H), 7.29~7.24 (m, 5H), 7.19~7.17(m, 2H). |
| I195 | δ = 9.08(d, 2H), 8.92(d, 2H), 8.33~8.32(m, 2H), 8.21(d, 2H), 8.19(s, 1H), 8.17(d, 1H), 7.92(d, 1H), 7.46~7.39(m, 7H), 7.29~7.24 (m, 5H), 7.19~7.17 (m, 2H). |

TABLE 4-continued

| Example | $^1$H NMR (CDCL$_3$, 200 Mz) |
|---|---|
| I196 | δ = 8.78(d, 2H), 8.70(d, 2H), 8.46(d, 2H), 8.23~8.22(m, 2H), 8.21(d, 2H), 8.14(s, 1H), 8.16(d, 1H), 7.89(d, 1H), 7.48(d, 2H), 7.46~7.41(m, 8H), 7.31~7.26 (m, 5H), 7.16~7.15(m, 2H). |
| I198 | δ = 9.19(dd, 2H), 8.73(d, 1H), 8.67(d, 1H), 8.49(s, 1H), 8.41(s, 1H), 8.29(d, 1H), 8.25~8.20(m, 3H), 8.15~8.07(m, 3H), 8.03(d, 1H), 7.98-7.91(m, 2H), 7.85~7.78(m, 3H), 7.66~7.42 (m, 12H), 7.34-7.30 (m, 1H) |
| I199 | δ = 9.16(dd, 2H), 8.70(d, 1H), 8.59(d, 1H), 8.46(s, 1H), 8.40(s, 1H), 8.19(s, 1H), 8.19(d, 1H), 8.27~8.22(m, 4H), 8.14-8.06(m, 2H), 8.01(d, 1H), 7.97~7.92(m, 2H), 7.88~7.79(m, 4H), 7.65~7.41 (m, 14H), 7.34-7.30(m, 1H) |
| I200 | δ = 9.08(d, 2H), 9.01(d, 1H), 8.82(d, 1H), 8.77~8.76(m, 2H), 8.62(s, 1H), 8.59(d, 1H), 8.58(s, 1H), 8.23(dd, 2H), 8.20(d, 1H), 7.74~7.66(m, 8H), 7.39~7.34(m, 8H). |
| I204 | δ = 8.89(d, 2H), 8.64(d, 1H), 8.52(s, 1H), 8.44(s, 1H), 8.29~8.25(m, 5H), 8.15(d, 1H), 8.11(d, 2H), 8.04(d, 1H), 8.00(d, 1H), 7.97(d, 1H), 7.92(s, 1H), 7.89(d, 1H), 7.80~7.61(m, 9H), 7.56~7.54(m, 3H), 7.45~7.43(m, 3H), 7.37(t, 1H). |
| I206 | δ = 9.02(s, 1H), 8.80(d, 1H), 8.79(d, 1H), 8.57(d, 1H), 8.49(s, 1H), 8.46(d, 1H), 8.38~8.36(m, 2H), 7.49~7.42(m, 8H), 7.40~7.36(m, 5H), 7.36~7.30(m, 5H), 7.20(s, 1H), 7.06(t, 1H). |
| I214 | δ = 9.29(d, 1H), 9.24 (d, 2H), 9.06 (d, 3H), 8.39 (d, 1H), 8.29 (s, 1H), 8.15(d, 1H), 8.11(d, 2H), 8.04(t, 1H), 8.00~7.89 (m, 4H), 7.80~7.61(m, 8H), 7.56(t, 1H). |
| I218 | δ = 9.18(d, 2H), 9.15(d, 1H), 8.90(d, 1H), 8.80(d, 1H), 8.79~8.78(m, 2H), 8.66(s, 1H), 8.59(d, 1H), 8.26(dd, 2H), 8.23(d, 1H), 7.76~7.67 (m, 11H), 7.47~7.41 (m, 6H). |
| I222 | δ = 8.88(d, 2H), 8.87(d, 1H), 8.69(d, 1H), 8.46(s, 1H), 8.31~8.29(m, 4H), 8.23(d, 1H), 7.46(d, 2H), 7.44~7.37 (m, 14H), 7.27~7.24(m, 6H), 7.21(t, 2H). |
| I229 | δ = 9.23(d, 2H), 8.91(d, 2H), 8.73~8.70(m, 3H), 8.68(s, 1H), 8.49(d, 2H), 8.32~8.29(m, 3H), 8.28~8.25(m, 2H), 7.59~7.56(m, 2H), 7.49~7.44(m, 5H), 7.40~7.38(m, 3H). |
| I230 | Δ = 9.16(s, 2H), 8.74~8.71(m, 3H), 8.70(d, 2H), 8.61(s, 1H), 8.41(d, 1H), 8.26(d, 1H), 8.22~8.21(m, 2H), 7.90~7.84(m, 5H), 7.38~7.32(m, 9H), 7.27~7.23(m, 5H), 7.14(t, 2H). |
| I232 | δ = 9.08(d, 2H), 9.04(d, 1H), 8.82(d, 1H), 8.76~8.75(m, 2H), 8.71~8.69(m, 3H), 8.68(d, 1H), 8.61(s, 1H), 8.44(d, 1H), 8.38~8.33(m, 4H), 7.80~7.72(m, 9H), 7.48~7.44(m, 3H), 7.33~7.31(m, 2H). |
| I233 | δ = 8.82(d, 2H), 8.69(d, 1H), 8.68~8.67(m, 3H), 8.64(d, 1H), 8.58(s, 1H), 8.38(d, 1H), 8.29~8.25(m, 5H), 7.64~7.55 (m, 11H), 7.38~7.34(m, 4H), 7.29 (t, 2H). |
| I235 | δ = 9.19(dd, 2H), 8.73(d, 1H), 8.61(d, 1H), 8.58(d, 1H), 8.46(s, 1H), 8.28(d, 1H), 8.26~8.22(m, 3H), 8.12~8.10(m, 2H), 8.03(d, 1H), 7.95~7.93(m, 3H), 7.87~7.76(m, 3H), 7.58~7.44(m, 12H), 7.30(t, 1H) |
| I244 | δ = 9.22(d, 2H), 8.91(d, 2H), 8.74~8.72(m, 3H), 8.48(d, 2H), 8.32~8.29(m, 3H), 8.26~8.24(m, 2H), 7.58(d, 1H), 7.49~7.44(m, 6H), 7.39~7.35(m, 4H). |
| I245 | δ = 8.82(d, 2H), 8.74~8.72(m, 3H), 8.62(d, 2H), 8.36(d, 2H), 8.26(d, 1H), 8.23~8.22(m, 2H), 7.88~7.85(m, 3H), 7.38~7.33(m, 8H), 7.39~7.36(m, 6H). |
| I246 | δ = 9.18(s, 2H), 8.76~8.73(m, 3H), 8.72(d, 2H), 8.38(d, 1H), 8.29(d, 1H), 8.26~8.24(m, 2H), 7.90~7.85(m, 5H), 7.39~7.31(m, 12H), 7.29~7.26(m, 3H), 7.18(t, 2H). |
| I247 | δ = 8.59(d, 2H), 8.32(d, 1H), 8.20~8.12(m, 4H), 7.99~7.79(m, 9H), 7.60~7.34(m, 13H), 7.23(t, 1H), 7.10(t, 2H). |
| I248 | δ = 8.69(d, 2H), 8.36(d, 2H), 8.24~8.12(m, 5H), 7.99(d, 1H), 7.86~7.79(m, 4H), 7.74(d, 1H), 7.59~7.34(m, 10H), 7.23~7.11(m, 7H). |
| I249 | δ = 8.79(d, 2H), 8.39(d, 1H), 8.24~8.11(m, 5H), 7.99(d, 2H), 7.86~7.72(m, 11H), 7.57~7.34(m, 12H), 7.20(t, 1H). |
| I250 | δ = 8.88(d, 3H), 8.24~8.11(m, 3H), 7.99~7.87(m, 3H), 7.79~7.61(m, 9H), 7.54~7.45 (m, 8H), 7.35(t, 1H) 7.16(t, 2H). |
| I252 | δ = 8.81(d, 2H), 8.67~8.49(m, 5H), 8.38~8.29(m, 10H), 8.24~8.11(m, 10H), 7.54(t, 2H), 7.44~7.34 (m, 2H), 6.78 (d, 1H). |
| I258 | δ = 8.91(d, 1H), 8.61(d, 1H), 8.54(d, 1H), 8.34~8.21(m, 8H), 7.89(d, 1H), 7.70~7.54(m, 10H), 7.41(t, 2H), 7.35(d, 1H), 7.22(d, 1H). |
| I261 | δ = 9.21(d, 4H), 8.91(d, 1H), 8.58(d, 1H), 8.44(d, 1H), 8.13(t, 1H), 7.79~7.64(m, 8H), 7.51~7.37(m, 7H). 7.22~7.15(m, 8H). 7.03(s, 2H). |
| I262 | δ = 9.20(d, 1H), 9.16(d, 1H), 8.72(d, 1H), 8.65(d, 1H), 8.51(s, 1H), 8.42(s, 1H), 8.34(s, 1H), 8.29(d, 1H), 8.26~8.20(m, 3H), 8.12(d, 1H), 8.09(d, 1H), 8.03(d, 1H), 7.97~7.90(m, 2H), 7.86~7.78(m, 3H), 7.63~7.41(m, 12H), 7.34~7.30(m, 1H). |
| I263 | δ = 9.01(d, 2H), 8.72(d, 2H), 8.58(d, 1H), 8.45(d, 4H), 8.37(d, 2H), 8.27~8.19(m, 7H), 8.11~8.02(m, 8H), 7.94~7.89(m, 8H), 7.67~7.56(m, 1H). |
| I266 | δ = 8.59(d, 2H), 8.52(d, 2H), 8.45(d, 1H), 8.31(d, 1H), 8.16~8.02(m, 4H), 7.79~7.64(m, 4H), 7.68~7.46(m, 5H), 7.35(t, 1H), 7.16(t, 1H). |
| I267 | δ = 8.65(d, 1H), 8.48(d, 2H), 8.25(d, 2H), 8.11(d, 1H), 7.89~7.71(m, 8H), 7.65~7.48(m, 8H), 7.17(s, 2H). |
| I268 | δ = 8.85(d, 2H), 8.76(d, 1H), 8.27(d, 1H), 8.10~7.94(m, 4H), 7.81~7.70(m, 6H), 7.58~7.36(m, 6H), 7.29~7.17(m, 5H). |
| I274 | δ = 8.7(d, 3H), 8.19~8.14(m, 3H), 7.90~7.82(m, 7H), 7.75~7.67(m, 8H), 7.59~7.50(m, 6H), 7.35(t, 1H), 7.20(t, 2H). |
| I275 | δ = 8.60(d, 1H), 8.57(d, 1H), 8.20(d, 1H), 8.11(s, 1H), 7.98(d, 2H), 7.93~7.89(m, 3H), 7.70~7.59(m, 6H), 7.50~7.37(m, 9H), 7.24(t, 2H), 7.01(d, 6H), 6.54(d, 1H). |
| I276 | δ = 8.56(d, 1H), 8.54(d, 1H), 8.19(d, 1H), 8.11(s, 1H), 7.99(d, 2H), 7.90~7.79(m, 10H), 7.61~7.49(m, 11H), 7.24(t, 2H), 7.10~7.02(m, 4H), 6.55(d, 1H). |
| I278 | δ = 8.71(d, 1H), 8.69(d, 1H), 8.19(d, 1H), 8.13(d, 1H), 7.99~7.91(m, 3H), 7.82~7.78(m, 4H), 7.61~7.55(m, 7H), 7.51~7.45(m, 6H), 7.40(s, 1H), 7.35(t, 1H), 7.20(t, 1H), 7.12(t, 1H). |
| I279 | δ = 8.55(d, 1H), 8.54(d, 2H), 8.13(d, 1H), 7.99~7.89(m, 6H), 7.85~7.79(m, 4H), 7.62~7.56(m, 7H), 7.52~7.47(m, 6H), 7.35(t, 1H), 7.21(d, 1H), 7.16(t, 1H). |

TABLE 4-continued

| Example | $^1$H NMR (CDCL$_3$, 200 Mz) |
|---|---|
| I281 | δ = 9.1(d, 1H), 9.08(d, 1H), 8.86(d, 1H), 8.67(d, 1H), 8.59(d, 1H), 8.47(d, 1H), 8.23~8.19(m, 3H), 8.17~8.15(m, 2H), 7.96(d, 2H), 7.89~7.87(m 3H), 7.59~7.46(m, 5H), 7.40(s, 1H), 7.36~7.35(m, 1H) |
| I282 | δ = 8.76(d, 1H), 8.75(d, 1H), 8.73~8.71(m, 3H), 8.21(d, 1H), 8.19(d, 1H), 7.99~7.92(m, 7H), 7.66~7.59(m, 5H), 7.48(d, 1H), 7.39(s, 1H), 7.29~7.26 (m, 3H), 7.18~7.16(m, 3H). |
| I283 | δ = 9.18(d, 1H), 8.79(d, 1H), 8.64(d, 1H), 8.60(d, 1H), 8.36(d, 2H), 8.28~8.19(m, 5H), 8.14(d, 1H), 7.87~7.74(m, 5H), 7.72~7.68(m, 4H), 7.58~7.42(m, 4H), 7.37~7.34(m, 2H). |
| I285 | δ = 9.20(d, 1H), 8.82(d, 1H), 8.66(d, 1H), 8.58(s, 1H), 8.36(d, 2H), 8.31~8.24(m, 5H), 8.10(d, 1H), 7.84~7.74(m, 5H), 7.72~7.68(m, 4H), 7.54~7.44(m, 4H), 7.38~7.35(m, 2H). |
| I286 | δ = 9.14(d, 1H), 8.75(d, 1H), 8.61(d, 1H), 8.50(s, 1H), 8.38(d, 2H), 8.29~8.20(m, 5H), 8.13(d, 1H), 7.79~7.72(m, 5H), 7.69~7.64(m, 4H), 7.60~7.49(m, 4H), 7.36~7.32(m, 2H). |
| I290 | δ = 9.14(d, 1H), 8.75(d, 1H), 8.61(d, 1H), 8.53(d, 1H), 8.40(d, 2H), 8.29(d, 1H), 8.28~8.20(m, 4H), 8.12(d, 1H), 7.79~7.75(m, 2H), 7.74~7.70(m, 3H), 7.69~7.63(m, 4H), 7.60~7.51(m, 4H), 7.36~7.34(m, 2H). |
| I293 | δ = 9.27(d, 1H), 9.08(d, 1H), 8.72(d, 1H), 8.62(d, 1H), 8.56(d, 2H), 8.31(d, 1H), 8.29(d, 1H), 8.27~8.24(m, 3H), 8.16(d, 1H), 7.85~7.74(m, 5H), 7.73~7.68(m, 4H), 7.57~7.52(m, 4H), 7.38~7.35(m, 2H). |
| I294 | δ = 9.22(d, 1H), 8.98(d, 1H), 8.69(d, 1H), 8.59(d, 1H), 8.55(d, 2H), 8.34(d, 1H), 8.29~8.24(m, 3H), 8.11(d, 1H), 7.79~7.71(m, 5H), 7.70(d, 2H), 7.69~7.66(m, 3H), 7.57~7.50(m, 4H), 7.40~7.37(m, 2H). |
| I295 | δ = 9.22(s, 1H), 9.09(d, 1H), 8.66(s, 1H), 8.62(d, 1H), 8.53(s, 1H), 8.40~8.26(m, 2H), 8.24~8.17(m, 3H), 8.07(d, 1H), 7.91(d, 1H), 7.87~7.76(m, 5H), 7.65~7.63(q, 2H), 7.56~7.52(m, 4H), 7.43~7.33(m, 5H) |
| I296 | δ = 9.24(s, 1H), 9.09(d, 1H), 8.63(s, 1H), 8.62(d, 1H), 8.55(d, 1H), 8.40~8.26(m, 2H), 8.20~8.13(m, 3H), 8.09(d, 1H), 8.0(d, 1H), 7.86~7.76(m, 5H), 7.66~7.64(m, 2H), 7.57~7.54(m, 4H), 7.43~7.27 (m, 5H). |
| I297 | δ = 9.19(s, 1H), 9.14(d, 2H), 8.63(d, 1H), 8.37~8.27(m, 3H), 8.26~8.16(m, 3H), 8.10(d, 1H), 7.96(d, 1H), 7.88~7.77(m, 5H), 7.67~7.64(m, 2H), 7.56~7.52(m, 4H), 7.44~7.32(m, 5H) |
| I298 | δ = 9.29(s, 1H), 914(d, 1H), 8.67(s, 1H), 8.64(d, 1H), 8.59(s, 1H), 8.41~8.26(m, 2H), 8.26~8.16(m, 3H), 8.10(d, 1H), 8.0(d, 1H), 7.86~7.76(m, 5H), 7.68~7.65(m, 2H), 7.54~7.51(m, 4H), 7.45~7.36(m, 5H) |
| I299 | δ = 932(s, 1H), 916(d, 1H), 8.66(s, 1H), 8.65(s, 1H), 8.57(d, 1H), 8.41~8.26(m, 2H), 8.26~8.16(m, 3H), 8.10(d, 1H), 8.0(d, 1H), 7.88~7.76(m, 5H), 7.66~7.64(m, 2H), 7.57~7.54(m, 4H), 7.43~7.31(m, 3H), 7.33~7.30(m, 2H) |
| I300 | δ = 9.30(s, 1H), 9.17(0, 2H), 8.64(d, 1H), 8.41~8.27(m, 3H), 8.26~8.16(m, 3H), 8.10(d, 1H), 7.96(d, 1H), 7.88~7.77(m, 5H), 7.67~7.64(m, 2H), 7.56~7.52(m, 4H), 7.44~7.32(m, 5H) |
| I304 | δ = 9.27(s, 1H), 8.79(d, 1H), 8.63(d, 1H), 8.41~8.26(m, 2H), 8.26~8.16(m, 3H), 8.10(d, 1H), 8.0(d, 1H), 7.86~7.76(m, 5H), 7.68~7.65(m, 2H), 7.59(d, 1H), 7.54~7.51(m, 3H), 7.45~7.40(m, 3H) |
| I305 | δ = 9.19(s, 1H), 9.11(d, 1H), 8.79(d, 1H), 8.69(d, 1H), 8.62~8.58(m, 3H), 8.49~8.46(m, 2H), 8.37~8.32(m, 3H), 8.19(d, 1H), 7.66~7.57(m, 6H), 7.48(d, 1H), 7.39~7.29 (m, 3H). |
| I306 | δ = 9.18(s, 1H), 9.11(d, 1H), 8.80(d, 1H), 8.68(d, 1H), 8.54~8.48(m, 3H), 8.47~8.46(m, 2H), 8.38~8.31(m, 5H), 8.20(d, 1H), 7.66~7.59(m, 4H), 7.47(d, 1H), 7.37~7.30 (m, 3H). |
| I308 | δ = 9.12(s, 1H), 9.06(d, 2H), 8.96(d, 1H), 8.69(d, 1H), 8.68(d, 2H), 8.26(d, 1H), 7.89~7.82(m, 3H), 7.67~7.62(m, 3H), 7.55~7.49(m, 4H), 7.43~7.38(m, 3H), 7.37~7.35(m, 2H). 7.32~7.29(m, 2H). |
| I316 | δ = 9.17(s, 1H), 9.13(d, 1H), 9.08(d, 1H), 8.82~8.77(m, 3H), 8.84~8.81(m, 2H), 8.71(d, 1H), 8.68(d, 1H), 8.59(s, 1H), 7.79~7.74(m, 3H), 7.68~7.61(m, 2H), 7.57~7.52(m, 3H), 7.50(d, 1H), 7.48(d, 1H), 7.44~7.41(m, 4H), 7.37~7.29(m, 5H). |
| I317 | δ = 9.09(d, 1H), 9.06(d, 1H), 8.92(s, 1H), 8.81~8.78(m, 3H), 8.82~8.80(m, 2H), 8.69(d, 1H), 8.66(d, 1H), 8.58(s, 1H), 7.77~7.74(m, 3H), 7.66~7.59(m, 2H), 7.56~7.52(m, 3H), 7.47(d, 1H), 7.46~7.42(m, 5H), 7.37~7.32(m, 5H). |
| I321 | δ = 9.18(d, 1H), 9.09(d, 1H), 9.07(s, 1H), 8.92(d, 1H), 8.81(d, 1H), 8.69(d, 1H), 8.23~8.18(m, 2H), 7.94~7.90(m, 2H), 7.79~7.72(m, 3H), 7.59~'7.56(m, 2H), 7.49~7.44(m, 4H), 7.42~7.36(m, 4H). |
| I322 | δ = 9.23(d, 1H), 9.21(s, 1H), 9.17(d, 1H), 8.92(d, 1H), 8.80(d, 1H), 8.66(s, 1H), 8.59(s, 1H), 8.23~8.18(m, 2H), 7.98(d, 2H), 7.74~7.70(m, 5H), 7.55~7.51(m, 3H), 7.54~7.52(m, 3H), 7.49~7.44(m, 5H), 7.29~7.22(m, 4H). 7.18(t, 1H). |
| I325 | δ = 9.21(s, 1H), 9.06(d, 1H), 8.63(s, 1H), 8.59(d, 1H), 8.53(s, 1H), 8.39~8.26(m, 2H), 8.24~8.19(m, 3H), 8.06(d, 1H), 7.91(d, 1H), 7.87~7.77(m, 5H), 7.65~7.63(m, 2H), 7.56~7.51(m, 4H), 7.43~7.33(m, 5H) |
| I334 | δ = 9.16(s, 1H), 9.08(s, 2H), 8.66(d, 1H), 8.48~8.45(m, 3H), 8.39(d, 1H), 8.24 (s, 2H), 7.67~7.64(m, 2H), 7.56~7.51(m, 4H), 7.52~7.49(m, 4H), 7.43~7.39(m, 2H), 7.38~7.35(m, 3H). |

Example

1) Manufacture of Organic Light Emitting Device (Red Host)

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was performed for 5 minutes using UV in a UV cleaner. After that, the substrate was transferred to a plasma cleaner (PT), and plasma treatment was performed under vacuum for ITO work function and residual film removal, and the substrate was transferred to a thermal deposition apparatus for organic deposition.

On the transparent ITO electrode (anode), a hole injection layer 2-TNATA (4,4',4''-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 500 Å by, using a compound described in the following Table 5 as a host, and $(piq)_2(Ir)(acac)$ as a red phosphorescent dopant, 3% doping the $(piq)_2(Ir)(acac)$ to the host. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-6}$ torr to $10^{-8}$ torr for each material to be used in the OLED manufacture.

2) Driving Voltage and Light Emission Efficiency of Organic Electroluminescent Device For the organic electroluminescent devices manufactured as above, electroluminescent light emission (EL) properties were measured using M7000 manufactured by McScience Inc., and with the measurement results, T90 was measured when standard luminance was 6,000 cd/m² was using a lifetime measurement system (M6000) manufactured by McScience Inc. Properties of the organic electroluminescent devices of the present disclosure are as shown in the following Table 5.

TABLE 5

| | Compound | Driving Voltage (V) | Efficiency (cd/A) | Color Coordinate (x, y) | Lifetime ($T_{90}$) |
|---|---|---|---|---|---|
| Comparative Example 1 | A | 5.69 | 17.9 | (0.661, 0.332) | 21 |
| Comparative Example 2 | B | 5.58 | 16.1 | (0.661, 0.333) | 33 |
| Comparative Example 3 | C | 5.39 | 18.8 | (0.664, 0.331) | 11 |
| Comparative Example 4 | D | 5.50 | 15.6 | (0.665, 0.333) | 44 |
| Comparative Example 5 | E | 5.60 | 15.5 | (0.662, 0.333) | 21 |
| Comparative Example 6 | F | 5.65 | 16.2 | (0.661, 0.333) | 21 |
| Comparative Example 7 | G | 5.50 | 18.0 | (0.661, 0.332) | 39 |
| Comparative Example 8 | H | 5.49 | 16.9 | (0.661, 0.334) | 40 |
| Comparative Example 9 | I | 5.68 | 16.8 | (0.661, 0.335) | 69 |
| Comparative Example 10 | J | 5.78 | 17.7 | (0.661, 0.333) | 39 |
| Comparative Example 11 | K | 5.66 | 15.9 | (0.661, 0.333) | 30 |
| Comparative Example 12 | L | 5.59 | 14.8 | (0.661, 0.333) | 28 |
| Comparative Example 13 | M | 5.18 | 15.2 | (0.661, 0.333) | 0 |
| Comparative Example 14 | N | 5.08 | 15.4 | (0.661, 0.333) | 39 |
| Comparative Example 15 | O | 4.79 | 16.8 | (0.661, 0.336) | 26 |
| Comparative Example 16 | P | 4.80 | 17.2 | (0.661, 0.331) | 55 |
| Comparative Example 17 | Q | 4.69 | 15.9 | (0.661, 0.333) | 32 |
| Example 1 | I1 | 4.49 | 18.2 | (0.661, 0.332) | 91 |
| Example 2 | I2 | 4.40 | 18.0 | (0.661, 0.332) | 99 |
| Example 3 | I4 | 4.48 | 18.7 | (0.661, 0.332) | 121 |
| Example 4 | I5 | 4.47 | 17.2 | (0.662, 0.333) | 100 |
| Example 5 | I6 | 4.52 | 19.2 | (0.662, 0.333) | 124 |
| Example 6 | I10 | 4.40 | 20.6 | (0.661, 0.333) | 127 |
| Example 7 | I11 | 4.39 | 17.0 | (0.661, 0.333) | 130 |
| Example 8 | I12 | 4.42 | 17.2 | (0.662, 0.334) | 120 |
| Example 9 | I17 | 4.38 | 18.4 | (0.663, 0.332) | 119 |
| Example 10 | I18 | 4.30 | 18.7 | (0.661, 0.333) | 109 |
| Example 11 | I19 | 4.10 | 19.2 | (0.659, 0.333) | 103 |
| Example 12 | I27 | 4.05 | 17.2 | (0.658, 0.332) | 100 |
| Example 13 | I28 | 4.29 | 17.1 | (0.661, 0.331) | 121 |
| Example 14 | I29 | 3.97 | 18.0 | (0.661, 0.331) | 118 |
| Example 15 | I31 | 4.22 | 18.8 | (0.663, 0.332) | 142 |
| Example 16 | I32 | 3.93 | 19.0 | (0.662, 0.331) | 97 |
| Example 17 | I33 | 3.99 | 18.7 | (0.663, 0.334) | 98 |
| Example 18 | I34 | 3.91 | 19.9 | (0.664, 0.332) | 94 |
| Example 19 | I35 | 3.98 | 18.0 | (0.663, 0.33) | 89 |
| Example 20 | I37 | 4.12 | 18.5 | (0.662, 0.332) | 94 |
| Example 21 | I38 | 3.85 | 17.9 | (0.662, 0.331) | 106 |
| Example 22 | I39 | 4.09 | 19.4 | (0.661, 0.331) | 89 |
| Example 23 | I40 | 3.92 | 20.7 | (0.661, 0.333) | 86 |
| Example 24 | I41 | 3.97 | 20.3 | (0.659, 0.332) | 108 |
| Example 25 | I42 | 3.90 | 17.6 | (0.660, 0.333) | 112 |
| Example 26 | I43 | 4.11 | 18.6 | (0.660, 0.332) | 127 |
| Example 27 | I45 | 4.06 | 19.9 | (0.660, 0.332) | 122 |
| Example 28 | I46 | 4.21 | 17.9 | (0.661, 0.332) | 132 |
| Example 29 | I47 | 4.30 | 18.9 | (0.66, 0.331) | 127 |
| Example 30 | I48 | 4.21 | 20.9 | (0.66, 0.331) | 118 |
| Example 31 | I54 | 3.92 | 17.9 | (0.66, 0.332) | 109 |
| Example 32 | I55 | 3.98 | 18.9 | (0.659, 0.333) | 132 |
| Example 33 | I56 | 4.03 | 19.8 | (0.661, 0.332) | 125 |
| Example 34 | I57 | 3.99 | 20.7 | (0.661, 0.333) | 117 |
| Example 35 | I61 | 3.97 | 19.8 | (0.661, 0.333) | 121 |
| Example 36 | I62 | 3.92 | 19.5 | (0.66, 0.332) | 124 |
| Example 37 | I63 | 3.95 | 18.9 | (0.66, 0.338) | 109 |
| Example 38 | I64 | 3.97 | 20.4 | (0.660, 0.330) | 109 |
| Example 39 | I65 | 4.12 | 19.9 | (0.660, 0.331) | 99 |
| Example 40 | I67 | 4.08 | 19.8 | (0.659, 0.332) | 94 |
| Example 41 | I68 | 4.17 | 20.9 | (0.661, 0.331) | 83 |
| Example 42 | I76 | 3.93 | 21.2 | (0.662, 0.332) | 99 |
| Example 43 | I77 | 3.89 | 22.9 | (0.662, 0.333) | 107 |
| Example 44 | I79 | 4.12 | 16.6 | (0.661, 0.332) | 121 |
| Example 45 | I80 | 3.88 | 19.7 | (0.663, 0.330) | 109 |
| Example 46 | I81 | 3.90 | 17.9 | (0.662, 0.330) | 107 |
| Example 47 | I82 | 4.22 | 20.5 | (0.661, 0.330) | 102 |
| Example 48 | I83 | 4.18 | 20.6 | (0.660, 0.330) | 100 |
| Example 49 | I85 | 3.99 | 20.7 | (0.660, 0.330) | 99 |
| Example 50 | I86 | 4.12 | 21.9 | (0.660, 0.331) | 109 |
| Example 51 | I87 | 3.98 | 19.9 | (0.659, 0.332) | 132 |
| Example 52 | I88 | 4.00 | 21.5 | (0.660, 0.330) | 99 |
| Example 53 | I89 | 4.22 | 21.6 | (0.660, 0.331) | 96 |
| Example 54 | I90 | 4.28 | 21.7 | (0.662, 0.332) | 89 |
| Example 55 | I91 | 4.22 | 21.9 | (0.662, 0.332) | 88 |
| Example 56 | I92 | 4.18 | 22.9 | (0.661, 0.332) | 90 |
| Example 57 | I93 | 3.89 | 21.9 | (0.661, 0.332) | 103 |
| Example 58 | I94 | 4.10 | 21.7 | (0.662, 0.332) | 101 |
| Example 59 | I95 | 4.01 | 21.9 | (0.661, 0.331) | 109 |
| Example 60 | I96 | 3.99 | 19.9 | (0.662, 0.331) | 121 |
| Example 61 | I101 | 3.98 | 19.9 | (0.662, 0.333) | 118 |
| Example 62 | I102 | 3.98 | 19.0 | (0.663, 0.332) | 121 |
| Example 63 | I107 | 4.00 | 18.8 | (0.66, 0.331) | 119 |
| Example 64 | I117 | 3.92 | 19.9 | (0.661, 0.332) | 110 |
| Example 65 | I118 | 4.11 | 18.9 | (0.661, 0.332) | 137 |
| Example 66 | I119 | 4.10 | 19.9 | (0.659, 0.332) | 129 |
| Example 67 | I120 | 3.99 | 22.9 | (0.660, 0.332) | 121 |
| Example 68 | I127 | 4.21 | 22.0 | (0.660, 0.332) | 118 |
| Example 69 | I128 | 4.15 | 18.8 | (0.661, 0.331) | 120 |
| Example 70 | I130 | 3.98 | 23.9 | (0.662, 0.332) | 94 |
| Example 71 | I132 | 3.88 | 22.6 | (0.662, 0.332) | 98 |
| Example 72 | I142 | 3.86 | 22.7 | (0.662, 0.332) | 96 |
| Example 73 | I143 | 3.85 | 21.9 | (0.663, 0.332) | 99 |
| Example 74 | I144 | 3.96 | 22.5 | (0.663, 0.331) | 101 |

TABLE 5-continued

| Compound | Driving Voltage (V) | Efficiency (cd/A) | Color Coordinate (x, y) | Lifetime (T90) |
|---|---|---|---|---|
| Example 75 | I145 | 3.97 | 18.6 | (0.664, 0.332) | 121 |
| Example 76 | I152 | 4.09 | 20.22 | (0.663, 0.333) | 98 |
| Example 77 | I158 | 3.98 | 21.9 | (0.662, 0.332) | 100 |
| Example 78 | I160 | 3.81 | 20.8 | (0.662, 0.332) | 97 |
| Example 79 | I162 | 3.99 | 19.9 | (0.661, 0.332) | 96 |
| Example 80 | I163 | 3.97 | 21.3 | (0.660, 0.332) | 92 |
| Example 81 | I164 | 3.99 | 22.8 | (0.659, 0.332) | 101 |
| Example 82 | I171 | 4.01 | 22.9 | (0.659, 0.332) | 112 |
| Example 83 | I172 | 4.01 | 22.7 | (0.659, 0.332) | 109 |
| Example 84 | I173 | 4.08 | 19.9 | (0.660, 0.332) | 107 |
| Example 85 | I174 | 4.07 | 20.9 | (0.660, 0.332) | 104 |
| Example 86 | I179 | 4.00 | 19.8 | (0.660, 0.332) | 102 |
| Example 87 | I180 | 4.10 | 18.9 | (0.662, 0.332) | 109 |
| Example 88 | I186 | 4.03 | 20.4 | (0.660, 0.339) | 112 |
| Example 89 | I191 | 4.08 | 20.9 | (0.660, 0.332) | 119 |
| Example 90 | I192 | 4.00 | 22.9 | (0.660, 0.331) | 109 |
| Example 91 | I195 | 4.11 | 19.8 | (0.661, 0.331) | 121 |
| Example 92 | I196 | 4.09 | 22.8 | (0.661, 0.331) | 124 |
| Example 93 | I198 | 4.03 | 20.9 | (0.662, 0.33) | 117 |
| Example 94 | I199 | 4.03 | 17.3 | (0.662, 0.331) | 112 |
| Example 95 | I200 | 4.09 | 18.8 | (0.662, 0.331) | 111 |
| Example 96 | I204 | 4.03 | 18.9 | (0.663, 0.331) | 109 |
| Example 97 | I206 | 4.03 | 18.9 | (0.661, 0.331) | 109 |
| Example 98 | I214 | 4.12 | 19.8 | (0.662, 0.332) | 99 |
| Example 99 | I218 | 3.96 | 20.3 | (0.661, 0.331) | 89 |
| Example 100 | I222 | 3.96 | 19.8 | (0.661, 0.331) | 98 |
| Example 101 | I229 | 3.97 | 22.0 | (0.661, 0.331) | 95 |
| Example 102 | I230 | 3.87 | 24.9 | (0.661, 0.331) | 89 |
| Example 103 | I232 | 3.98 | 23.9 | (0.660, 0.331) | 88 |
| Example 104 | I233 | 3.99 | 21.1 | (0.662, 0.331) | 89 |
| Example 105 | I235 | 4.01 | 19.9 | (0.66, 0.331) | 90 |
| Example 106 | I244 | 3.99 | 18.7 | (0.662, 0.331) | 97 |
| Example 107 | I245 | 3.89 | 22.0 | (0.662, 0.332) | 99 |
| Example 108 | I246 | 3.99 | 21.0 | (0.662, 0.331) | 104 |
| Example 109 | I247 | 3.98 | 23.8 | (0.660, 0.331) | 113 |
| Example 110 | I248 | 3.98 | 22.0 | (0.666, 0.331) | 112 |
| Example 111 | I249 | 4.12 | 22.9 | (0.661, 0.332) | 118 |
| Example 112 | I250 | 4.09 | 20.9 | (0.661, 0.332) | 121 |
| Example 113 | I252 | 4.11 | 21.1 | (0.661, 0.332) | 120 |
| Example 114 | I258 | 4.10 | 20.9 | (0.661, 0.333) | 120 |
| Example 115 | I261 | 4.09 | 20.7 | (0.662, 0.333) | 119 |
| Example 116 | I262 | 4.11 | 22.7 | (0.660, 0.333) | 121 |
| Example 117 | I263 | 4.11 | 18.7 | (0.660, 0.333) | 126 |
| Example 118 | I266 | 4.11 | 19.2 | (0.660, 0.332) | 109 |
| Example 119 | I267 | 4.00 | 19.0 | (0.660, 0.332) | 107 |
| Example 120 | I268 | 4.03 | 23.1 | (0.660, 0.332) | 89 |
| Example 121 | I274 | 3.97 | 22.0 | (0.660, 0.332) | 98 |
| Example 122 | I275 | 3.96 | 22.9 | (0.660, 0.339) | 90 |
| Example 123 | I276 | 3.94 | 22.8 | (0.662, 0.331) | 95 |
| Example 124 | I278 | 3.99 | 18.9 | (0.662, 0.332) | 104 |
| Example 125 | I279 | 3.99 | 19.0 | (0.661, 0.331) | 110 |
| Example 126 | I281 | 3.99 | 21.9 | (0.661, 0.332) | 87 |
| Example 127 | I282 | 3.91 | 22.6 | (0.661, 0.332) | 80 |
| Example 128 | I283 | 3.87 | 22.9 | (0.661, 0.337) | 89 |
| Example 129 | I285 | 3.89 | 22.7 | (0.661, 0.339) | 90 |
| Example 130 | I286 | 3.92 | 23.8 | (0.660, 0.339) | 88 |
| Example 131 | I290 | 3.88 | 22.0 | (0.659, 0.339) | 92 |
| Example 132 | I293 | 3.90 | 21.9 | (0.660, 0.339) | 90 |
| Example 133 | I294 | 3.88 | 22.4 | (0.660, 0.339) | 88 |
| Example 134 | I295 | 3.99 | 22.9 | (0.671, 0.327) | 100 |
| Example 135 | I297 | 3.78 | 21.9 | (0.666, 0.322) | 108 |
| Example 136 | I298 | 3.83 | 22.3 | (0.667, 0.321) | 119 |
| Example 137 | I299 | 3.97 | 19.8 | (0.665, 0.328) | 89 |
| Example 138 | I300 | 3.82 | 21.8 | (0.668, 0.324) | 88 |
| Example 139 | I304 | 3.84 | 22.1 | (0.669, 0.322) | 110 |
| Example 140 | I305 | 3.90 | 20.6 | (0.662, 0.330) | 94 |
| Example 141 | I306 | 3.94 | 20.6 | (0.663, 0.329) | 90 |
| Example 142 | I308 | 3.84 | 21.9 | (0.663, 0.330) | 92 |
| Example 143 | I316 | 3.80 | 20.7 | (0.662, 0.329) | 89 |
| Example 144 | I317 | 4.01 | 20.8 | (0.663, 0.324) | 100 |
| Example 145 | I321 | 3.97 | 19.4 | (0.667, 0.329) | 92 |
| Example 146 | I322 | 3.89 | 19.9 | (0.669, 0.327) | 78 |
| Example 147 | I325 | 3.99 | 18.5 | (0.671, 0.319) | 85 |
| Example 148 | I334 | 3.78 | 17.9 | (0.672, 0.320) | 86 |

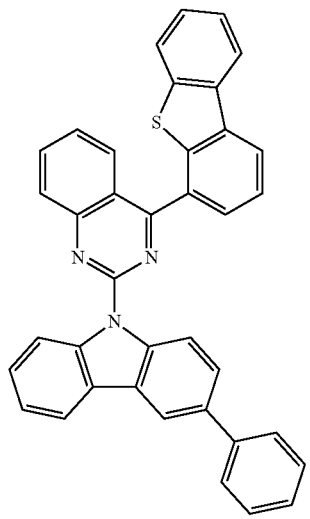

A

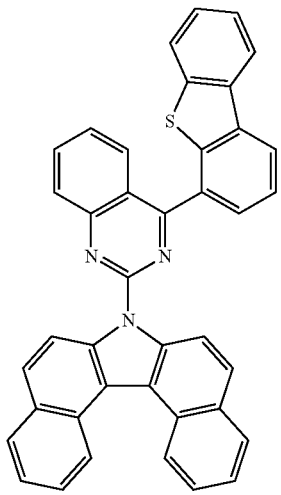

B

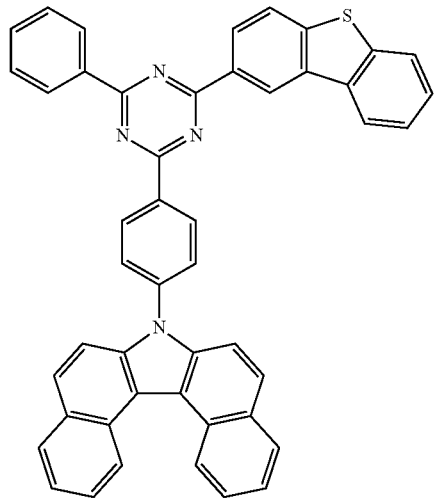

C

D
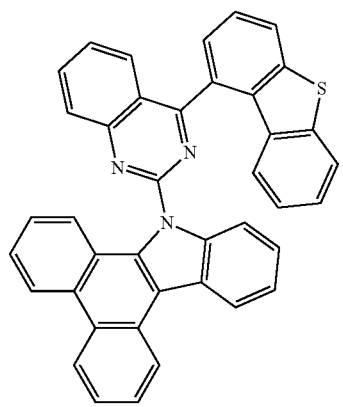
E
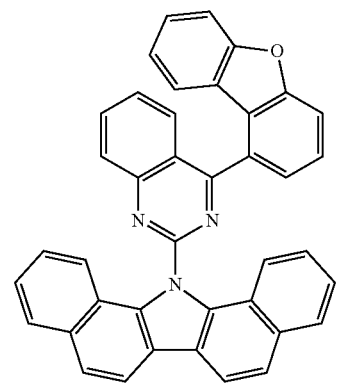
F
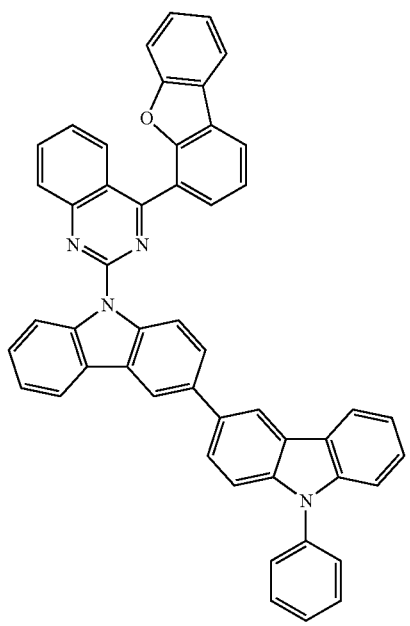
G
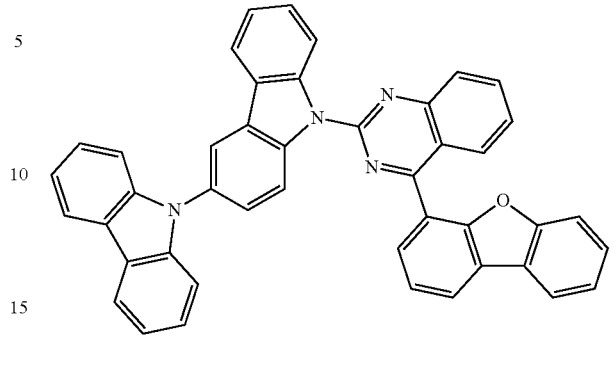
H
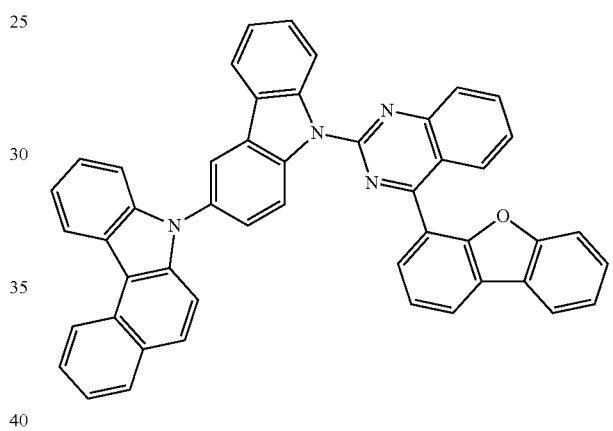
I
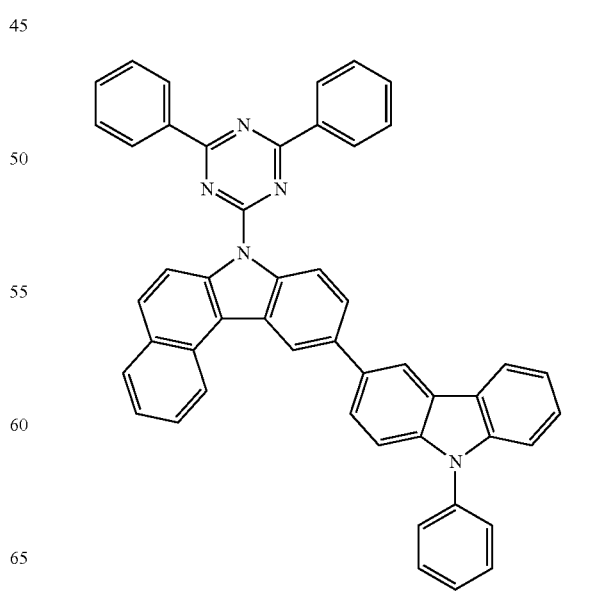

J
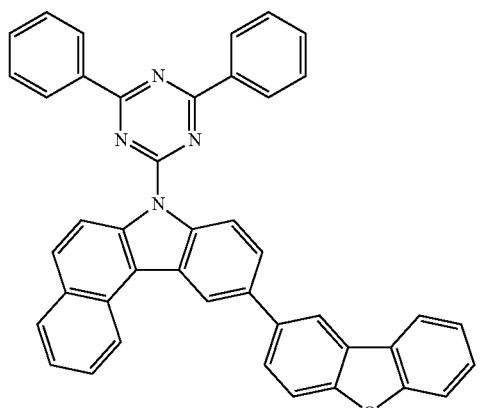
K
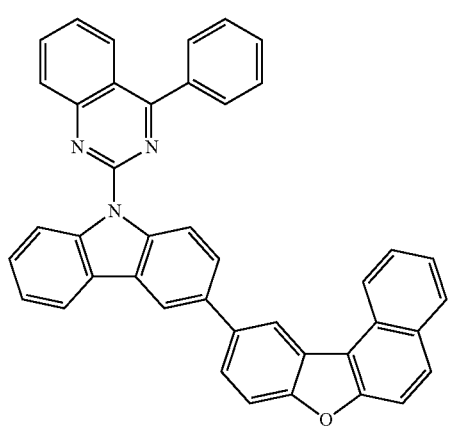
L
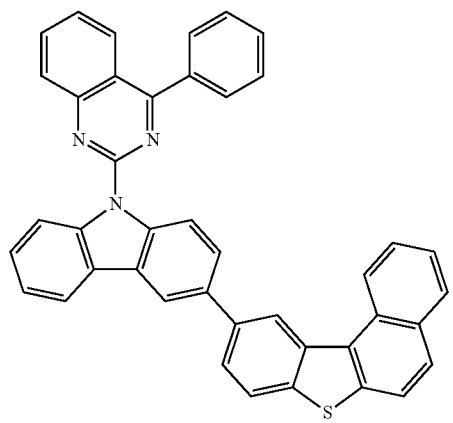
M
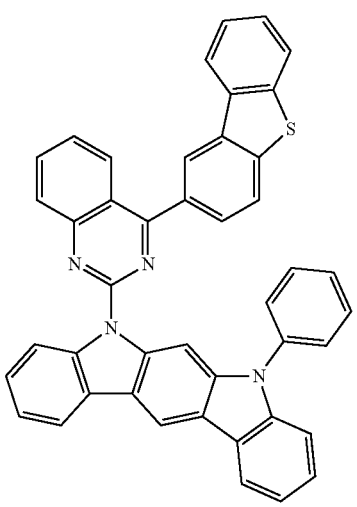
N
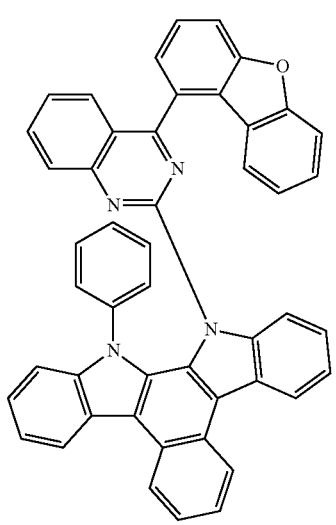
O
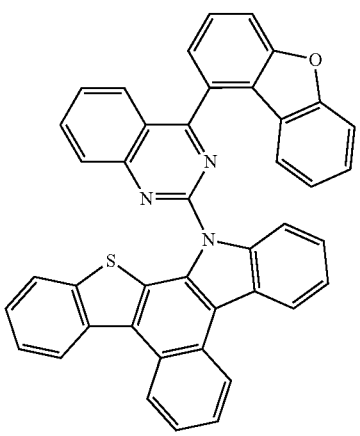

189
-continued

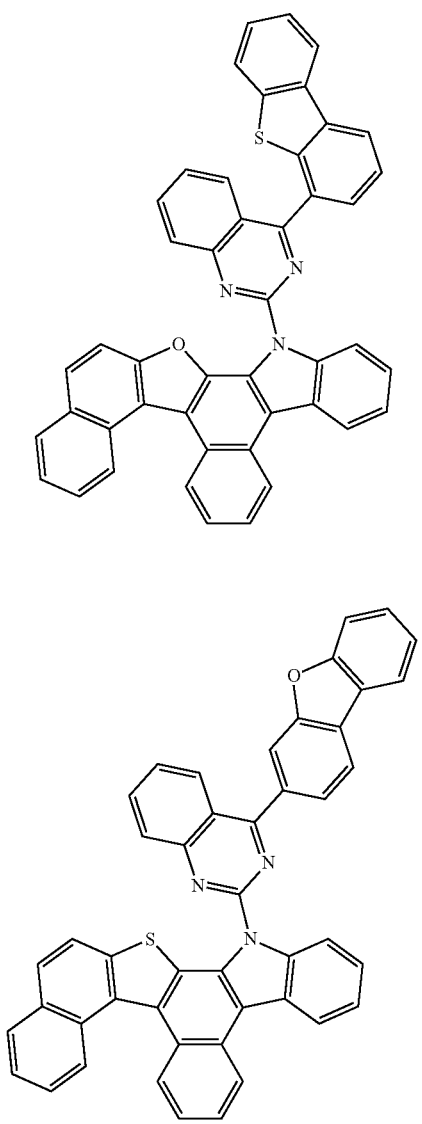

P

Q

When substituting the heteroring that facilitates electron transfer with dibenzofuran that does not have a fused ring as in the compounds of E, F, G, N, O and Q, the dibenzofuran pushes electrons simultaneously lowering HOMO and LUMO. As a result, electrons and holes become unbalanced, and it was identified that a lifetime was reduced in the organic light emitting device as shown in Table 5.

In addition, it was identified that the compounds of A, B, C, D, M and P substituted with dibenzothiophene that does not have a fused ring tended to have a relatively decreased driving voltage when compared to the dibenzothiophene that does not have a fused ring, but had a reduced lifetime due to imbalance of charges as in the case of being substituted with the dibenzofuran that does not have a fused ring.

No special effects were obtained when substituting the carbazole derivative (carbazole moiety) with dibenzofuran or other substituents as in the compounds of J, K and L, and it is considered that such a substituent degrades a hole transfer ability based on the fact that the lifetime was reduced compared to the structure of I.

190

The invention claimed is:

1. A heterocyclic compound represented by any one of the following Chemical Formulae 6 to 9:

[Chemical Formula 6]

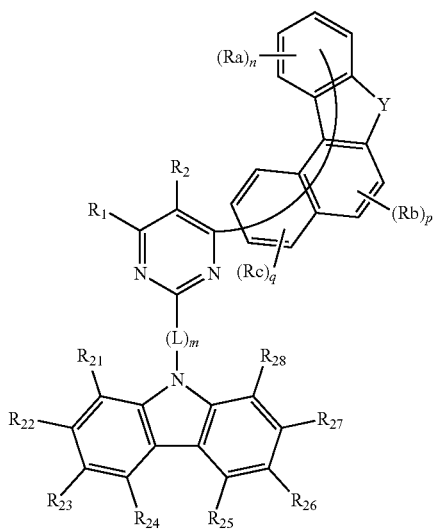

[Chemical Formula 7]

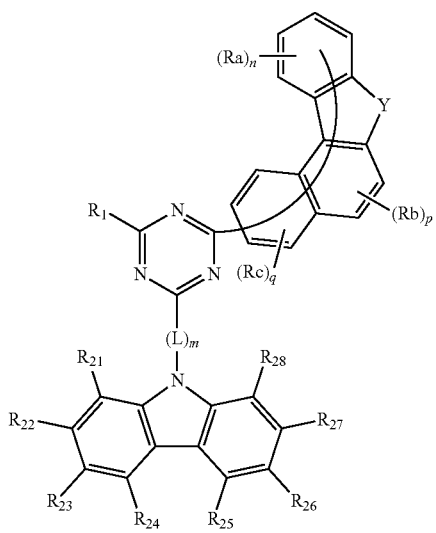

[Chemical Formula 8]

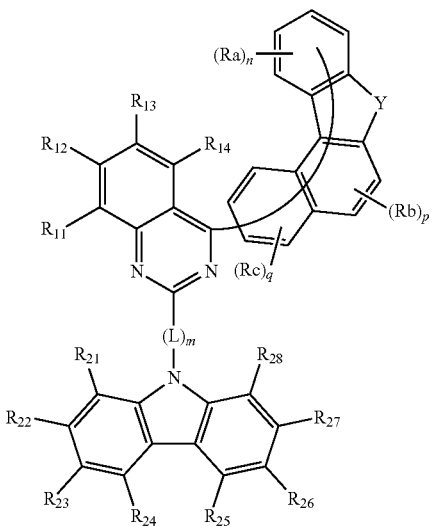

[Chemical Formula 9]

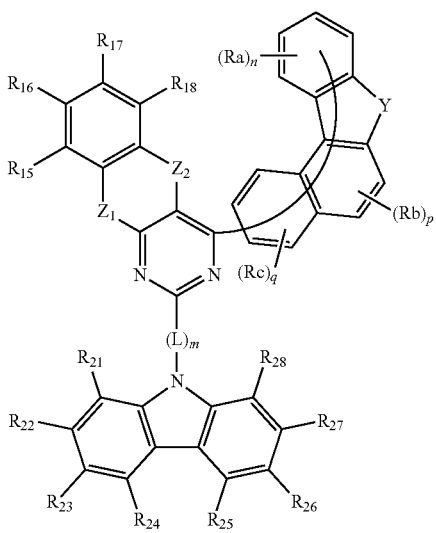

in Chemical Formulae 6 to 9, $R_1$, $R_2$, and $R_{11}$ to $R_{18}$ are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group;

$R_{21}$ to $R_{28}$ are the same as or different from each other, and each independently selected from the group consisting of hydrogen; a substituted or unsubstituted C6 to C40 aryl group; a substituted or unsubstituted C2 to C40 heteroaryl group; and a diarylamine group, or two or more groups adjacent to each other bond to each other to form a substituted or unsubstituted C6 to C40 aromatic hydrocarbon ring or a substituted or unsubstituted C2 to C40 aromatic heteroring, in chemical formula 8, wherein when $R_{22}$ and $R_{23}$; or $R_{26}$ and $R_{27}$; bond to each other to form a ring, a ring is indene ring unsubstituted or substituted with a methyl group; a benzofuran ring; a benzothiophene ring; or an indole ring unsubstituted or substituted with a phenyl group, $Z_1$ and $Z_2$ are the same as or different from each other, and each independently a direct bond; O; or S; one of $Z_1$ and $Z_2$ is a direct bond, Y is O; S; or CRR';

L is a direct bond; a substituted or unsubstituted arylene group; or a substituted or unsubstituted heteroarylene group;

m is an integer of 0 to 5;

$R_a$ to $R_c$, R, and R' are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or a substituted or unsubstituted aliphatic or aromatic heteroring, n and q are each an integer of 0 to 4, and when n is 2 or greater, $R_a$s are the same as or different from each other, and when q is 2 or greater, $R_c$s are the same as or different from each other, p is an integer of 0 to 2, and when p is an integer of 2, $R_b$s are the same as or different from each other; and $n+p+q \leq 9$, wherein in chemical formulae 6 and 7, at least one of $R_{21}$ to $R_{28}$ is a substituted or unsubstituted C2 to C40 heteroaryl group; or a diarylamine group, or two or more groups adjacent to each other bond to each other to form a substituted or unsubstituted C6 to C40 aromatic hydrocarbon ring or a substituted or unsubstituted C2 to C40 aromatic heteroring.

2. The heterocyclic compound of claim 1, wherein

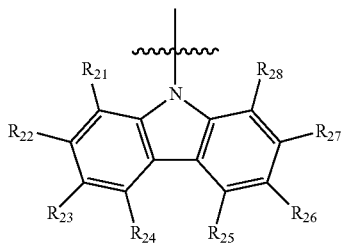

is represented by the following Chemical Formula 10:

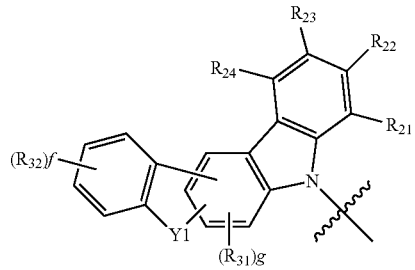

in Chemical Formula 10,

is a site linked to L of Chemical Formulae 6 to 9;

$R_{21}$ to $R_{24}$ and $R_{31}$ are the same as or different from each other, and each independently selected from the group consisting of hydrogen; a substituted or unsubstituted C6 to C40 aryl group; a substituted or unsubstituted C2 to C40 heteroaryl group; and a diarylamine group, or two or more groups adjacent to each other bond to each other to form a substituted or unsubstituted C6 to C40 aromatic hydrocarbon ring or a substituted or unsubstituted C2 to C40 aromatic heteroring, Y1 is O, S, $CR_{41}R_{42}$; or $NR_{43}$;

$R_{32}$ and $R_{41}$ to $R_{43}$ are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, f is an integer of 0 to 4, and when f is 2 or greater, $R_{32}$s are the same as or different from each other, g is an integer of 0 to 2, and when g is 2 or greater, $R_{31}$s are the same as or different from each other.

3. The heterocyclic compound of claim 1, wherein $R_a$ to $R_c$ are hydrogen.

4. The heterocyclic compound of claim 1, wherein any one of the following Chemical Formulae 6 to 9 is represented by any one of the following compounds:

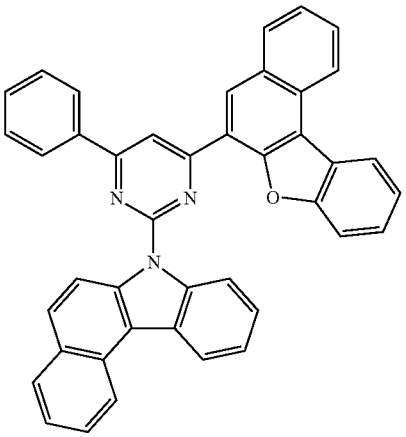

I1

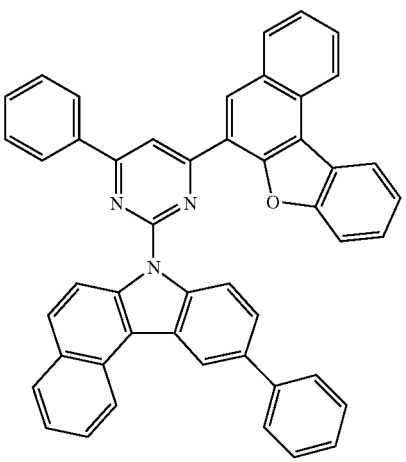

I2

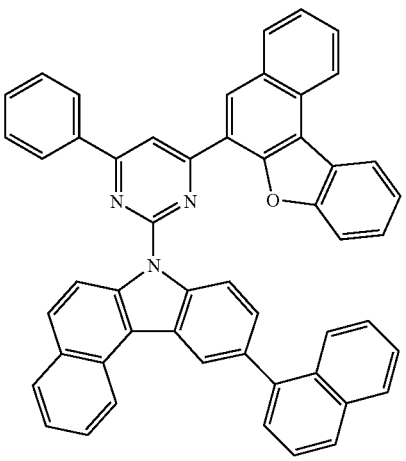

I3

I4
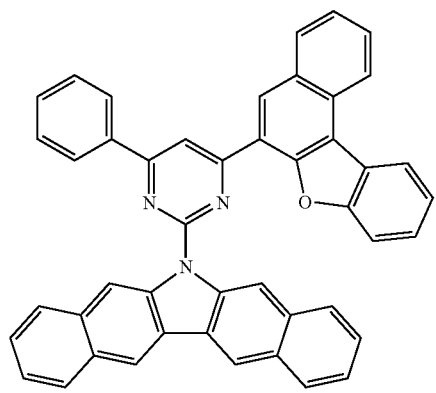
I5
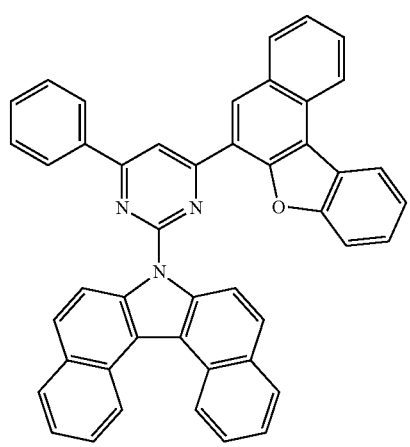
I6
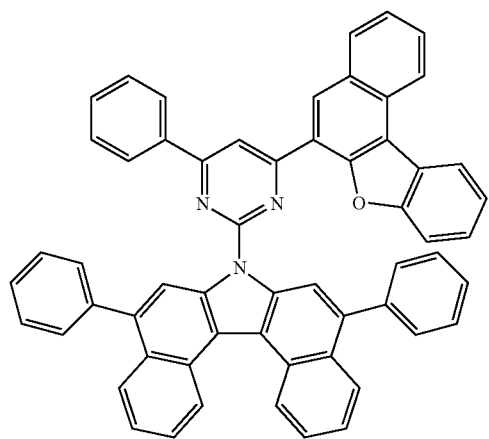
I7
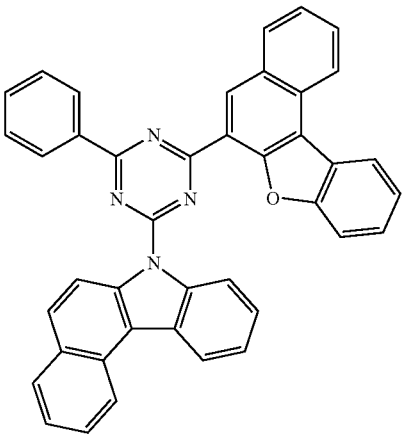
I8
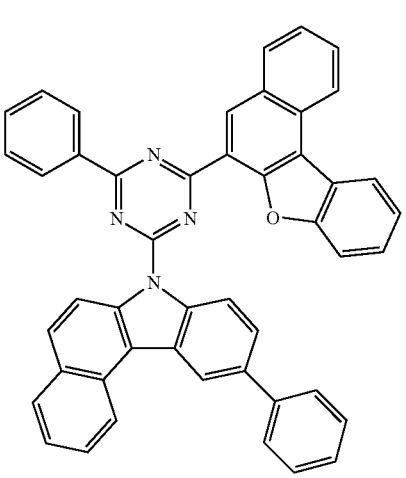
I9
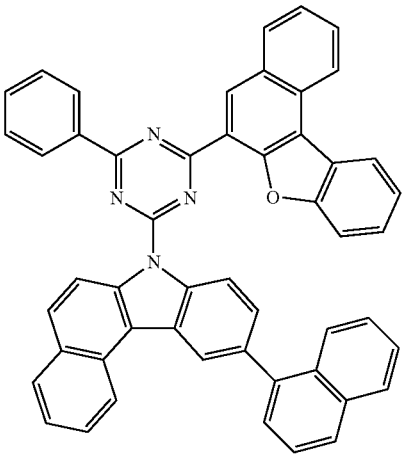

I10
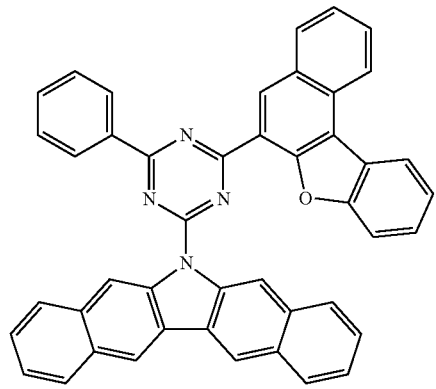
I11
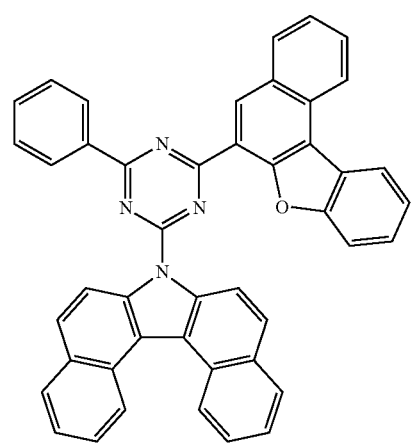
I12
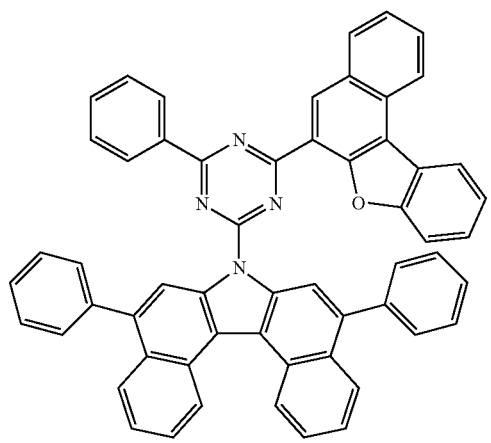
I13
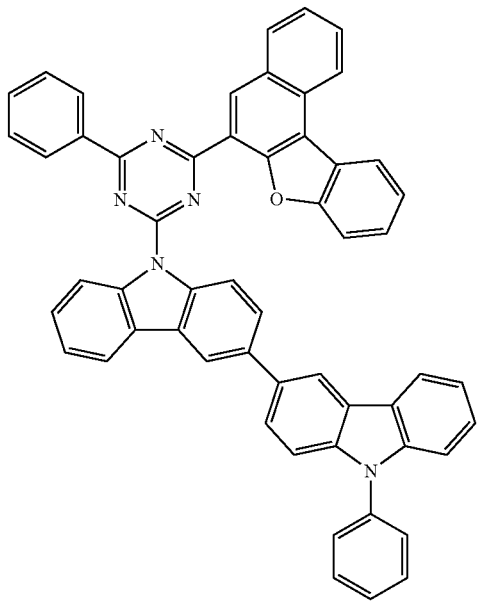
I14
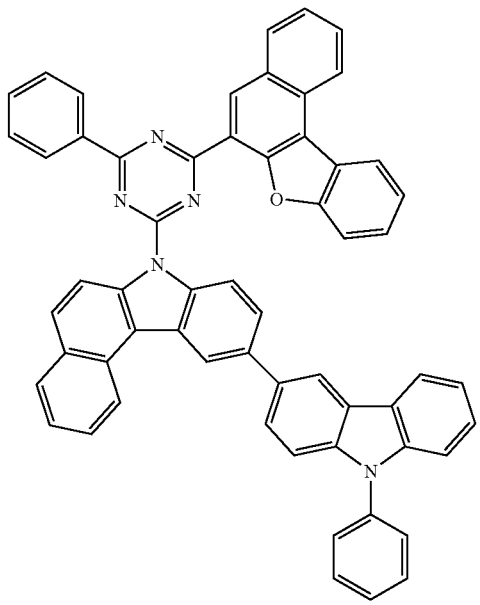

I15
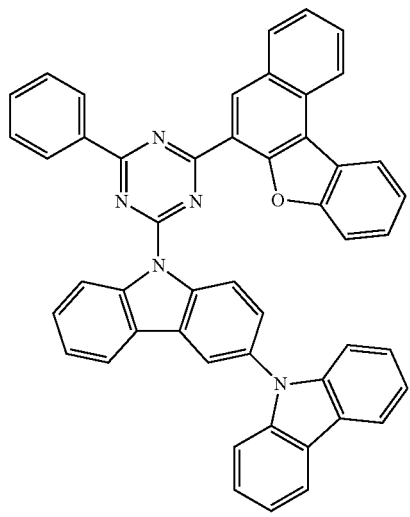
I16
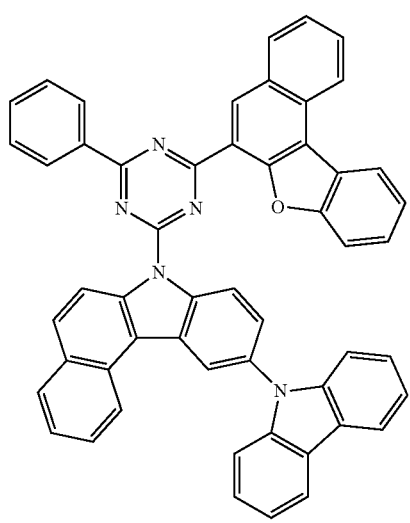
I17
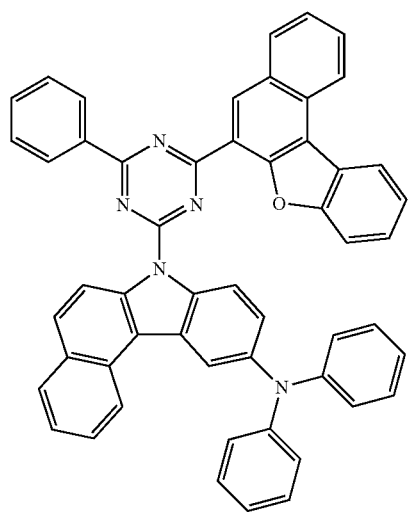
I18
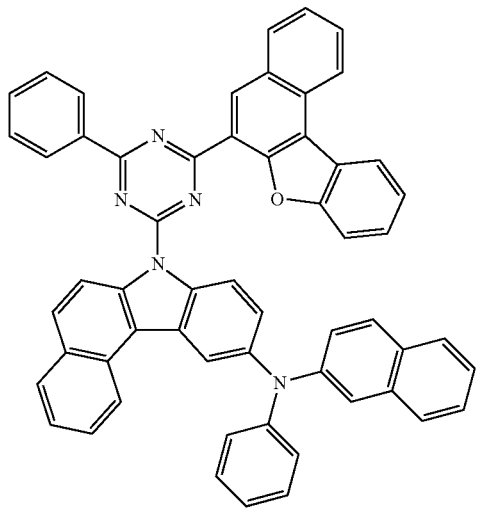
I19
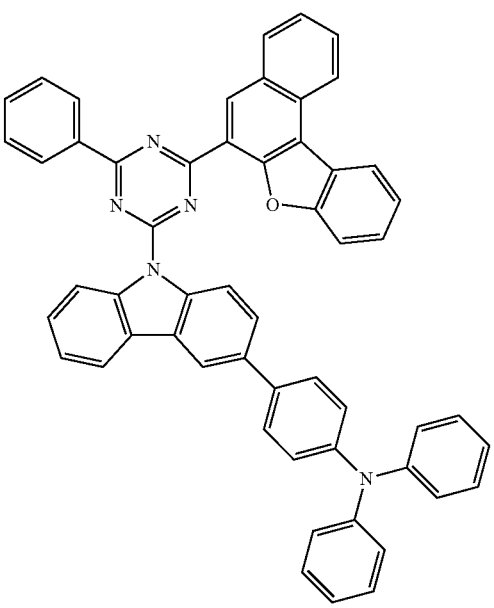
I20
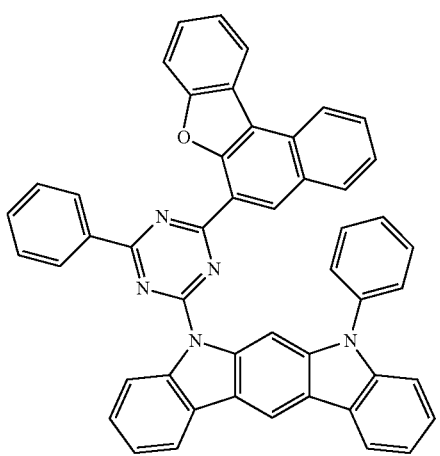

-continued
I21
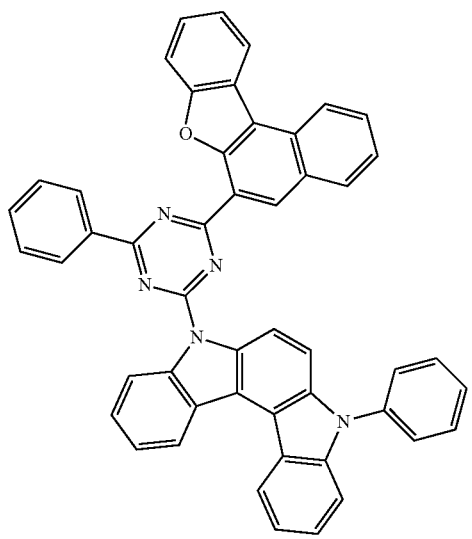
I22
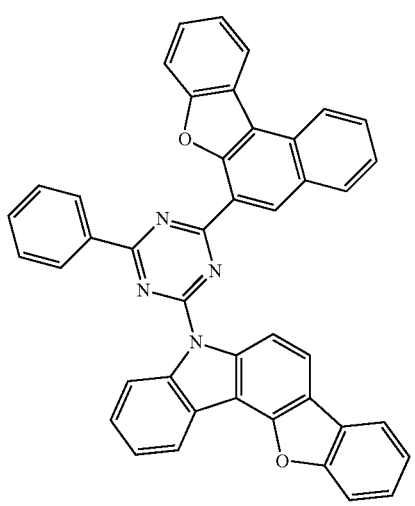
I23
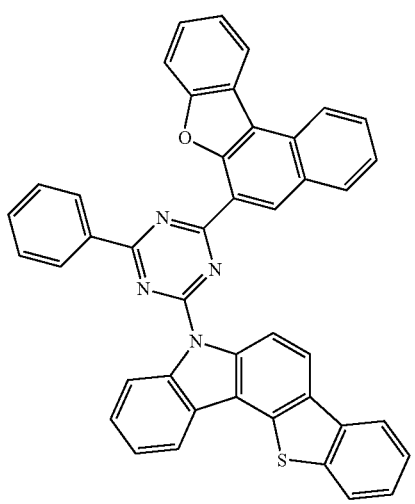
-continued
I24
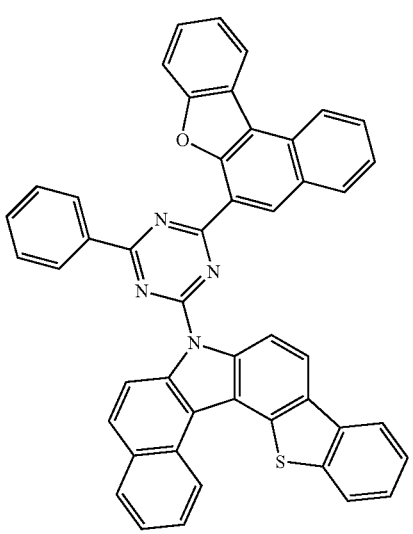
I25
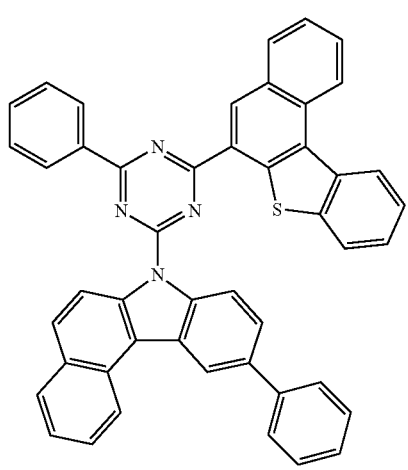
I26
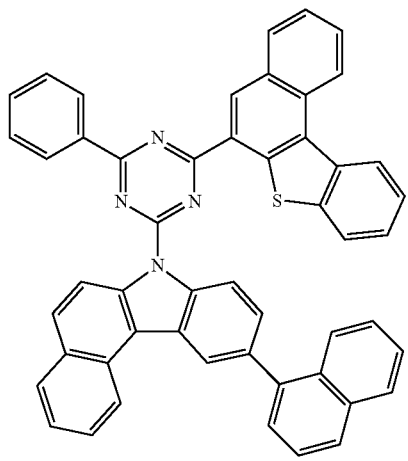

I 27
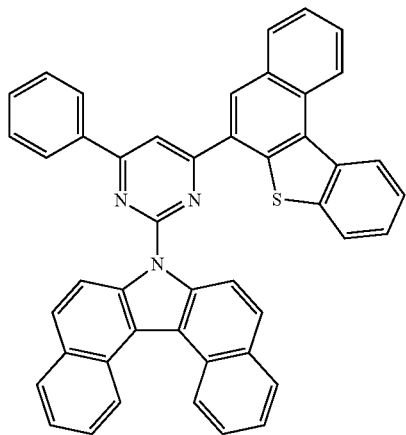
I 28
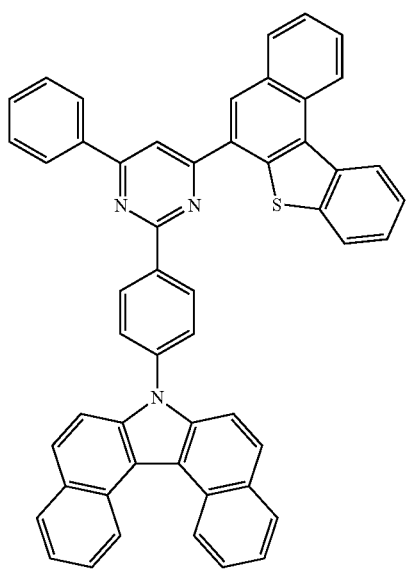
I 29
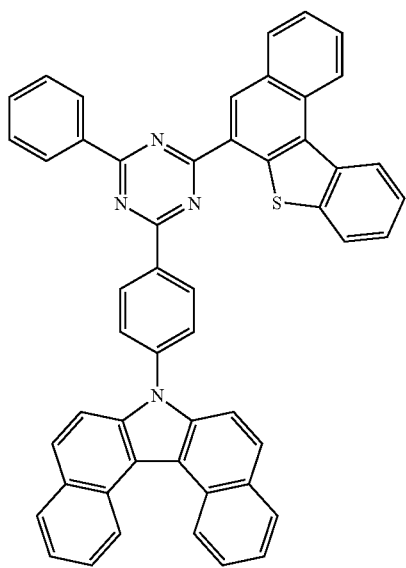
I 30
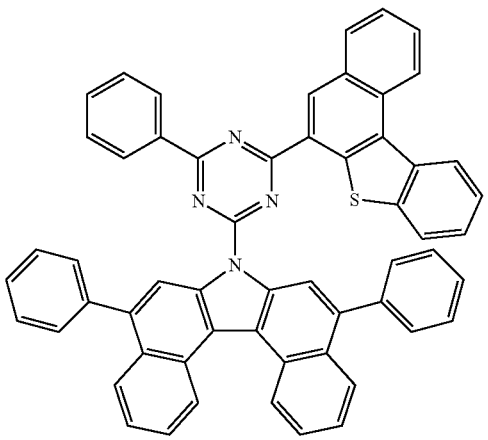
I 31
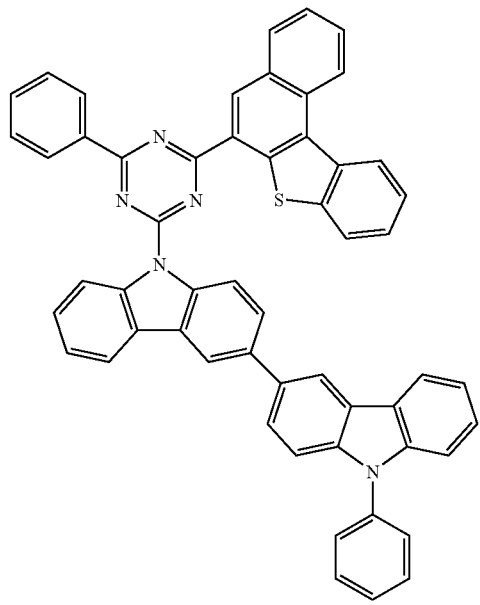
I 32
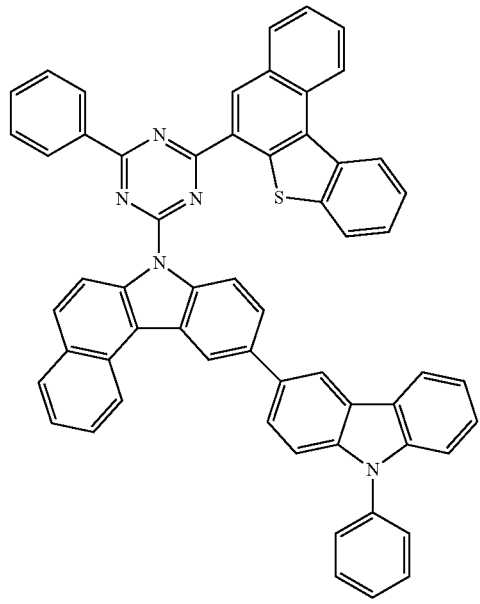

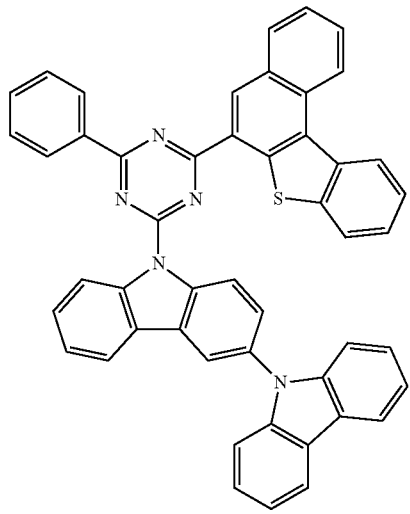
I 33
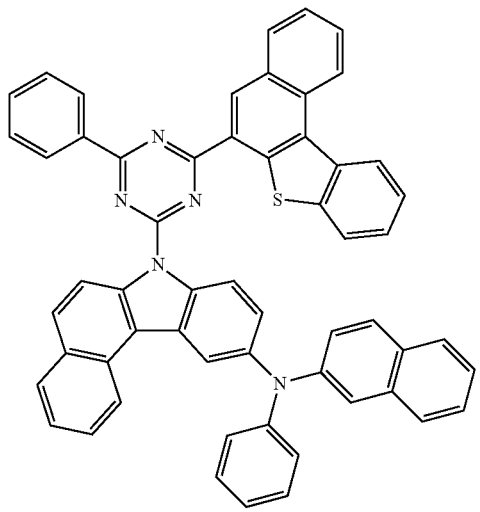
I 36
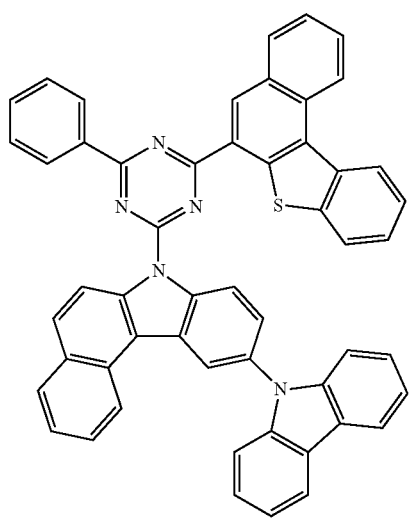
I 34
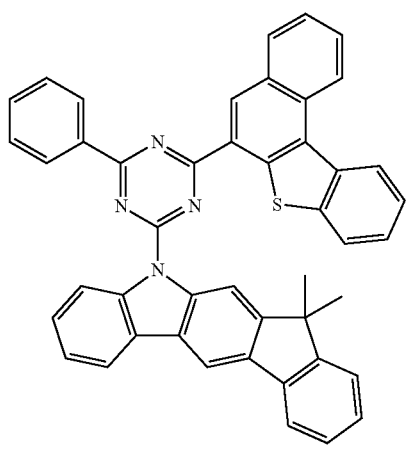
I 37
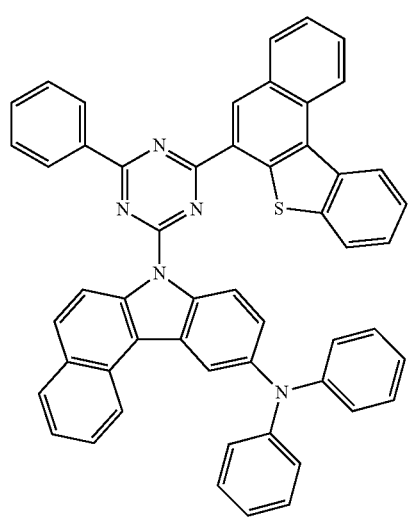
I 35
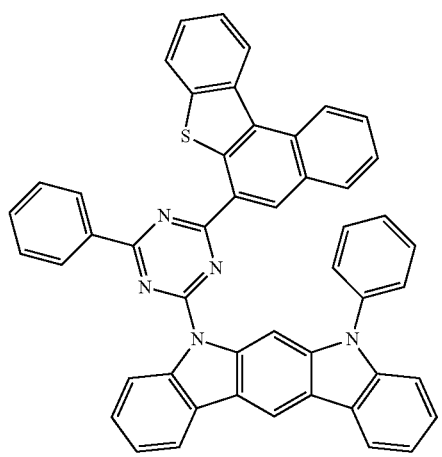
I 38

I 39
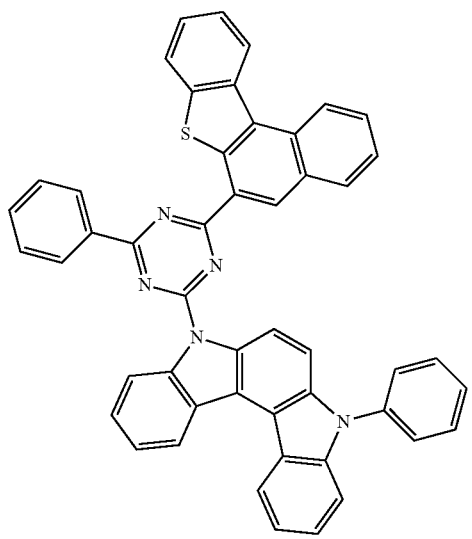
I 40
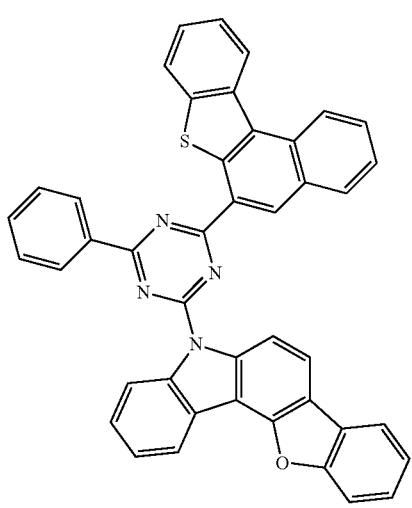
I 41
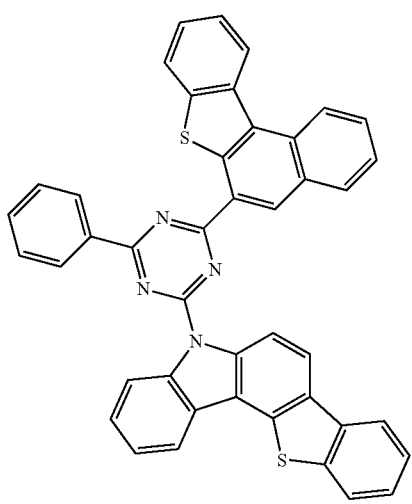
I 42
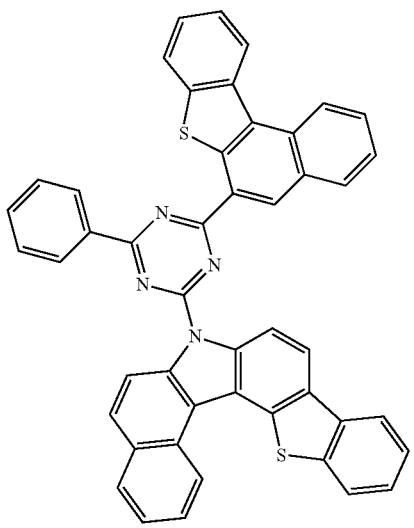
I 43
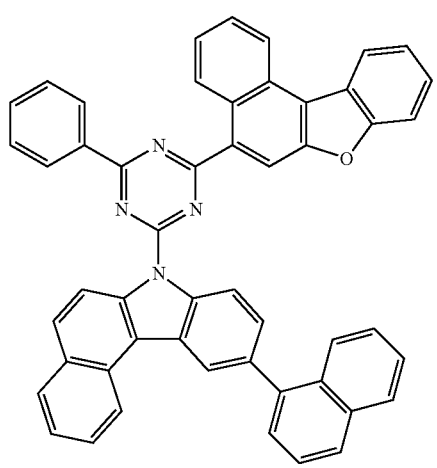
I 44
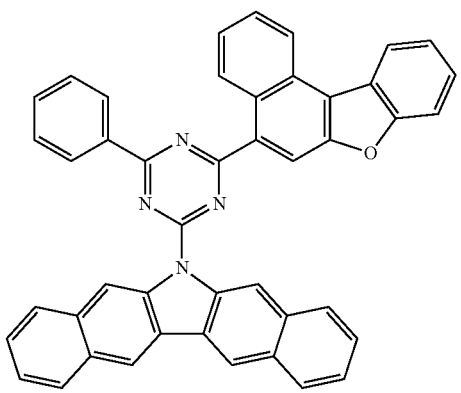

I 45
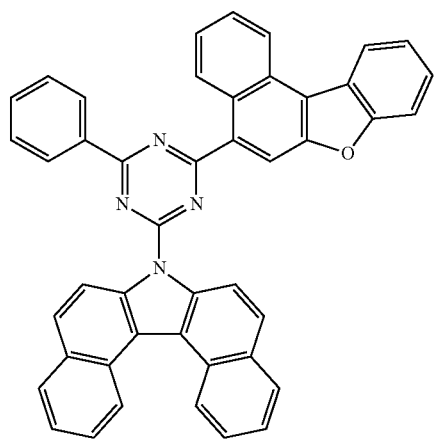
I 46
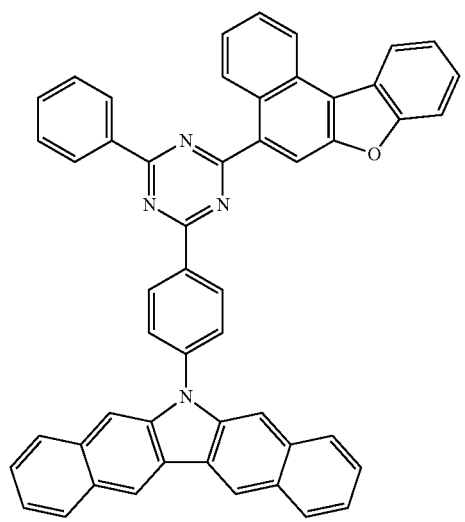
I 47
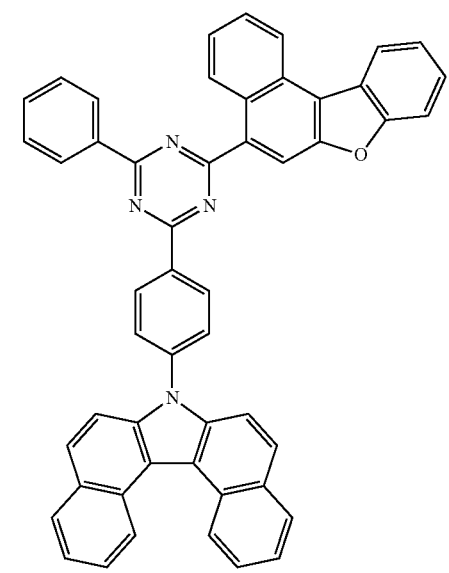
I 48
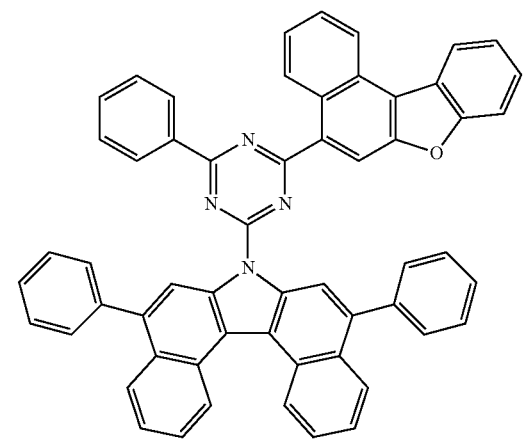
I 49
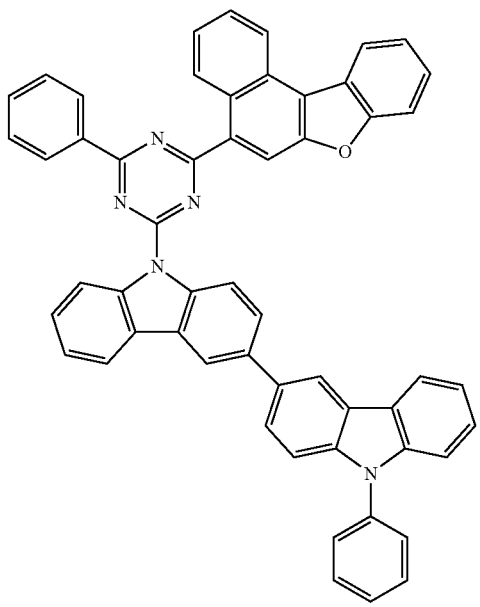
I 50
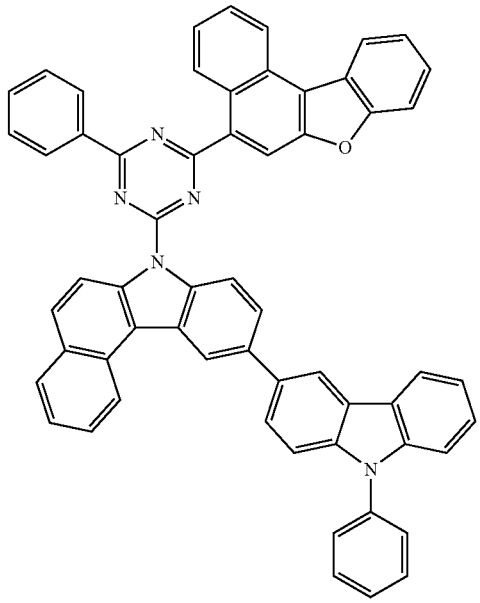

I51
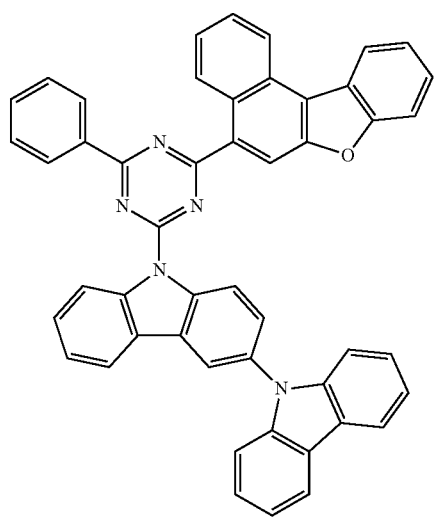
I52
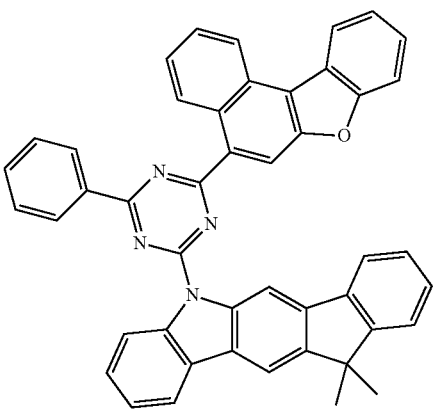
I53
I54
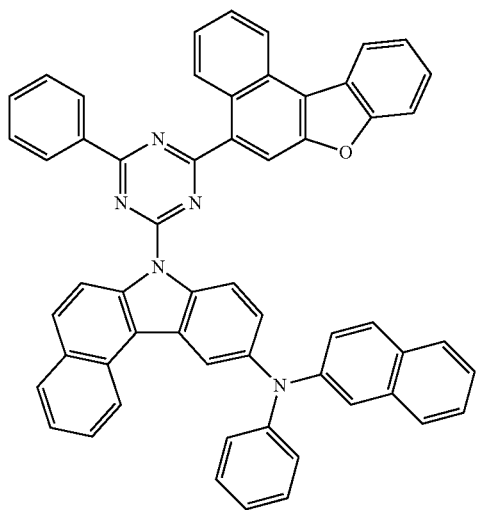
I55
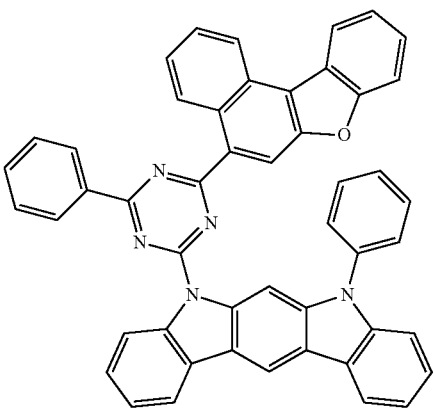
I56

-continued
I 57
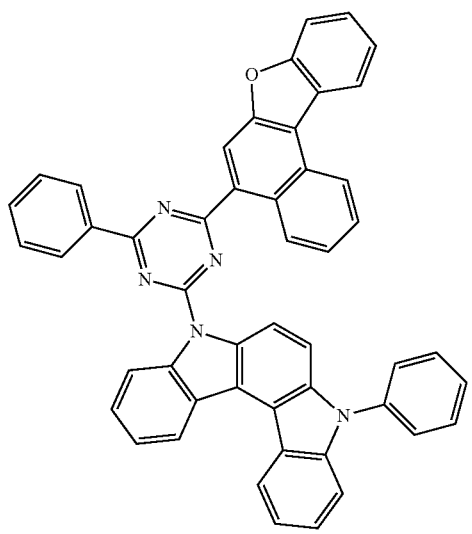
I 58
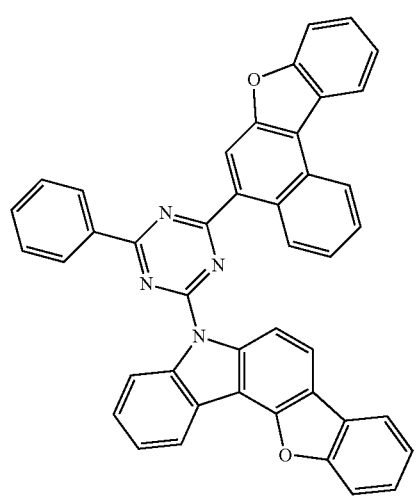
I 59
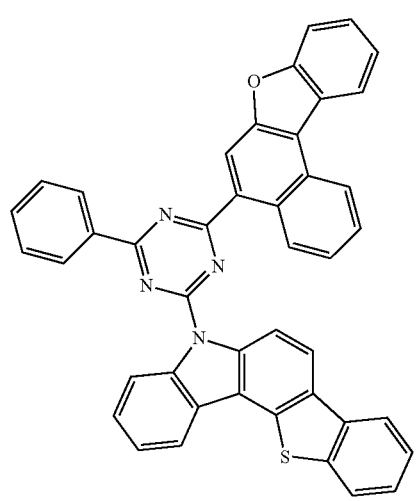
-continued
I 60
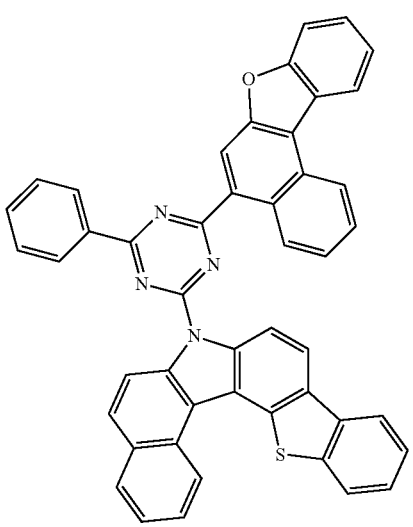
I 61
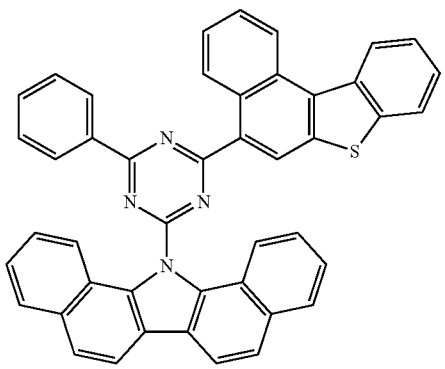
I 62
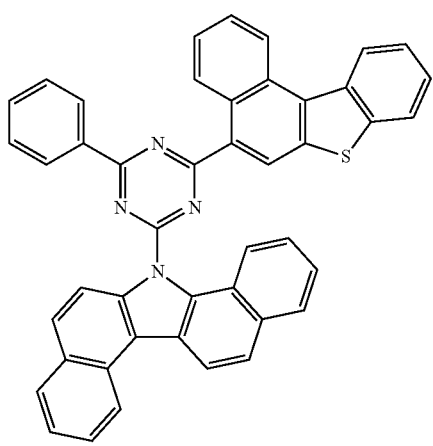

I 63
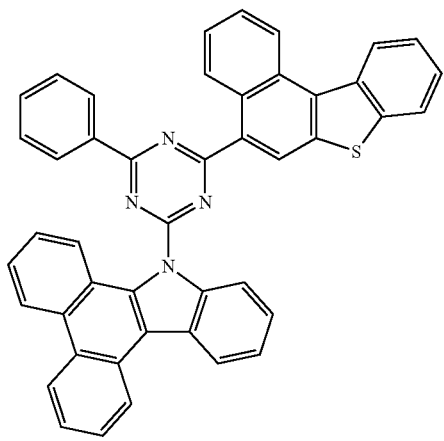
I 64
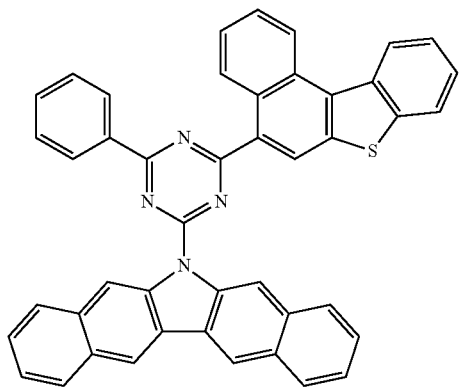
I 65
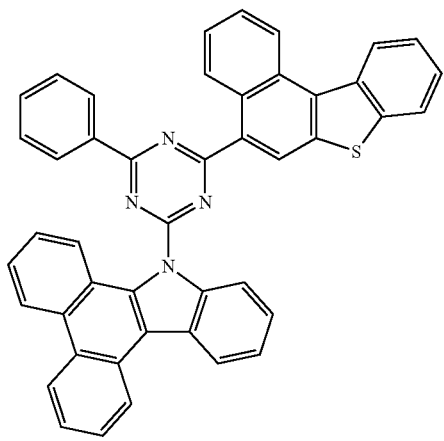
I 66
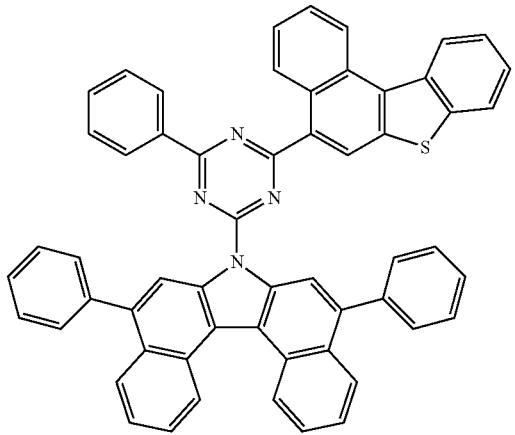
I 67
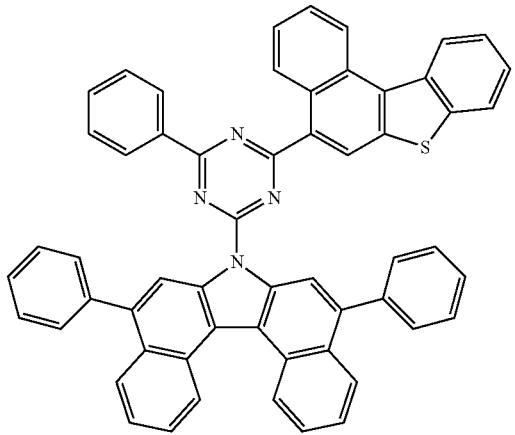
I 68
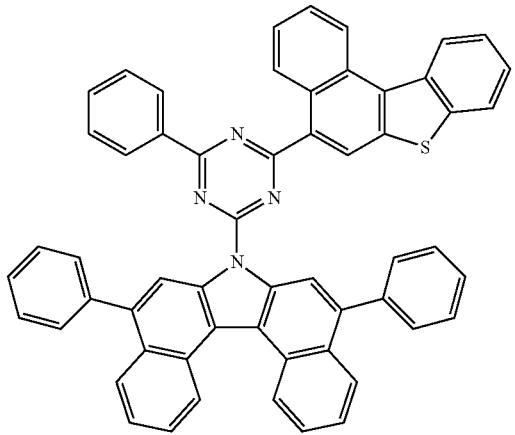

I 69
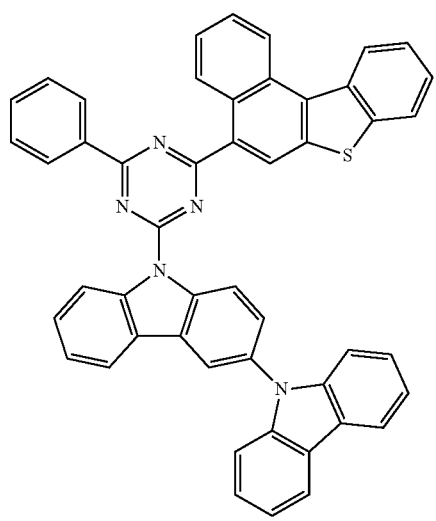
I 70
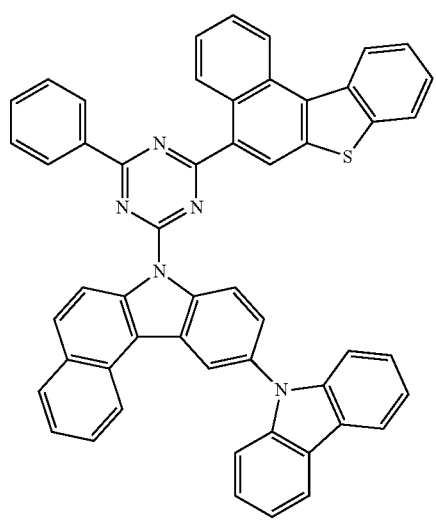
I 71
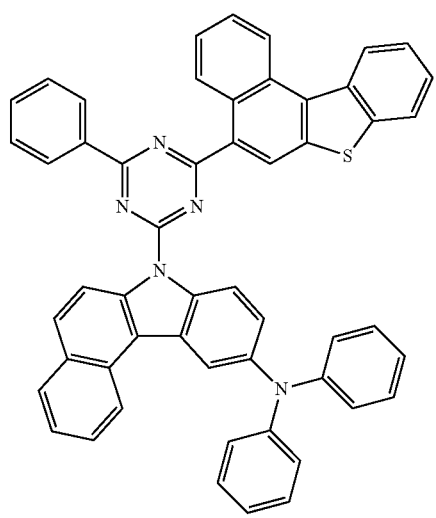
I 72
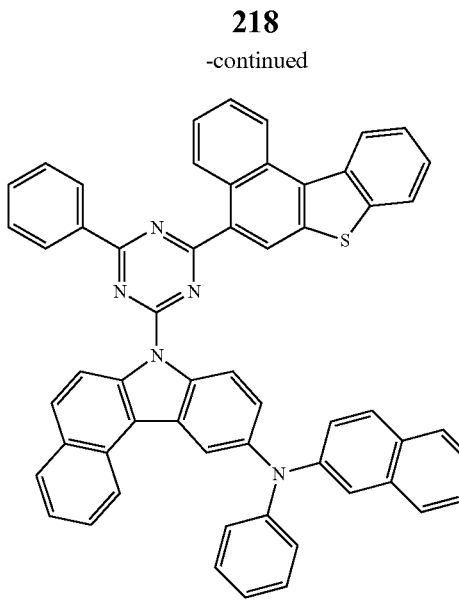
I 73
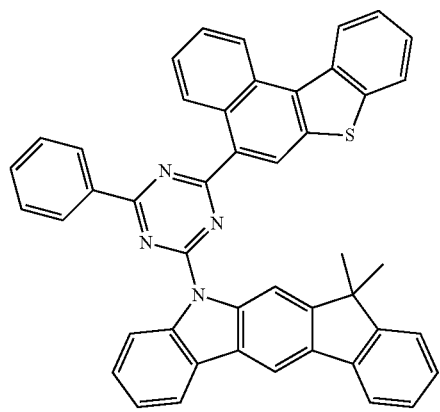
I 74
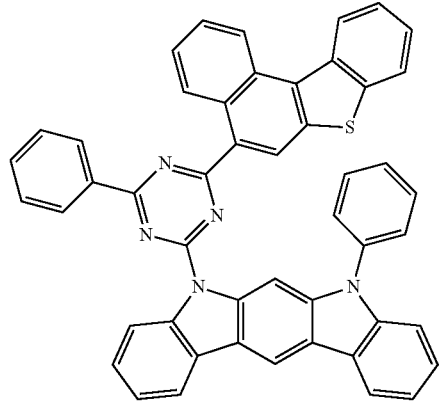

-continued
I 75
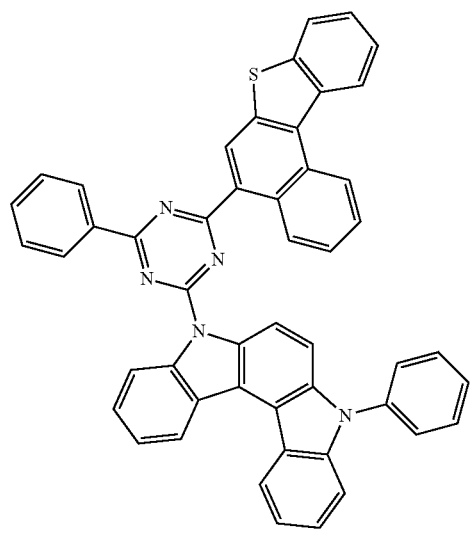
I 76
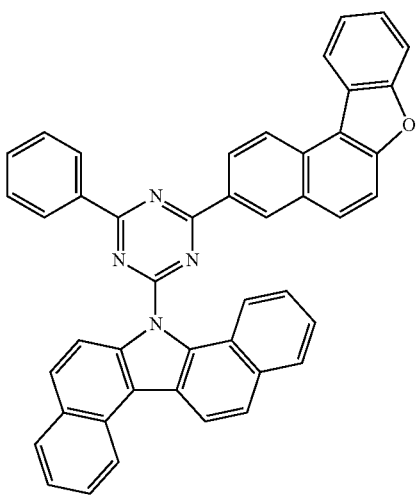
I 77
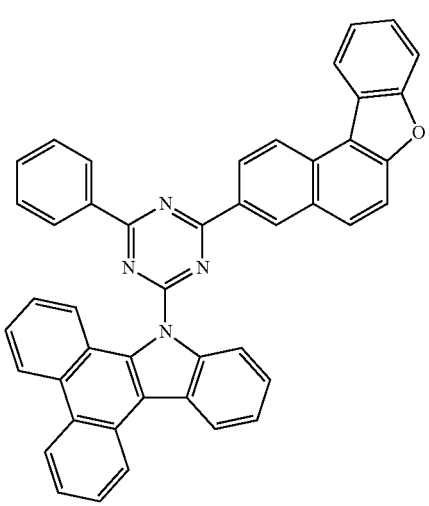
-continued
I 78
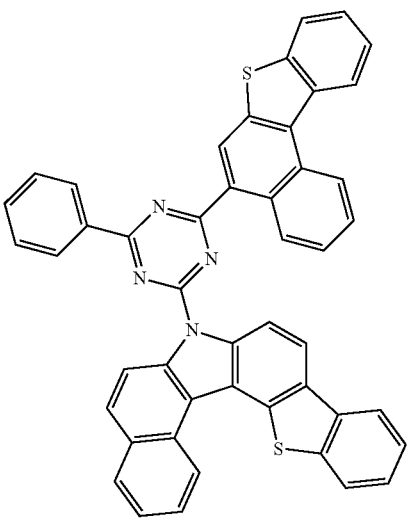
I 79
I 80

I 81
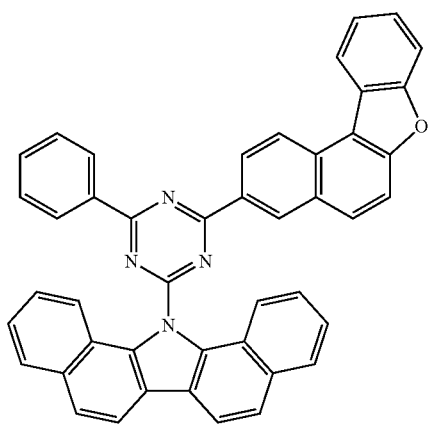
I 82
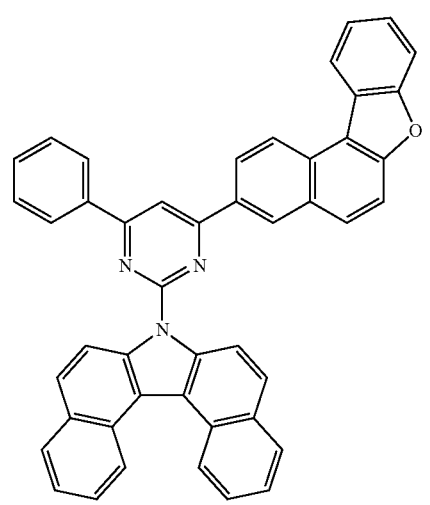
I 83
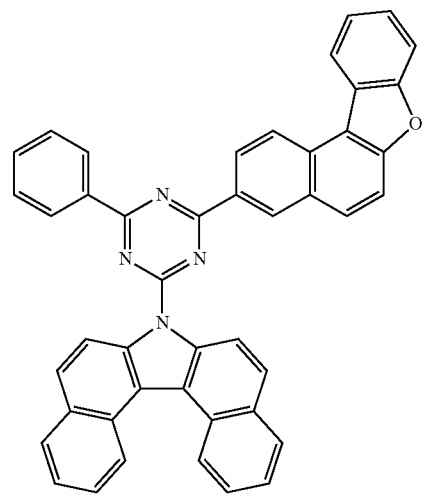
I 84
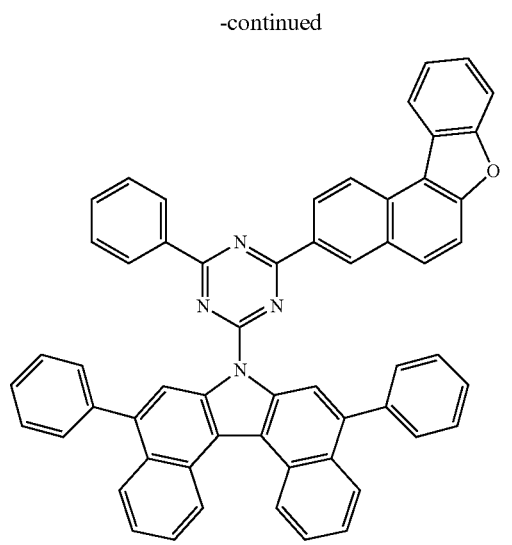
I 85
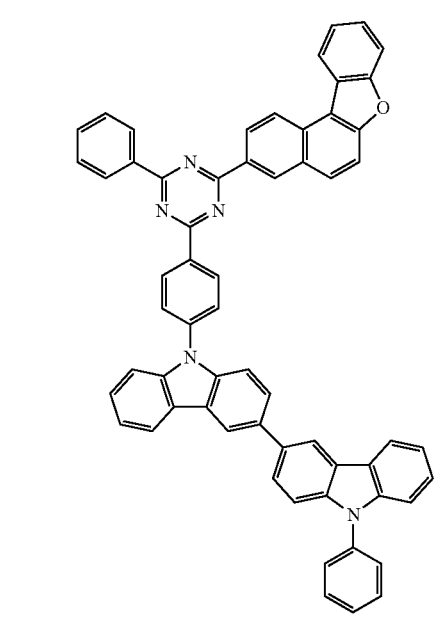
I 86
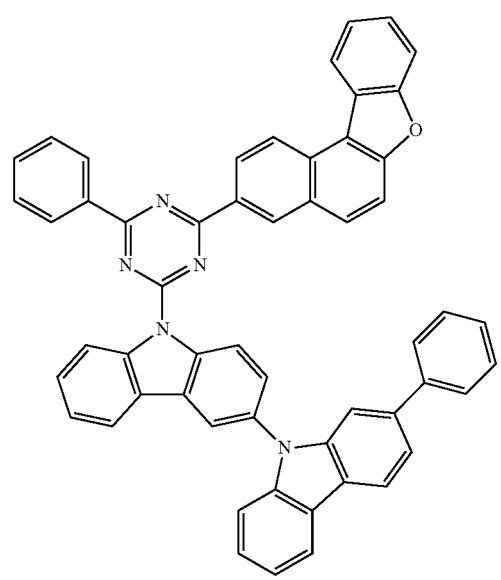

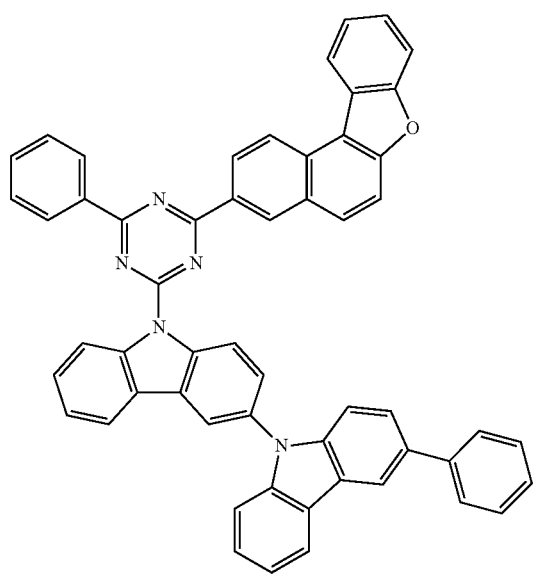
I 87
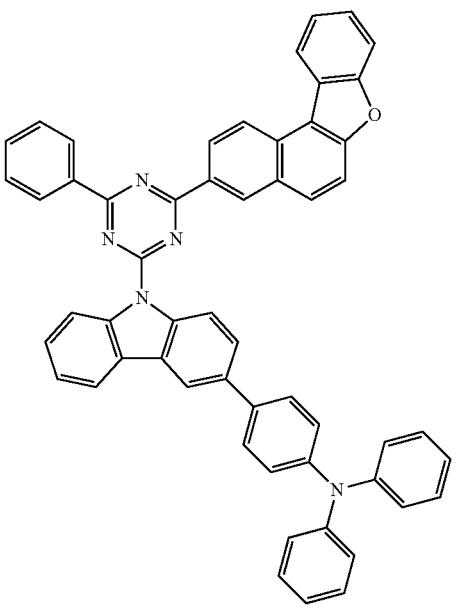
I 89
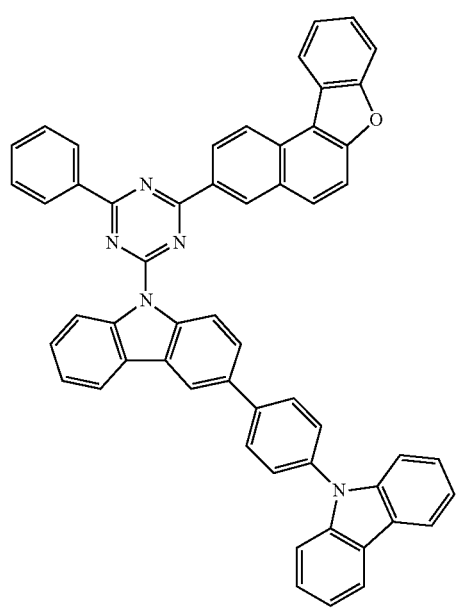
I 88
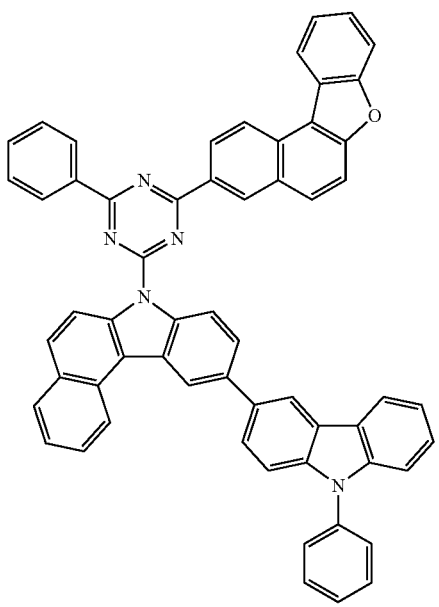
I 90

I91
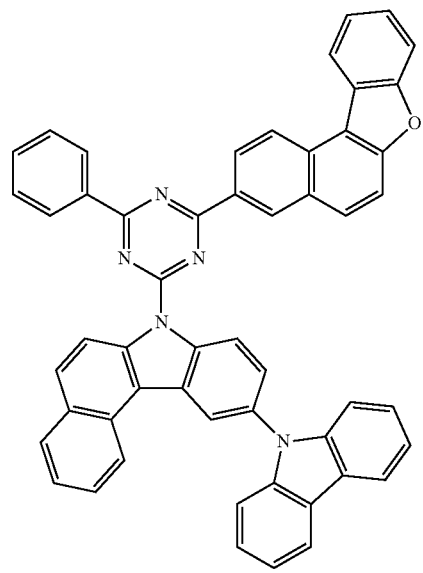
I92
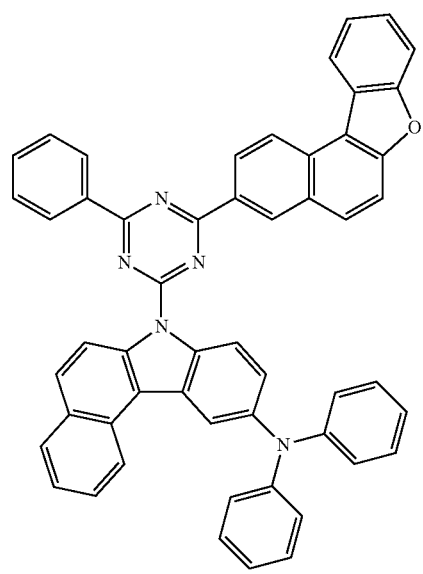
I93
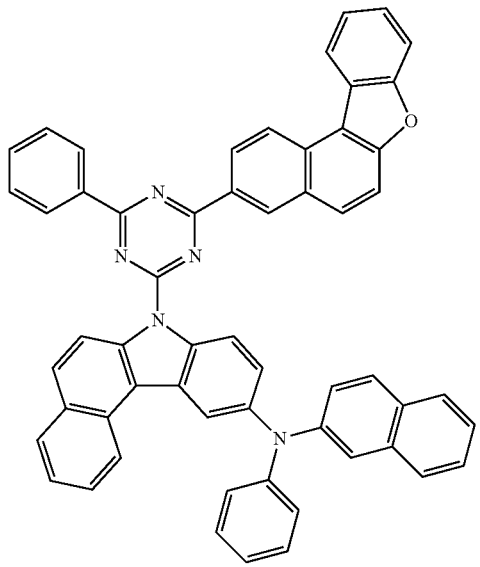
I94
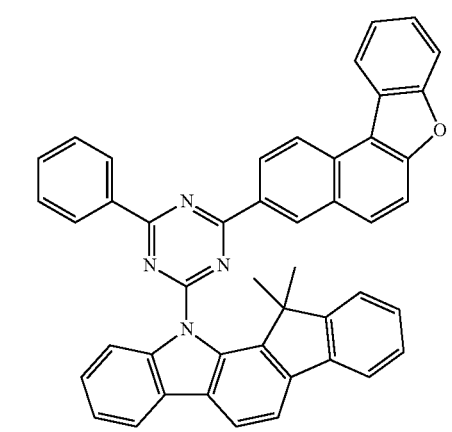
I95
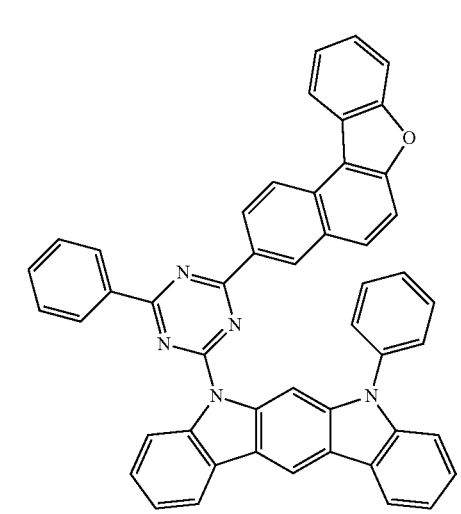

I96
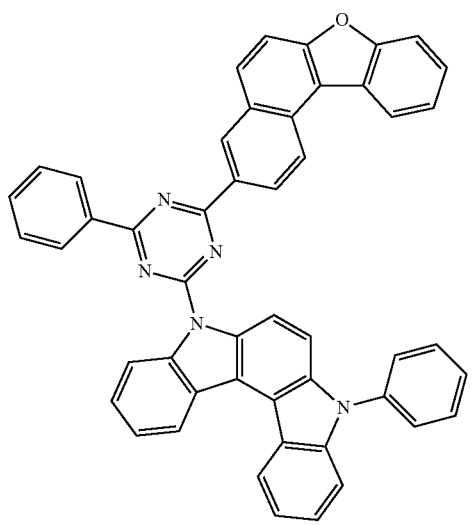
I97
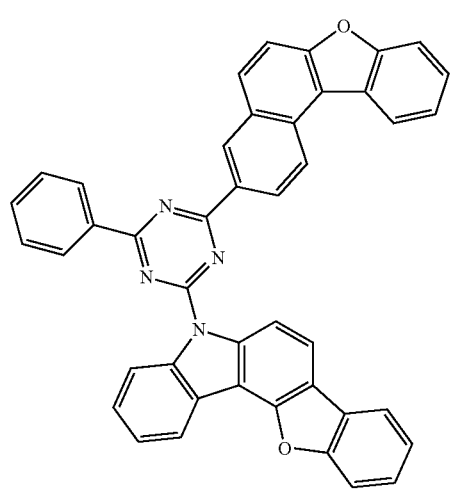
I98
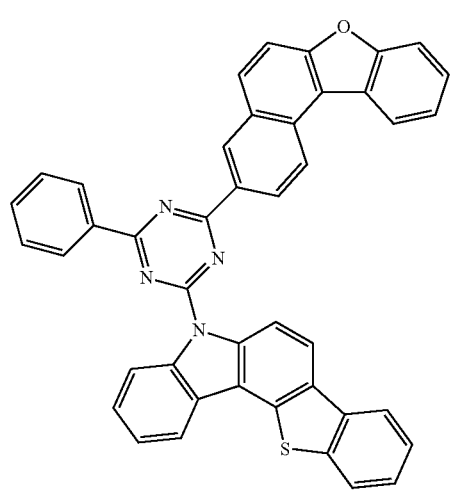
I99
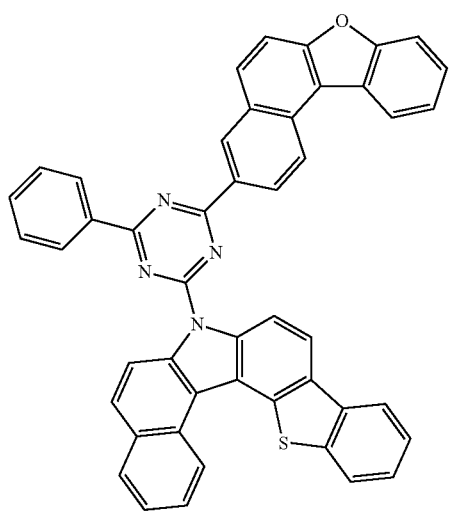
I100
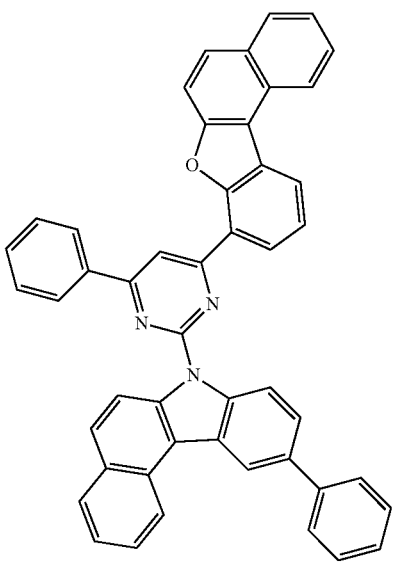
I101
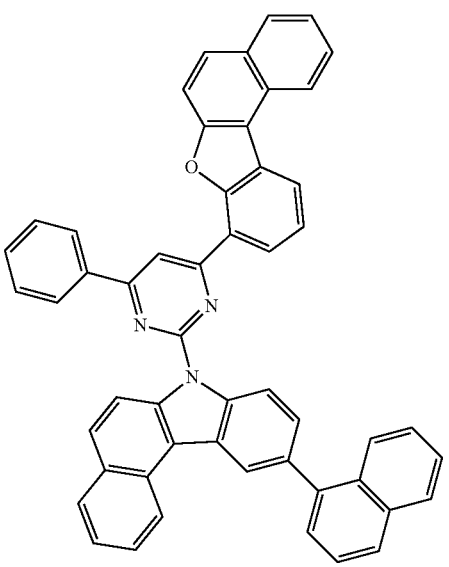

I 102
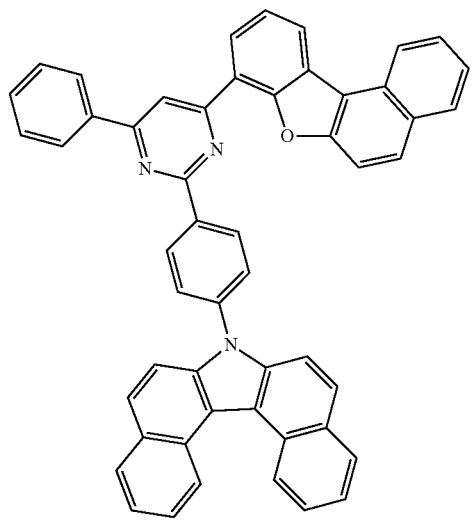
I 103
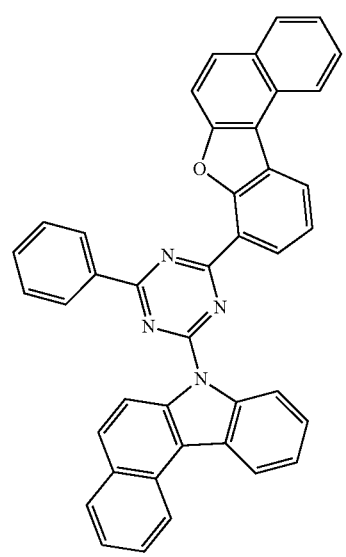
I 104
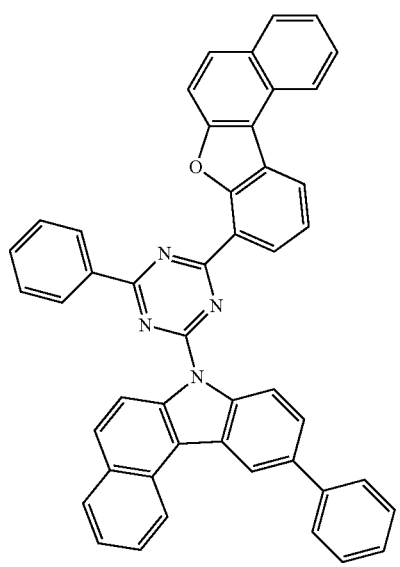
I 105
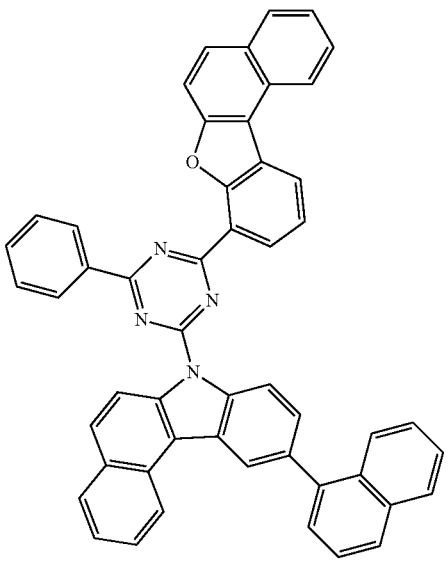
I 106
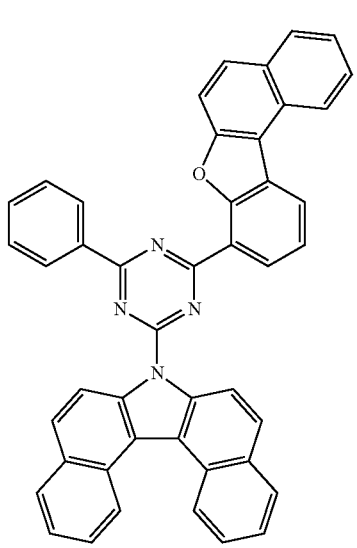
I 107
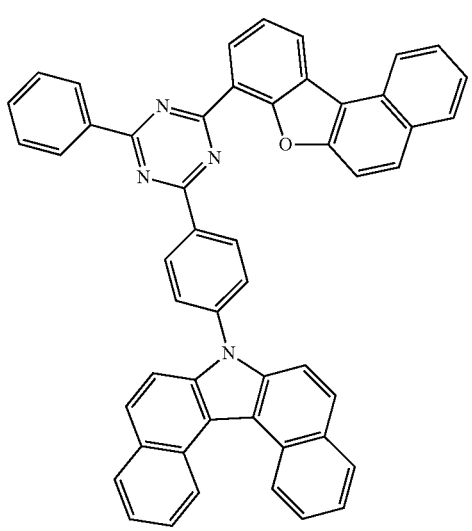

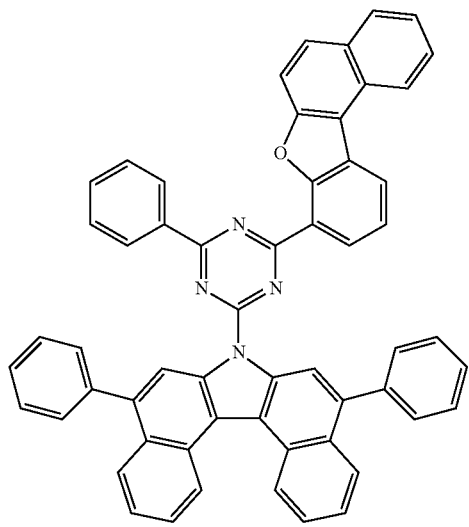
I 108
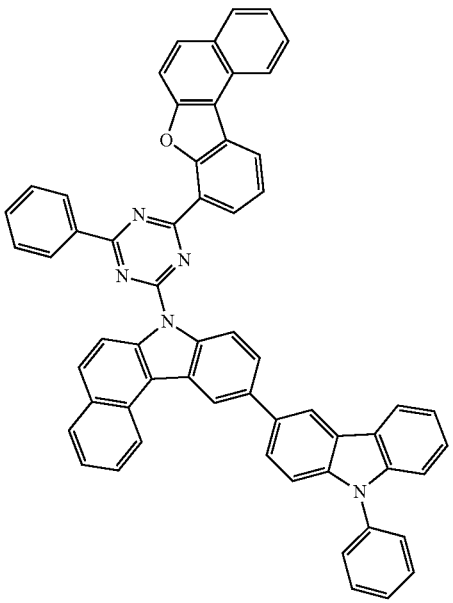
I 110
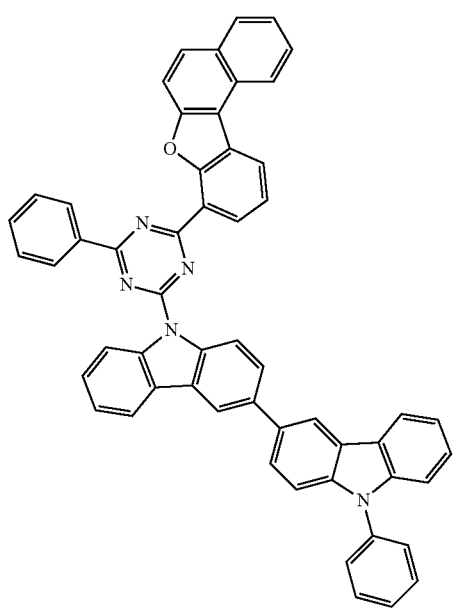
I 109
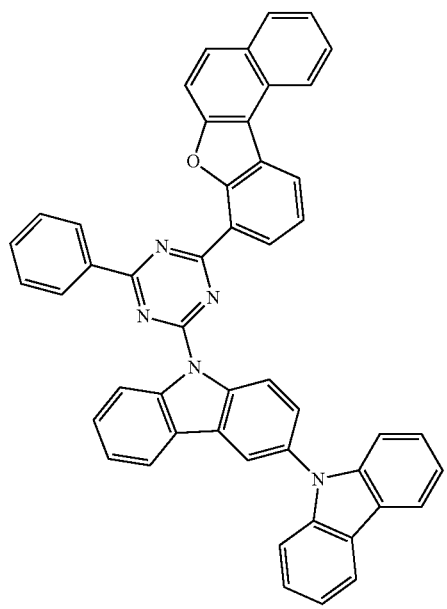
I 111

I-112
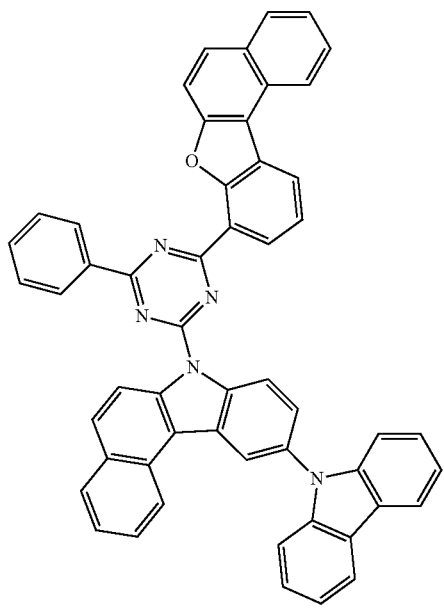
I-113
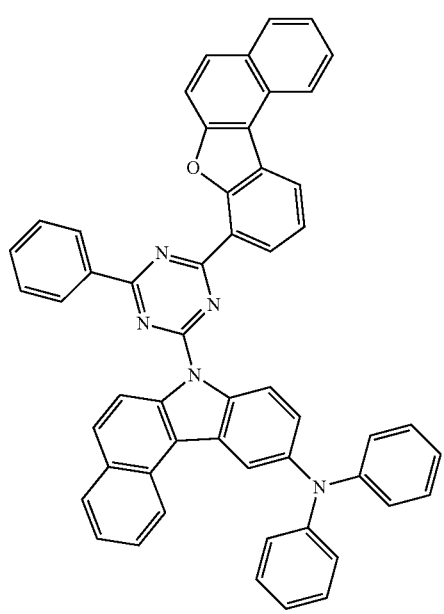
I-114
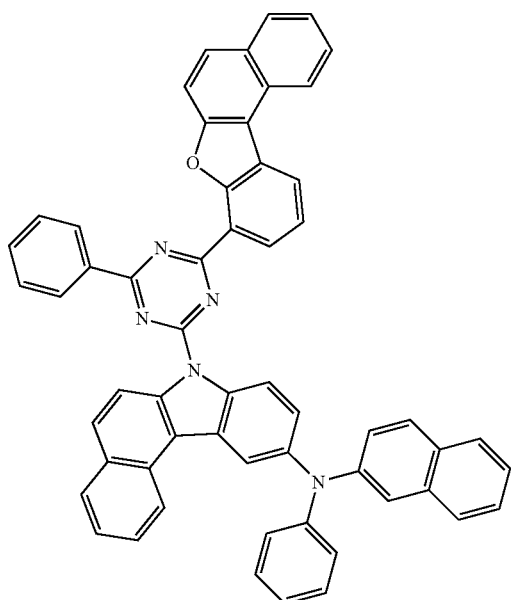
I-115
I-116
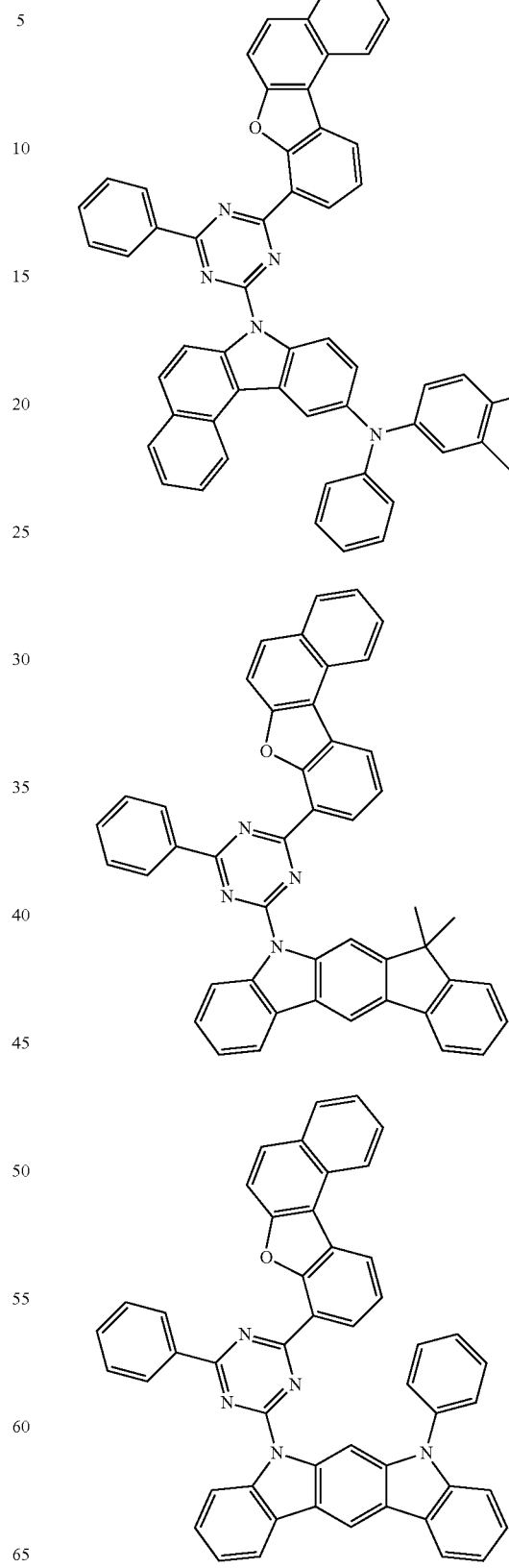

-continued
I117
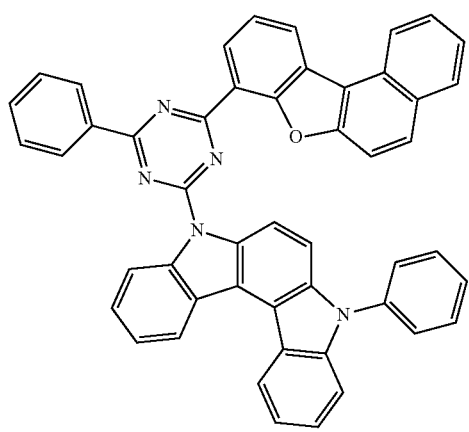
I118
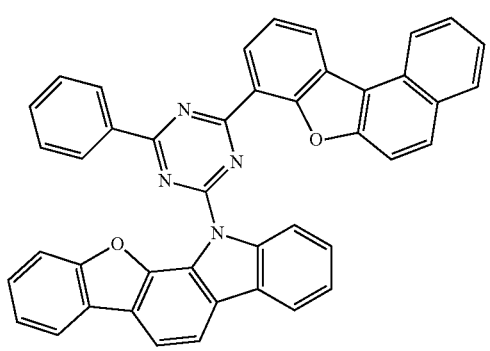
I119
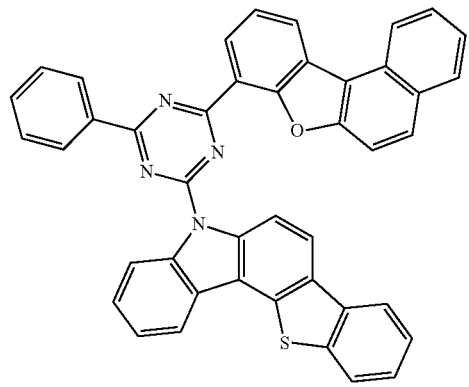
I120
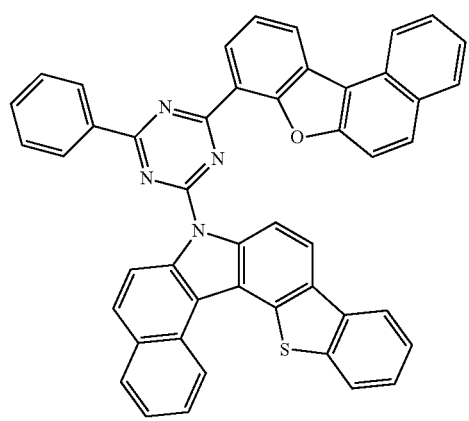
-continued
I121
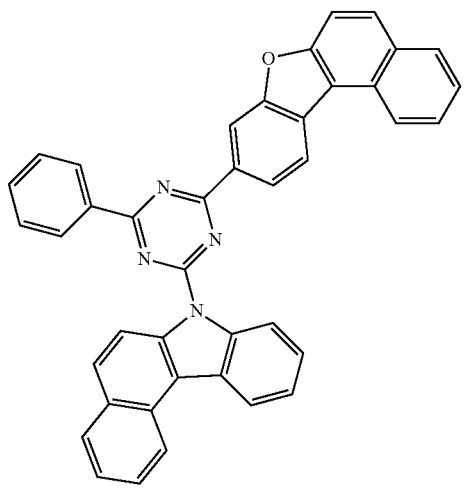
I122
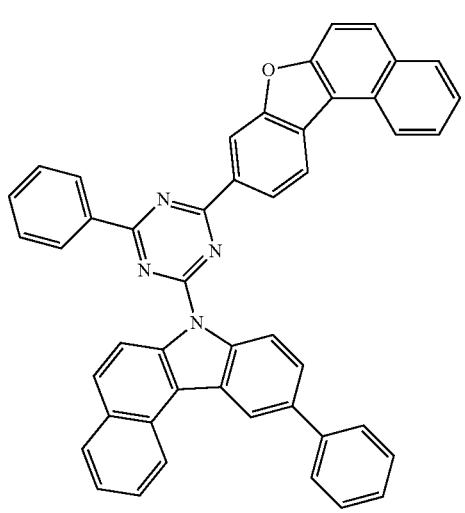
I123
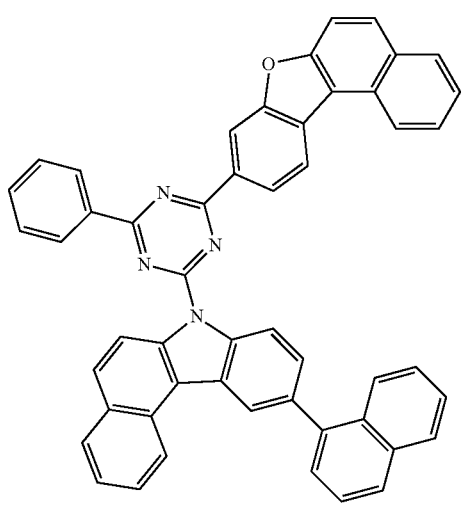

I-124
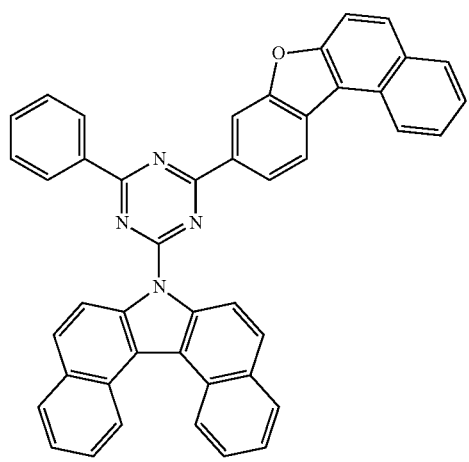
I-125
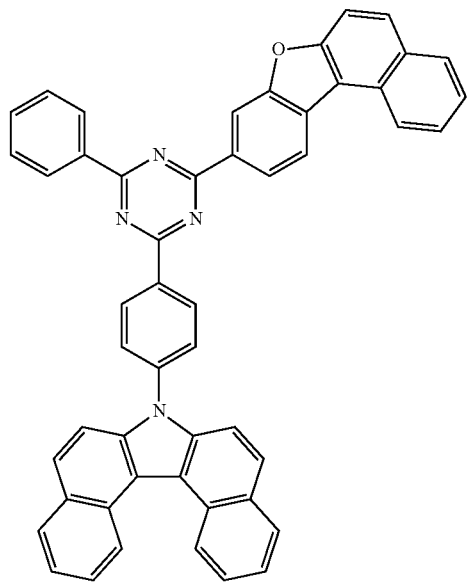
I-126
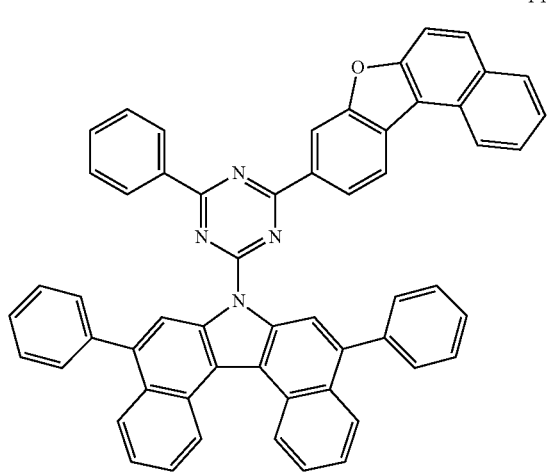
I-127
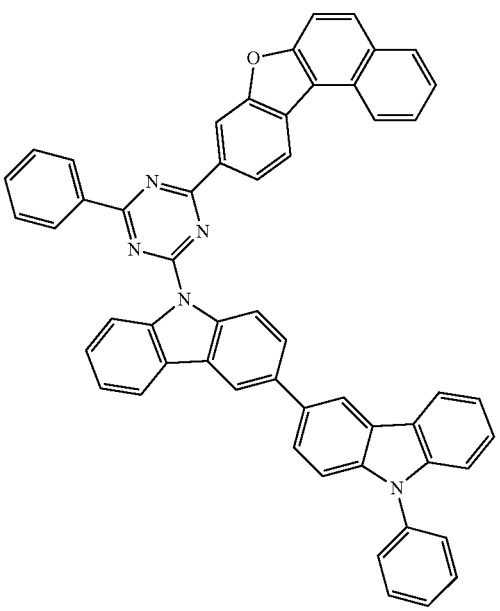
I-128
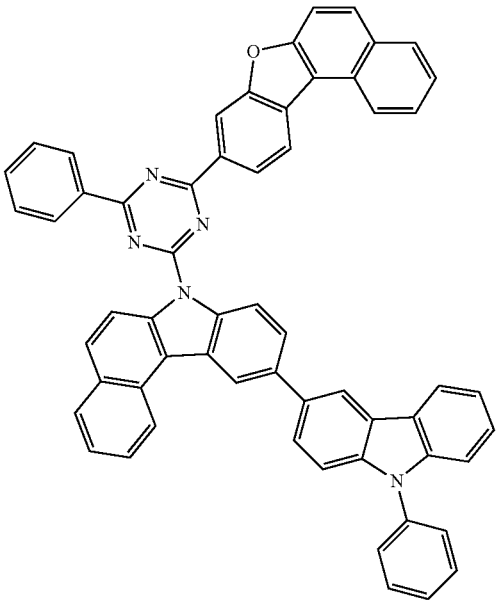

I 129
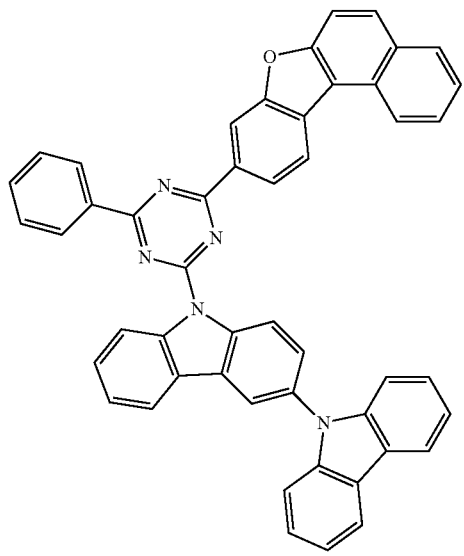
I 130
I 131
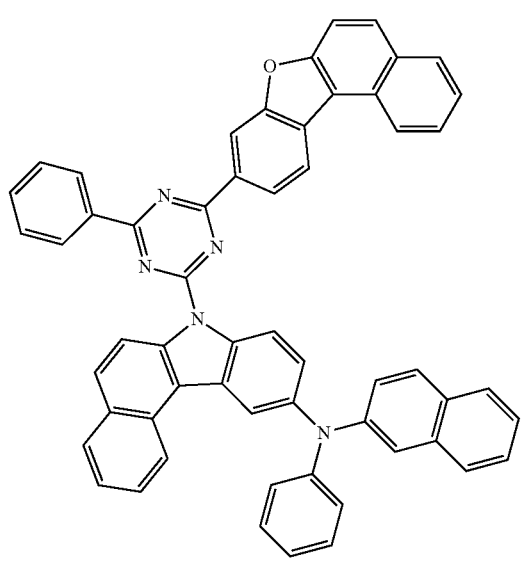
I 132
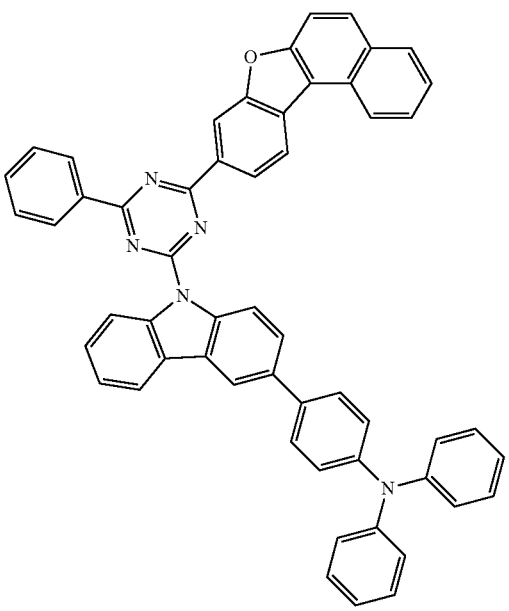
I 133
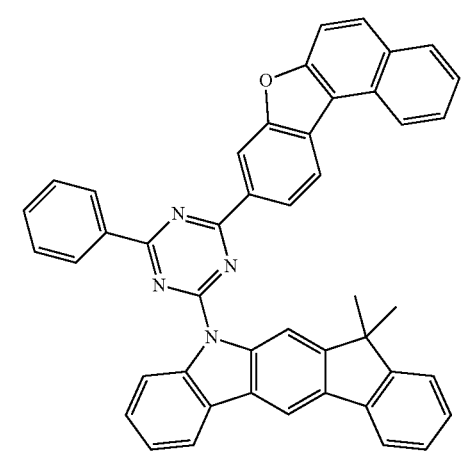
I 134
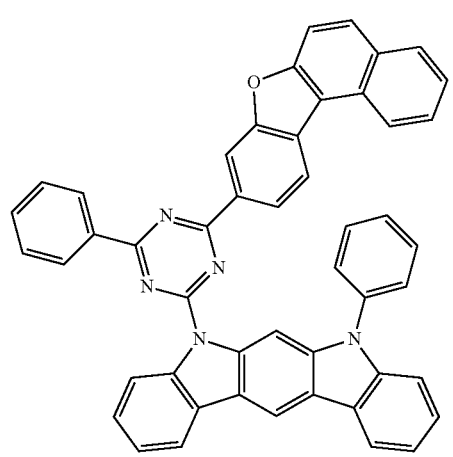

I 135
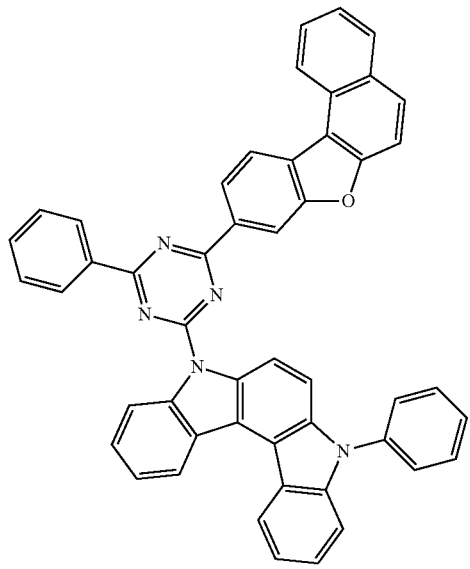
I 136
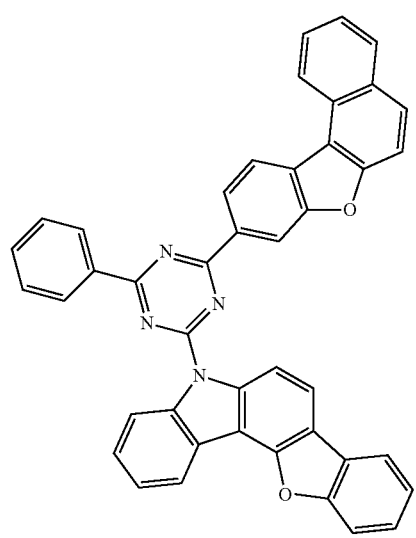
I 137
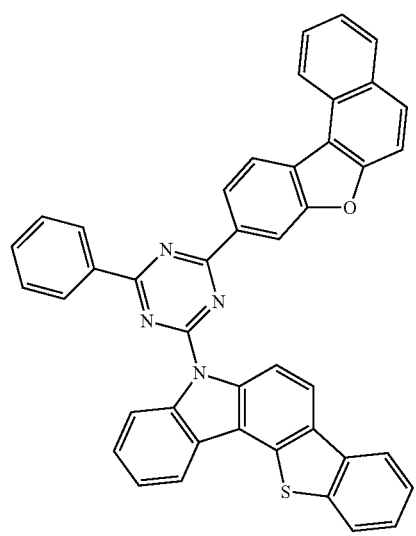
I 138
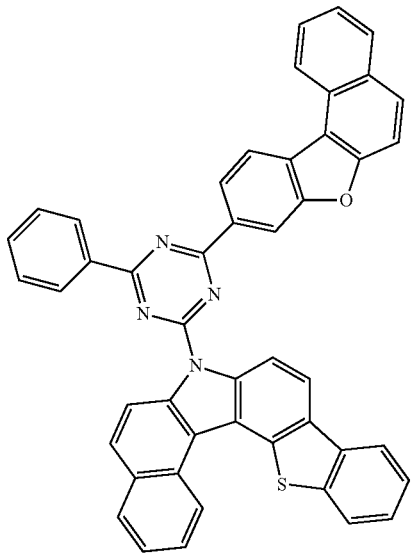
I 139
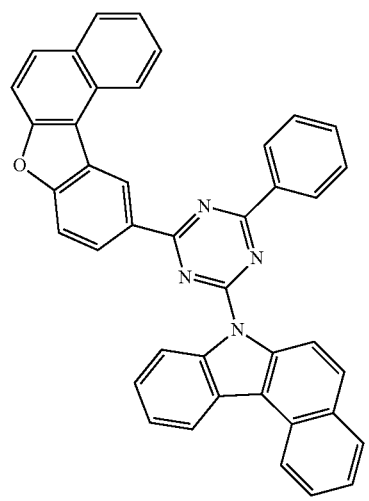
I 140
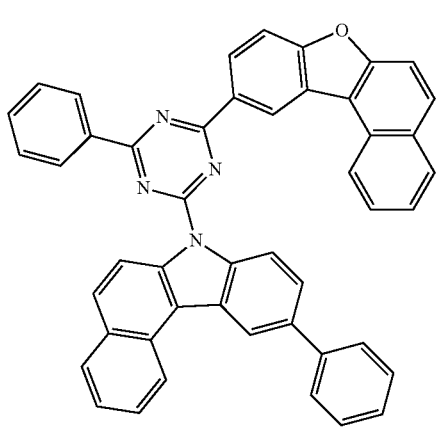

I 141
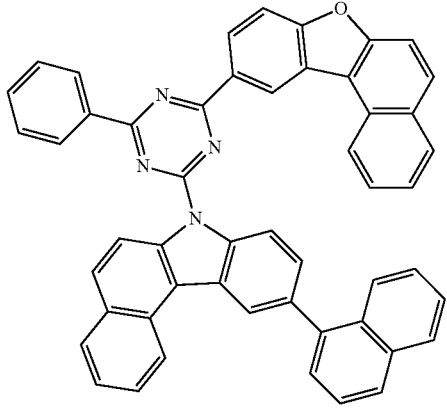
I 142
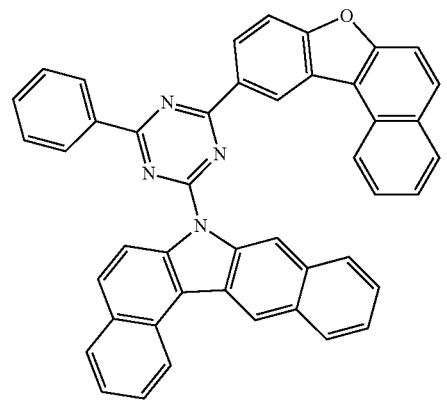
I 143
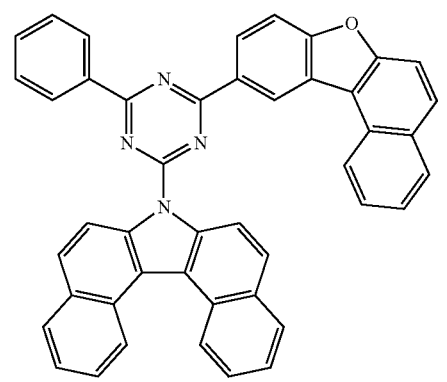
I 144
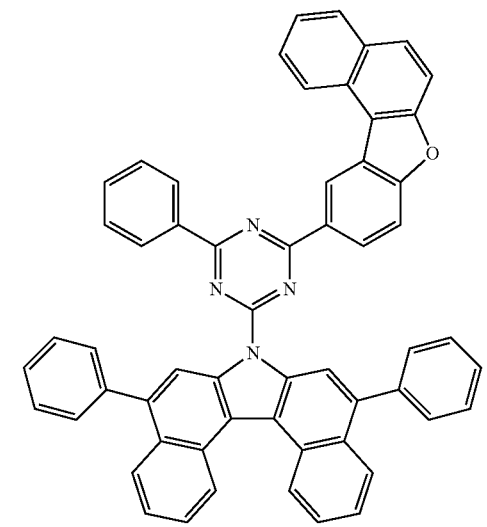
I 145
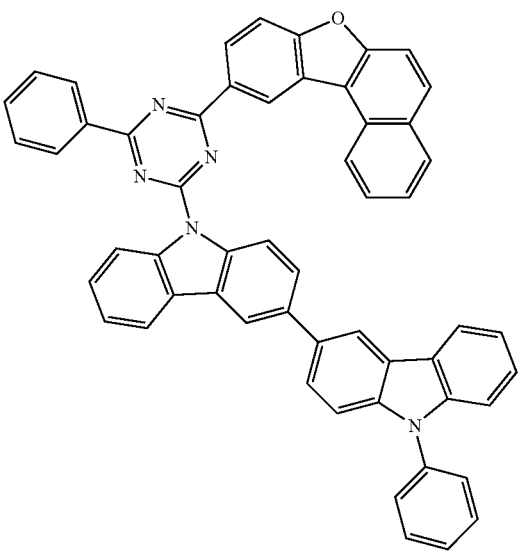
I 146
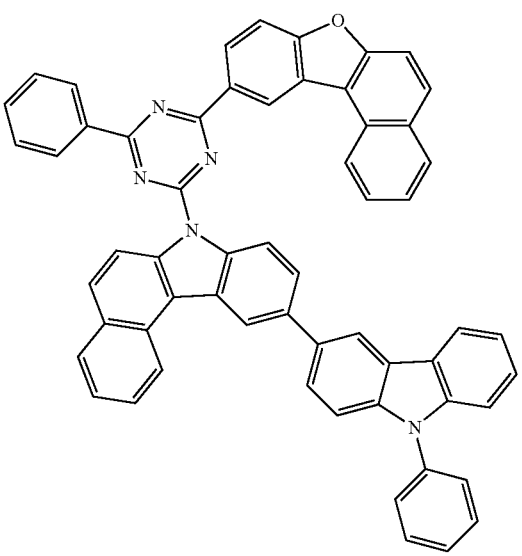

I 147
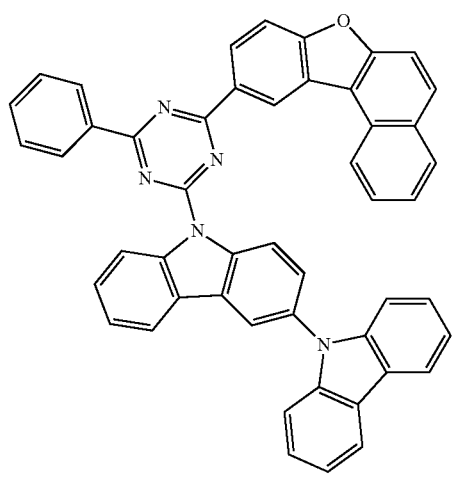
I 148
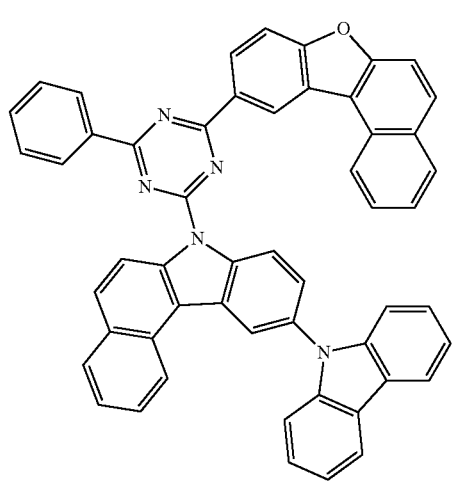
I 149
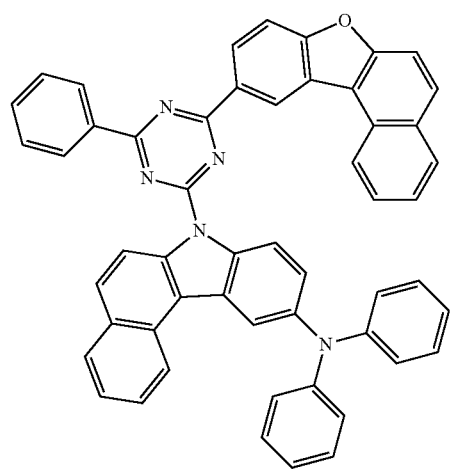
I 150
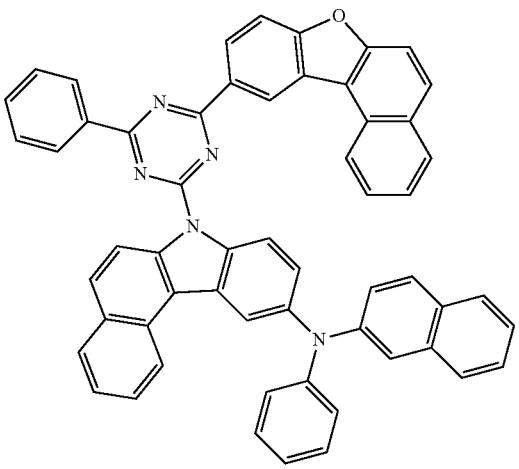
I 151
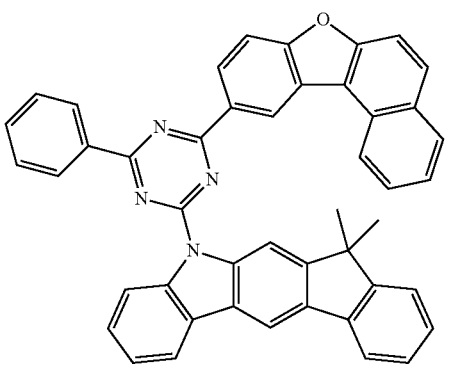
I 152
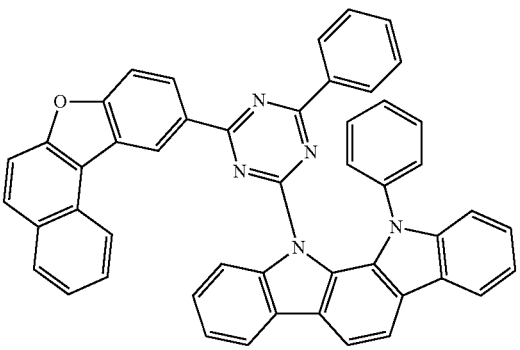

I 153
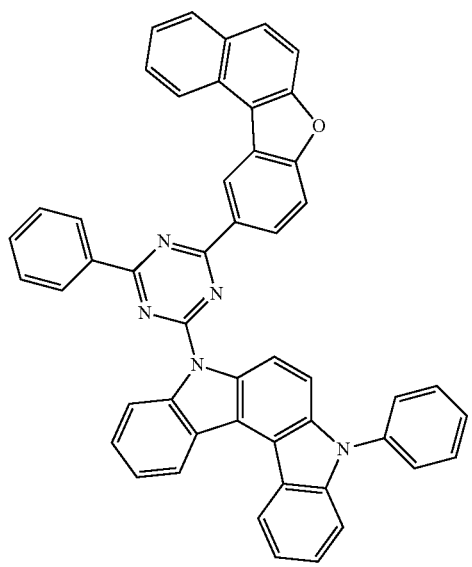
I 154
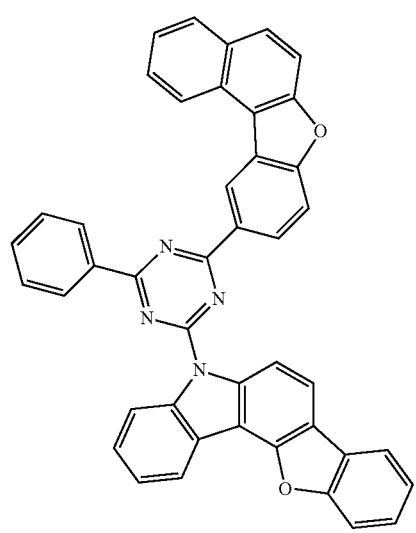
I 155
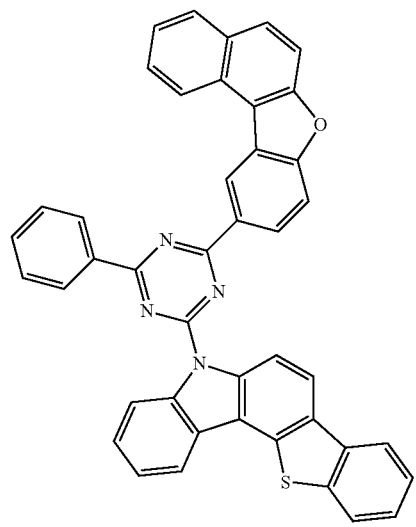
I 156
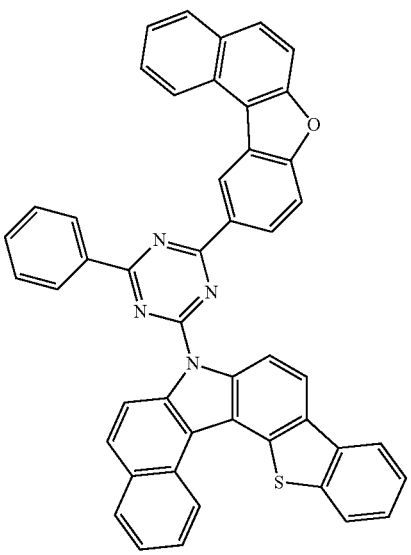
I 157
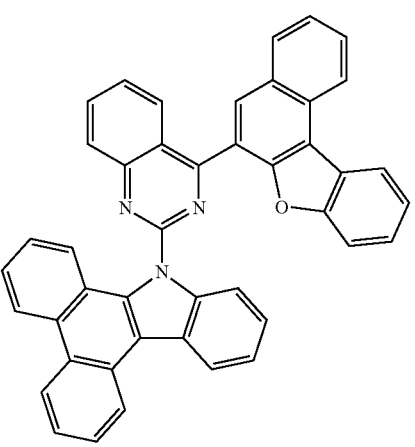
I 158
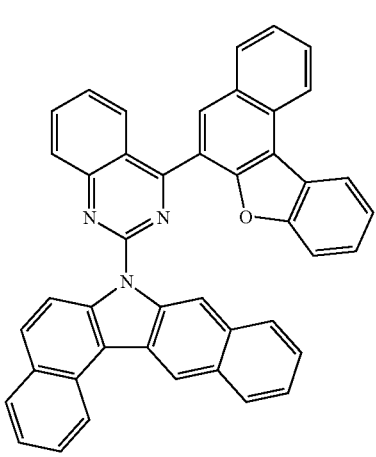

I159
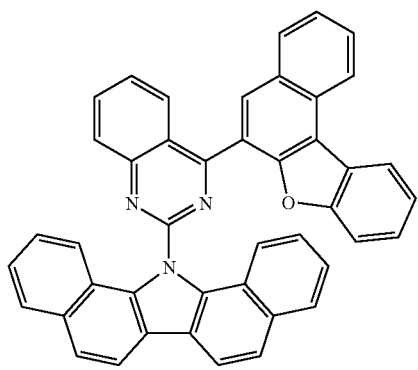
I160
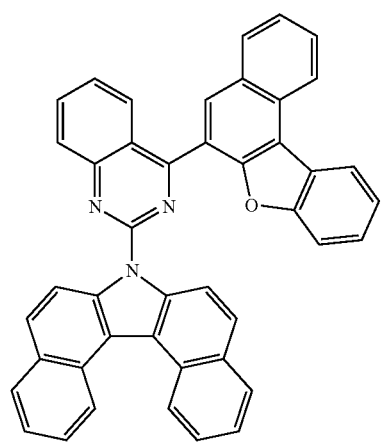
I161
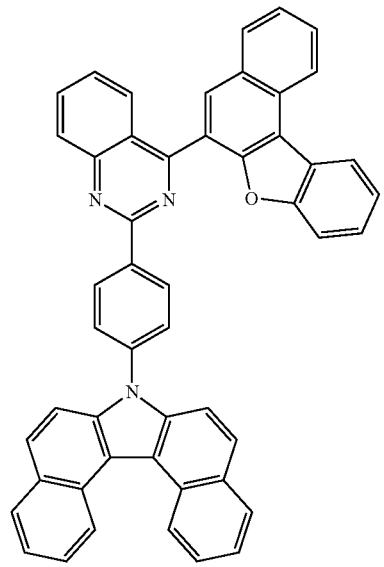
I162
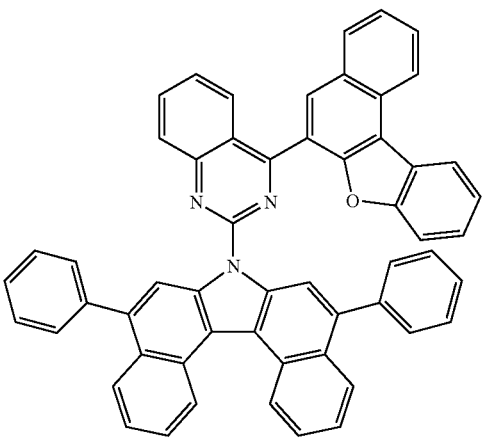
I163
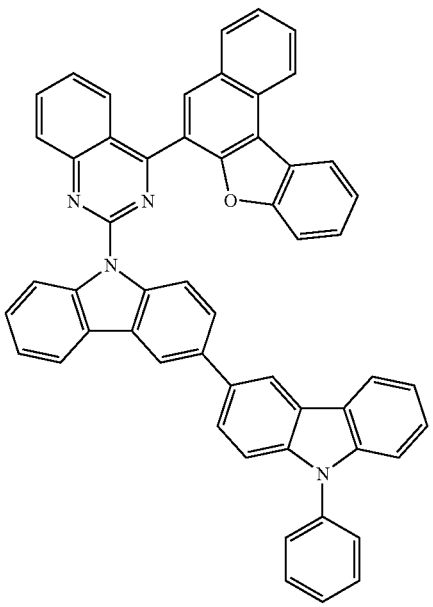

I 164
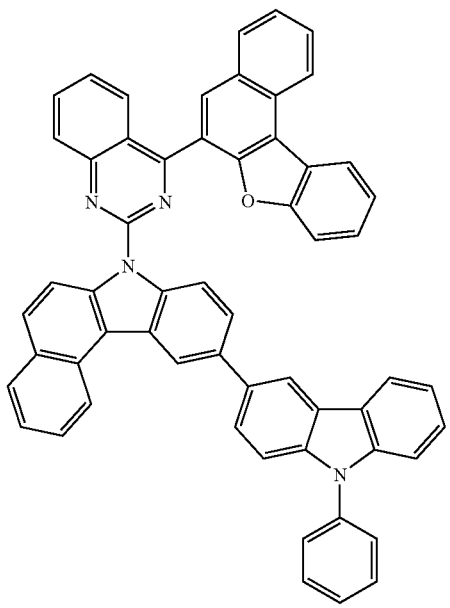
I 165
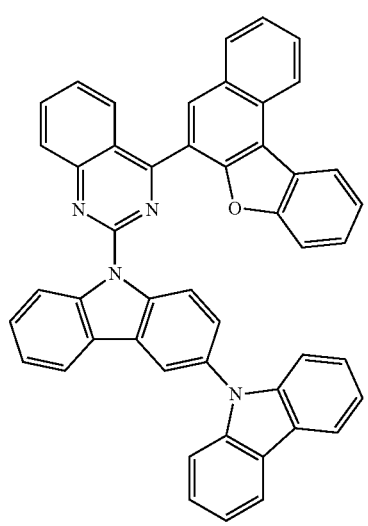
I 166
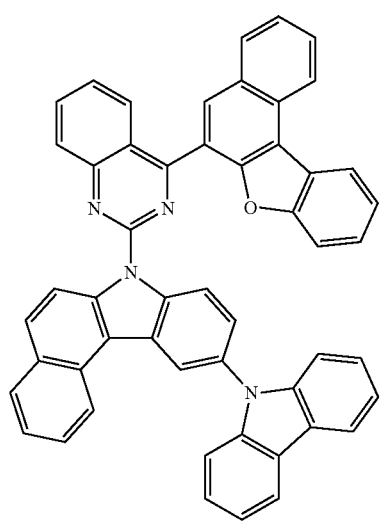
I 167
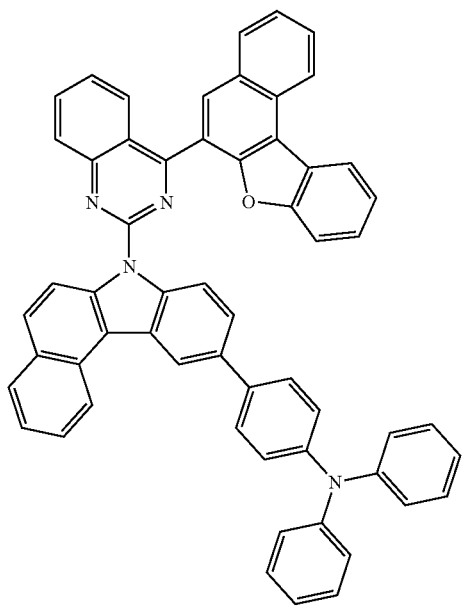
I 168
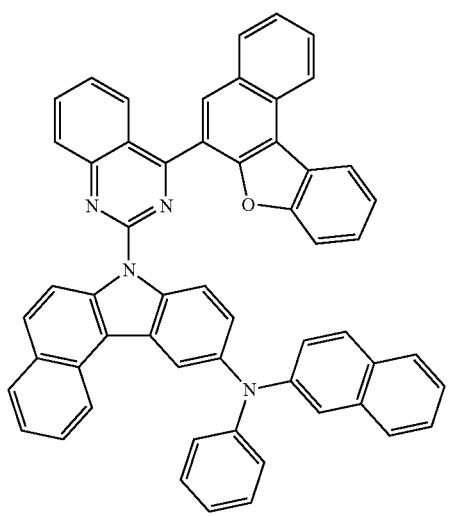
I 169
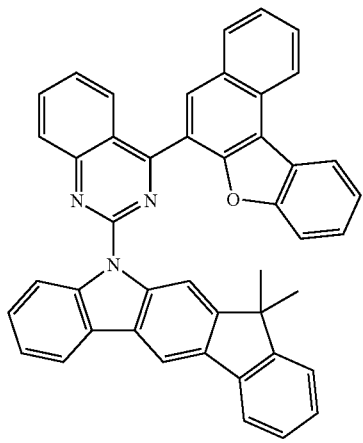

I-170
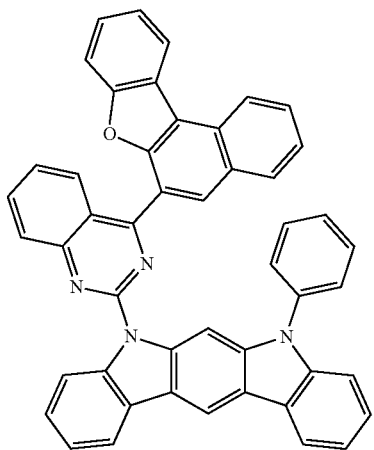
I-171
I-173
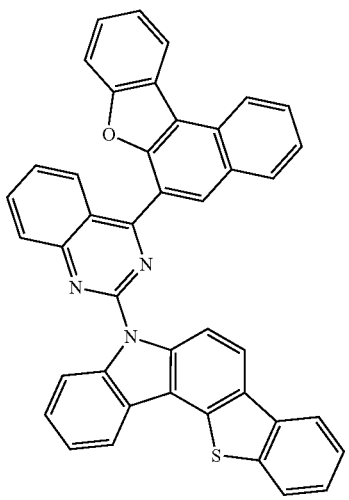
I-174
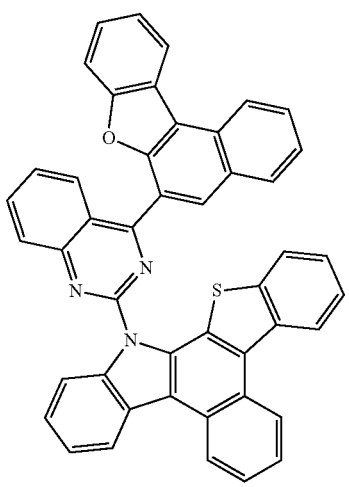
I-172
I-175
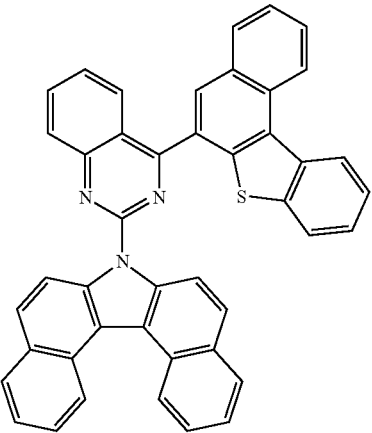

-continued
I-176
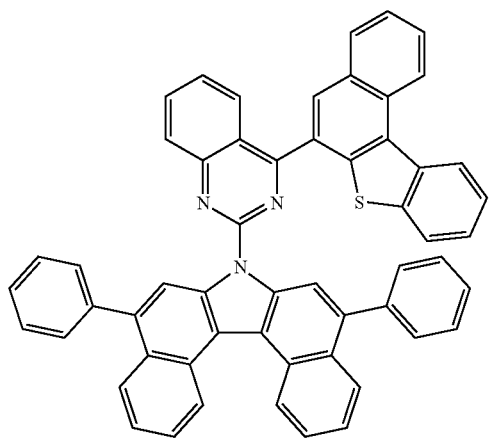
I-177
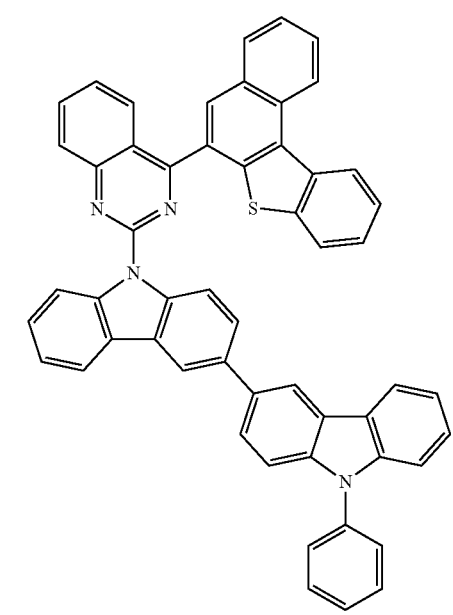
I-178
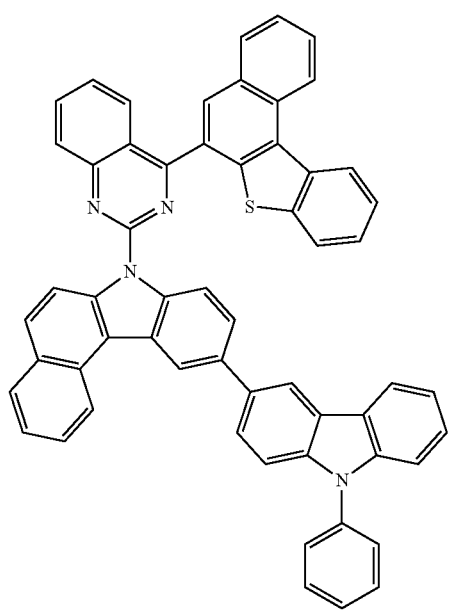
-continued
I-179
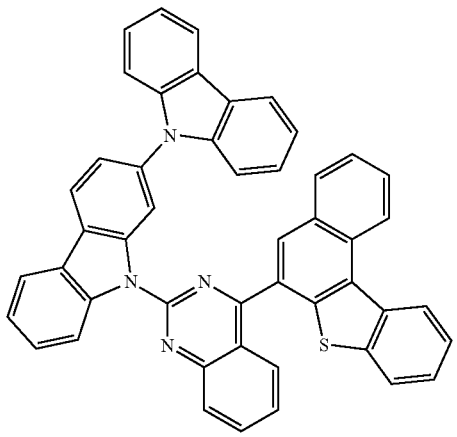
I-180
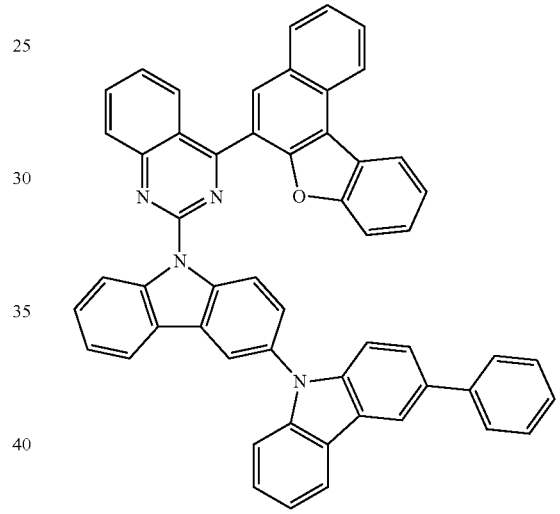
I-181
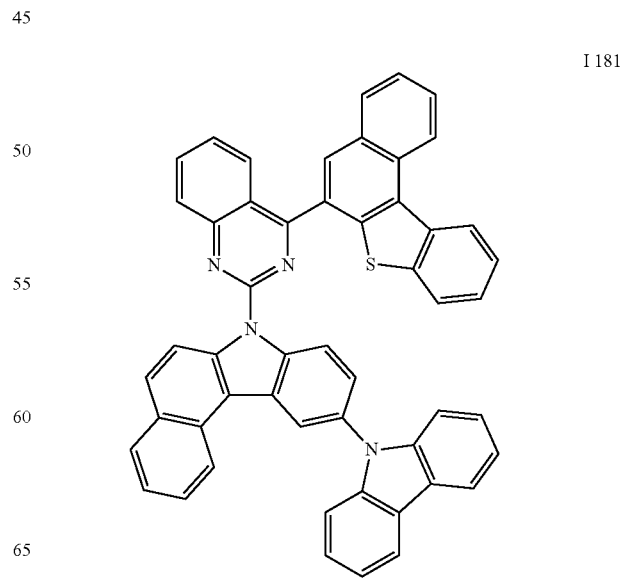

I182
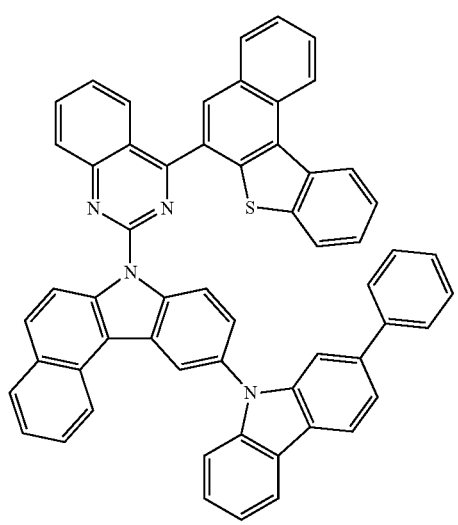
I183
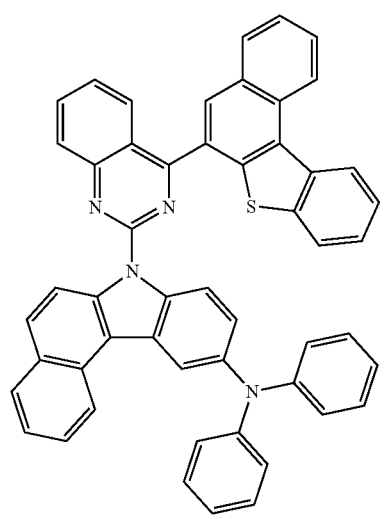
I184
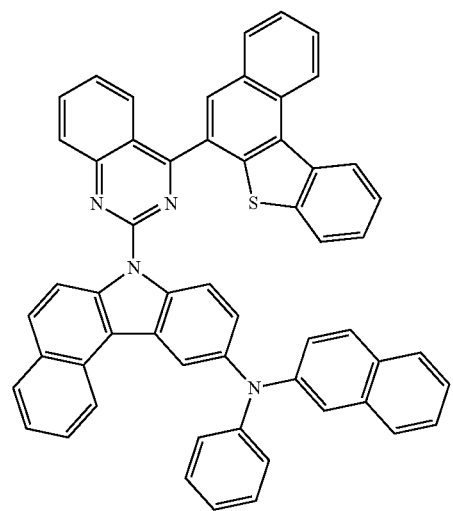
I185
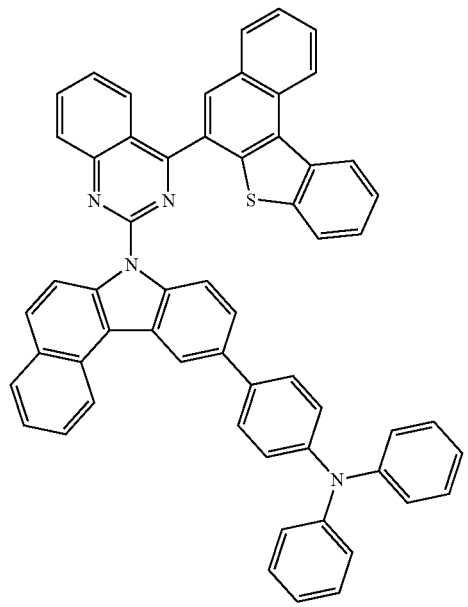
I186
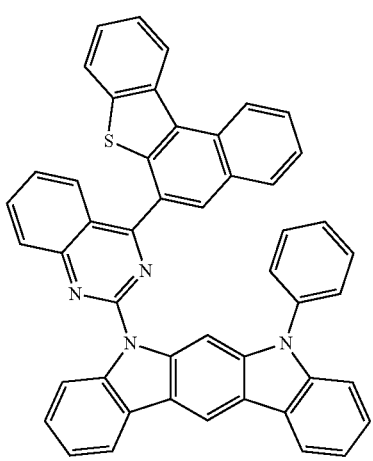
I187
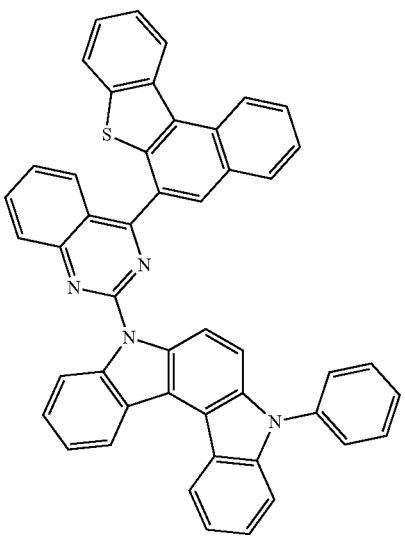

I 188
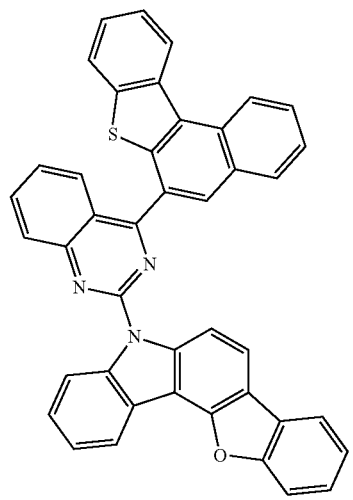
I 189
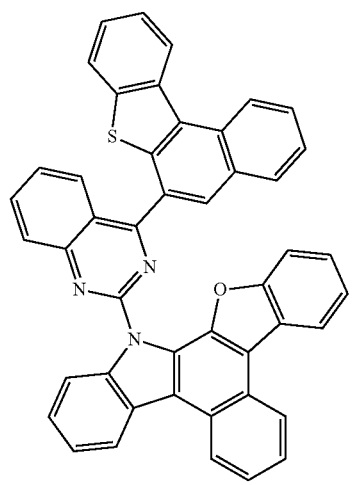
I 190
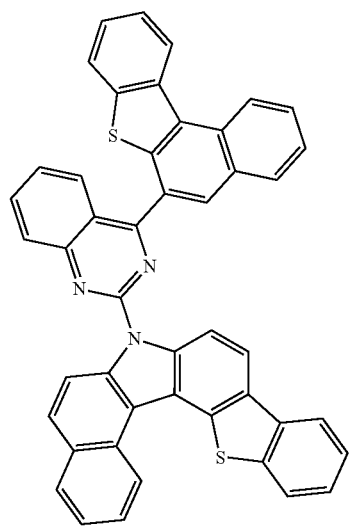
I 191
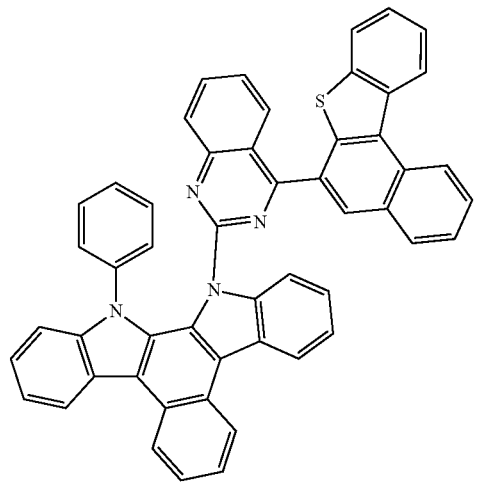
I 192
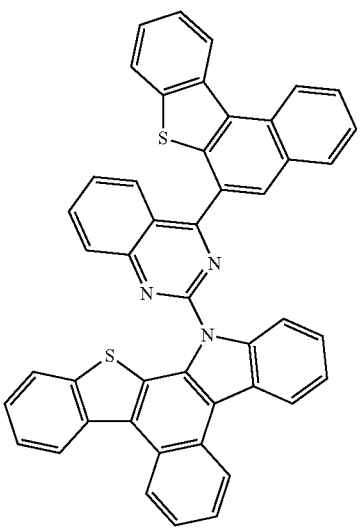
I 193
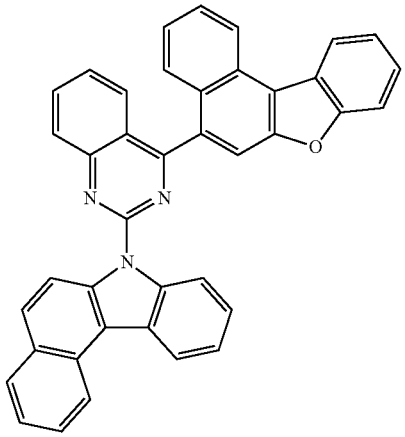

-continued
I 194
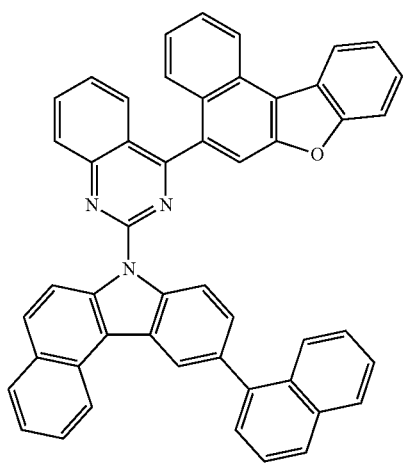
I 195
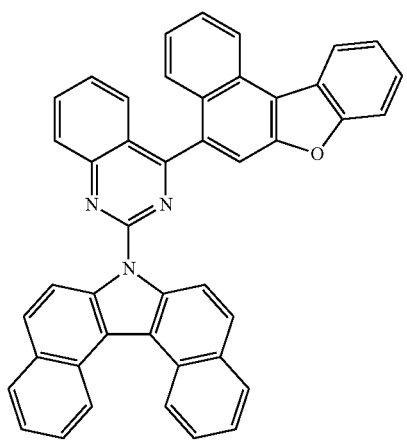
I 196
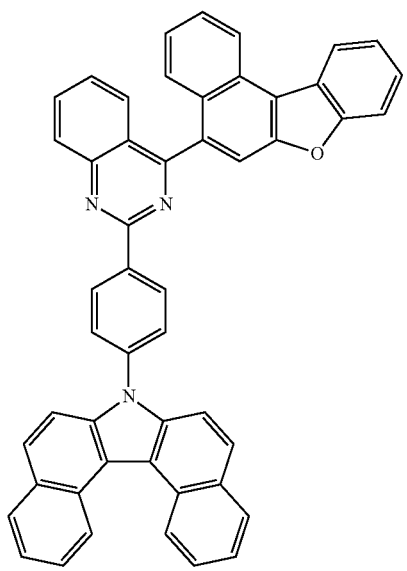
-continued
I 197
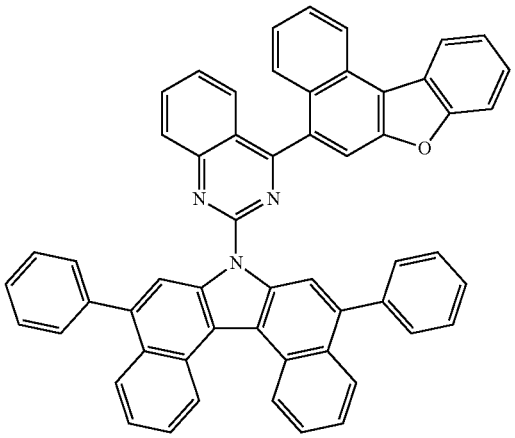
I 198
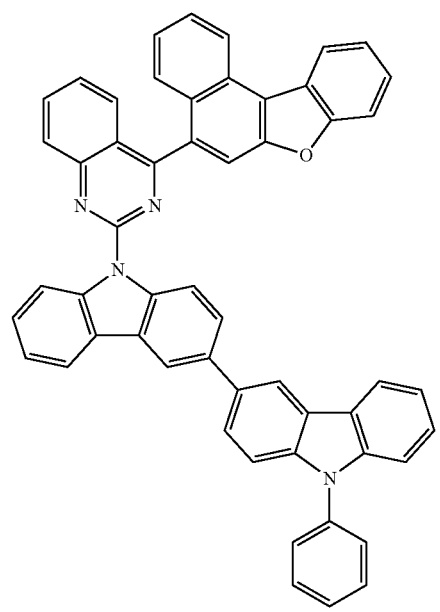
I 199
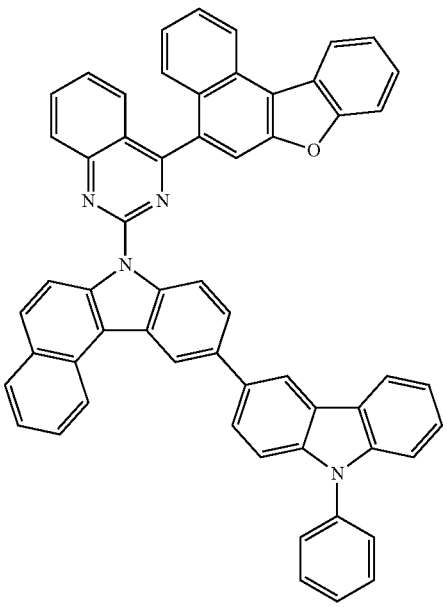

I 200
I 201
I 202
I 203 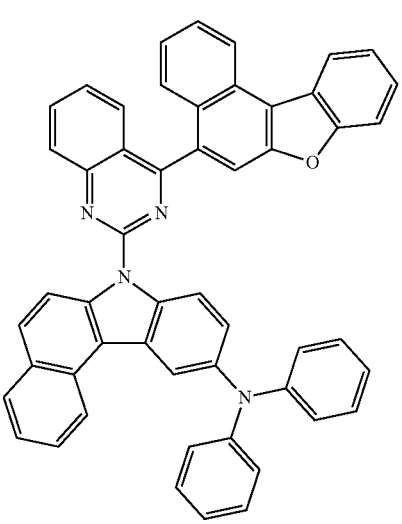
I 204 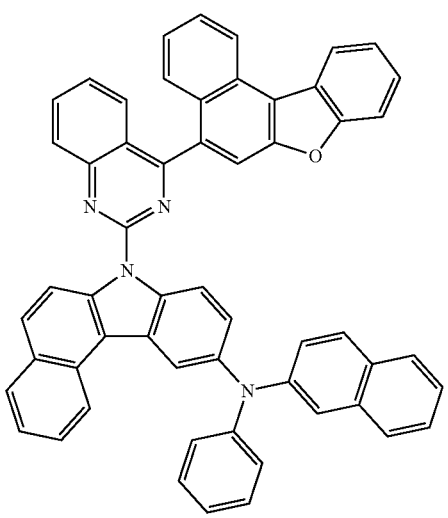
I 205 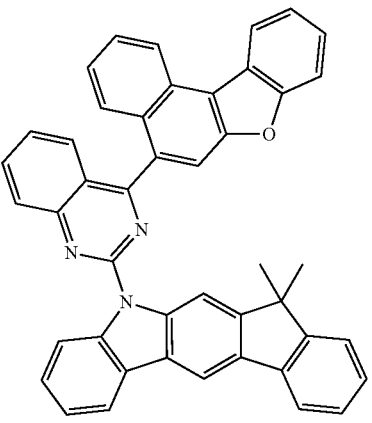

-continued
I 206
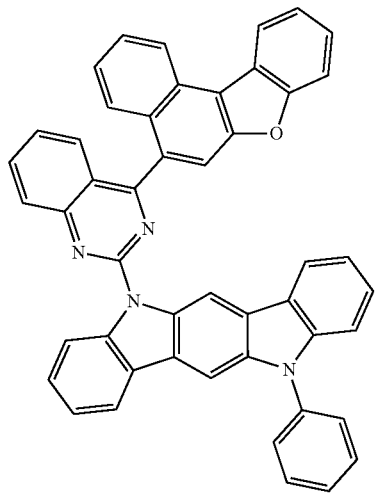
I 207
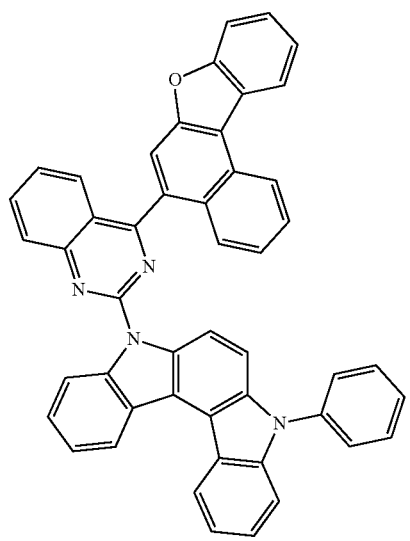
I 208
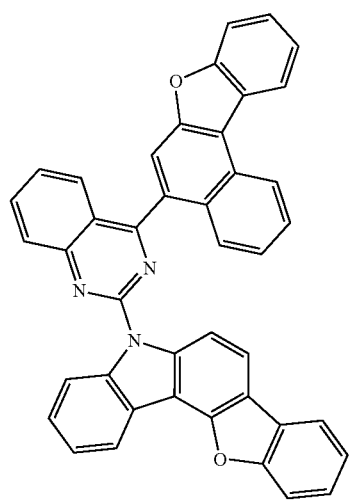
-continued
I 209
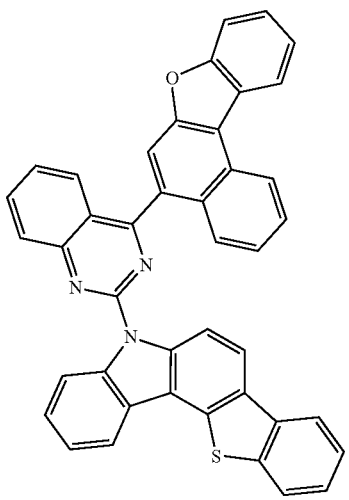
I 210
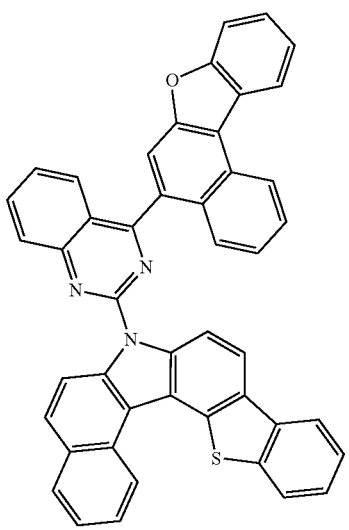
I 211
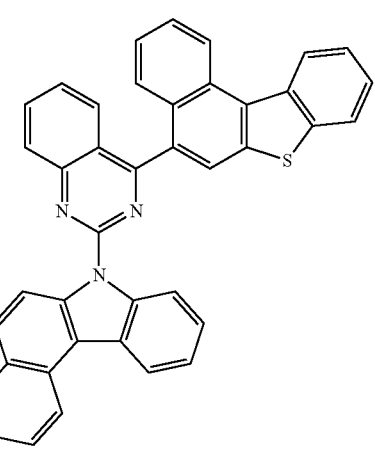

-continued
I 212
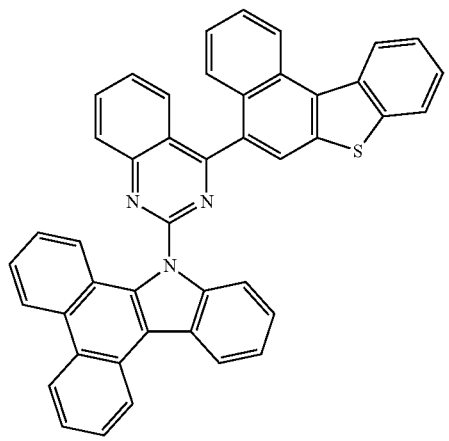
I 213
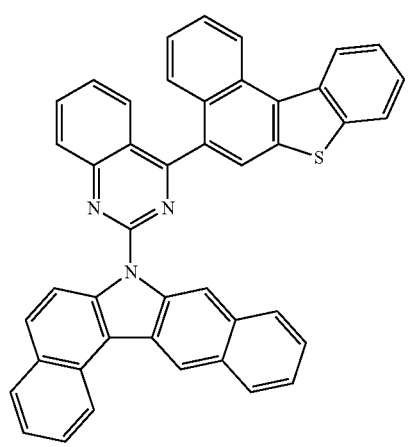
I 214
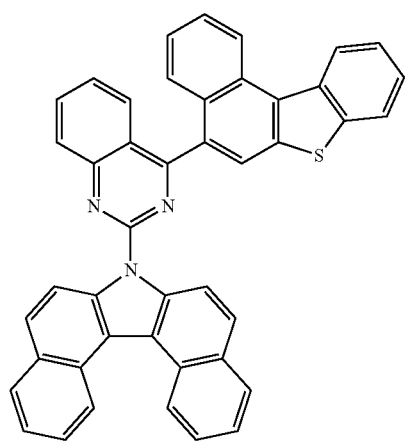
-continued
I 215
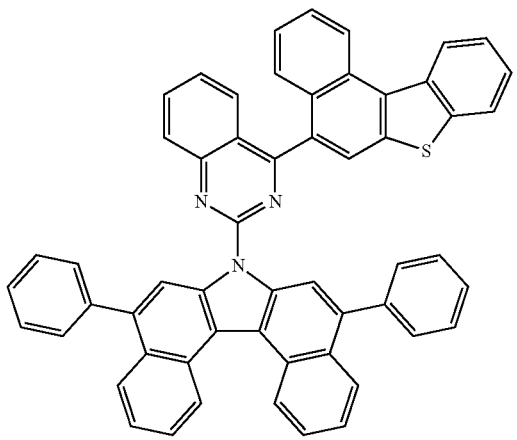
I 216
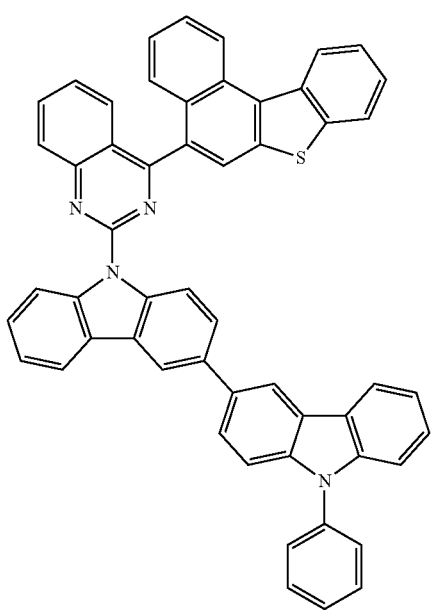
I 217
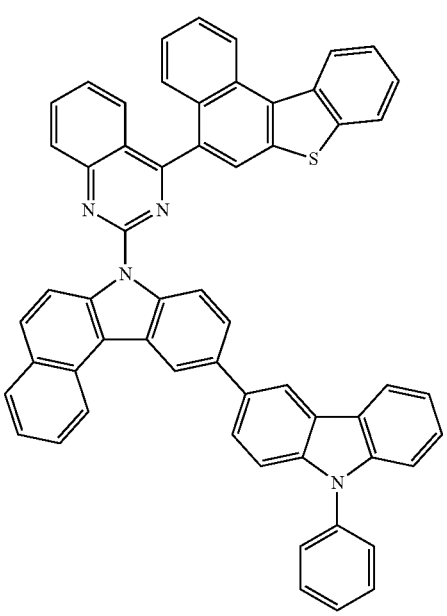

I 218
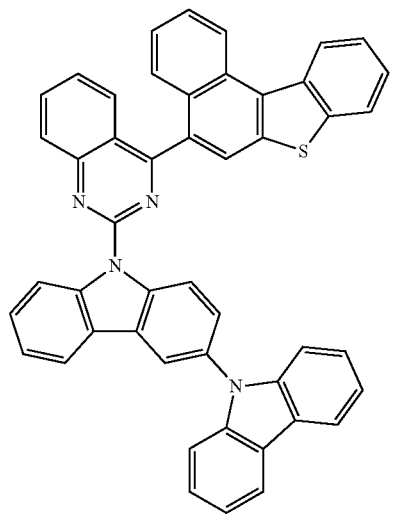
I 219
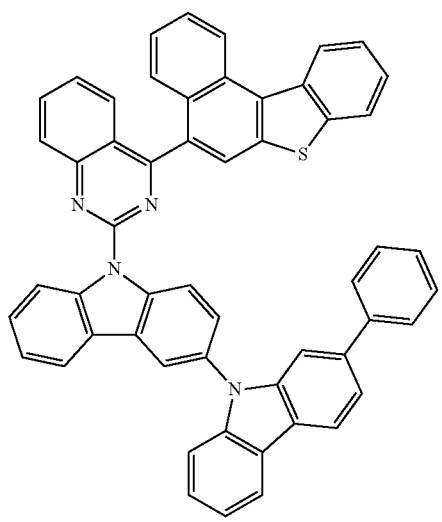
I 220
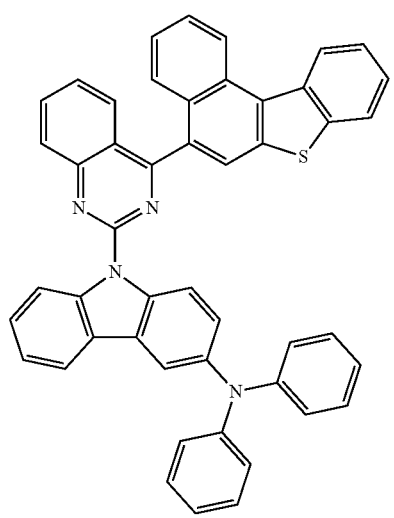
I 221
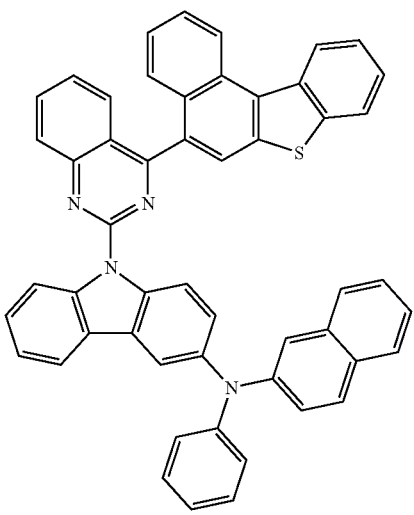
I 222
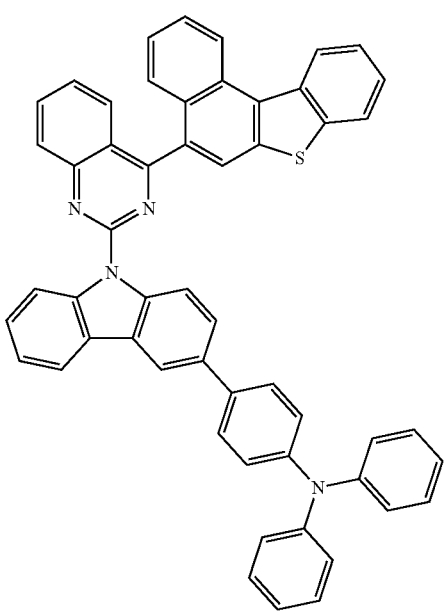
I 223
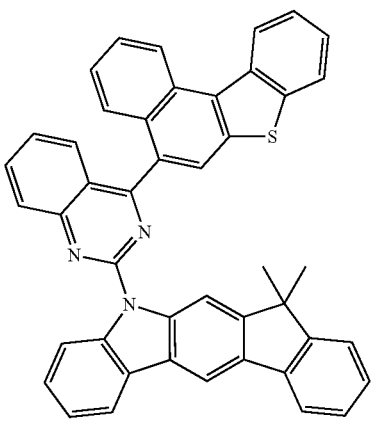

-continued
I 224
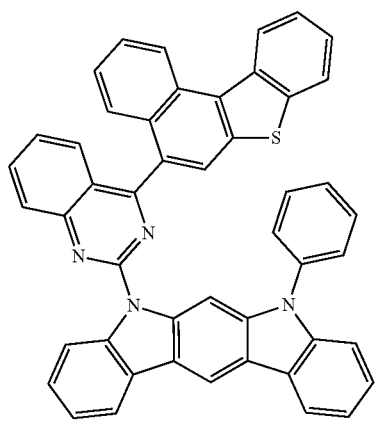
I 225
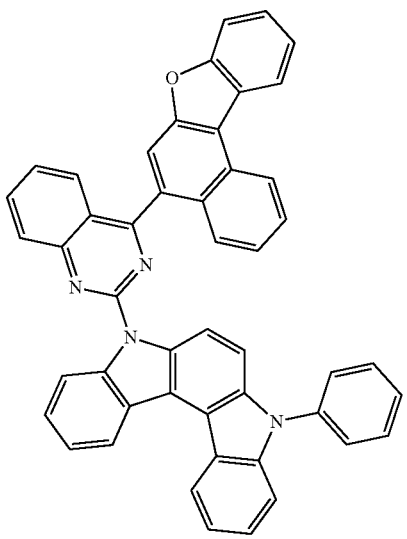
I 226
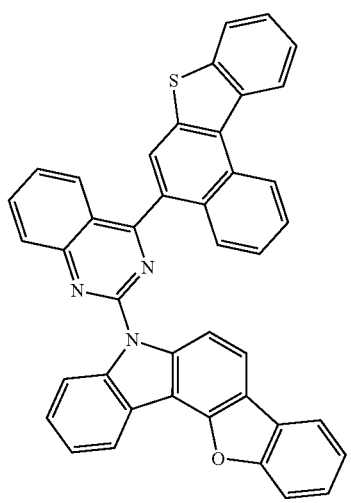
-continued
I 227
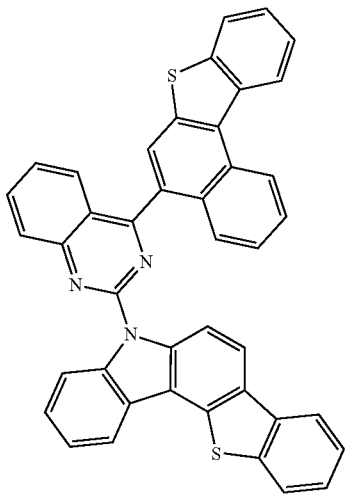
I 228
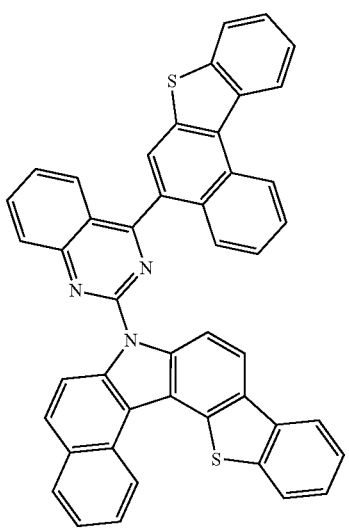
I 229
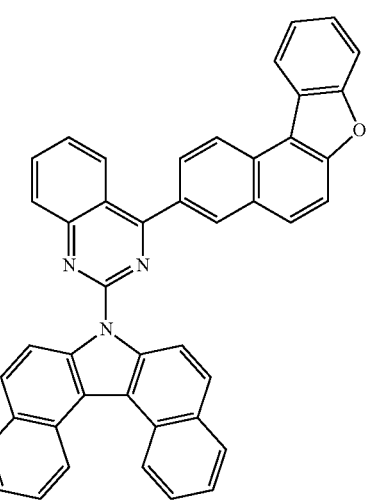

I230
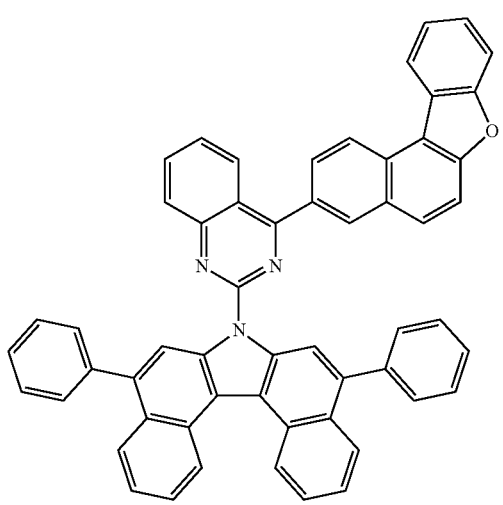
I231
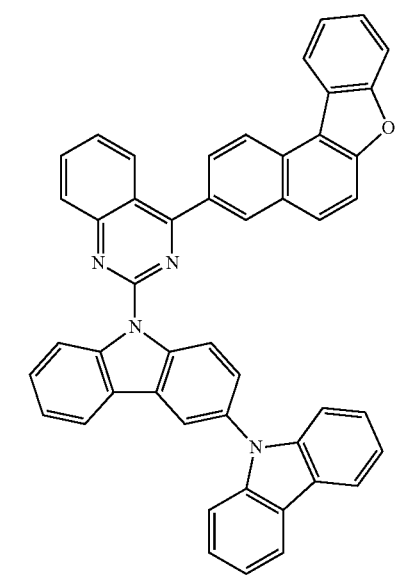
I232
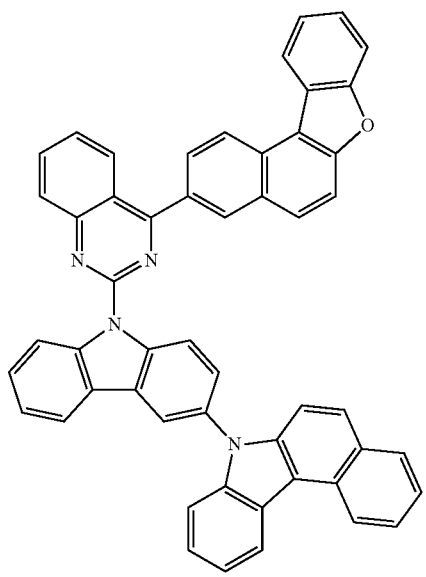
I233
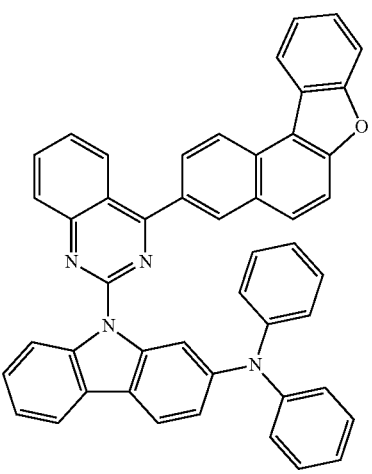
I234
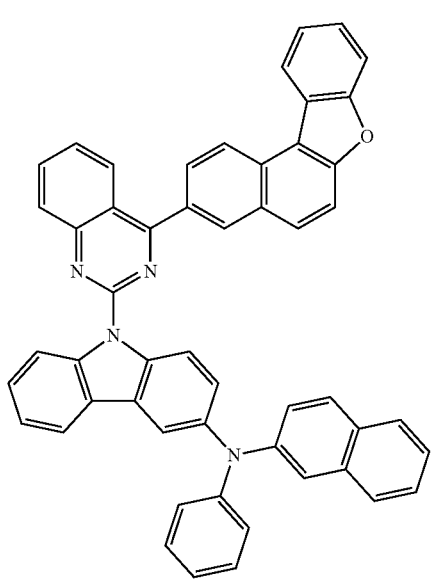
I235
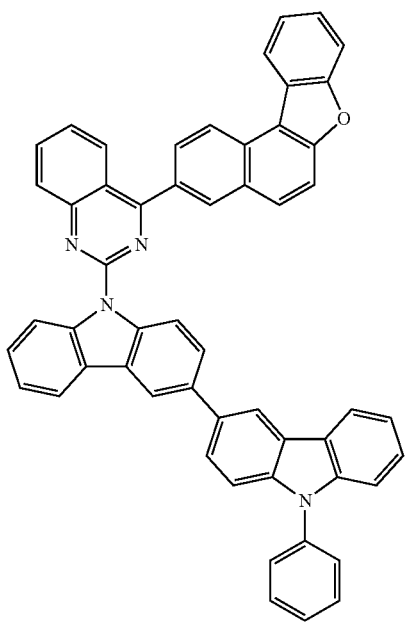

I 236
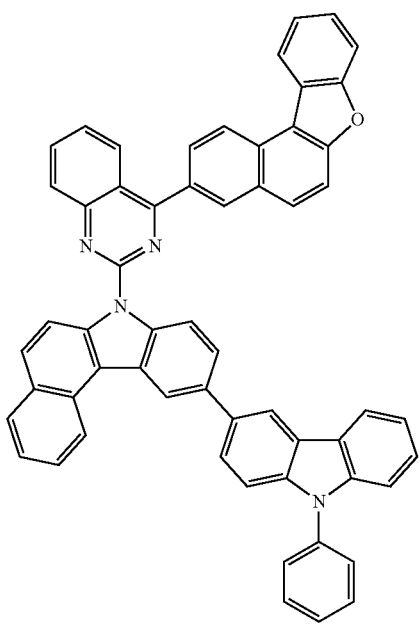
I 238
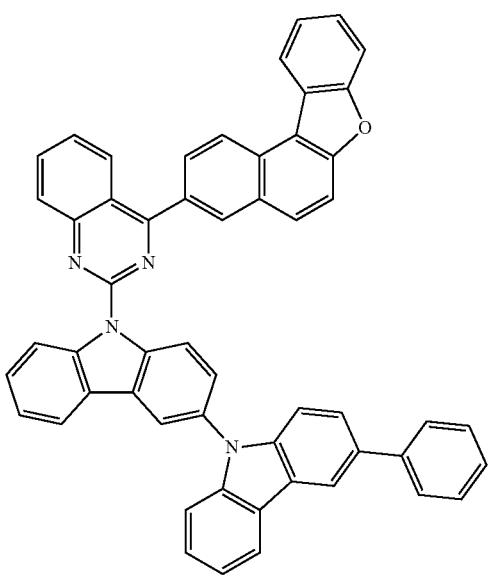
I 237
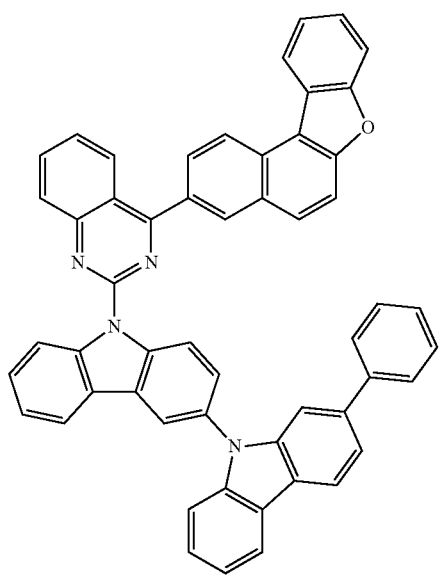
I 239

I 240
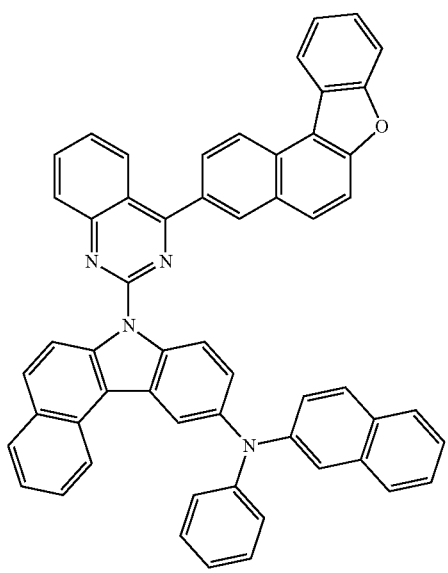
I 241
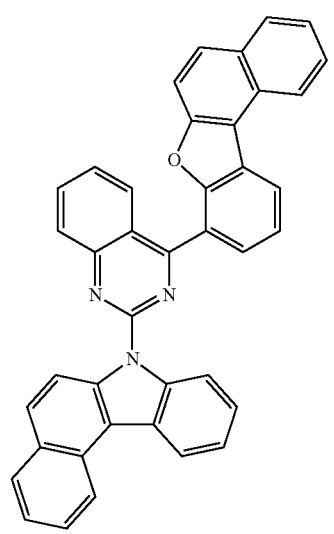
I 242
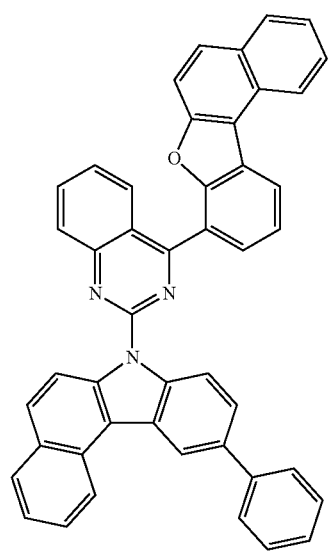
I 243
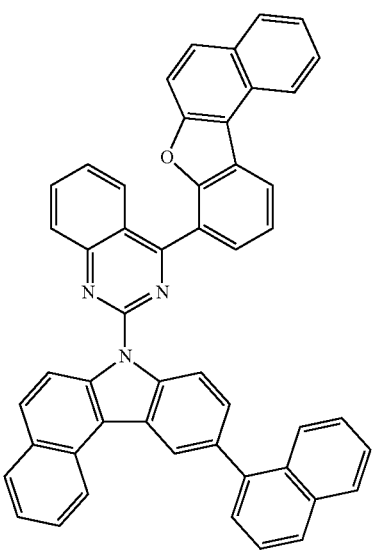
I 244
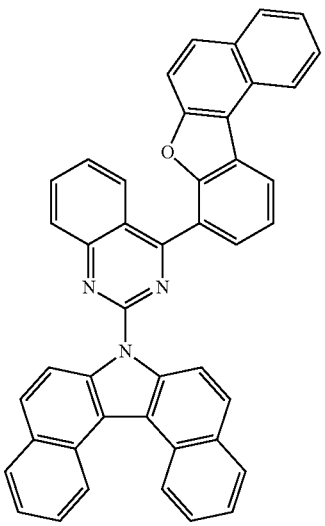

I 245
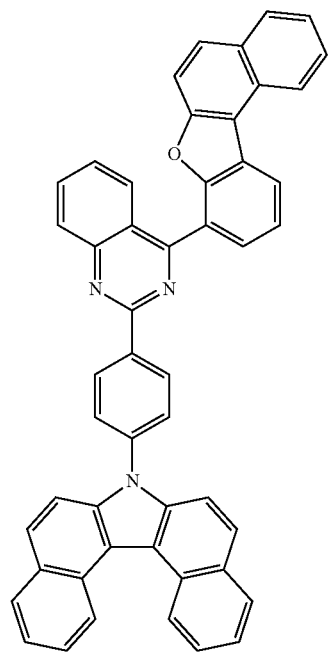
I 246
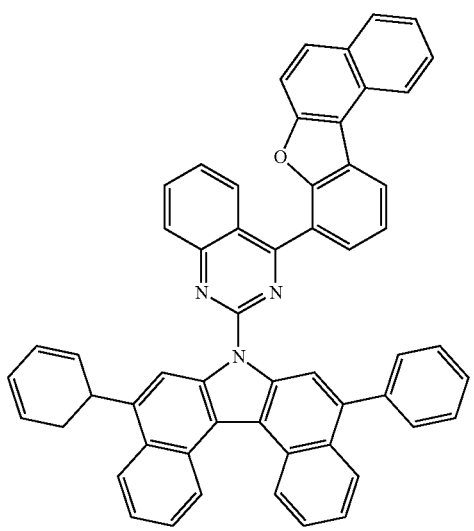
I 247
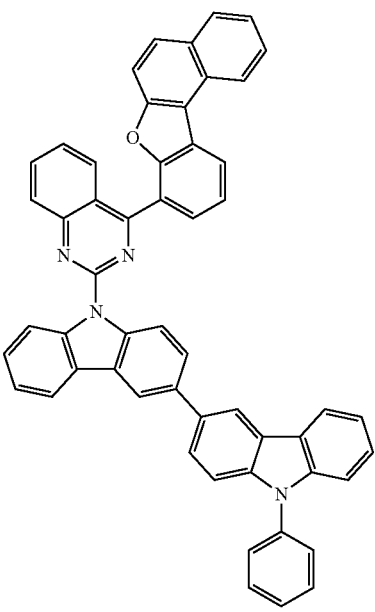
I 248
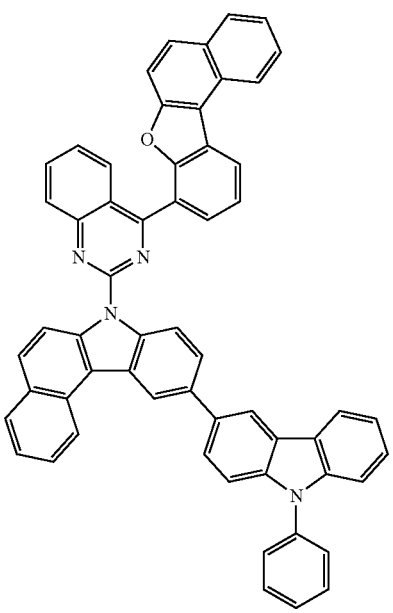

-continued
I 249
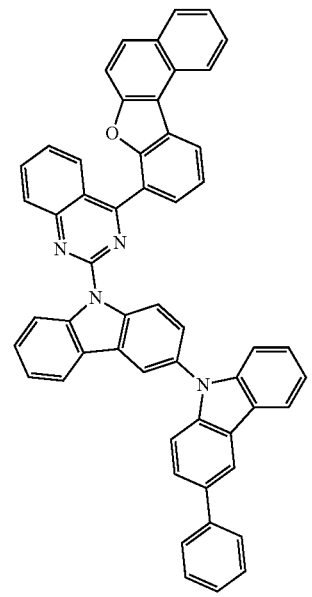
I 250
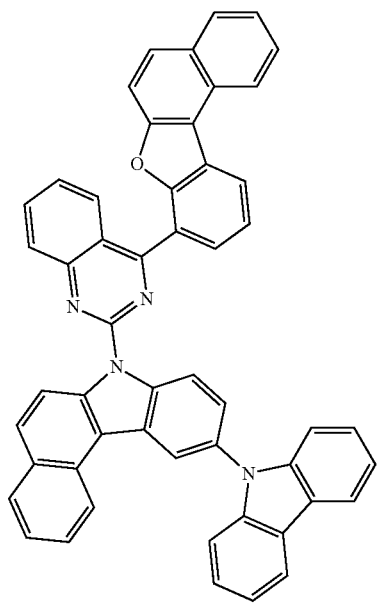
I 251
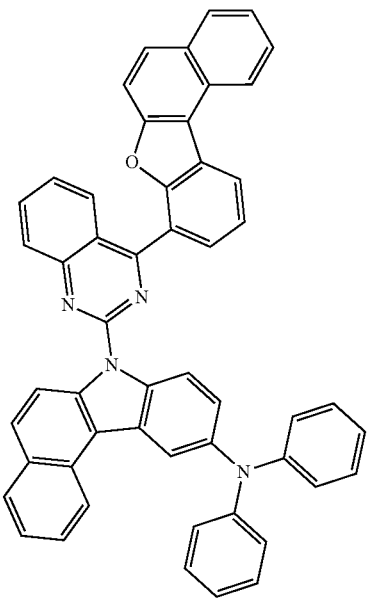
I 252
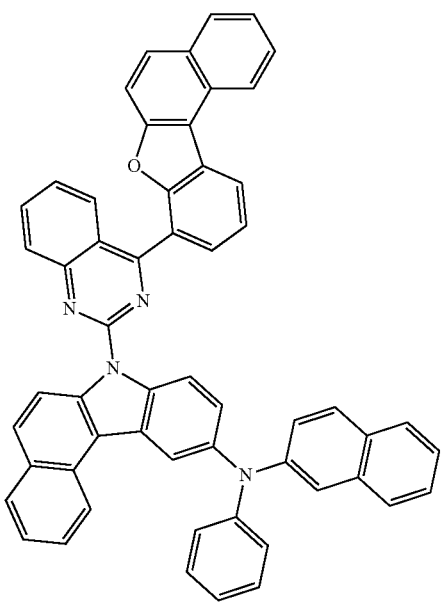

I 253
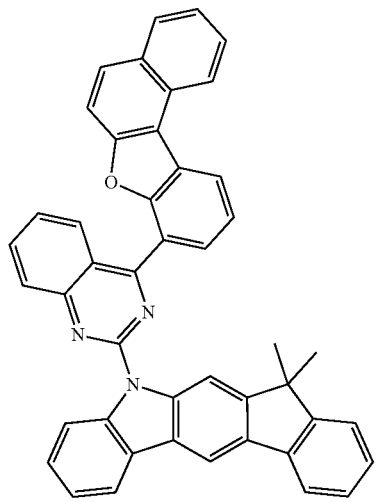
I 254
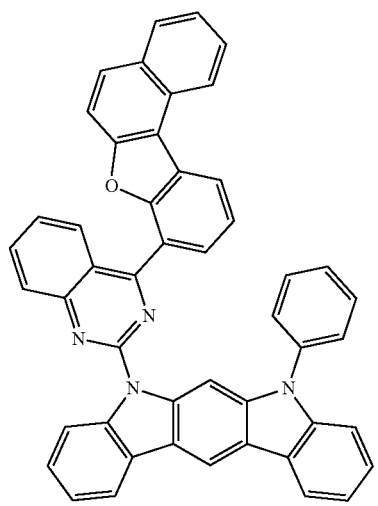
I 255
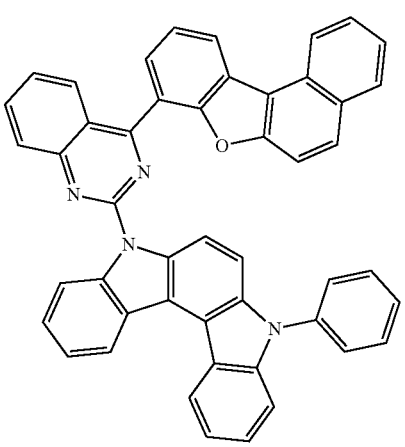
I 256
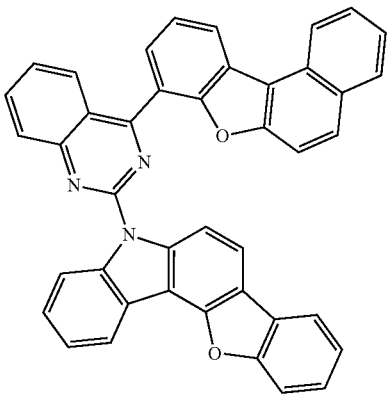
I 257
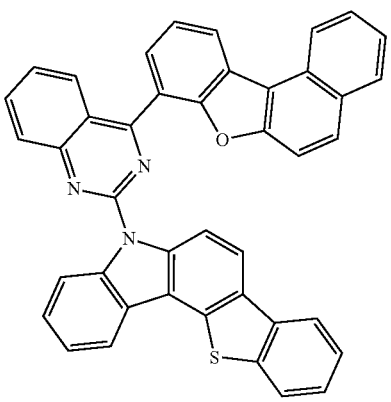
I 258
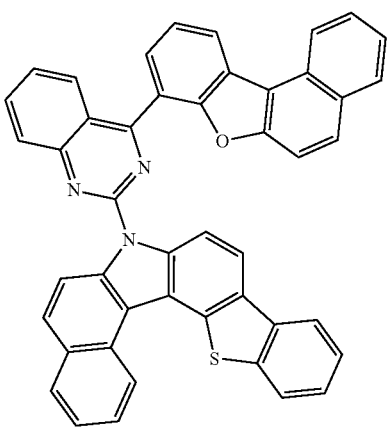
I 259
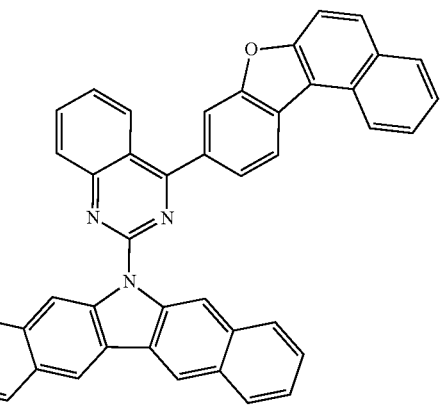

I 260
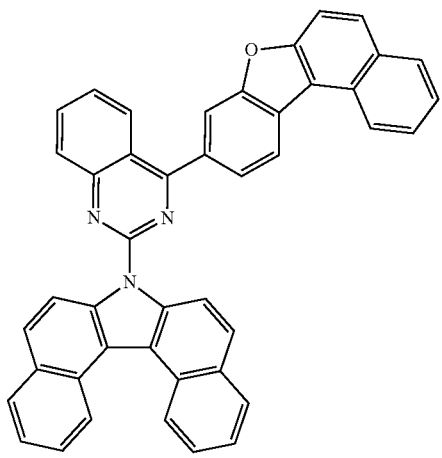
I 261
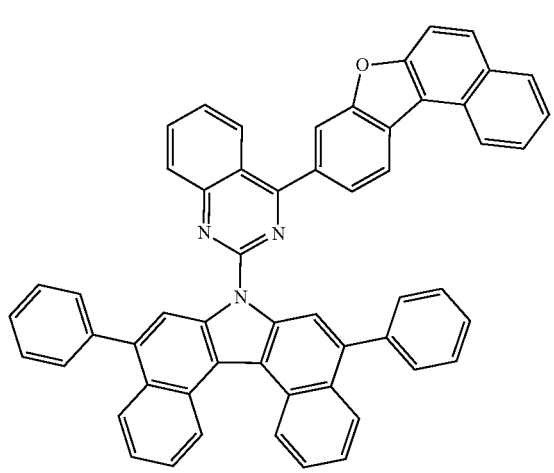
I 262
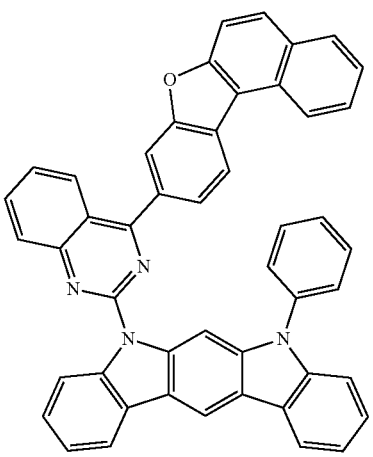
I 263
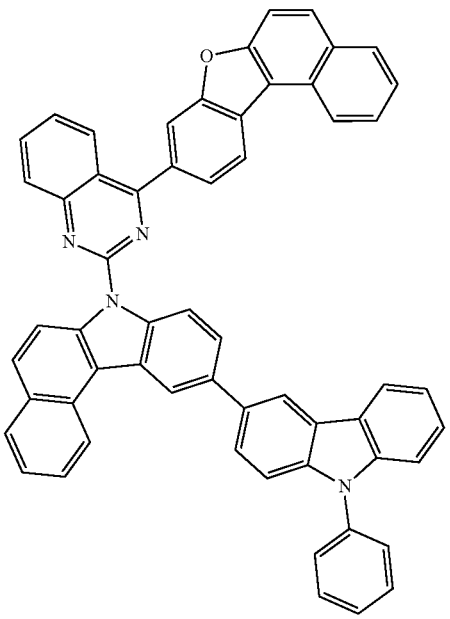
I 264
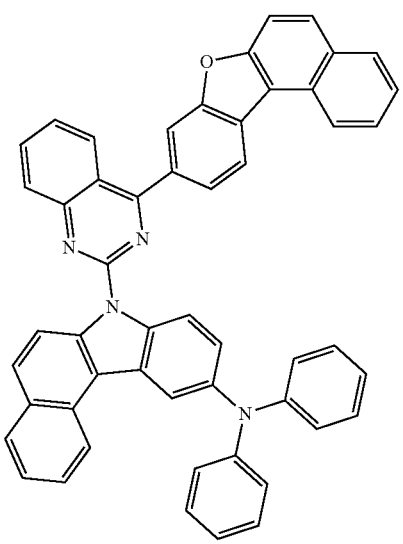
I 265

-continued
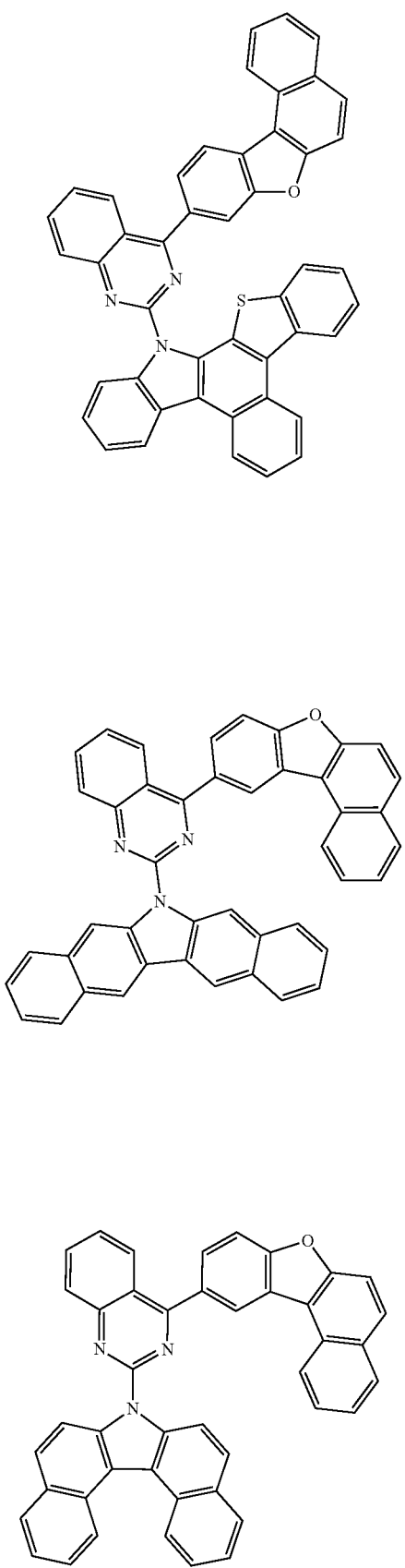
I 266
I 267
I 268
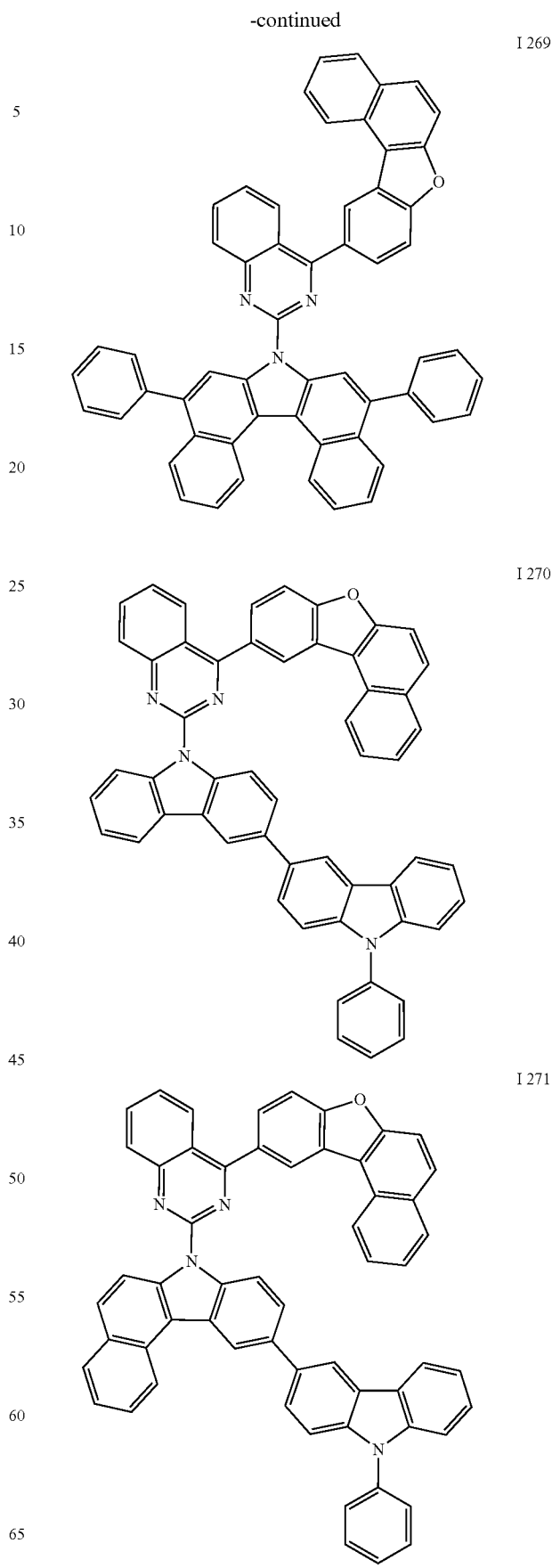
I 269
I 270
I 271

I 272
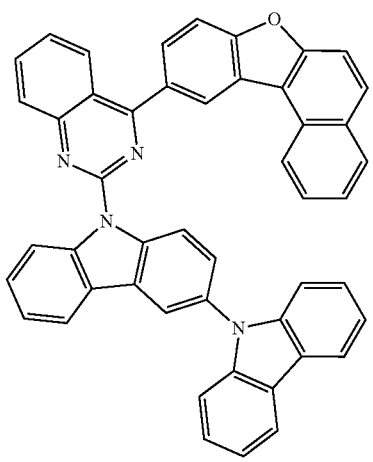
I 273
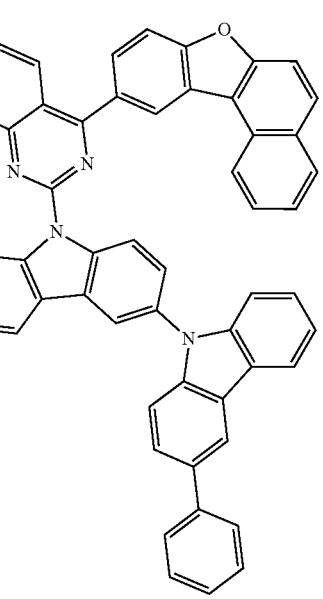
I 274
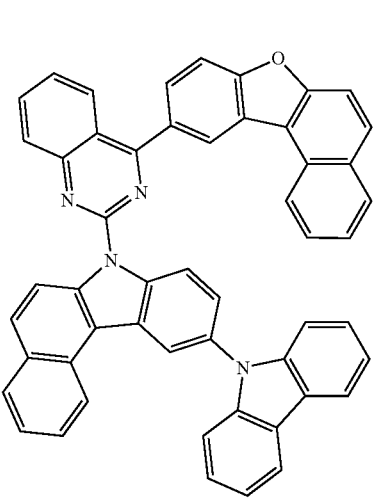
I 275
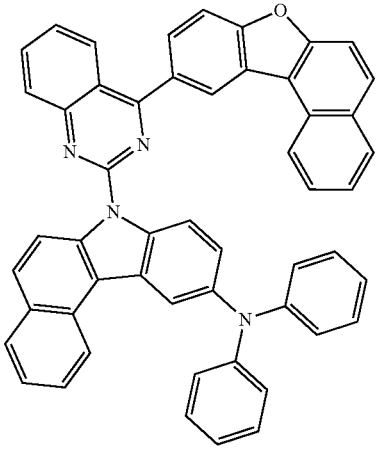
I 276
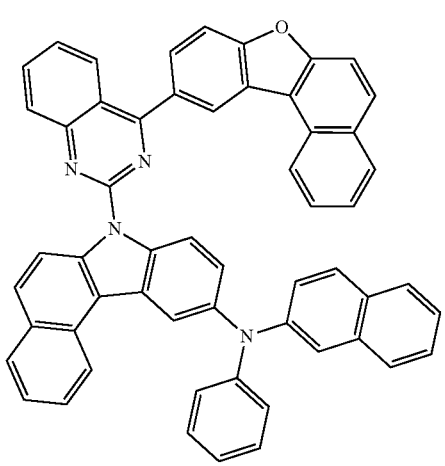
I 277
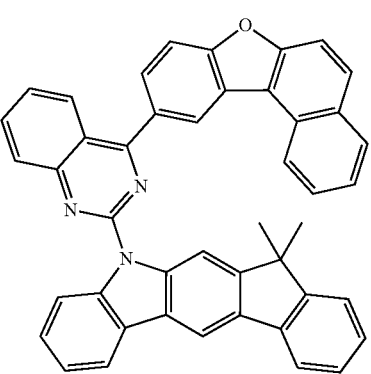

I 278
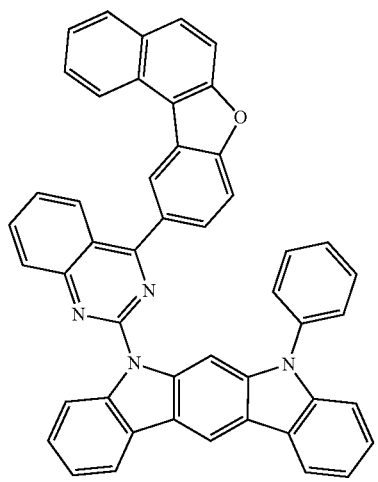
I 281
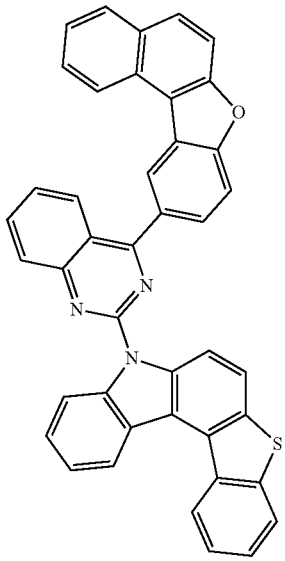
I 279
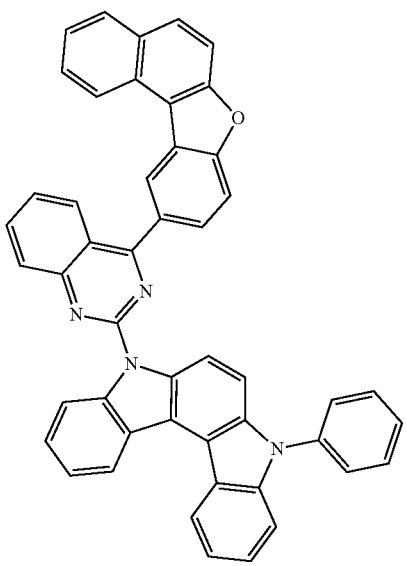
I 280
I 282
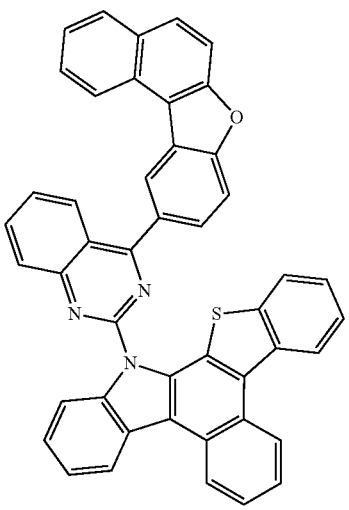

I 283
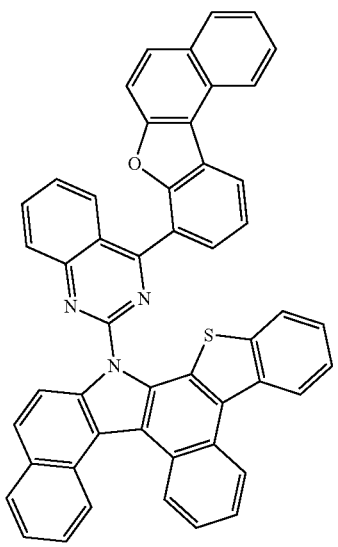
I 284
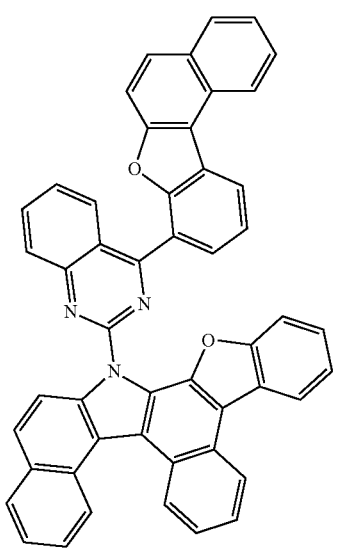
I 285
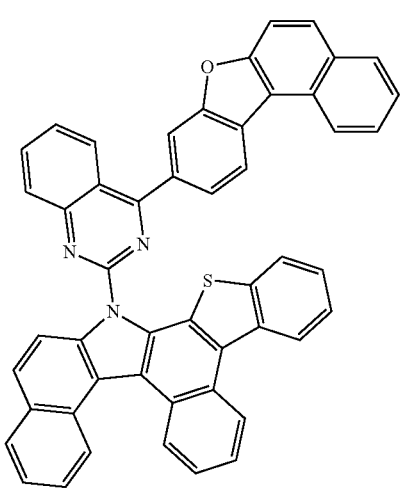
I 286
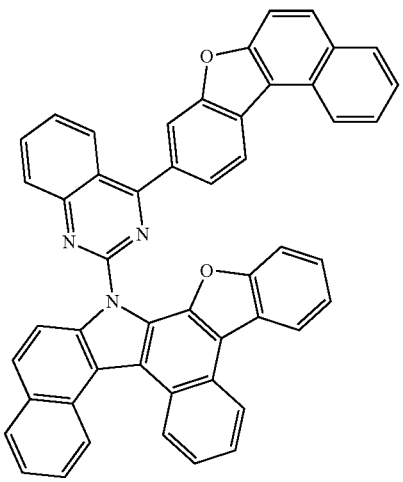
I 287
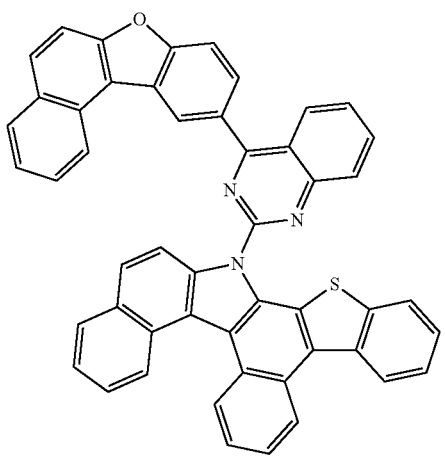
I 288
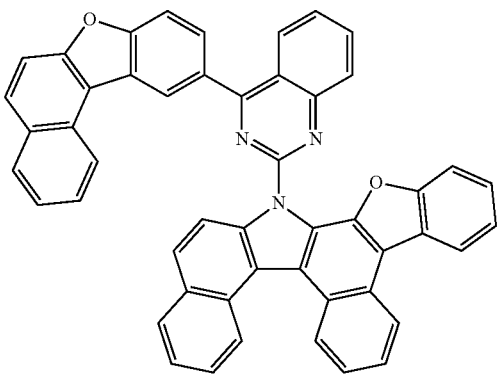

I 289
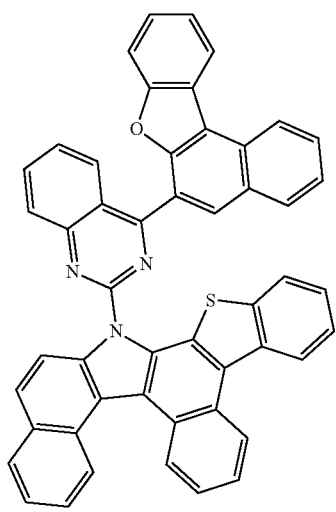
I 290
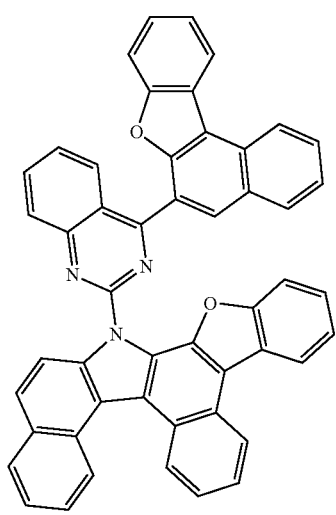
I 291
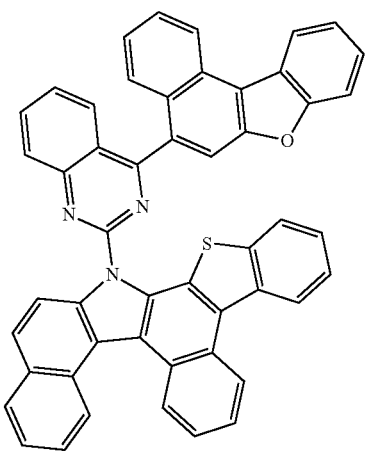
I 292
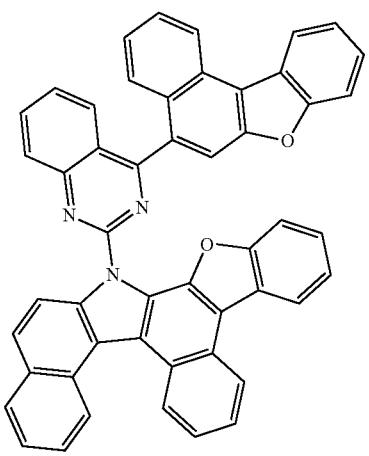
I 293
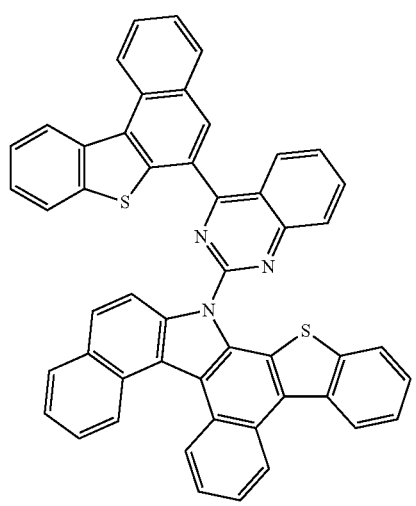
I 294
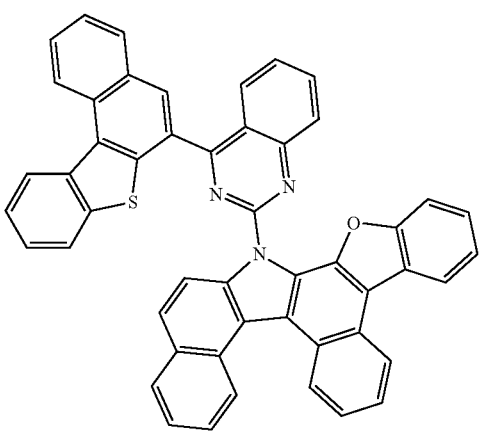

-continued
I 295
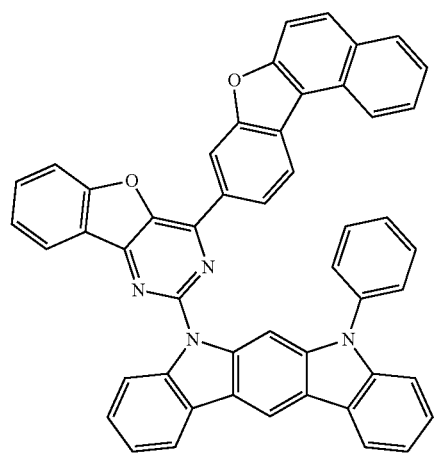
I 296
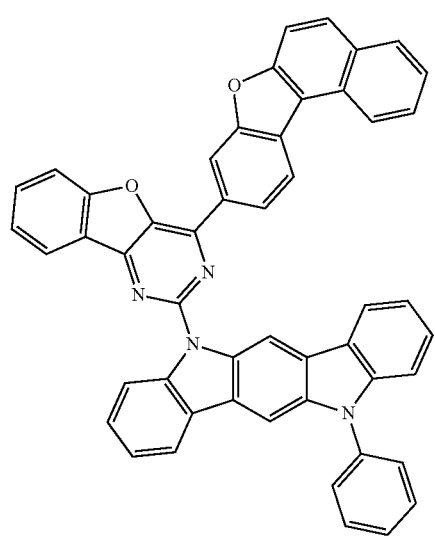
I 297
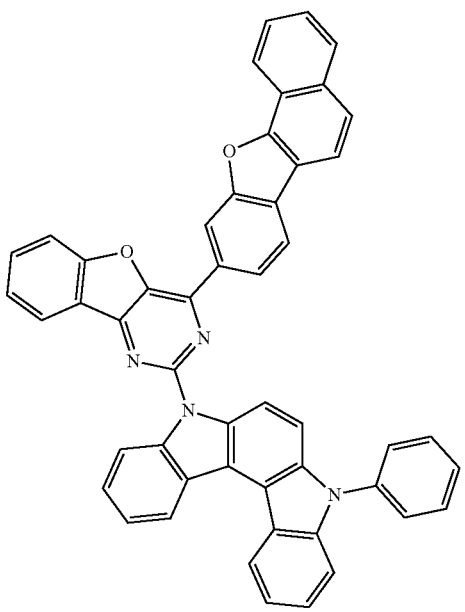
-continued
I 298
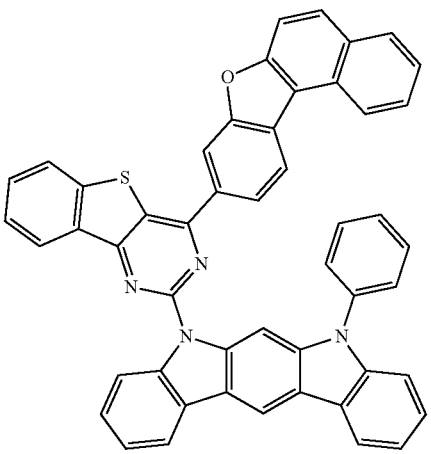
I 299
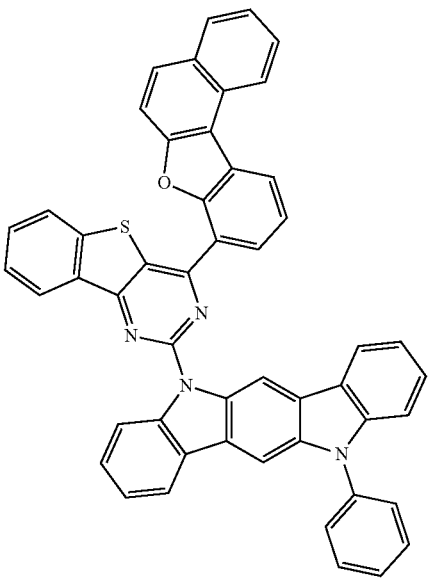
I 300
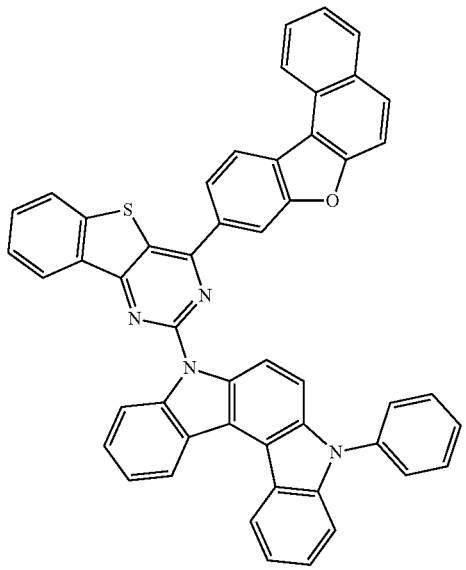

-continued
I 301
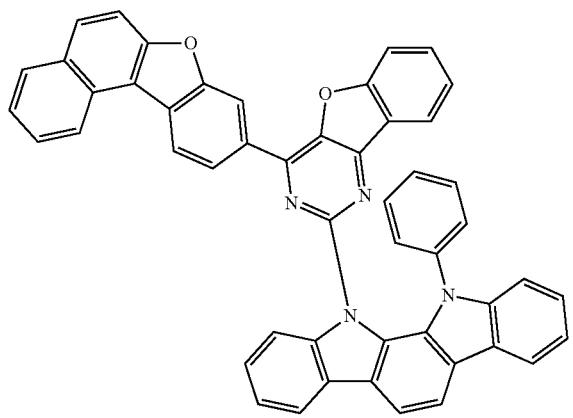
I 302
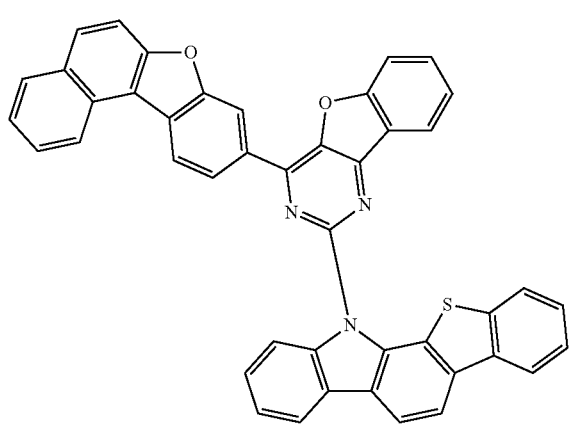
I 303
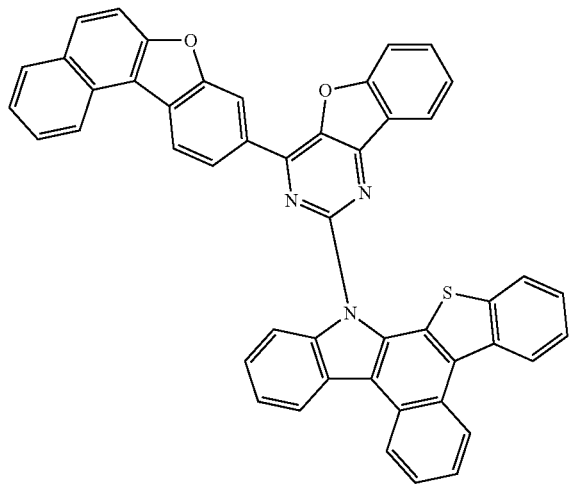
-continued
I 304
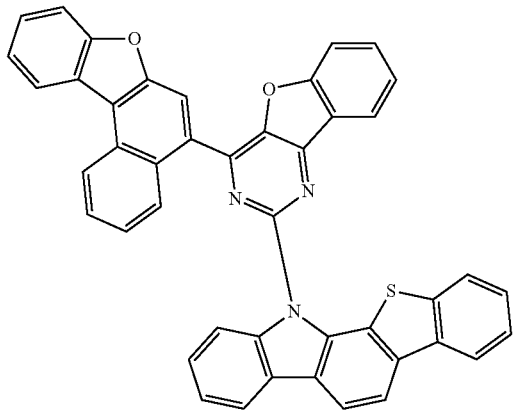
I 305
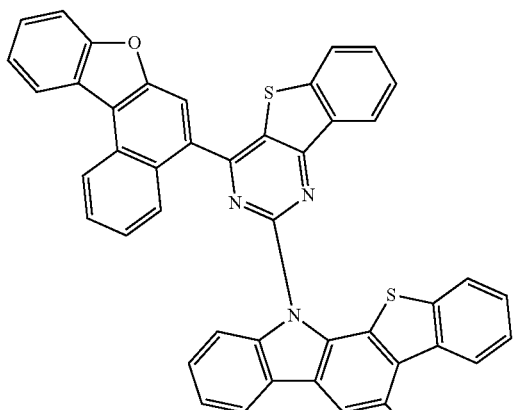
I 306
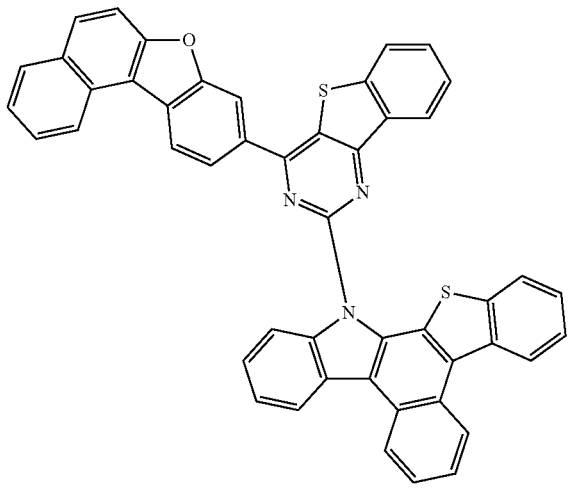

-continued
I 307
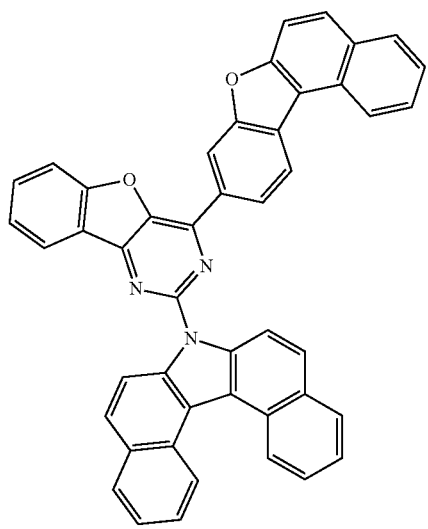
I 308
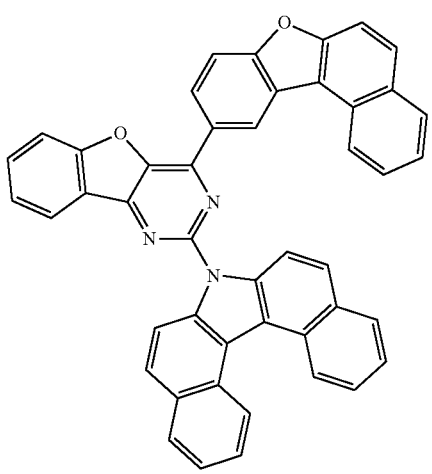
I 309
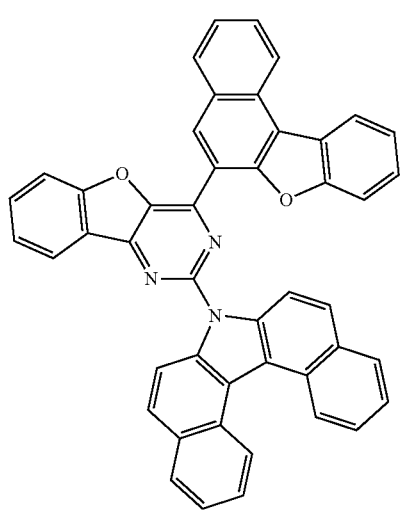
-continued
I 310
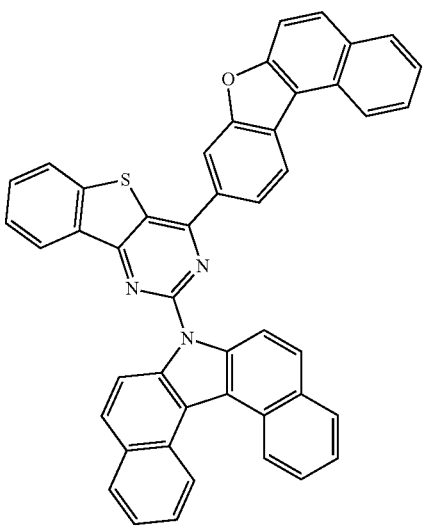
I 311
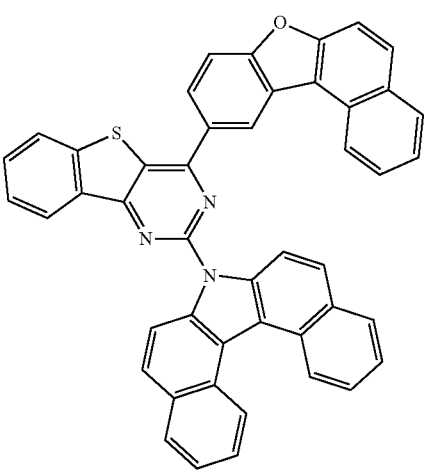
I 312
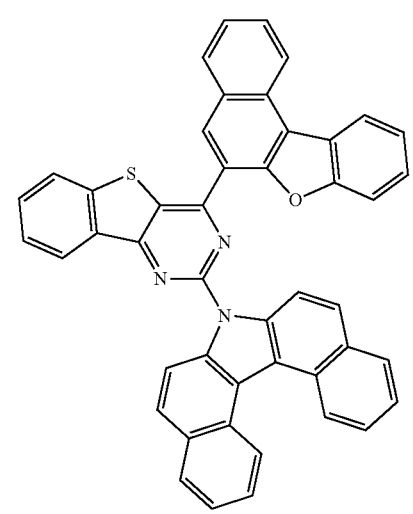

I 313
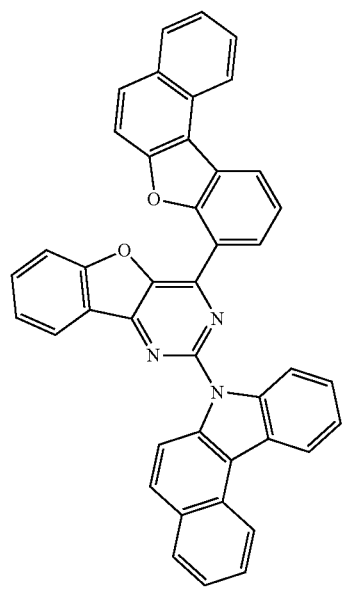
I 314
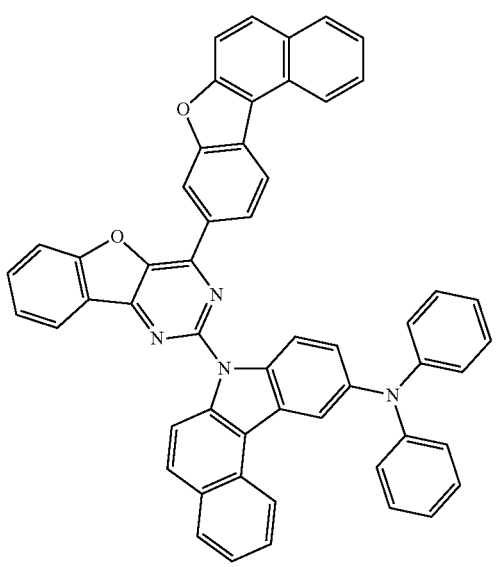
I 315
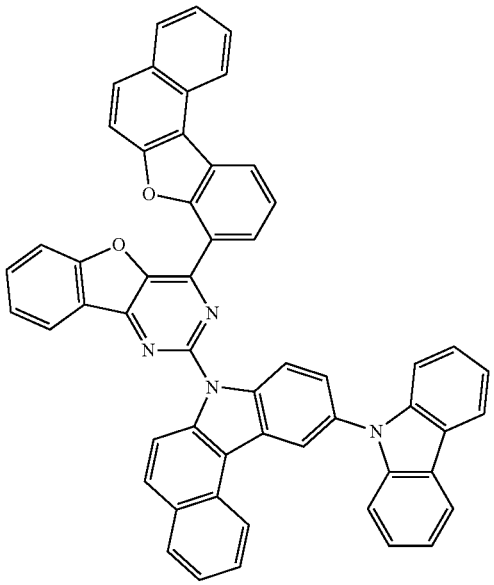
I 316
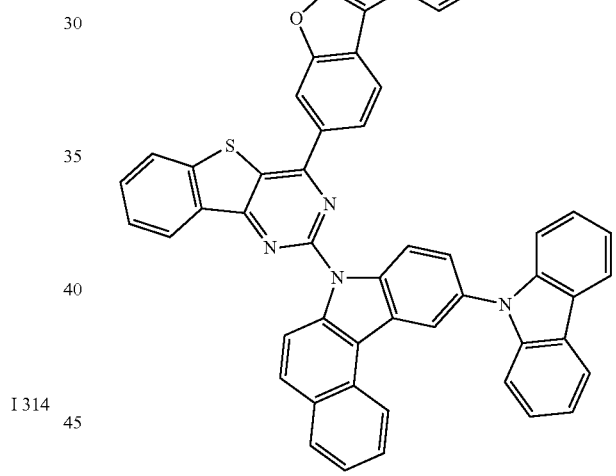
I 317
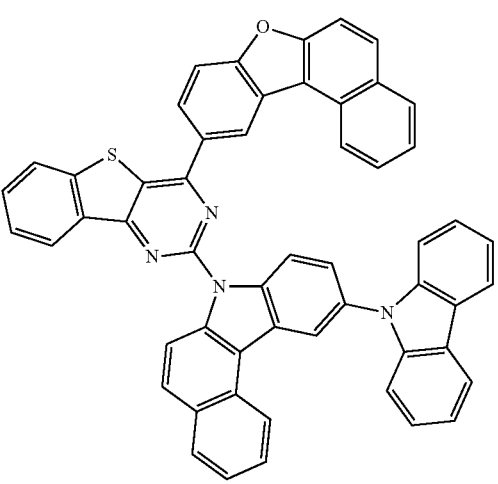

I-318
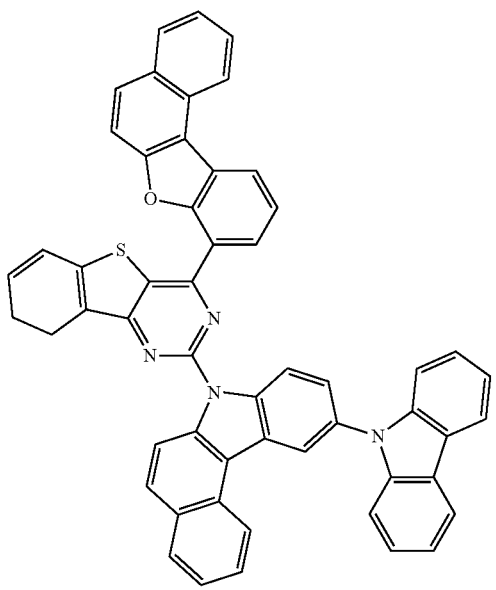
I-319
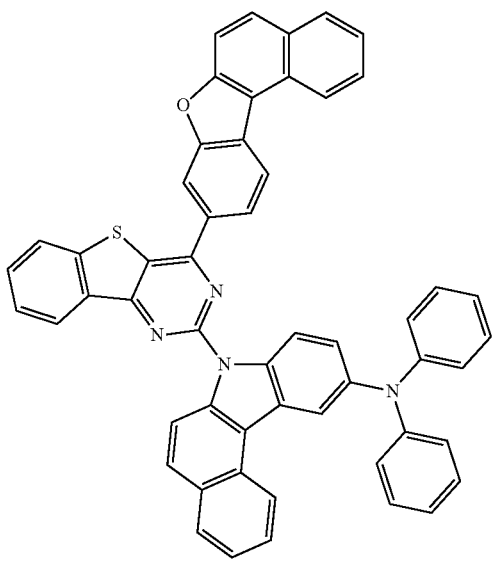
I-320
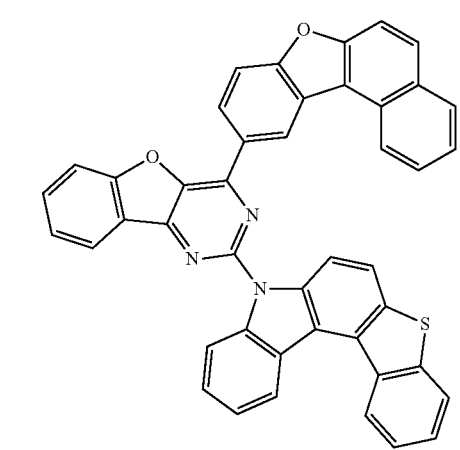
I-321
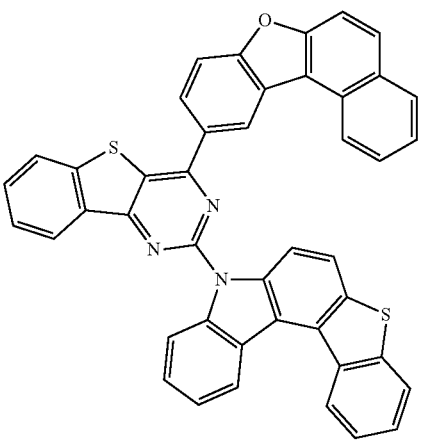
I-322
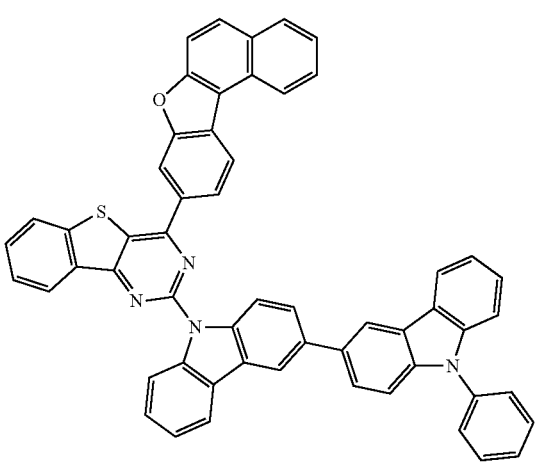
I-323
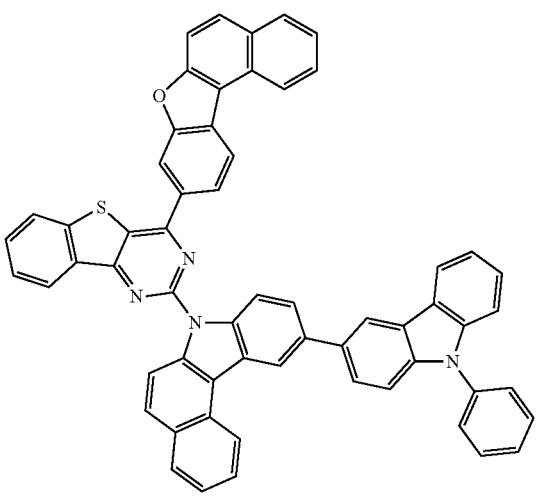

I 324
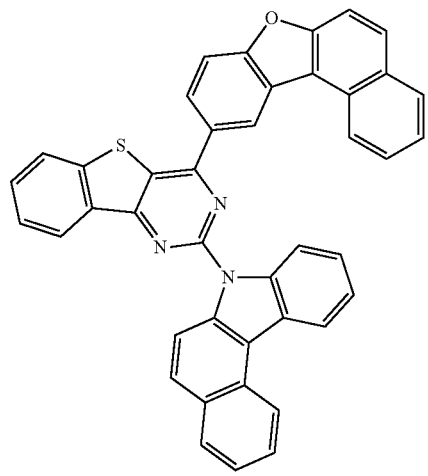
I 325
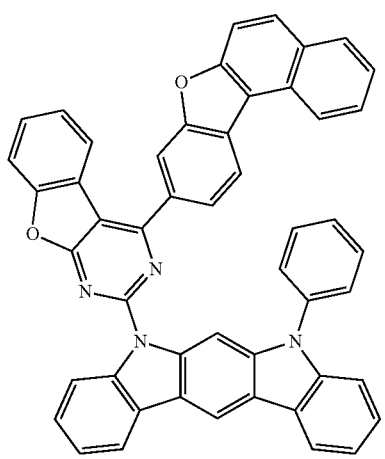
I 326
I 327
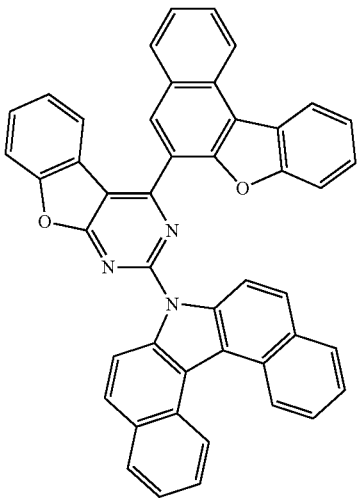
I 328
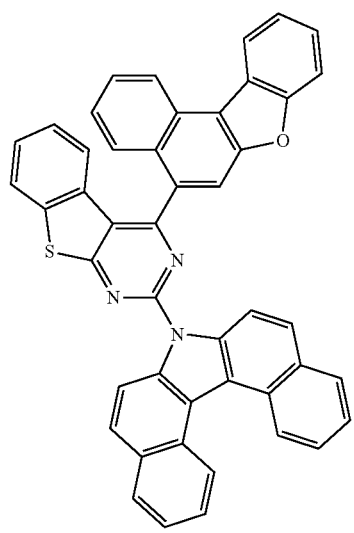
I 329
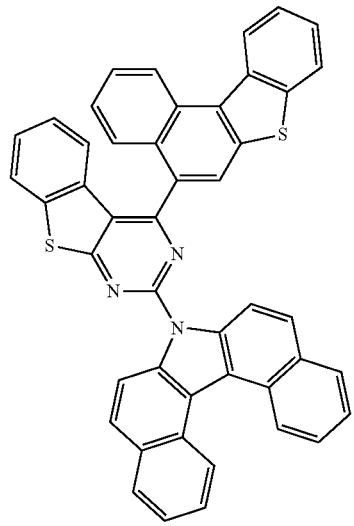

I 330
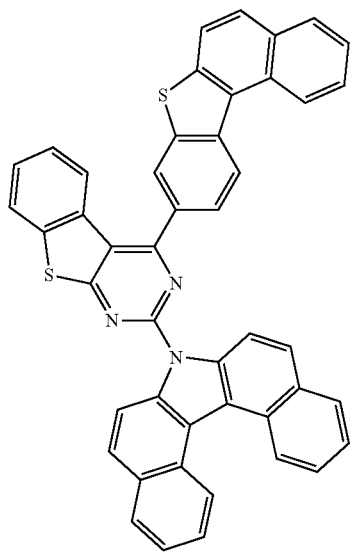
I 331
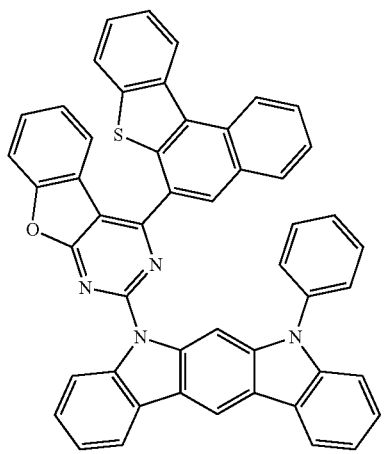
I 332
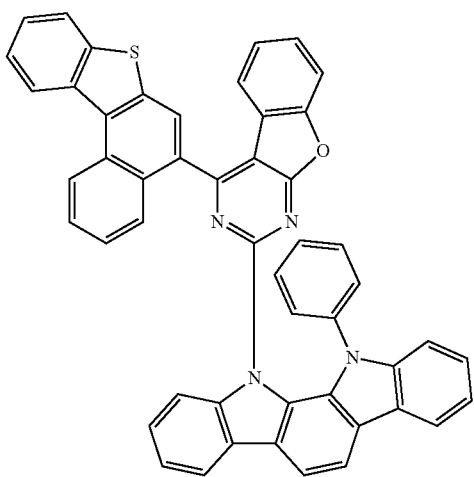
I 333
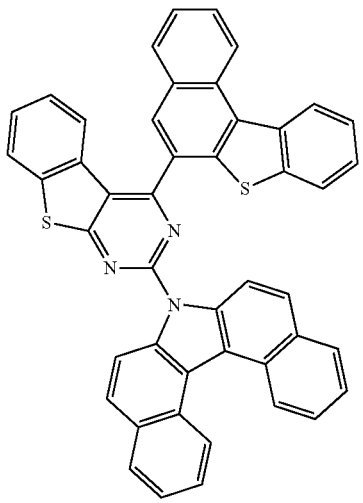
I 334
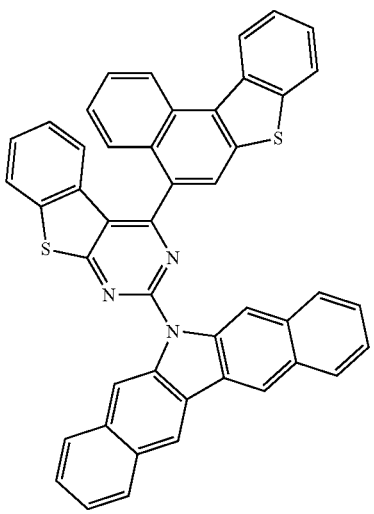
I 335
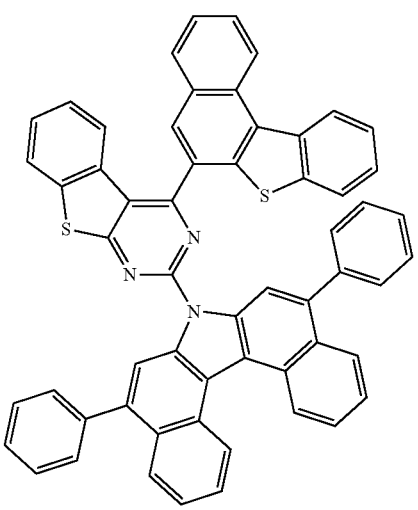

-continued

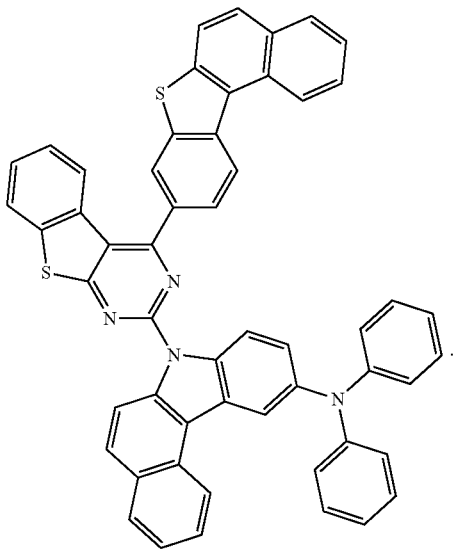

I 336

5. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

6. The organic light emitting device of claim 5, wherein the organic material layer comprises a light emitting layer, and the light emitting layer comprises the heterocyclic compound.

7. The organic light emitting device of claim 5, wherein the organic material layer comprises a light emitting layer, the light emitting layer comprises a host material, and the host material comprises the heterocyclic compound.

8. The organic light emitting device of claim 5, wherein the organic material layer comprises an electron injection layer or an electron transfer layer, and the electron transfer layer or the electron injection layer comprises the heterocyclic compound.

9. The organic light emitting device of claim 5, wherein the organic material layer comprises an electron blocking layer or a hole blocking layer, and the electron blocking layer or the hole blocking layer comprises the heterocyclic compound.

10. The organic light emitting device of claim 5, further comprising one, two or more layers selected from the group consisting of a light emitting layer, a hole injection layer, a hole transfer layer, an electron injection layer, an electron transfer layer, an electron blocking layer and a hole blocking layer.

* * * * *